(12) United States Patent
Hakii et al.

(10) Patent No.: US 9,871,220 B2
(45) Date of Patent: Jan. 16, 2018

(54) TRANSPARENT ELECTRODE, AND ELECTRONIC DEVICE

(71) Applicant: Konica Minolta, Inc., Tokyo (JP)

(72) Inventors: Takeshi Hakii, Tokyo (JP); Hiroshi Ishidai, Tokyo (JP); Toshiyuki Kinoshita, Tokyo (JP); Kazuhiro Yoshida, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 291 days.

(21) Appl. No.: 14/646,611

(22) PCT Filed: Nov. 28, 2013

(86) PCT No.: PCT/JP2013/082097
§ 371 (c)(1),
(2) Date: May 21, 2015

(87) PCT Pub. No.: WO2014/084323
PCT Pub. Date: Jun. 5, 2014

(65) Prior Publication Data
US 2015/0311467 A1 Oct. 29, 2015

(30) Foreign Application Priority Data
Nov. 28, 2012 (JP) .................................. 2012-260040

(51) Int. Cl.
H01L 51/00 (2006.01)
H01L 51/52 (2006.01)
(Continued)

(52) U.S. Cl.
CPC ........ *H01L 51/5203* (2013.01); *C07C 211/54* (2013.01); *C07D 209/86* (2013.01);
(Continued)

(58) Field of Classification Search
None
See application file for complete search history.

(56) References Cited

U.S. PATENT DOCUMENTS 6,861,800 B2 * 3/2005 Tyan ................... H01L 51/5265
313/113
7,642,714 B2 * 1/2010 Bechtel ................. H01L 27/322
313/506
(Continued)

FOREIGN PATENT DOCUMENTS

JP 2002015623 A 1/2002
JP 2006001271 A 1/2006
(Continued)

OTHER PUBLICATIONS

International Search Report dated Mar. 4, 2014 for PCT/JP2013/082097 and English translation.

Primary Examiner — Robert S Loewe
(74) Attorney, Agent, or Firm — Lucas & Mercanti, LLP

(57) ABSTRACT

A transparent electrode is configured which is provided with: a nitrogen-containing layer; a conductive layer which is provided abutting the nitrogen-containing layer, and which has silver as a main component thereof; a high refractive index layer having a refractive index higher than that of the nitrogen-containing layer; and a low refractive index layer having a refractive index lower than that of the high refractive index layer. In the nitrogen-containing layer, a compound is used which includes nitrogen atoms, and which has, in cases when n represents the number of unshared electron pairs which are not involved in aromaticity and which are not coordinated to metal, from among the unshared electron pairs of the nitrogen atoms, and M represents molecular weight, an effective unshared-electron-pair content [n/M] that satisfies $2.0 \times 10^{-3} \leq [n/M]$.

26 Claims, 5 Drawing Sheets

(51) Int. Cl.

| | |
|---|---|
| *C07D 401/14* | (2006.01) |
| *C07D 409/14* | (2006.01) |
| *C07D 471/04* | (2006.01) |
| *C07D 471/14* | (2006.01) |
| *C07D 491/048* | (2006.01) |
| *C07D 213/24* | (2006.01) |
| *H05B 33/02* | (2006.01) |
| *H05B 33/28* | (2006.01) |
| *C07D 405/14* | (2006.01) |
| *C07D 417/14* | (2006.01) |
| *C07D 493/04* | (2006.01) |
| *C07D 495/04* | (2006.01) |
| *C07D 495/14* | (2006.01) |
| *C07D 519/00* | (2006.01) |
| *C07C 211/54* | (2006.01) |
| *C07D 209/86* | (2006.01) |
| *C07D 409/10* | (2006.01) |

(52) U.S. Cl.
CPC ......... *C07D 213/24* (2013.01); *C07D 401/14* (2013.01); *C07D 405/14* (2013.01); *C07D 409/10* (2013.01); *C07D 409/14* (2013.01); *C07D 417/14* (2013.01); *C07D 471/04* (2013.01); *C07D 471/14* (2013.01); *C07D 491/048* (2013.01); *C07D 493/04* (2013.01); *C07D 495/04* (2013.01); *C07D 495/14* (2013.01); *C07D 519/00* (2013.01); *H01L 51/5215* (2013.01); *H05B 33/02* (2013.01); *H05B 33/28* (2013.01)

(56) References Cited

U.S. PATENT DOCUMENTS

| | | | | |
|---|---|---|---|---|
| 8,487,527 | B2 * | 7/2013 | Aziz | H01L 51/5012 257/40 |
| 8,878,206 | B2 * | 11/2014 | Lee | H01L 27/3211 257/89 |
| 2003/0085652 | A1 * | 5/2003 | Weaver | H01L 51/5262 313/506 |
| 2004/0140757 | A1 * | 7/2004 | Tyan | H01L 51/5265 313/504 |
| 2004/0245917 | A1 * | 12/2004 | Lu | H01L 51/5203 313/503 |
| 2005/0037232 | A1 * | 2/2005 | Tyan | H01L 27/3211 428/690 |
| 2009/0284138 | A1 * | 11/2009 | Yasukawa | C09K 11/06 313/504 |
| 2010/0123126 | A1 * | 5/2010 | Kitamura | H01L 51/5231 257/40 |
| 2010/0156277 | A1 * | 6/2010 | Visser | H01L 51/5237 313/504 |
| 2011/0057920 | A1 | 3/2011 | Matsuura et al. | |
| 2012/0211743 | A1 * | 8/2012 | Ito | C07D 213/22 257/40 |
| 2012/0261654 | A1 | 10/2012 | Yasukawa et al. | |

FOREIGN PATENT DOCUMENTS

| | | |
|---|---|---|
| JP | 2006164961 A | 6/2006 |
| JP | 2009151963 A | 7/2009 |
| JP | 2010251675 A | 11/2010 |
| JP | 2011054419 A | 3/2011 |
| JP | 2011077028 A | 4/2011 |
| WO | 2009054253 A1 | 4/2009 |
| WO | 2011004807 A1 | 1/2011 |

* cited by examiner

TBAC

Ir(ppy)₃

TRANSPARENT ELECTRODE, AND ELECTRONIC DEVICE

CROSS REFERENCE TO RELATED APPLICATION

This Application is a 371 of PCT/JP2013/082097 filed on Nov. 28, 2013 which, in turn, claimed the priority of Japanese Patent Application No. JP2012-260040 filed on Nov. 28, 2012, both applications are incorporated herein by reference.

TECHNICAL FIELD

The present invention relates to a transparent electrode, and an electronic device, particularly relates to a transparent electrode having both electrical conductivity and light transmission property, and to an electronic device using the transparent electrode.

BACKGROUND ART

An organic electroluminescent element (hereinafter, referred to as "organic EL element") utilizing electroluminescence (hereinafter, referred to as "EL") of an organic material is a thin-film type completely-solid state element capable of emitting light at a low voltage of several volts to several ten volts, and has many excellent features such as high luminance, high light emission efficiency, small thickness and light weight. Accordingly, in recent years, the element has attracted attention, as backlights for various kinds of displays, display boards such as a signboard and an emergency lamp, and surface emitting bodies such as illumination light sources.

Such an organic electroluminescent element has a configuration obtained by holding a light-emitting layer formed of an organic material between two electrodes, the emitted light generated in the light-emitting layer is extracted to the outside through the electrode. Therefore, at least one of the two electrodes is constituted as a transparent electrode.

As the transparent electrode, there is used generally a material of an oxide semiconductor type such as indium tin oxide ($SnO_2$-$In_2O_3$:Indium Tin Oxide:ITO), and examination aiming at lowering electric resistance by laminating ITO and silver has been carried out (e.g. referring to the following Patent Literatures 1, 2). In addition, ITO has a high raw cost because of using a rare metal indium, and is required to be subjected to annealing treatment at about 300° C. after the formation in order to lower its electric resistance. Accordingly, there have been proposed a configuration in which a metallic material such as silver having a high electrical conductivity is made into a thin film, and a configuration in which an electrical conductivity is ensured even at a film thickness smaller than that of silver alone by blending aluminum with silver (e.g. refer to the following Patent Literature 3).

CITATION LIST

Patent Literature

PTL 1: Japanese Patent Laid-Open No. 2002-15623
PTL 2: Japanese Patent Laid-Open No. 2006-164961
PTL 3: Japanese Patent Laid-Open No. 2009-151963

SUMMARY OF INVENTION

Technical Problem

However, even by using the transparent electrode constituted using silver and aluminum with a high electrical conductivity, it has been difficult to attain sufficient electrical conductivity and light transmission property, at the same time.

In order to solve the above-described problems, the present invention provides a transparent electrode excellent in both electrical conductivity and light transmission property, and an electronic device.

Solution to Problem

The transparent electrode of the present invention includes a nitrogen-containing layer, a conductive layer provided adjacent to the nitrogen-containing layer and having silver as a main component, a high refractive index layer provided to sandwich the nitrogen-containing layer between the conductive layer and the high refractive index layer and having a higher refractive index than that of the nitrogen-containing layer, and a low refractive index layer provided in contact with the high refractive index layer and having a lower refractive index than that of the high refractive index layer. The nitrogen-containing layer is constituted using a compound which contains nitrogen atoms, and has an effective unshared electron pair content [n/M] of $2.0 \times 10^{-3} \leq [n/M]$, when n is the number of unshared electron pairs which are not involved in aromaticity and which are not coordinated to a metal in the unshared electron pairs of the nitrogen atoms, and M is a molecular weight.

In addition, the electronic device of the present invention includes the above-described transparent electrode.

According to the transparent electrode of the present invention, the conductive layer containing silver as a main component is provided adjacent to the nitrogen-containing layer constituted using the compound including a nitrogen atom. The nitrogen-containing layer is constituted of the compound having an effective unshared electron pair content [n/M] of $2.0 \times 10^{-3} \leq [n/M]$. Furthermore, the transparent electrode of the present invention has the high refractive index layer and the low refractive index layer.

By the formation of the conductive layer containing silver as a main component on the above-described nitrogen-containing layer, the agglomeration of the silver is suppressed due to interaction of the silver atom and the compound constituting the nitrogen-containing layer, and thus the conductive layer having a uniform thickness was obtained although the thickness is small. The reflection caused on the conductive layer containing silver as a main component is suppressed by laminating the low refractive index layer, the high refractive index layer, the nitrogen-containing layer and the conductive layer in this order.

Accordingly, in the transparent electrode using silver, it becomes possible to enhance both of electrical conductivity and light transmission property. In addition, the electronic device excellent in electrical conductivity and light transmission property can be constituted by using the transparent electrode.

Advantageous Effects of Invention

According to the present invention, the transparent electrode and the electronic device being excellent in electrical conductivity and light transmission property can be provided.

DESCRIPTION OF EMBODIMENTS

Hereinafter, the embodiments according to the present invention will be explained by referring drawings in the order mentioned below.
1. Transparent electrode
2. A first embodiment of organic electroluminescent element (bottom emission type)
3. A second embodiment of organic electroluminescent element (reverse laminate configuration)
4. Lighting device Note that, in each common constituent, the same symbol is attached to the common constituent element, and an overlapped explanation will be omitted.

<1. Transparent Electrode>

Hereinafter, the specific embodiment of the transparent electrode of the present invention will be explained.

Figure 1:
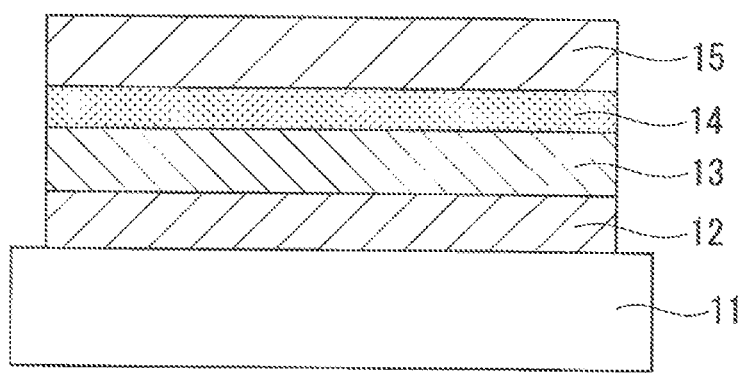
FIG. 1 is a cross-sectional view of a configuration of an embodiment of a transparent electrode.

In FIG. 1, the schematic configuration diagram (cross-sectional view) of the transparent electrode of the present embodiment is shown. AS shown in FIG. 1, a transparent electrode 10 includes a low refractive index layer 12, a high refractive index layer 13, a nitrogen-containing layer 14 and a conductive layer 15. The conductive layer 15 is formed adjacent to the nitrogen-containing layer 14. The nitrogen-containing layer 14 is sandwiched between the conductive layer 15 and the high refractive index layer 13. One surface of the high refractive index layer 13 is in contact with the nitrogen-containing layer 14, and the low refractive index layer 12 is formed in contact with the other surface.

The lamination structure constituted of the low refractive index layer 12, the high refractive index layer 13, the nitrogen-containing layer 14 and the conductive layer 15 I provided on a base material 11.

In the above construction, the high refractive index layer 13 is a layer having a refractive index higher than that of the nitrogen-containing layer 14. In addition, the low refractive index layer 12 is a layer having a refractive index lower than the high refractive index layer 13. The conductive layer 15 constituting an electrode part of the transparent electrode 10 is a layer constituted using silver (Ag) as a main component. The nitrogen-containing layer 14 adjacent to the conductive layer 15 is constituted using a compound which contains a nitrogen atom (N). Particularly, the nitrogen-containing layer 14 is constituted of a compound in which a content of an unshared electron pair (effective unshared electron pair) of a nitrogen atom stably bonding to the silver being a main material of the conductive layer 15 is within a predetermined range.

Hereinafter, as to the transparent electrode 10 of the example, a detailed configuration will be explained in order of the base material 11, the low refractive index layer 12, the high refractive index layer 13, the nitrogen-containing layer 14, and the conductive layer 15. Note that, in the transparent electrode 10 of the example, translucency means that light transmittance at a wavelength of 550 nm is 50% or more.

[Base Material 11]

The base material 11 on which the transparent electrode 10 is formed includes, for example, glass, plastics, or the like, but is not limited to these. In addition, the base material 11 may be transparent or opaque. When the transparent electrode 10 is used as an electronic device in which light is taken out from the side of the base material 11, the base material 11 is preferably transparent. Preferably used transparent base material 11 can include glass, quartz, and transparent resin film. When the transparent electrode 10 is used for an electronic device in which light is taken out from the opposite side of the base material 11, the base material 11 may be transparent or opaque.

[Glass]

Examples of the glasses include silica glass, soda lime silica glass, lead glass, borosilicate glass, alkali-free glass, and the like. From the viewpoint of a close adhesive characteristic to the laminate structure of the transparent electrode 10, durability and smoothness, a physical treatment such as polishing may be given as necessary, or a film made of an inorganic material or an organic material, or a hybrid film obtained by combining these coating films may be formed on the surfaces of these glass materials.

Examples of the resin film include polyesters such as polyethylene terephthalate (PET) and polyethylene naphthalate (PEN), polyethylene, polypropylene, cellulose esters or derivative thereof such as cellophane, cellulose diacetate, cellulose triacetate (TAC), cellulose acetate butylate, cellulose acetate propionate (CAP), cellulose acetate phthalate and cellulose nitrate, polyvinylidene chloride, polyvinyl alcohol, polyethylene vinyl alcohol, syndiotactic polystyrene, polycarbonate, norbornen resin, polymethylpenten, polyether ketone, polyimide, polyether sulphone (PES), polyphenylene sulfide, polysluphones, polyether imide, polyether ketone imide, polyamide, fluororesin, Nylon, polymethyl methacrylate, acryl or polyallylates, cycloolefin-based resins such as Alton (commercial name of JSR) or APEL (commercial name of Mitsui Chemicals), and the like.

A coating film made of inorganic materials or organic materials, or a hybrid coating film obtained by combining those coating films may be formed on the surface of the resin film. These coating films or hybrid coating films are preferably a barrier film (also referred to as barrier membrane, or the like) having a water vapor transmittance (25±0.5° C., relative humidity 90±2% RH) measured by the method in accordance with JIS-K-7129-1992 of 0.01 g/(m$^2$·24 hrs) or less. Furthermore, these films are preferably a high barrier film having an oxygen transmittance measured by the method in accordance with JIS-K-7126-1987 of $10^{-3}$ ml/(m$^2$·24 hrs·atm) or less and a water vapor transmittance of $10^{-5}$ g/(m$^2$·24 hrs) or less.

A material for forming the above barrier film may be a material having a function of suppressing penetration of substances such as water vapor and oxygen which deteriorate the resin film. For example, there can be used silicon oxide, silicon dioxide, silicon nitride, and the like. Furthermore, in order to improve fragility of the barrier film, it is more preferably to give a lamination structure of the inorganic layer and a layer of organic material (organic layer). The order of lamination of the inorganic layer and the organic layer is not particularly limited, and is preferable to alternately laminate both of the layers a plurality of times.

The method of forming the barrier film is not particularly limited, and there can be used, for example, vacuum deposition method, spattering method, reactive spattering method, molecular beam epitaxial method, cluster ion beam method, ion platting method, plasma polymerization method, atmospheric pressure plasma polymerization method, plasma CVD method, laser CVD method, thermal CVD method, coating method, and the like. Particularly preferable is the atmospheric pressure plasma polymerization method described in Japanese Patent Application Laid-Open Publication No. 2004-68143.

In contrast, when the base material 11 is opaque, there can be used, for example, a metal substrate such as aluminum or stainless steel, an opaque resin substrate, a substrate made of ceramics, and the like. These substrates may be a film-like substrate which can be bended flexibly.

[Low Refractive Index Layer]

The low refractive index layer 12 is a layer having a refractive index lower than the high refractive index layer 13 in contact with the low refractive index layer 12. Particularly, a refractive index at a wavelength of 550 nm is preferably lower than the high refractive index layer by 0.1 or more, particularly preferably lower than the high refractive index layer 13 by 0.3 or more. The low refractive index layer 12 as described above is constituted of a material having a low refractive index and a light transmittance property. For example, there can be used a low refractive index material generally used for an optical film such as magnesium fluoride ($MgF_2$: n=1.37), lithium fluoride (LiF: n=1.39), Calcium fluoride ($CaF_2$: n=1.43), or aluminum fluoride ($AlF_3$: n=1.38); a polymeric material such as Poly(1,1,1,3,3,3-hexafluoroisopropyl acrylate): n=1.38, Poly(2,2,3,3,4,4,4-heptafluorobutyl acrylate): n=1.38, Poly(2,2,3,3,4,4,4-heptafluorobutyl methacrylate): n=1.38, Poly(2,2,3,3,3-pentafluoropropyl acrylate): n=1.39, Poly(1,1,1,3,3,3-hexafluoroisopropyl methacrylate): n=1.39, Poly(2,2,3,4,4,4-hexafluorobutyl acrylate): n=1.39, Poly(2,2,3,3,3-pentafluoropropyl methacrylate): n=1.40, Poly(2,2,2-trifluoroethyl acrylate): n=1.41, Poly(2,2,3,3-tetrafluoropropyl acrylate): n=1.42, Poly(2,2,3,3-tetrafluoropropyl methacrylate): n=1.42, or Poly(2,2,2-trifluoroethyl methacrylate): n=1.42; and the like.

In addition, as is shown in FIG. 1, when the low refractive index layer 12 and the high refractive index layer 13 are laminated on the base material 11, the low refractive index layer 12 is set to be a layer having a refractive index lower than the high refractive index layer 13 and the base material 11. At this time, the base material 11 is constituted of a material having a refractive index lower than the high refractive index layer 13, and the low refractive index layer 12 is set to be a layer having a refractive index lower than the base material 11. Preferably, a refractive index at a wavelength of 550 nm of the low refractive index layer 12 is preferably lower than the base material 11 by 0.1 or more. Thereby, the transmittance of the transparent electrode 10 can be further enhanced.

Note that, when the refractive index of the base material 11 is lower than the high refractive index layer 13, the base material 11 may be a low refractive index layer 12 by forming the high refractive index layer 13 directly on the base material 11, without separately providing the low refractive index layer 12. Therefore, the configuration may be such that there is employed the lamination structure formed of the high refractive index layer 13, the nitrogen-containing layer 14 and the conductive layer 15 is provided on the base material by using the base material 11 itself as a low refractive index layer. Alternatively, in the case where the low refractive index layer 12 has a property required for the base material, the low refractive index layer 12 can be used as the base material without separately preparing the base material.

[High Refractive Layer]

The high refractive layer 13 has a refractive index higher than the nitrogen-containing layer 14. It is preferable that the refractive index of the high refractive layer 13 at a wavelength of 550 nm is higher than a refractive index of the nitrogen-containing layer 14 (n=1.7 to 1.8) by 0.1 or more, more preferable by 0.3 or more. The high refractive layer 13 is constituted by the materials having a high refractive index and light transmission property. Examples include high refractive materials which are generally used for optical films such as titanium oxide ($TiO_2$: n=2.3 to 2.4), zirconium oxide (ZrO: n=2.4), cadmium oxide (CdO: n=2.49), indium tin oxide (ITO: n=2.1 to 2.2), hafnium oxide ($HfO_2$: n=1.9 to 2.1), tantalum pentoxide ($Ta_2O_5$: n=2.16), niobium oxide ($Nb_2O_5$: n=2.2 to 2.4), and the like.

[Nitrogen-Containing Layer]

The nitrogen-containing layer 14 is formed adjacent to the conductive layer 15 and is a layer sandwiched between the high refractive index layer 13 and the conductive layer 15.

As the result of the formation of the nitrogen-containing layer 14 in contact with the conductive layer 15, diffusion distance of silver atoms at the surface of the nitrogen-containing layer is reduced due to the interaction between silver being the principal component of the conductive layer 15 and a compound containing a nitrogen atom constituting the nitrogen-containing layer 14, and thus aggregation of the silver is suppressed. Therefore, generally, a thin silver layer that tends to be easily isolated in an island shape as the result of the growth by a nuclear growth-type (Volumer-Weber: VW type) is formed by the growth of a single layer growth type (Frank-van der Merwe: FM type). Accordingly, the conductive layer 15 having a uniform thickness, although the thickness is small, can be obtained by forming the conductive layer 15 containing silver as the principal component in contact with the nitrogen-containing layer 14.

The nitrogen-containing layer 14 preferably has the thickness of 5 nm or less. This is because a smaller thickness of the nitrogen-containing layer 14, that is, a smaller distance between the high refractive index layer 13 and the conductive layer 15 gives higher light transmittance of the transparent electrode 10. Note that the thickness of the nitrogen-containing layer 14 is set to be a thickness that does not prevent the FM type growth of the conductive layer 15 formed on the nitrogen-containing layer 14, that is, to be approximately a thickness of the extent that the nitrogen-containing layer 14 is formed not in an island shape but as a continuous layer covering the high refractive index layer 13.

Furthermore, the nitrogen-containing layer 14 is a layer provided adjacent to the conductive layer 15, and is constituted using a compound containing a nitrogen atom (N). An unshared electron pair of a nitrogen atom that is bonded stably to silver being the main material for constituting the conductive layer 15 in the compound containing a nitrogen atom is referred to as an "effective unshared electron pair." Additionally, the compound constituting the nitrogen-containing layer 14 is characterized in that the content ratio of the effective unshared electron pair" is within a prescribed range.

Here, the "effective unshared electron pair" is defined as an unshared electron pair that is not involved in aromaticity and is not coordinated to a metal, among unshared electron pairs of a nitrogen atom contained in a compound. The aromaticity means an unsaturated ring structure in which atoms having a π electron are arranged in a ring shape, and the aromaticity follows the so-called "Huckel's rule" which requires a condition in which the number of electrons contained in the π electron system on the ring is "4n+2" (n=0, or a natural number).

The "effective unshared electron pair" is selected based on whether or not the unshared electron pair of a nitrogen atom is involved in the aromaticity irrespective of whether or not the nitrogen atom itself including the unshared electron pair is a hetero atom constituting the aromatic ring. For example, even if a certain nitrogen atom is a hetero atom constituting an aromatic ring, when the nitrogen atom has an unshared electron pair that is not directly involved in the aromaticity as the essential element, the unshared electron pair is counted as one of the "effective unshared electron pair." Namely, if there is an unshared electron pair which is not involved in aromaticity expression as the essential element in the delocalized π electron system in the conjugated unsaturated ring structure (aromatic ring), the unshared electron pair is counted as one of the "effective unshared electron pair." In contrast, even in the case where a certain nitrogen atom is not a hetero atom constituting an aromatic ring, if all the unshared electron pairs of the nitrogen atom are involved in the aromaticity, the unshared electron pairs of the nitrogen atom are not the "effective unshared electron pair." Note that, in respective compounds, the number of the "effective unshared electron pair" n coincides with the number of the nitrogen atoms having the "effective unshared electron pair."

Next, the above-described "effective unshared electron pair" will be explained in detail by referring specific examples.

A nitrogen atom is an element of the group 15 and has 5 electrons on the outermost shell. Among them, three unpaired electrons are used for covalent bond with the other atoms, and the remaining two electrons serve as one pair of unshared electron pair. Therefore, usually, the number of bonds of nitrogen atom is 3.

Examples of the group having a nitrogen atom includes an amino group ($-NR^1R^2$), an amide group ($-C(=O)NR^1R^2$), nitro group ($-NO_2$), cyano group ($-CN$), diazo group ($-N_2$), azide group ($-N_3$), an urea group ($-NR^1C=ONR^2-$), isothiocyanate group ($-N=C=S$), a thioamide group ($-C(=S)NR^1R^2$), and the like. Note that R1 and R2 are each a hydrogen atom (H) or a substituent. The unshared electron pair of the nitrogen atom constituting these groups corresponds to [effective unshared electron pair] since the pair is not involved in aromatibity and does not coordinate with a metal. Among them, although the unshared electron pair of the nitrogen atom of nitro group ($-NO_2$) is utilized for resonance structure with oxygen atom, it is considered that the pair exists on the nitrogen atom as the [effective unshared electron pair] which is not involved in aromaticity and does not coordinate with a metal, since the good results are obtained as shown in the following examples.

Figure 2:
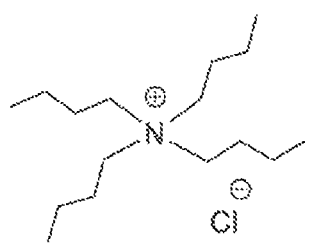
FIG. 2 is a drawing showing structural formulae of TBAC and Ir(ppy)$_3$ for explaining the manner of bonding of a nitrogen atom.
Figure 2:
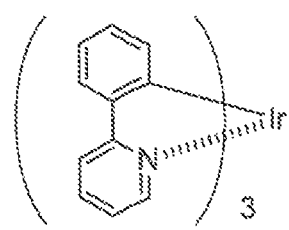

Furthermore, the nitrogen atom can produce the fourth bond by utilizing the unshared electron pair. One example of such a case will be explained by referring FIG. 2. FIG. 2 shows the structural formulae of tetrabutylammonium chloride (TBAC), and tris(2-phenylpyridine)iridium (III) [Ir(ppy)$_3$].

Among them, TBAC is a quaternary ammonium salt where one of four butyl groups ionically bonds to a nitrogen atom and has a chloride ion as a counter ion. In this case, one of the electrons constituting the unshared electron pair of a nitrogen atom is donated to the ionic bond with the butyl group. Therefore, the nitrogen atom of TBAC is equal to a state where an unshared electron pair does not exist initially. Accordingly, the unshared electron pair of the nitrogen constituting TBAC does not correspond to the "effective unshared electron pair" which is not involved in aromaticity and is not coordinated to a metal.

Further, Ir(ppy)$_3$ is a neutral metal complex in which the iridium atom and the nitrogen atom are coordinately bonded. The unshared electron pair of the nitrogen atom constituting Ir(ppy)$_3$ is coordinated to the iridium atom, and is utilized for coordinate bonding. Accordingly, the unshared electron pair of the nitrogen constituting Ir(ppy)$_3$ does not correspond to the "effective unshared electron pair" which is not involved in aromaticity and is not coordinated to a metal.

Nitrogen atom is a usual hetero atom that can constitute an aromatic ring, and can contribute to expression of aromaticity. Examples of the "nitrogen-containing aromatic ring" include pyridine ring, piperazine ring, pyrimidine ring, triazine ring, pyrrole ring, imidazole ring, pyrazole ring, triazole ting, tetrazole ring, and the like.

Figure 3:
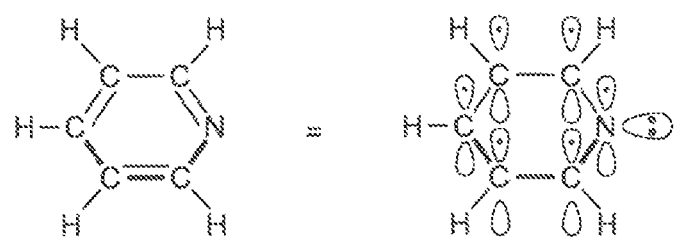
FIG. 3 is a drawing showing a structural formula and molecular orbital of a pyridine ring.

FIG. 3 shows the structural formula and the molecular orbital of the pyridine ring which is one of the above-described nitrogen-containing aromatic rings. AS shown in FIG. 3, the pyridine ring has 6 delocalized π electrons in the conjugated (resonant) unsaturated ring structure arranged in the form of a 6-membered ring, and thus satisfies 4n+2 (n=0 or natural numeral) of the "Hueckel's rule". Since the nitrogen atom in the 6-membered ring is the substituent of $-CH=$, only one unshared electron is used for the 6 π electron system, and the unshared electron pair is not involved in expression of aromaticity as an essential element.

Accordingly, the unshared electron pair of the nitrogen atom constituting the pyridine ring corresponds to the [effective unshared electron pair] which is not involved in aromaticity and is not coordinated to a metal.

Figure 4:
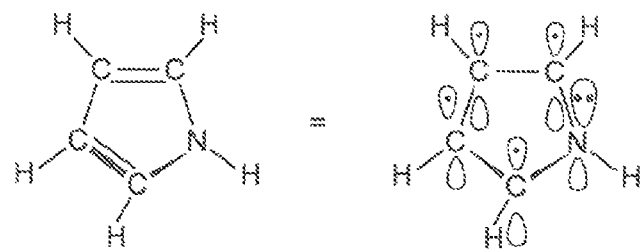
FIG. 4 is a drawing showing a structural formula and molecular orbital of a pyrrole ring.

FIG. 4 shows the structural formula and the molecular orbital of the pyrrole ring. AS shown in FIG. 4, the pyrrole ring has a structure in which one of the carbon atoms constituting five-membered ring is substituted with a nitrogen atom, and since the number of π electrons is six, the pyrrole ring is a nitrogen-containing aromatic ring which satisfies the "Hueckel's rule". Since the nitrogen atom of the pyrrole ring also bonds to a hydrogen atom, the unshared electron pair is used for the 6 π electron system.

Accordingly, though the nitrogen atom of the pyrrole ring has an unshared electron pair, the unshared electron pair is utilized for expressing the aromaticity as the essential element, and thus does not correspond to the "effective unshared electron pair" which is not involved in aromaticity and is not coordinated to a metal.

Figure 5:
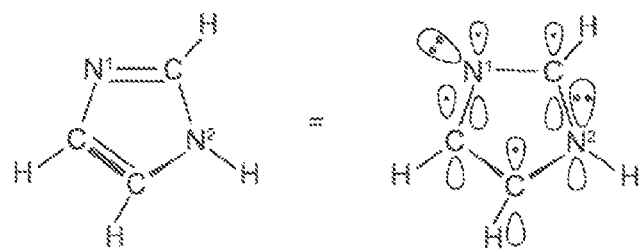
FIG. 5 is a drawing showing a structural formula and molecular orbital of an imidazole ring.

FIG. 5 shows the structural formula and the molecular orbital of the imidazole ring. As shown in FIG. 5, the imidazole ring has a structure in which the carbon atoms of 1-position and 3-position of the five-membered ring are substituted by the two nitrogen atoms $N^1$, $N^2$, and is also a nitrogen-containing aromatic ring having six π electrons. Among them, one nitrogen atom $N^1$ supplies only one unshared electron to the 6 π electron system, and thus, is the nitrogen atom of the pyridine ring-type nitrogen atom in which the unshared electron pair is not utilized for the expression of aromaticity. Accordingly, the unshared electron pair of the nitrogen atom $N^1$ corresponds to the [effective unshared electron pair]. In contrast to this, since the other nitrogen atom $N^2$ is the pyrrole ring-type nitrogen atom which supplies the unshared electron pair to the 6 π electron system, the unshared electron pair of the nitrogen atom $N^2$ does not correspond to the "effective unshared electron pair".

Accordingly, in the imidazole ring, among the two nitrogen atoms $N^1$, $N^2$, only the unshared electron pair of the nitrogen atom $N^1$ corresponds to the [effective unshared electron pair].

The selection of the unshared electron pair in the nitrogen atom of the "nitrogen-containing aromatic ring" as mentioned above also applies to the case of a condensed ring compound having a nitrogen-containing aromatic ring structure in the same way.

Figure 6:
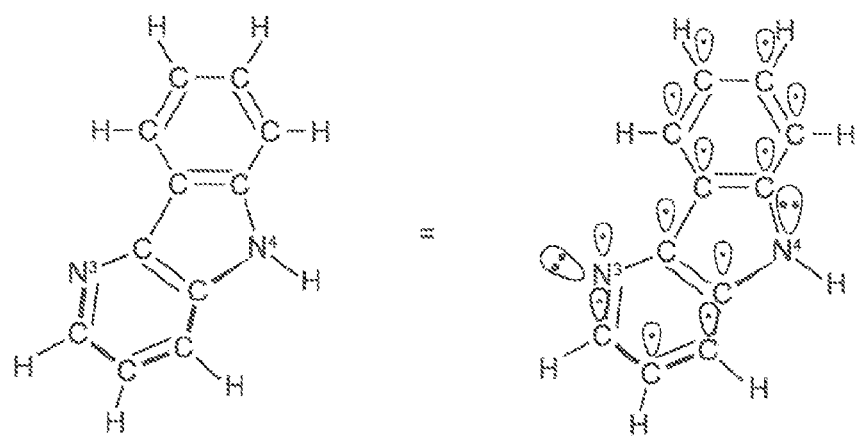
FIG. 6 is a drawing showing a structural formula and molecular orbital of a δ-carboline ring.

FIG. 6 shows the structural formula and the molecular orbital of the δ-carboline ring. As shown in FIG. 6, the δ-carboline ring is a condensed ring compound having a nitrogen-containing aromatic ring structure, and is an azacarbazole compound in which a benzene ring structure, a pyrrole ring structure and a pyridine ring structure are condensed in this order. In this compound, the nitrogen atom $N^3$ of the pyridine ring supplies only one unshared electron to the $\pi$ electron system, and the nitrogen atom. $N^4$ of the pyridine ring supplies one unshared electron pair to the $\pi$ electron system, and thus the number of the whole $\pi$ electrons is fourteen together with eleven $\pi$ electrons derived from the carbon atoms which form the rings.

Accordingly, among the two nitrogen atoms $N^3$ and $N^4$ of δ-carboline ring, the unshared electron pair of the nitrogen atom $N^3$ constituting the pyridine ring corresponds to the "effective unshared electron pair", but the unshared electron pair of the nitrogen atom $N^4$ constituting the pyrrole ring does not correspond to the "effective unshared electron pair".

As explained above, the unshared electron pair of the nitrogen atom constituting the condensed ring compound is involved in bonding in the condensed ring compound in the same way as bonding in the monocyclic rings such as pyridine ring and pyrrole ring constituting the condensed ring compound.

The "effective unshared electron pair" as explained above is important because it expresses a strong interaction with the silver which is a main component of the conductive layer 15. The nitrogen atoms having these "effective unshared electron pairs" are preferably nitrogen atoms in the nitrogen-containing aromatic ring from the viewpoint of stability, durability. Accordingly, the compound included in the nitrogen-containing layer 14 preferably has an aromatic heterocyclic ring which sets, as the hetero atom, the nitrogen atom having the "effective unshared electron pair".

In the present embodiment, the number n of the "effective unshared electron pair" relative to the molecular weight M of such a compound is defined as, for example, an effective unshared electron pair content ratio [n/M]. In addition, the nitrogen-containing layer 14 is characterized by being constituted using a compound that is selected so that the [n/M] is $2.0\times10^{-3}\leq[n/M]$. Furthermore, the nitrogen-containing layer 14 is preferable when the effective unshared electron pair content ratio [n/M] defined as described above is within the range of $3.9\times10^{-3}\leq[n/M]$, more preferable when the content ratio [n/M] is within the range of $6.5\times10^{-3}\leq[n/M]$. The above-described effect of suppressing the aggregation of silver constituting the conductive layer is obtained by constituting the nitrogen-containing layer using a compound having the effective unshared electron pair content ratio of [n/M].

Furthermore, it is sufficient that the nitrogen-containing layer 14 is constituted using a compound whose effective unshared electron pair content ratio [n/M] is within the above-described prescribed range, that the layer is also constituted only of such a compound, or that the layer is constituted mixing such a compound and another compound for use. Another compound may or may not contain a nitrogen atom, and furthermore, the effective unshared electron pair content ratio [n/M] may not be within the prescribed range.

When the nitrogen-containing layer 14 is constituted using a plurality of compounds, for example, the molecular weight M of the mixed compound obtained by mixing these compounds is obtained based on the mixing ratio of the compounds. Additionally, an average value of the effective unshared electron pair content ratio [n/M] is obtained from the total number n of "effective unshared electron pairs" relative to the molecular weight M. The value is preferably within the prescribed range. Namely, the effective unshared electron pair content ratio [n/M] of the nitrogen-containing layer 14 itself is preferably within the prescribed range.

Note that, in the case where the nitrogen-containing layer 14 is constituted using a plurality of compounds and has a configuration different in the mixing ratio (content ratio) of compounds in the thickness direction, it is sufficient that the effective unshared electron pair content ratio [n/M] in the surface layer of the nitrogen-containing layer 14 on the side in contact with the conductive layer 15 is within the prescribed range.

[Compound-1]

Hereinafter, specific examples of compounds (No. 1 to No. 48), which satisfy that the effective unshared electron pair content ratio [n/M] is $2.0\times10^{-3}\leq[n/M]$, will be shown as compounds constituting the nitrogen-containing layer 14. In respective compounds of No. 1 to No. 48, ○ is given to a nitrogen atom having the "effective unshared electron pair." In addition, in the Table 1 below, molecular weights M of these compounds of No. 1 to No. 48, numbers n of the "effective unshared electron pair," and effective unshared electron pair content ratios [n/M] are shown. In copper phthalocyanine of a compound 33 below, unshared electron pairs not coordinated to the copper, among unshared electron pairs of a nitrogen atom, are counted as the effective unshared electron pair.

[Chem. 1]

No. 1

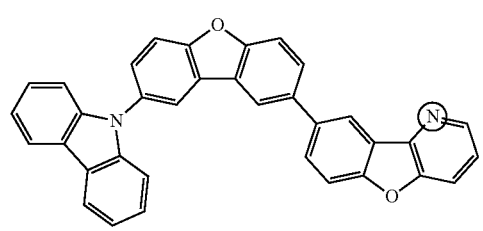

No. 2

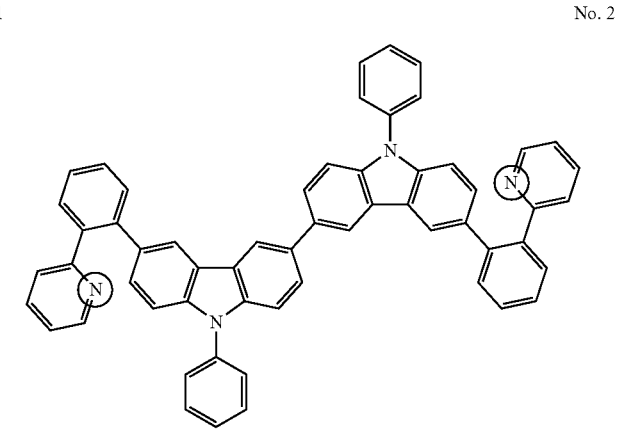

No. 3
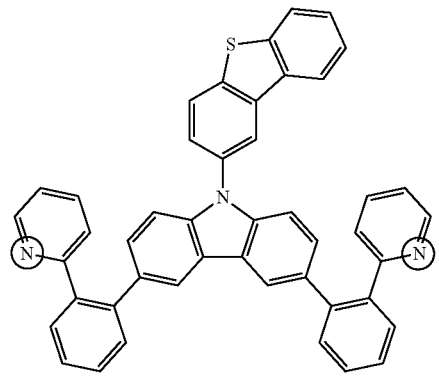
No. 4
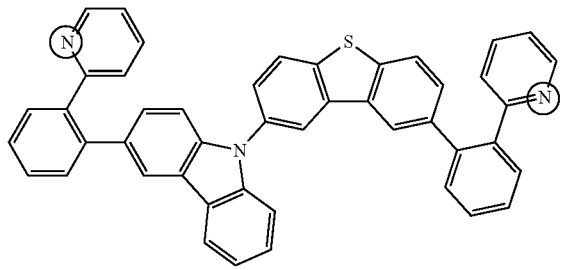
No. 5
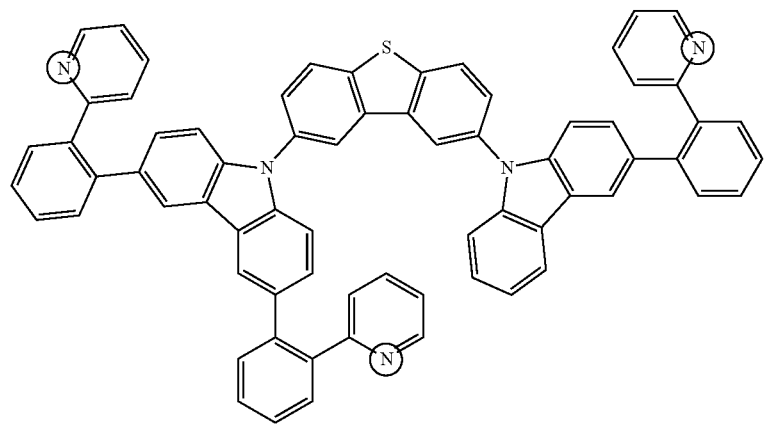
No. 6
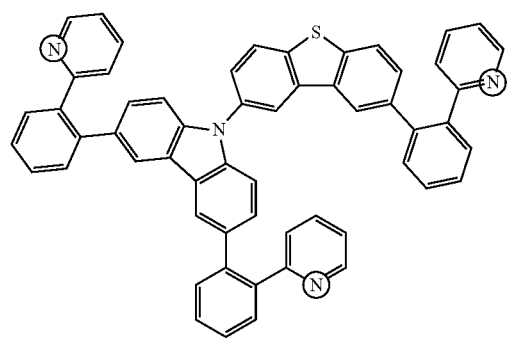
No. 7
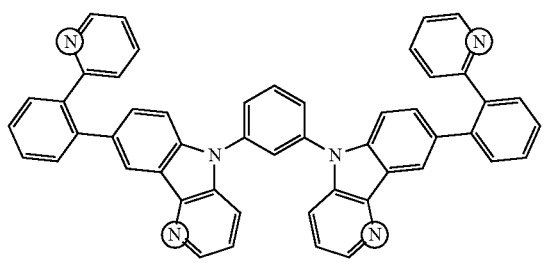

-continued
No. 8
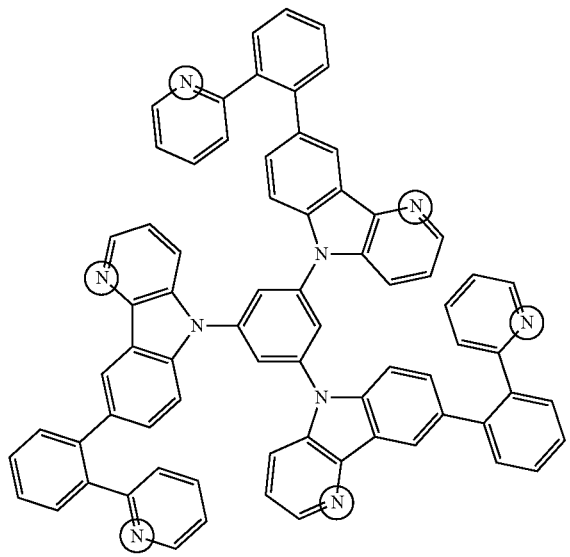
No. 9
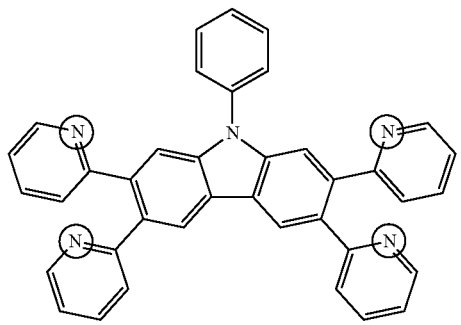
No. 10
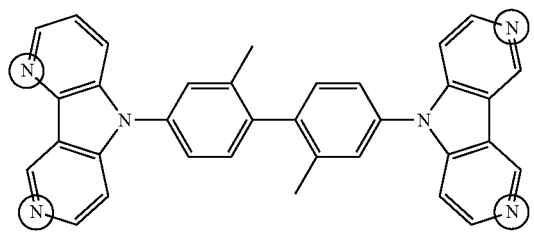
No. 11
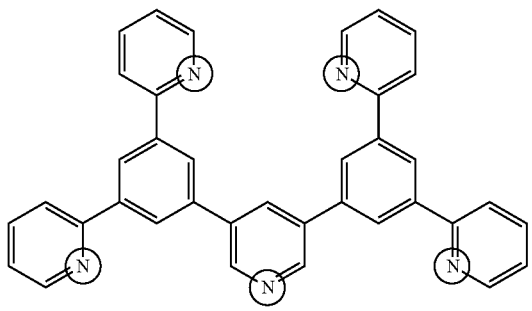
No. 12
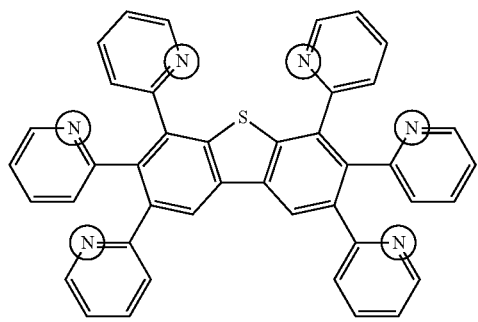
No. 13
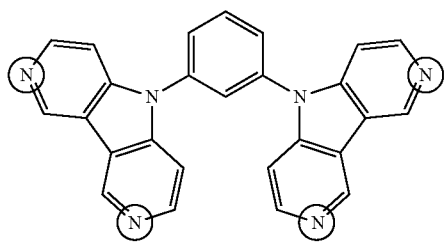
No. 14
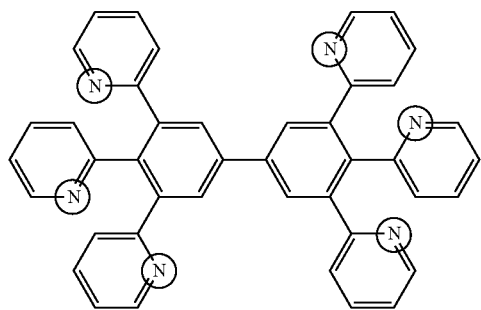
No. 15
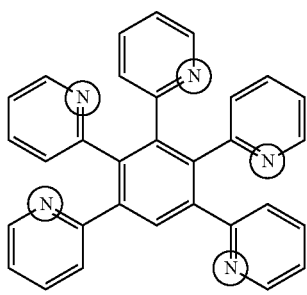

-continued
No. 16
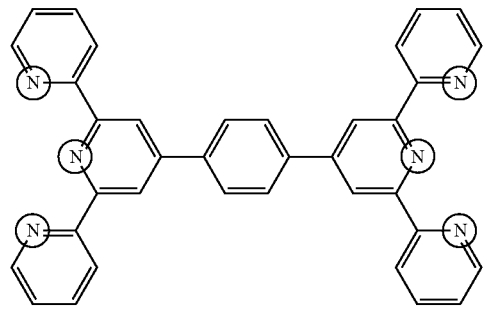
[Chem. 3]
No. 17   No. 18
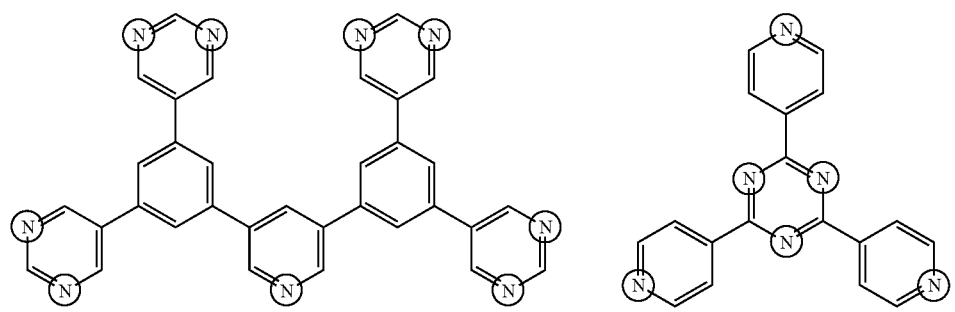
No. 19   No. 20
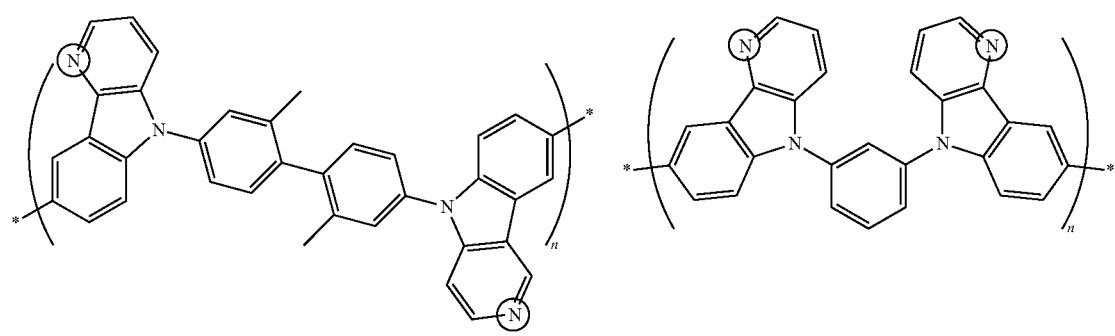
No. 21   No. 22
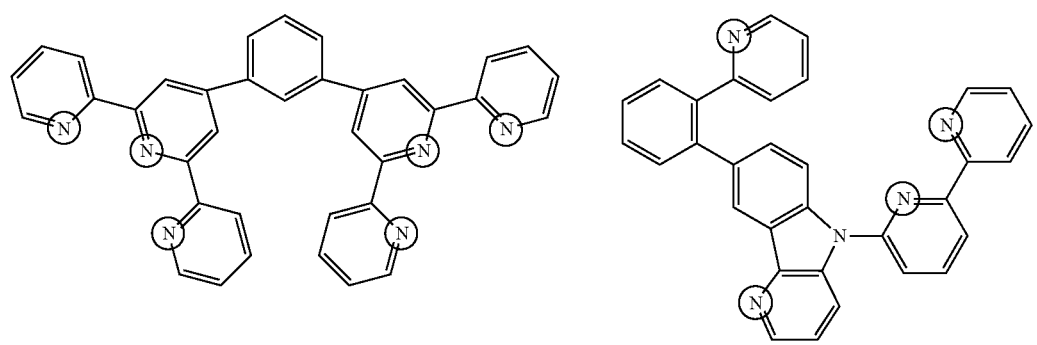

-continued
No. 23
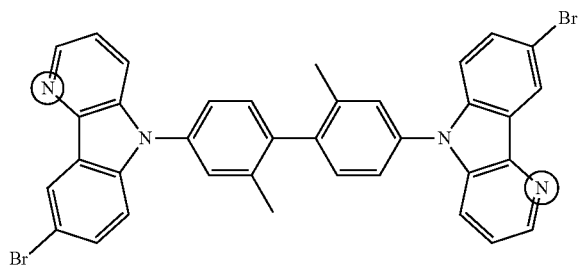
No. 24
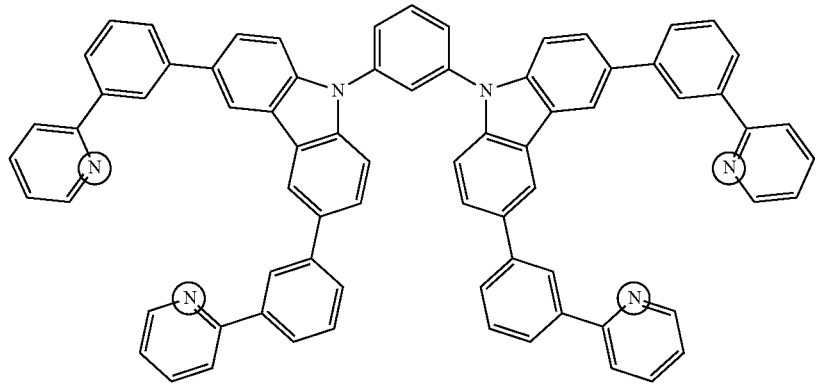
No. 25
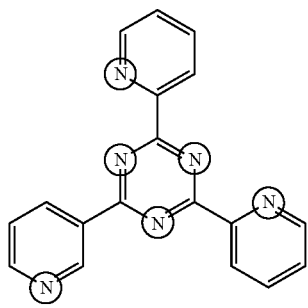
[Chem. 4]
No. 26
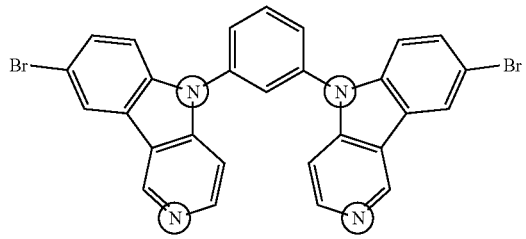
No. 27
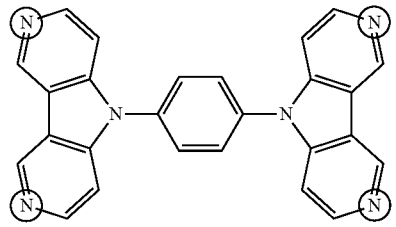
No. 28
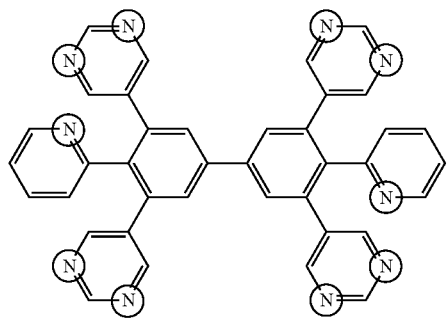
No. 29
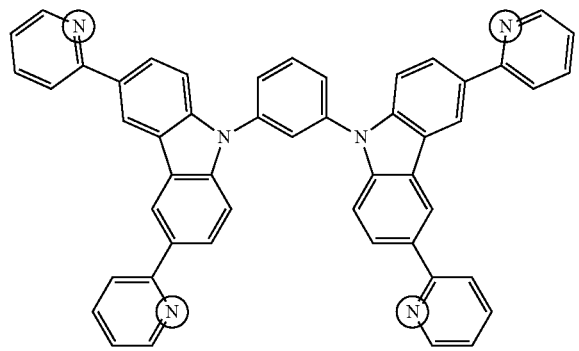

-continued
No. 30
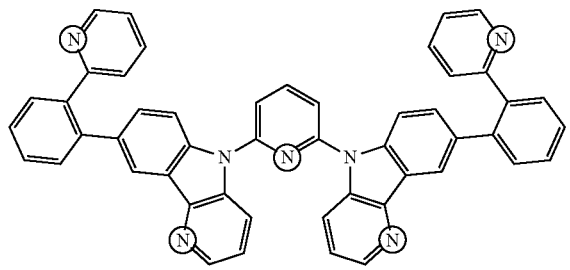
No. 31
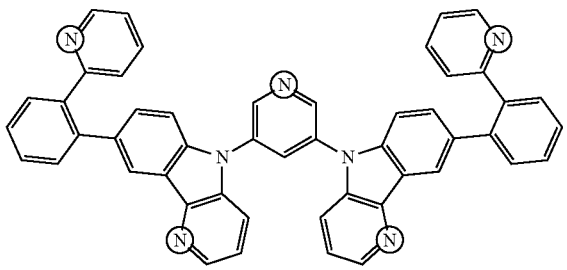
No. 32
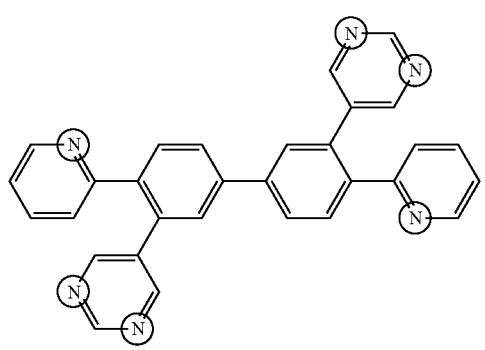
No. 33
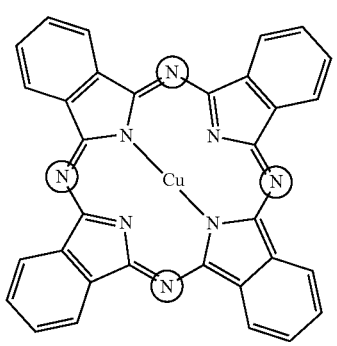
No. 34
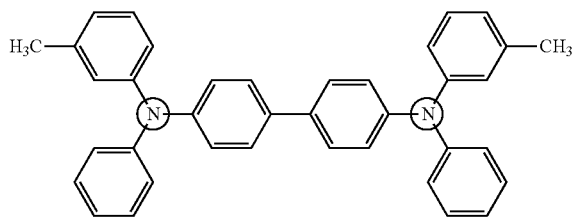
No. 35
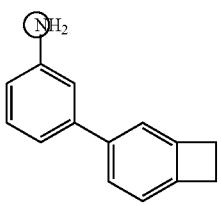
[Chem. 5]
No. 36
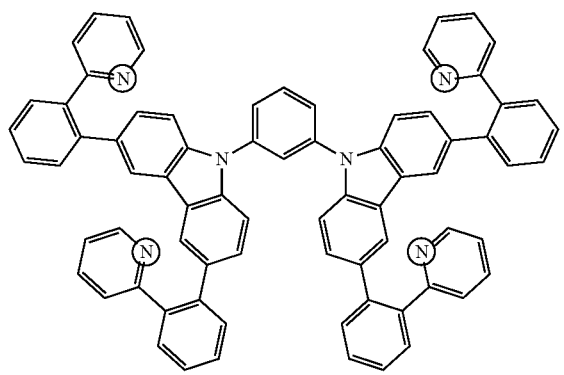
No. 37
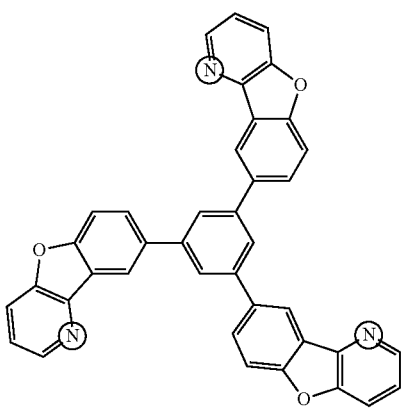

-continued
No. 38
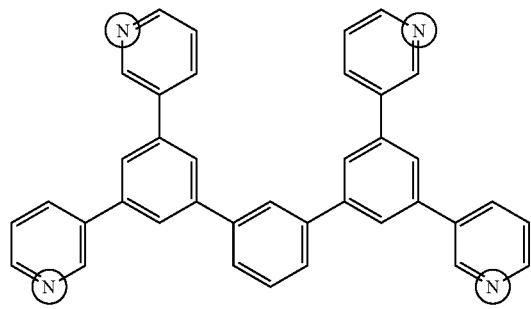
No. 39
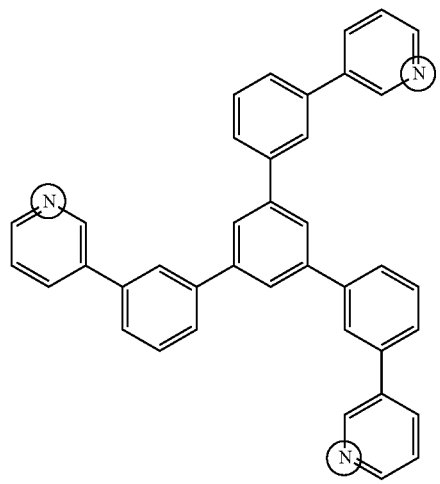
No. 40
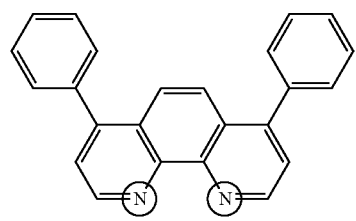
No. 41
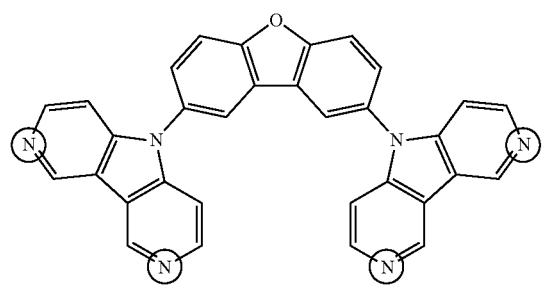
[Chem. 6]
No. 42
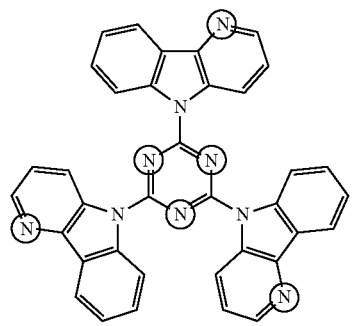
No. 43
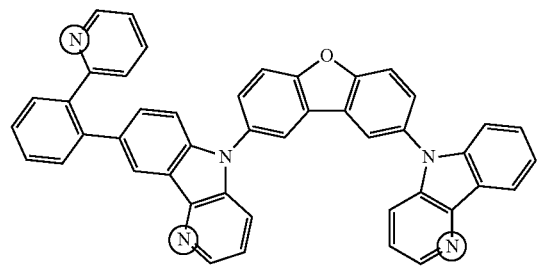
No. 44
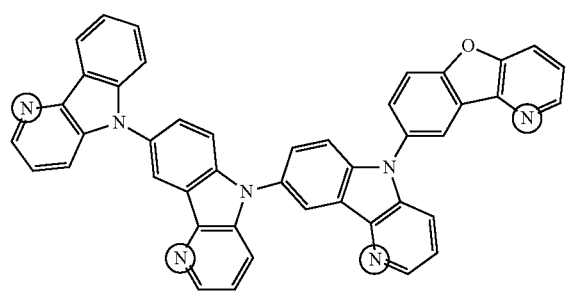
No. 45
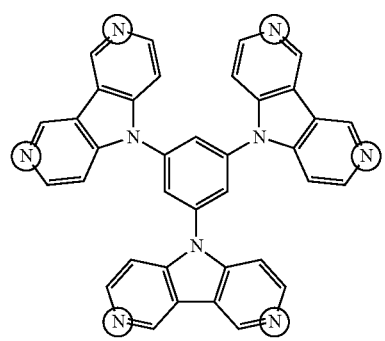

-continued

No. 46

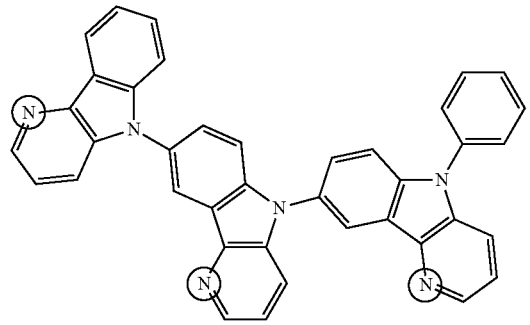

No. 47

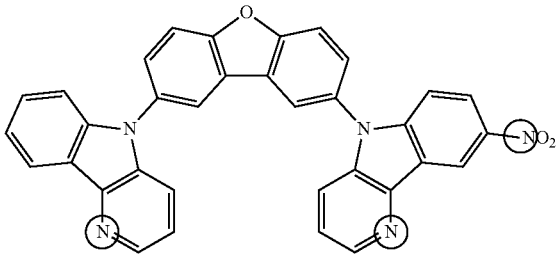

No. 48

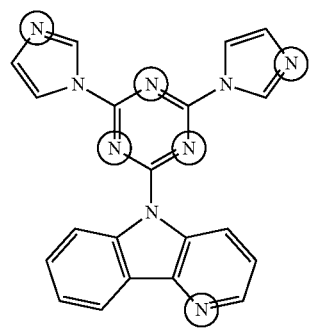

TABLE 1

| COMPOUND | NUMBER (N) OF EFFECTIVE UNSHARED ELECTRON PAIRS | MOLECULAR WEIGHT (M) | [N/M] | CORRESPONDING GENERAL FORMULA |
|---|---|---|---|---|
| No. 1 | 1 | 500.55 | 2.0E−03 | (1b) |
| No. 2 | 2 | 790.95 | 2.5E−03 | |
| No. 3 | 2 | 655.81 | 3.0E−03 | |
| No. 4 | 2 | 655.81 | 3.0E−03 | |
| No. 5 | 3 | 974.18 | 3.1E−03 | (2) |
| No. 6 | 3 | 808.99 | 3.7E−03 | |
| No. 7 | 4 | 716.83 | 5.6E−03 | (1a-1), (2) |
| No. 8 | 6 | 1036.19 | 5.8E−03 | (1a-1), (4) |
| No. 9 | 4 | 551.64 | 7.3E−03 | |
| No. 10 | 4 | 516.60 | 7.7E−03 | (1a-2), (3) |
| No. 11 | 5 | 539.63 | 9.3E−03 | |
| No. 12 | 6 | 646.76 | 9.3E−03 | (5) |
| No. 13 | 4 | 412.45 | 9.7E−03 | (1a-2), (3) |
| No. 14 | 6 | 616.71 | 9.7E−03 | (5) |
| No. 15 | 5 | 463.53 | 1.1E−02 | (2) |
| No. 16 | 6 | 540.62 | 1.1E−02 | (6) |
| No. 17 | 9 | 543.58 | 1.7E−02 | |
| No. 18 | 6 | 312.33 | 1.9E−02 | |
| No. 19 | 2 | 512.60 | 3.9E−03 | (1a-1) |
| No. 20 | 2 | 408.45 | 4.9E−03 | (1a-1) |
| No. 21 | 6 | 540.62 | 1.1E−02 | (6) |
| No. 22 | 4 | 475.54 | 8.4E−03 | (1a-1) |
| No. 23 | 2 | 672.41 | 3.0E−03 | (1a-1) |
| No. 24 | 4 | 1021.21 | 3.9E−03 | |
| No. 25 | 6 | 312.33 | 1.9E−02 | (6) |
| No. 26 | 2 | 568.26 | 3.5E−03 | (1a) |
| No. 27 | 4 | 412.45 | 9.7E−03 | (1a-2), (3) |
| No. 28 | 10 | 620.66 | 1.6E−02 | (5) |
| No. 29 | 4 | 716.83 | 5.6E−03 | |
| No. 30 | 5 | 717.82 | 7.0E−03 | (1a-1), (2) |
| No. 31 | 5 | 717.82 | 7.0E−03 | (1a-1), (2) |
| No. 32 | 6 | 464.52 | 1.3E−02 | |
| No. 33 | 4 | 576.10 | 6.9E−03 | |
| No. 34 | 2 | 516.67 | 3.9E−03 | |
| No. 35 | 1 | 195.26 | 5.1E−03 | |
| No. 36 | 4 | 1021.21 | 3.9E−03 | (2) |
| No. 37 | 3 | 579.60 | 5.2E−03 | (1b) |
| No. 38 | 4 | 538.64 | 7.4E−03 | |
| No. 39 | 3 | 537.65 | 5.6E−03 | |
| No. 40 | 2 | 332.40 | 6.0E−03 | |
| No. 41 | 4 | 502.15 | 8.0E−03 | (1a-2), (3) |
| No. 42 | 6 | 579.19 | 1.0E−02 | (1a-1) |
| No. 43 | 3 | 653.22 | 4.6E−03 | (1a-1) |
| No. 44 | 4 | 667.21 | 6.0E−03 | (1a-1), (1b) |
| No. 45 | 6 | 579.19 | 1.0E−02 | (1a-2), (3) |
| No. 46 | 3 | 576.65 | 5.2E−03 | (1a-1) |
| No. 47 | 3 | 545.55 | 5.5E−03 | (1a-1) |
| No. 48 | 6 | 379.38 | 1.6E−02 | (1a-1), (7), (8a) |

Note that, in the above Table 1, when those exemplified compounds are also involved in the general formulae (1) to (8a) which represent other compound-2 explained herein below, the corresponding general formulae are indicated.

[Compound-2]

In addition, as the compound constituting the nitrogen-containing layer 14, other than the above compound having the effective unshared electron pair content [n/M] of the above-described predetermined range, other compounds may be used. The other compounds used for the nitrogen-containing layer 14 are preferably compounds containing a nitrogen atom, regardless of whether or not the effective unshared electron pair content [n/M] is within the predetermined range. Among them, a compound containing the nitrogen atom having the [effective unshared electron pair] is particularly preferably used. In addition, there are used, as other compounds used for the nitrogen-containing layer 14, compounds having properties to be required for each of the electronic devices to which the transparent electrode 10 provided with the nitrogen-containing layer 14 is applied.

For example, in the case where the transparent electrode 10 is used as an electrode of an organic electroluminescent element, the following compounds represented by the general formulae (1) to (8a) are preferably used as the compound constituting the nitrogen-containing layer 14 from the viewpoints of film formation and electron transport property.

Among these compounds represented by the general formulae (1) to (8a), a compound which falls within the above-described range of the effective unshared electron pair content [n/M] is included, and such a compound can be used alone as the compound constituting the nitrogen-containing layer 14 (See Table 1). On the other hand, if a compound represented by the general formulae (1) to (8a) does not fall within the above-described range of the effective unshared electron pair content [n/M], the compound can be used as the compound constituting the nitrogen-containing layer 14 by mixing with the compound having the above-described range of the effective unshared electron pair content [n/M].

[Chem. 7]

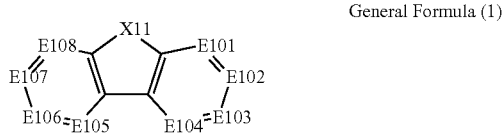

General Formula (1)

In the above general formula (1), X11 represents —N(R11) or —O—. In addition, in the general formula (1), E101 to E108 each represent —C(R12)═ or —N═; and at least one of E101 to E108 is —N═. In addition, the above-described R11 and R12 each represent hydrogen atom or a substituent.

Examples of the substituent include an alkyl group (for example, methyl group, ethyl group, propyl group, isopropyl group, tert-butyl group, pentyl group, hexyl group, octyl group, dodecyl group, tridecyl group, tetradecyl group, pentadecyl group and the like), a cycloalkyl group (for example, cyclopentyl group, cyclohexyl group and the like), an alkenyl group (for example, vinyl group, allyl group and the like), an alkynyl group (for example, ethynyl group, propargyl group and the like), an aromatic hydrocarbon group (also referred to as an aromatic carbon ring group, an aryl group or the like, for example; phenyl group, p-chlorophenyl group, mesityl group, tolyl group, xylyl group, naphthyl group, anthryl group, azulenyl group, acenaphthenyl group, fluorenyl group, phenanthryl group, indenyl group, pyrenyl group, biphenyryl group and the like), an aromatic heterocyclic ring group (for example, furyl group, thienyl group, pyridyl group, pyridazinyl group, pyrimidinyl group, pyrazinyl group, triazinyl group, imidazolyl group, pyrazolyl group, thiazolyl group, quinazolinyl group, carbazolyl group, carbolinyl group, diazacarbazolyl group (a group in which a certain carbon atom constituting the carboline ring of the carbolinyl group is substituted with a nitrogen atom), phtharazinyl group and the like), a ring group (for example, pyrrolidyl group, imidazolidyl group, morpholyl group, oxazolidyl group and the like), an alkoxy group (for example, methoxy group, ethoxy group, propyloxy group, pentyloxy group, hexyloxy group, octyloxy group, dodecyloxy group and the like), a cycloalkoxy group (for example, cyclopentyloxy group, cyclohexyloxy group and the like), an aryloxy group (for example, phenoxy group, naphthyloxy group and the like), an alkylthio group (for example, methylthio group, ethylthio group, propylthio group, pentylthio group, hexylthio group, octylthio group, dodecylthio group and the like), a cycloalkylthio group (for example, cyclopentylthio group, cyclohexylthio group and the like), an arylthio group (for example, phenylthio group, naphthylthio group and the like), an alkoxycarbonyl group (for example, methyloxycarbonyl group, ethyloxycarbonyl group, butyloxycarbonyl group, octyloxycarbonyl group, dodecyloxycarbonyl group and the like), an aryloxycarbonyl group (for example, phenyloxycarbonyl group, naphthyloxycarbonyl group and the like), a sulfamoyl group (for example, aminosulfonyl group, methylaminosulfonyl group, dimethylaminosulfonyl group, butylaminosulfonyl group, hexylaminosulfonyl group, cyclohexylaminosulfonyl group, octylaminosulfonyl group, dodecylaminosulfonyl group, phenylaminosulfonyl group, naphthylaminosulfonyl group, 2-pyridylaminosulfonyl group and the like), an acyl group (for example, acetyl group, ethylcarbonyl group, propylcarbonyl group, pentylcarbonyl group, cyclohexylcarbonyl group, octylcarbonyl group, 2-ethylhexylcarbonyl group, dodecylcarbonyl group, phenylcarbonyl group, naphthylcarbonyl group, pyridylcarbonyl group and the like), an acyloxy group (for example, acetyloxy group, ethylcarbonyloxy group, butylcarbonyloxy group, octylcarbonyloxy group, dodecylcarbonyloxy group, phenylcarbonyloxy group and the like), an amido group (for example, methylcarbonylamino group, ethylcarbonylamino group, dimethylcarbonylamino group, propylcarbonylamino group, pentylcarbonylamino group, cyclohexylcarbonylamino group, 2-ethylhexylcarbonylamino group, octylcarbonylamino group, dodecylcarbonylamino group, phenylcarbonylamino group, naphthylcarbonylamino group and the like), a carbamoyl group (for example, aminocarbonyl group, methylaminocarbonyl group, dimethylaminocarbonyl group, propylaminocarbonyl group, pentylaminocarbonyl group, cyclohexylaminocarbonyl group, octylaminocarbonyl group, 2-ethylhexylaminocarbonyl group, dodecylaminocarbonyl gropup, phenylaminocarbonyl group, naphthylaminocarbonyl group, 2-pyridylaminocarbonyl group and the like), an ureido group (for example, methylureido group, ethylureido group, pentylureido group, cyclohexylureido group, octylureido group, dodecylureido group, phenylureido group, naphthylureido group, 2-pyridylaminoureido group and the like), a sulfinyl group (for example, methylsulfinyl group, ethylsulfinyl group, butylsulfinyl group, cyclohexylsulfinyl group, 2-ethylhexylsulfinyl group, dodecylsulfinyl group, phenylsulfinyl group, naphthylsulfinyl group, 2-pyridylsulfinyl group and the like), an alkylsulfonyl group (for example, methylsulfonyl group, ethylsulfonyl group, butylsulfonyl group, cyclohexylsulfonyl group, 2-ethylhexylsulfonyl group, dodecylsulfonyl group and the like), an arylsulfonyl group or a heteroarylsulfonyl group (for example, phenylsulfonyl group, naphthylsulfonyl group, 2-pyridylsulfonyl group and the like), an amino group (for example, amino group, ethylamino group, dimethylamino group, butylamino group, cyclopentylamino group, 2-ethylhexylamino group, dodecylamino group, anilino group, naphthylamino group, 2-pyridylamino group, piperidyl group (also referred to as piperidinyl group), 2,2,6,6-tetramethylpiperidinyl group and the like), a halogen atom (for example, fluorine atom, chlorine atom, bromine atom and the like), a fluorinated hydrocarbon group (for example, fluoromethyl group, trifluoromethyl group, pentafluoroethyl group, pentafluorophenyl group and the like), cyano group, nitro group, hydroxyl group, mercapto group, a silyl group (for example, trimethylsilyl group, triisopropylsilyl group, triphenylsilyl group, phenyldiethylsilyl group and the like), a phosphate group (for example, dihexylphosphoryl group and the like), a phosphite group (for example, diphenylphosphinyl group and the like), phosphono group, and the like.

Some of these substituents may further be substituted by the above-described substituent. In addition, a plurality of the substituents may bind to each other to form a ring. The substituents which do not prevent the interaction between a compound and silver (Ag) are preferably used, and further the substituents having the nitrogen atom having the above-mentioned effective unshared electron pair are particularly preferably applied. Note that the above description as to the substituents is also applied to the substituents designated in the following explanation of the general formulae (2) to (8a).

The compound having the structure represented by the above general formula (1) is preferable because the strong interaction between the nitrogen atom in the compound and the silver constituting the conductive layer 15 can be expressed.

[Chem. 8]

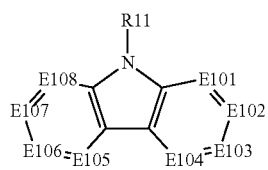

General Formula (1a)

The compound having the structure represented by the above general formula (1a) is one form of the compound having the structure expressed by the above general formula (1), and is a compound in which X11 is —N(R11)- in the general formula (1). This compound is preferable because the above interaction can be more strongly expressed.

[Chem. 9]

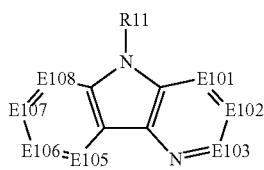

General Formula (1a-1)

The compound having the structure represented by the above general formula (1a-1) is one form of the compound having the structure expressed by the above general formula (1a), and is a compound in which E104 is —N= in the general formula (1a). This compound is preferable because the above interaction can be more effectively expressed.

[Chem. 10]

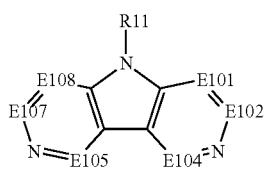

General Formula (1a-2)

The compound having the structure represented by the above general formula (1a-2) is another form of the compound having the structure expressed by the above general formula (1a), and is a compound in which E103 and E106 are —N= in the general formula (1a). This compound is preferable because the above interaction can be more strongly expressed.

[Chem. 11]

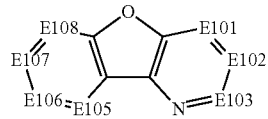

General Formula (1b)

The compound having the structure represented by the above general formula (1b) is another form of the compound having the structure expressed by the above general formula (1), and is a compound in which X11 is —O— and E104 is —N= in the general formula (1). This compound is preferable because the above interaction can be more effectively expressed.

Furthermore, the compounds having the structure represented by the following general formulae (2) to (8a) are preferable because the above interaction can be more effectively expressed.

[Chem. 12]

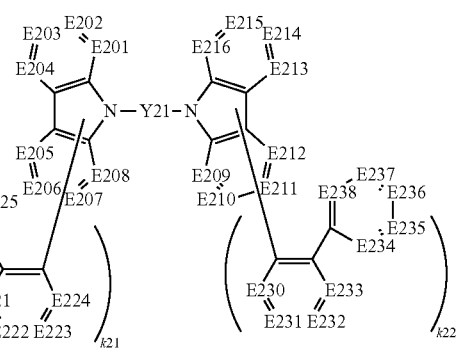

General formula (2)

The above-described general formula (2) is also one embodiment of the general formula (1). In the general formula (2), Y21 represents a divalent linking group of an arylene group, a heteroarylene group or a combination thereof. E201 to E216 and E221 to E238 each represent —C(R21)= or —N=, and R21 represents hydrogen atom (H) or a substituent. However, at least one of E221 to E229 and at least one of E230 to E238 represent —N=. k21 and k22 represent an integer of 0 to 4, and k21+k22 is an integer of 2 or more.

In the general formula (2), examples of an arylene group represented by Y21 include, for example, o-phenylene group, p-phenylene group, naphthalenediyl group, anthracenediyl group, naphthacenediyl group, pyrenediyl group, naphthylnaphthalenediyl group, biphenyldiyl group (for example, [1,1'-biphenyl]-4,4'-diyl group, 3,3'-biphenyldiyl group, 3,6-biphenyldiyl group and the like), terphenyldiyl group, quaterphenyldiyl group, quinquephenyldiyl group, sexiphenyldiyl group, septiphenyldiyl group, octiphenyldiyl group, nobiphenyldiyl group, deciphenyldiyl group and the like.

Furthermore, in the general formula (2), examples of a heteroarylene group represented by Y21 include, for example, a divalent group derived from a group consisting of carbazole ring, carboline ring, diazacarbazole ring (also referred to as monoazacarboline ring, and indicating a ring structure in which one carbon atom constituting the carboline ring is substituted with a nitrogen atom), triazole ring, pyrrole ring, pyridine ring, pyrazine ring, quinoxaline ring, thiophene ring, oxadiazole ring, dibenzofuran ring, dibenzothiophene ring, indole ring and the like.

As a preferable divalent linking group which is an arylene group, a heteroarylene group or a combination thereof represented by Y21 contain, among the heteroarylene groups, preferable is a group which is derived from a condensed aromatic heterocyclic ring formed by condensing three or more rings, and as the group derived from the condensed aromatic heterocyclic ring formed by condensing three or more rings, preferable is a group derived from dibenzofuran ring or a group derived from dibenzothiophene ring.

In the general formula (2), it is preferable that six or more of E201 to E208 and six or more of E209 to E216 each represent —C(R21)=.

In the general formula (2), it is preferable that at least one of E225 to E229 and at least one of E234 to E238 represent —N=.

Furthermore, in the general formula (2), it is preferable that at least one of E225 to E229 and at least one of E234 to E238 represent —N=.

In addition, in the general formula (2), preferable embodiment is that E221 to E224 and E230 to E233 each represent —C(R21)=.

Moreover, in the compound represented by the general formula (2), it is preferable that E203 represents —C(R21)=, and R21 represents a linking moiety, and in addition, it is preferable that E211 also represents —C(R21)=, and R21 represents a linking moiety.

Furthermore, it is preferable that E225 and E234 represent —N=, and it is preferable that E221 to E224 and E230 to E233 each represent —C(R21)=.

[Chem. 13]

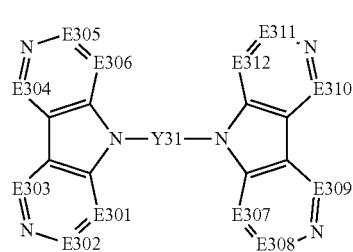

General formula (3)

The general formula (3) is also one embodiment of the general formula (1a-2). In the general formula (3), E301 to E312 each represent —C(R31)=, and the above-described R31 represents hydrogen atom (H) or a substituent. Y31 represents a divalent linking group of an arylene group, a heteroarylene group or combination thereof.

In addition, in the general formula (3), a preferable embodiment of the divalent linking group of an arylene group, a heteroarylene group or combination thereof represented by Y31, is the same as that in Y21 of the general formula (2).

[Chem. 14]

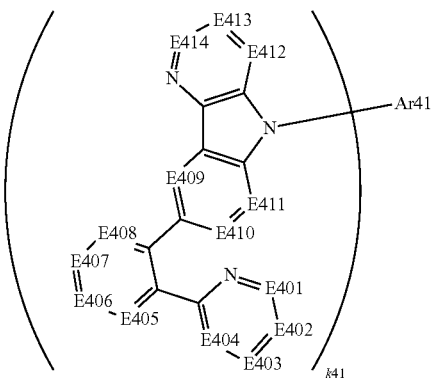

General formula (4)

The general formula (4) is also one embodiment of the general formula (1a-1). In the above-described the general formula (4), E401 to E414 each represent —C(R41)=, and the above-described R41 represents hydrogen atom (H) or a substituent. Ar41 represents a substituted or un-substituted aromatic hydrocarbon ring or a substituted or un-substituted aromatic heterocyclic ring. Furthermore, k41 represents an integer of 3 or more.

In addition, in the general formula (4), when Ar41 represents an aromatic hydrocarbon ring, examples of the aromatic hydrocarbon ring include benzene ring, biphenyl ring, naphthalene ring, azulene ring, anthracene ring, phenanthrene ring, pyrene ring, chrysene ring, naphthacene ring, triphenylene ring, o-terphenyl ring, m-terphenyl ring, p-terphenyl ring, acenaphthene ring, coronene ring, fluorene ring, fluoranthrene ring, naphthacene ring, pentacene ring, perylene ring, pentaphene ring, picene ring, pyrene ring, pyranthrene ring, anthranthrene ring, and the like. These rings may also have a substituent represented by R11, R12 of the general formula (1).

Additionally, in the general formula (4), when Ar41 represents an aromatic heterocyclic ring, examples of the aromatic heterocyclic ring include furan ring, thiophene ring, oxazole ring, pyrrole ring, pyridine ring, pyridazine ring, pyrimidine ring, pyrazine ring, triazine ring, benzimidazole ring, oxadiazole ring, triazole ring, imidazole ring, pyrazole ring, triazole ring, indole ring, benzimidazole ring, benzothiazole ring, benzoxazole ring, quinoxaline ring, quinazoline ring, phthalazine ring, carbazole ring, azacarbazole ring, and the like. Note that the azacarbazole ring means a ring obtained by substituting one or more of carbon atoms of a benzene ring with a nitrogen atom constituting a carbazole ring. These rings may also have a substituent represented by R11, R12 of the general formula (1).

[Chem. 15]

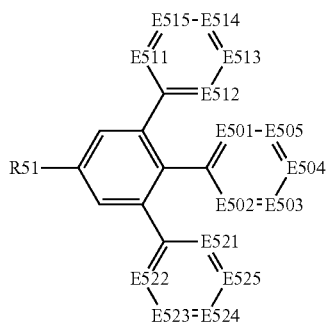

General formula (5)

In the above-described general formula (5), R51 represents a substituent, E501, E502, E511 to E515, E521 to E525 each represent —C(R52)= or —N=. E503 to E505 each represent —C(R52)=. R52 represents hydrogen atom (H) or a substituent. At least one of E501 and E502 is —N=, at least one of E511 to E515 is —N=, at least one of E521 to E525 is —N=.

[Chem. 16]

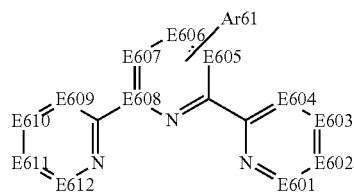

General formula (6)

In the above-described general formula (6), E601 to E612 each represent —C(R61)= or —N=, R61 represents hydrogen atom (H) or a substituent. In addition, Ar61 represents a substituted or un-substituted aromatic hydrocarbon ring or a substituted or un-substituted aromatic heterocyclic ring.

In addition, in the general formula (6), the substituted or un-substituted aromatic hydrocarbon ring or substituted or un-substituted aromatic heterocyclic ring represented by Ar61 is the same as that in Ar41 of the general formula (4).

[Chem. 17]

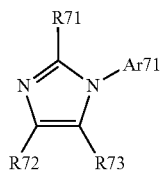

General Formula (7)

R71 to R73 in the above general formula (7) each represent a hydrogen atom (H) or a substituent, Ar71 represents an aromatic hydrocarbon ring group or an aromatic heterocyclic group.

Additionally, examples of the aromatic hydrocarbon ring group or an aromatic heterocyclic group represented by Ar71 in the above general formula (7) include the same as those of Ar41 of the general formula (4).

[Chem. 18]

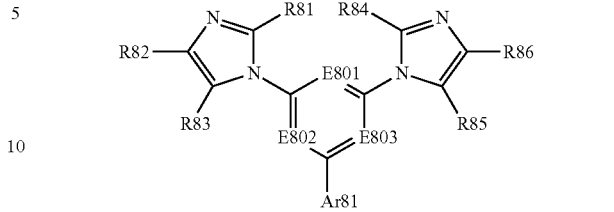

General Formula (8)

The above general formula (8) is also one form of the general formula (7). R81 to R86 in the above general formula (8) each represents a hydrogen atom (H) or a substituent. E801 to E803 each represents —C(R87)= or N=, and R87 represents a hydrogen atom (H) or a substituent. Ar81 represents an aromatic hydrocarbon ring group or an aromatic heterocyclic group.

In addition, examples of the aromatic hydrocarbon ring group or an aromatic heterocyclic group represented by Ar81 in the above general formula (8) include the same as those of Ar41 of the general formula (4).

[Chem. 19]

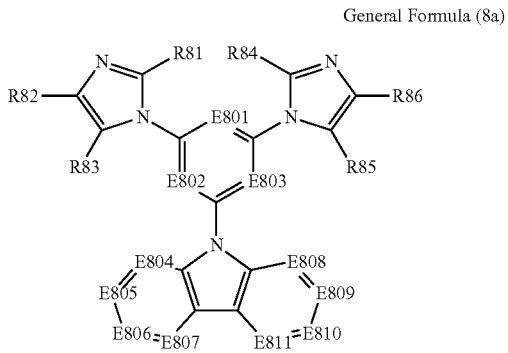

General Formula (8a)

The above general formula (8a) is also one form of the nitrogen-containing compound represented by the general formula (8), Ar81 in the above general formula (8) is a carbazole derivative. E804 to E811 in the above general formula (8a) each represents —C(R88)= or —N=, and R88 represents a hydrogen atom (H) or a substituent. At least one of E808 to E811 is —N=, and E804 to E807, E808 to E811 may bond each other to form a new ring.

[Compound-3]

In addition, as the other compound constituting the nitrogen-containing layer 14, there are compounds 1 to 166 specifically exemplified in the followings, other than the above compounds represented by the general formulae (1) to (8a). These compounds are compounds containing a nitrogen atom which interacts with silver constituting the conductive layer 15. Additionally, these compounds are materials having electron transport property or electron injection property. Accordingly, the transparent electrode 10 wherein the nitrogen-containing layer 14 is constituted using such a compound is suitable to a transparent electrode in the organic electroluminescent element, and the nitrogen-containing layer 14 can be used as an electron transport layer or an electron injection layer in the organic electroluminescent element. Note that, among these compounds 1 to 166, a compound which falls within the above-mentioned range of the effective unshared electron pair content [n/M] is included, and such a compound can be used alone as the compound constituting the nitrogen-containing layer 14. Furthermore, in the compounds 1 to 166, there are compounds which are applicable to the above-mentioned general formulae (1) to (8a).

[Chem. 20]

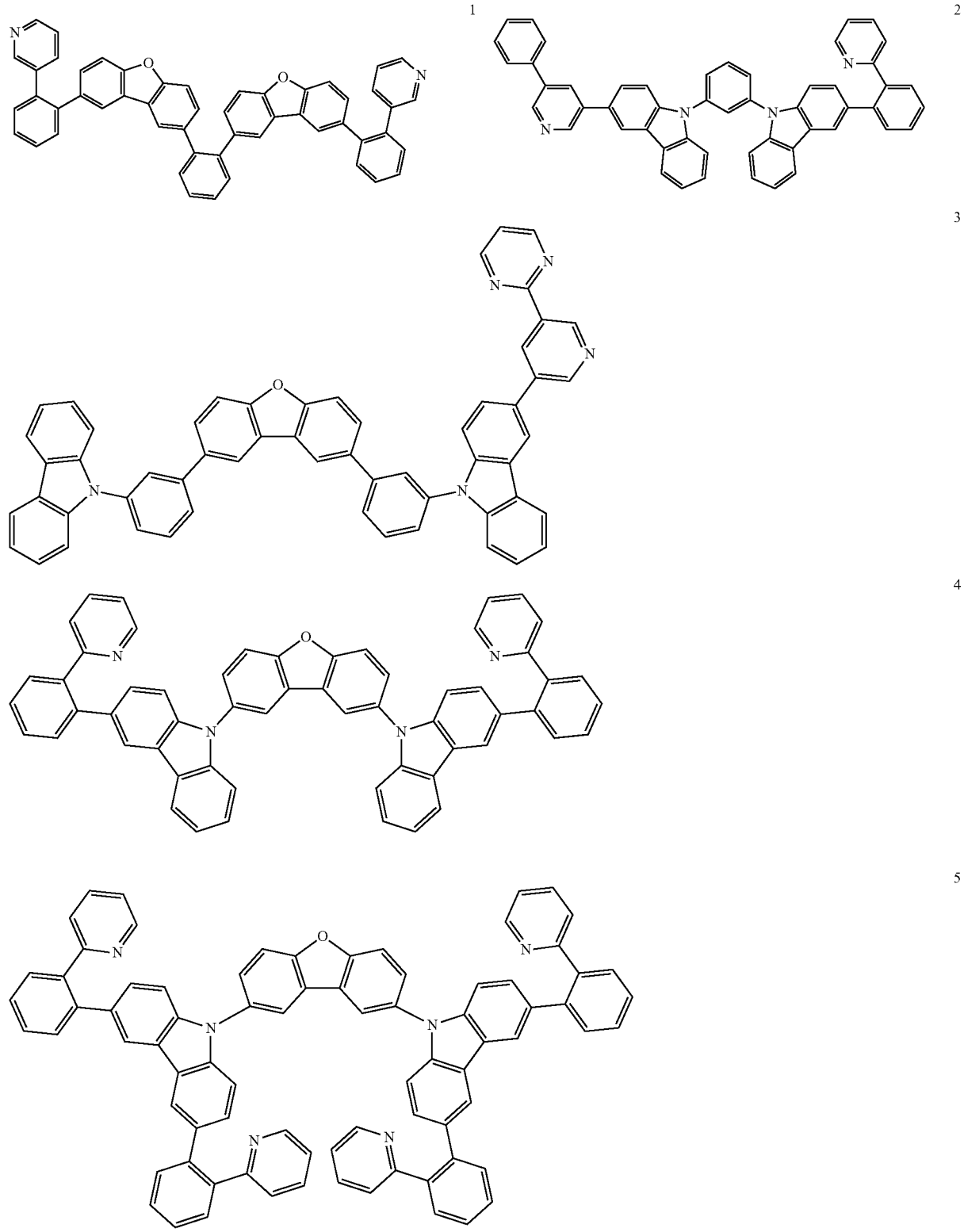

[Chem. 21]
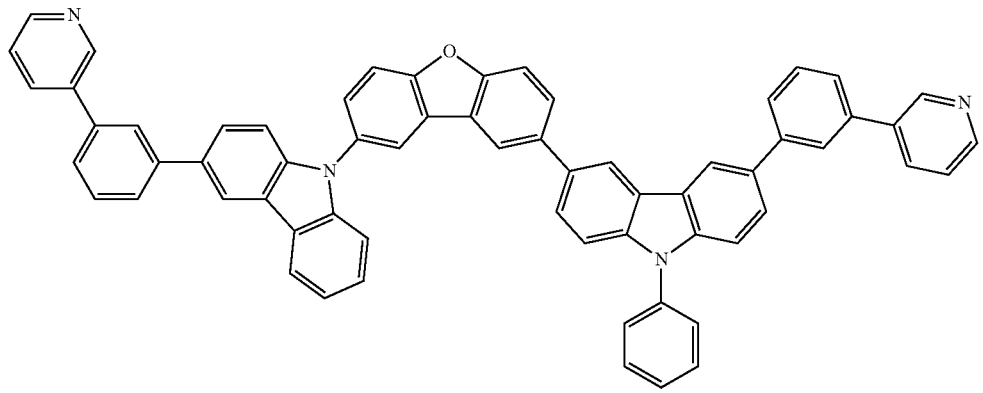
6
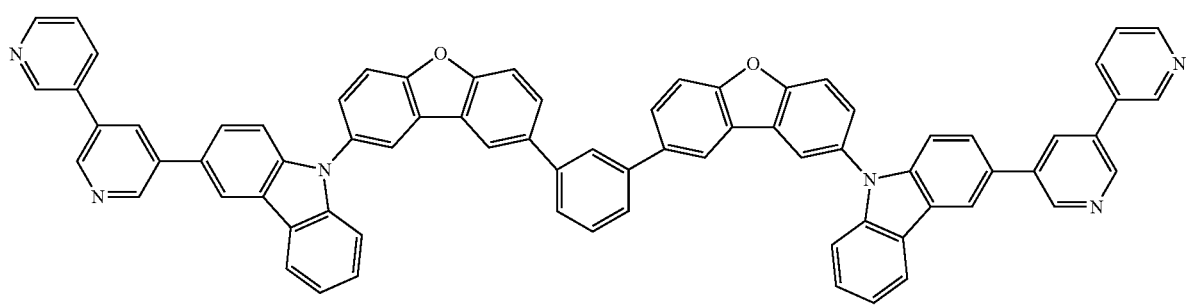
7
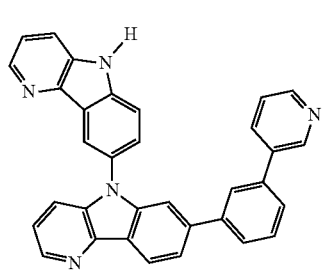
8
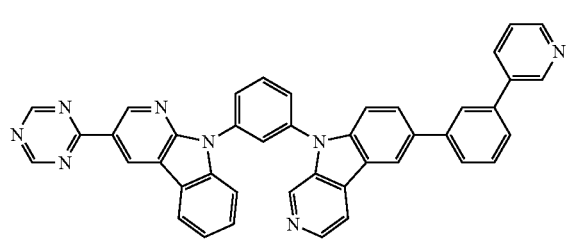
9
[Chem. 22]
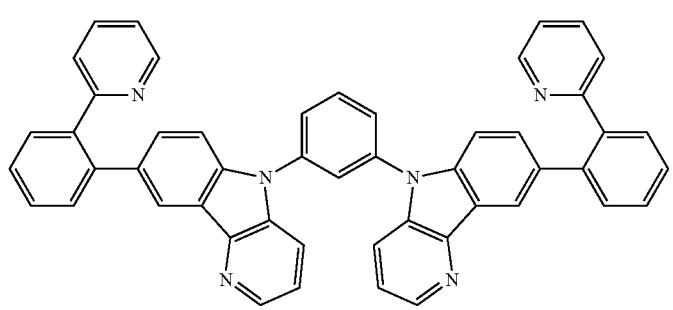
10

11
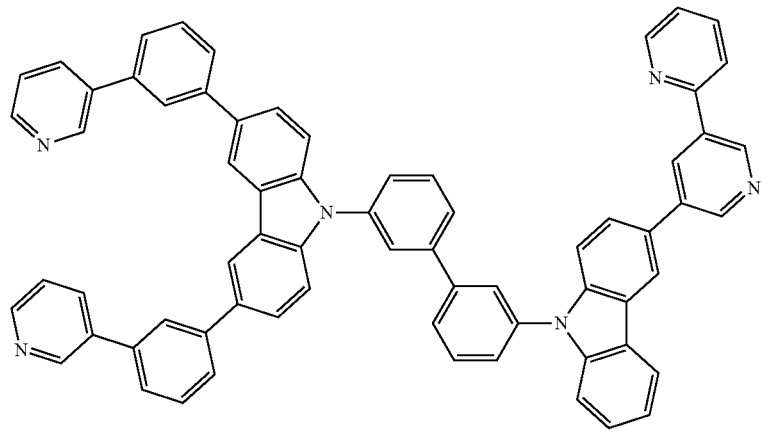
12
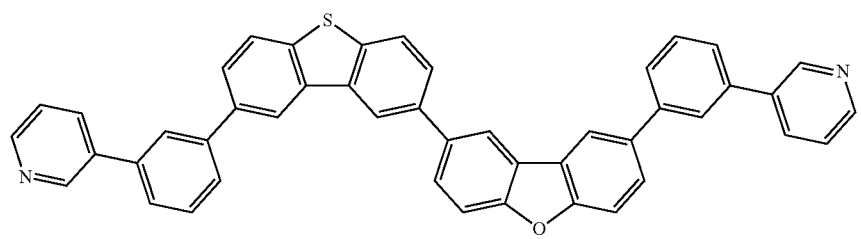
13
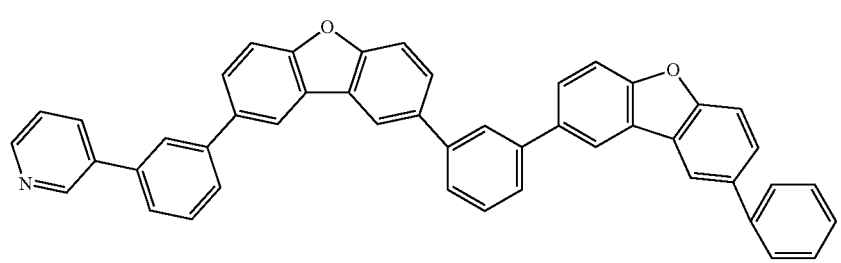
14
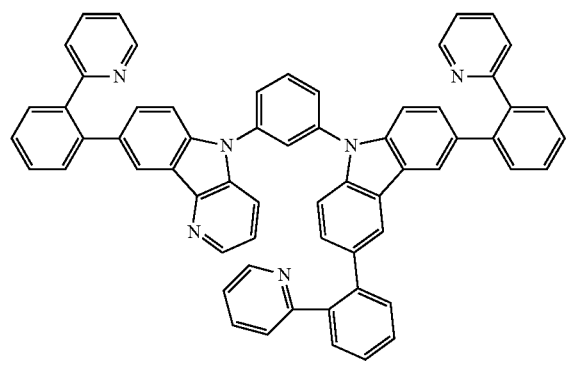
15
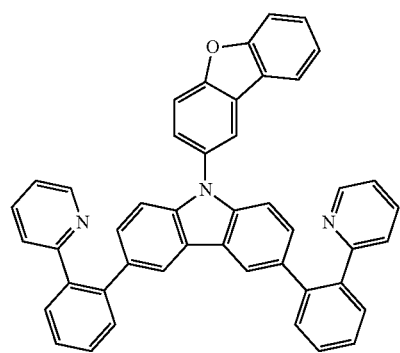

[Chem. 23]
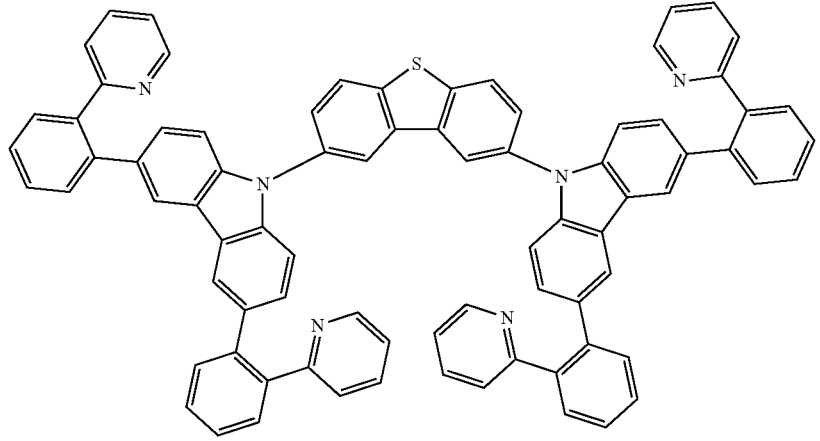
16
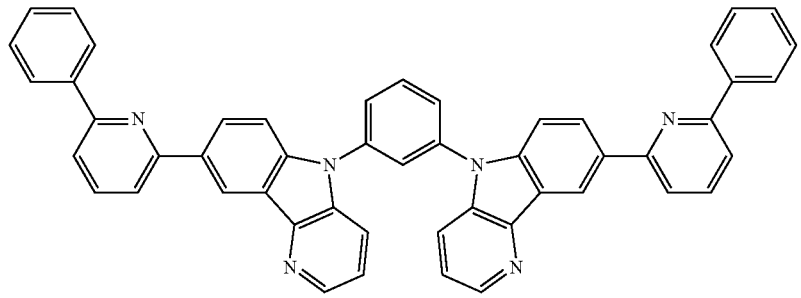
17
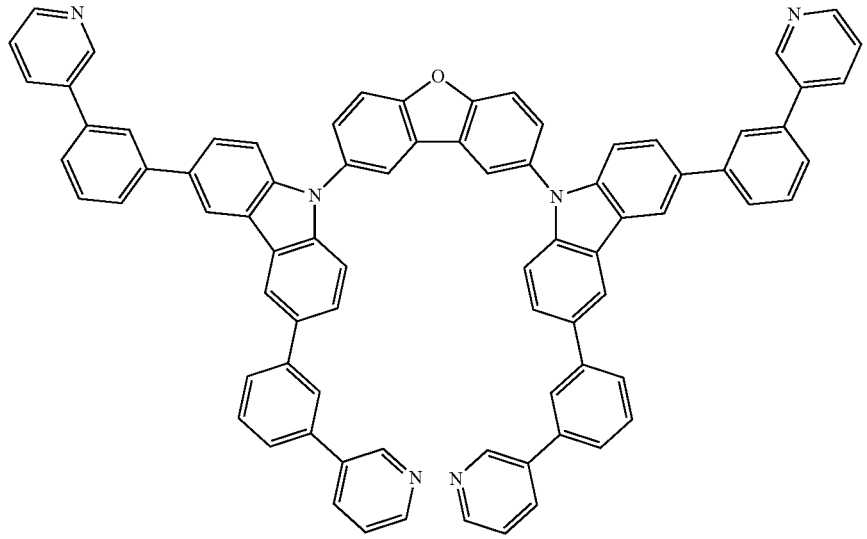
18
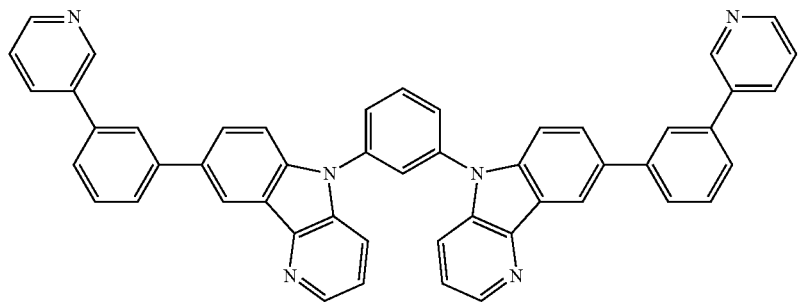
19

[Chem. 24]
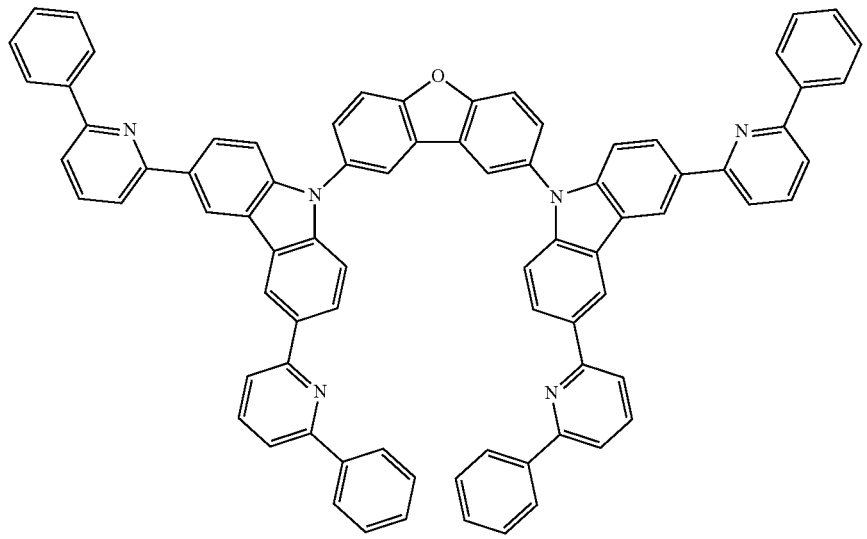
20
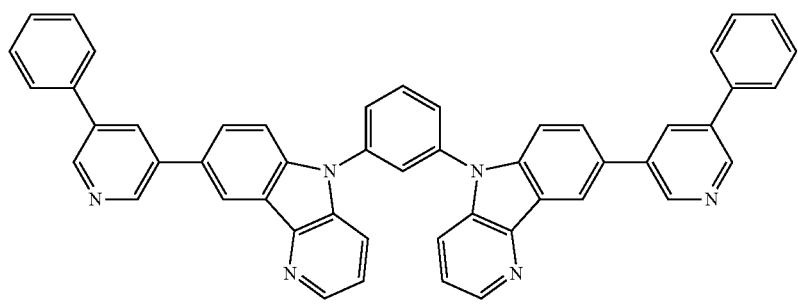
21
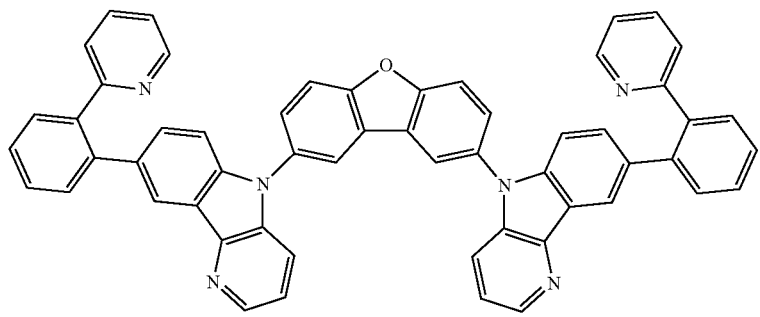
22
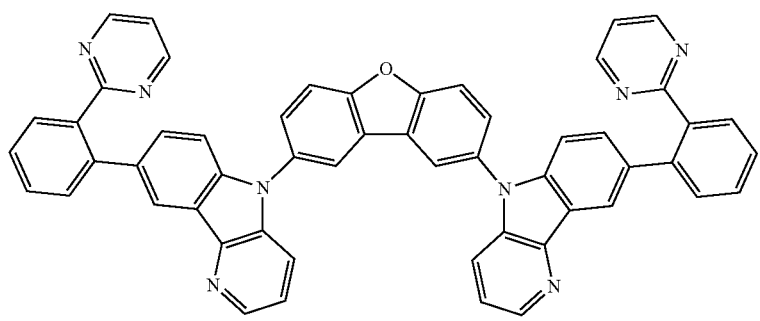
23

[Chem. 25]
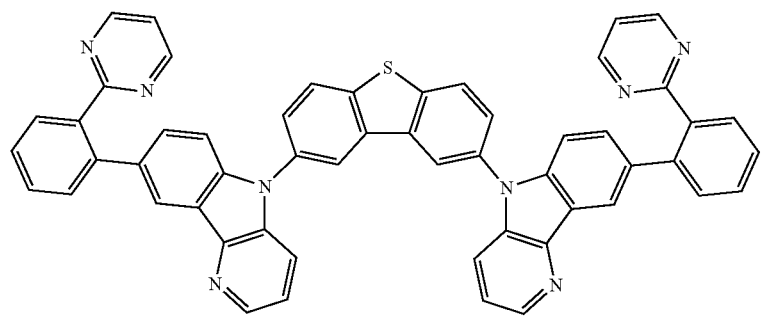
24
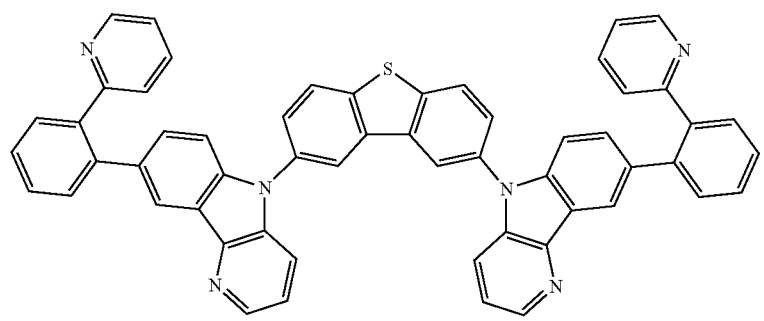
25
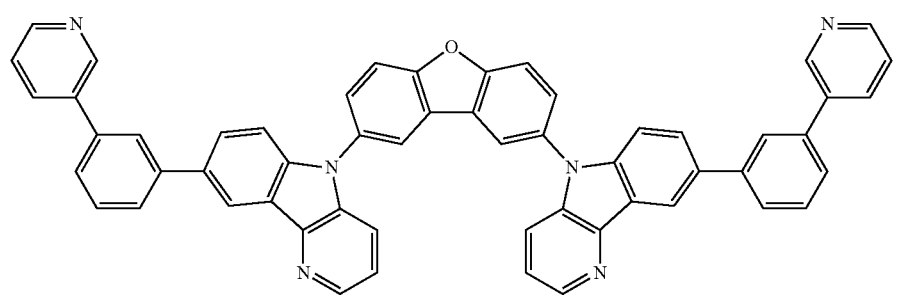
26
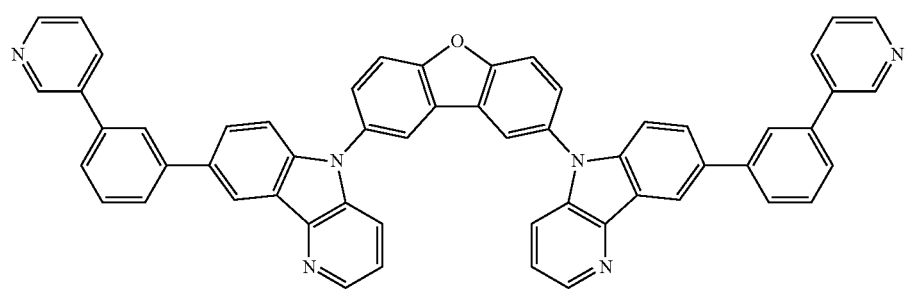
27
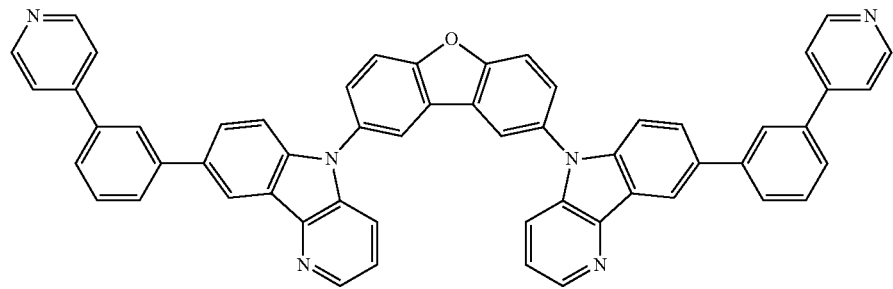
28

-continued
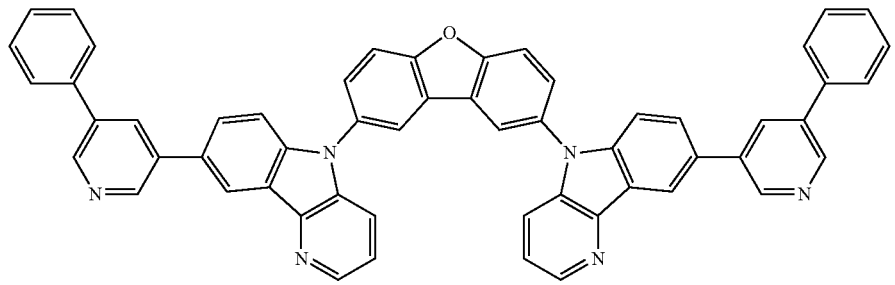
29
[Chem. 26]
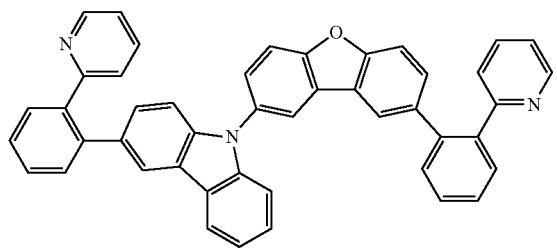
30
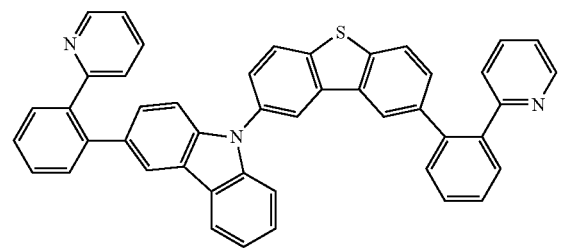
31
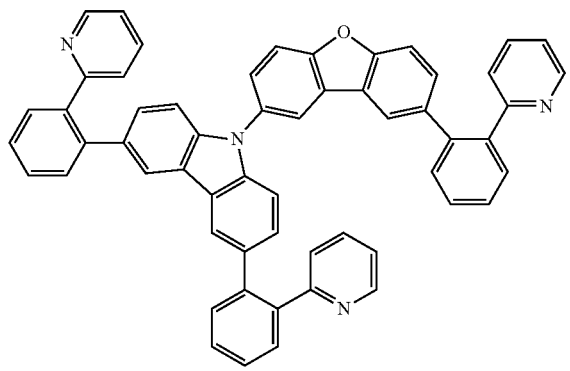
32
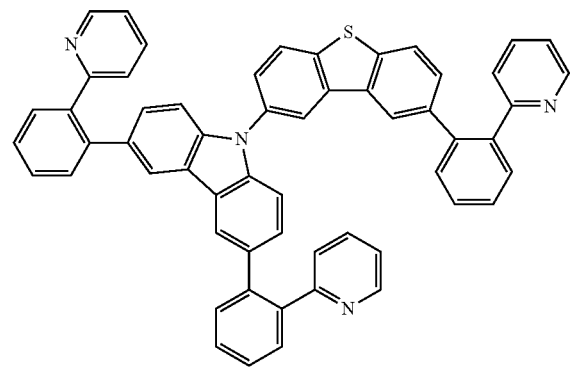
33
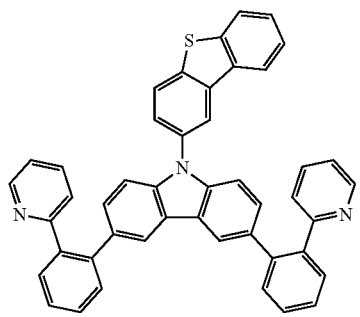
34
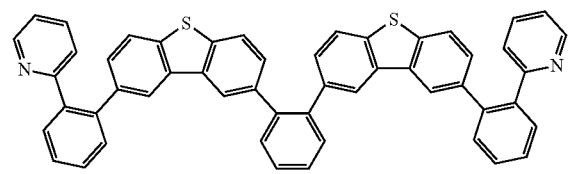
35
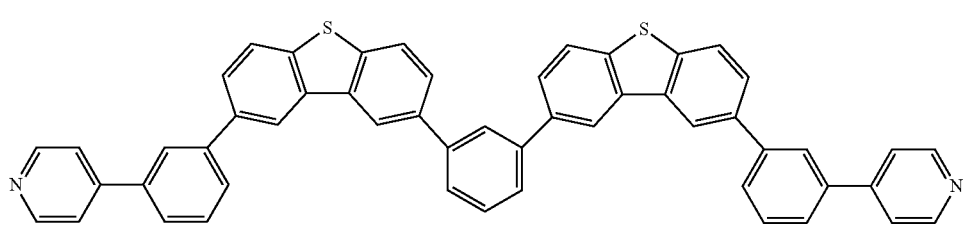
36

[Chem. 27]
-continued
37
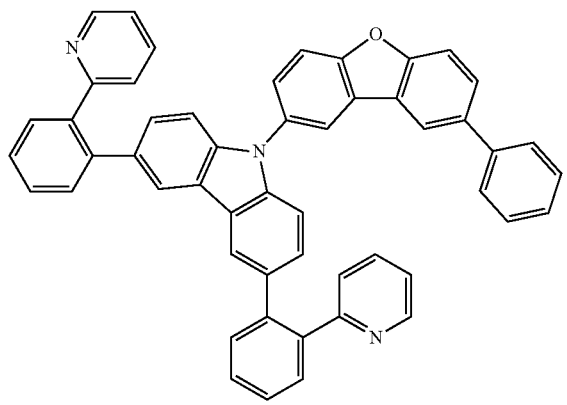
38
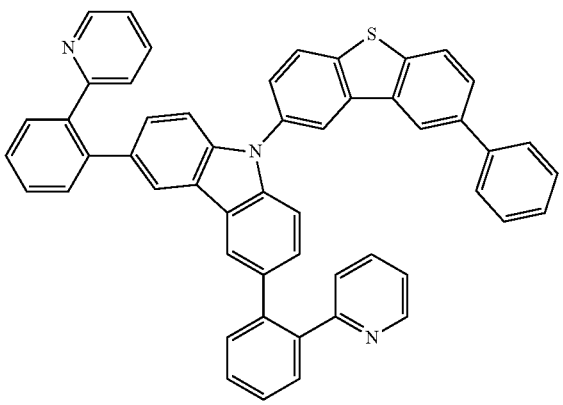
39
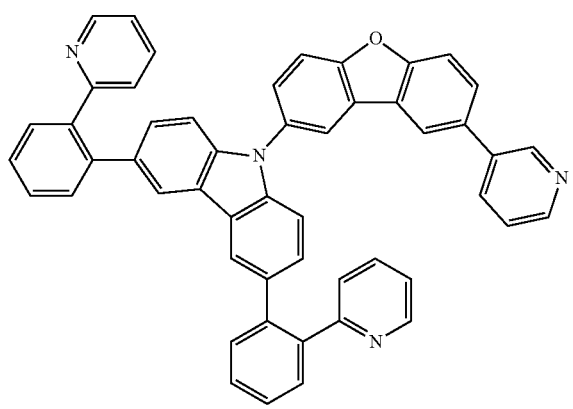
40
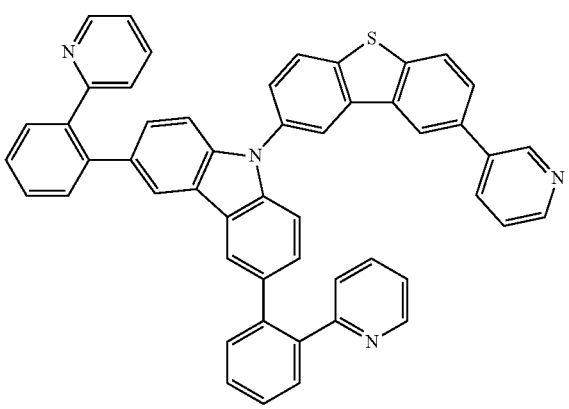
41
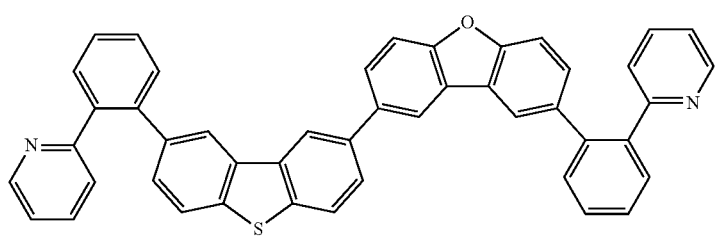
42
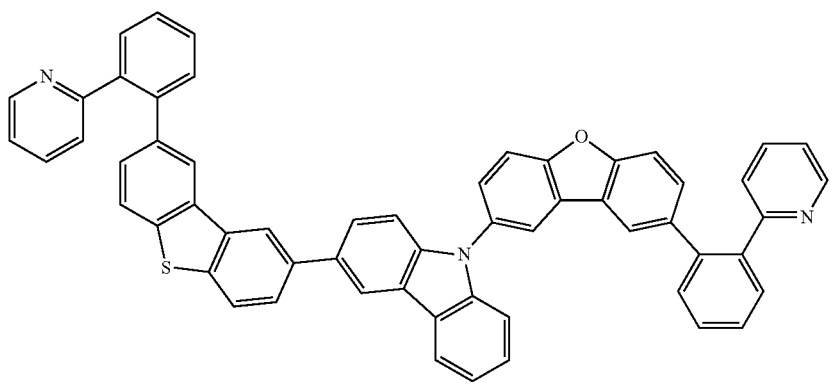

[Chem. 28]
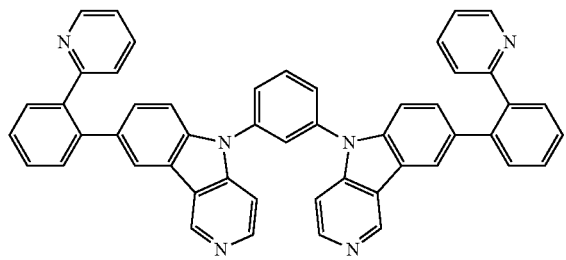
43
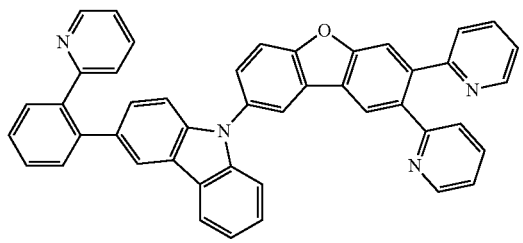
44
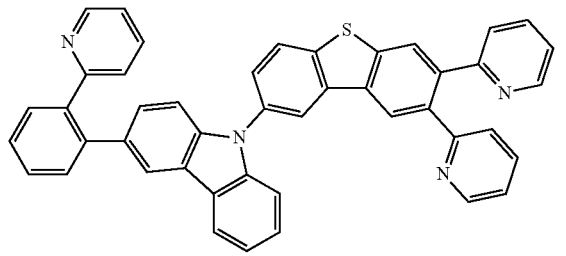
45
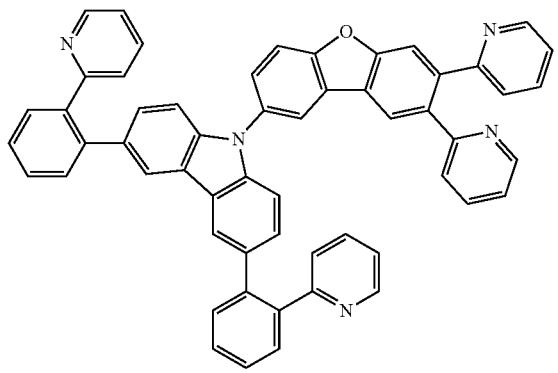
46
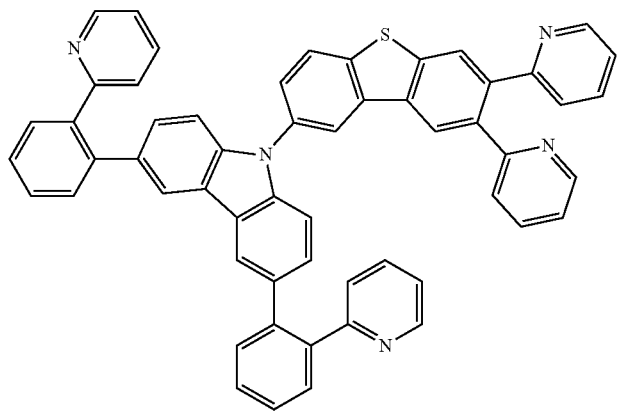
47
[Chem. 29]
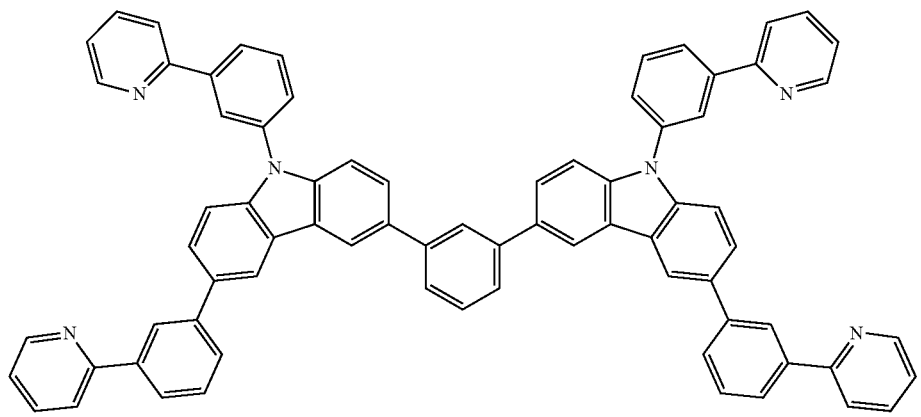
48

-continued
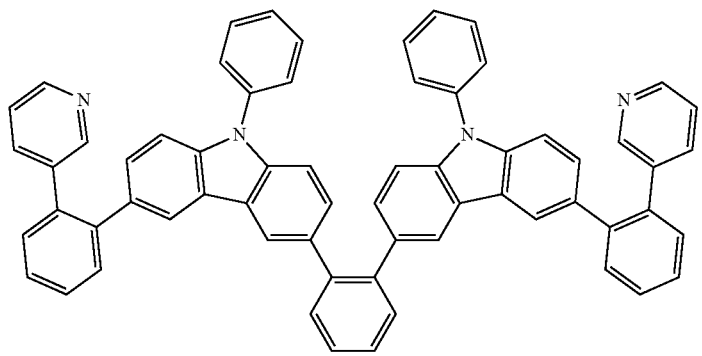
49
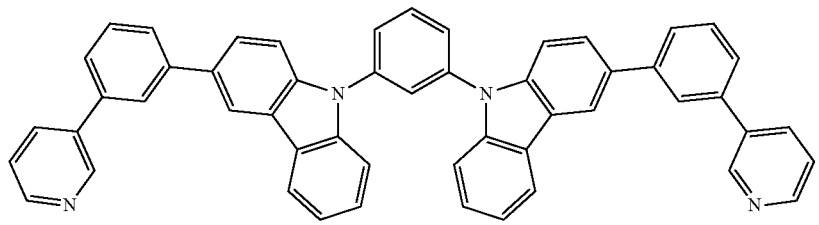
50
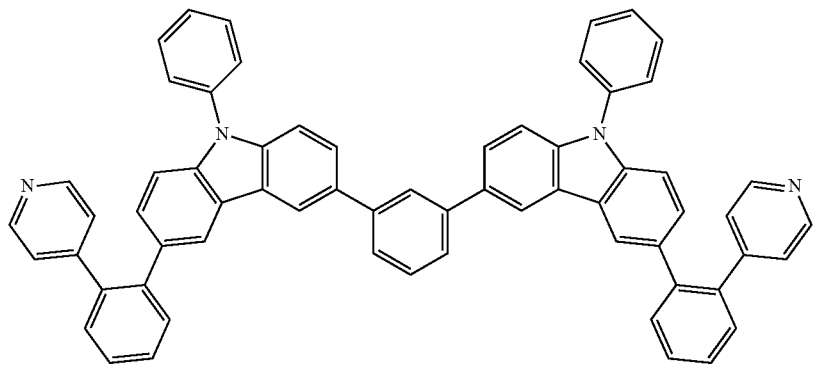
51
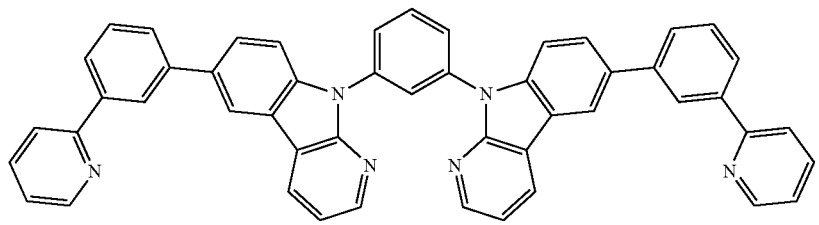
52
[Chem. 30]
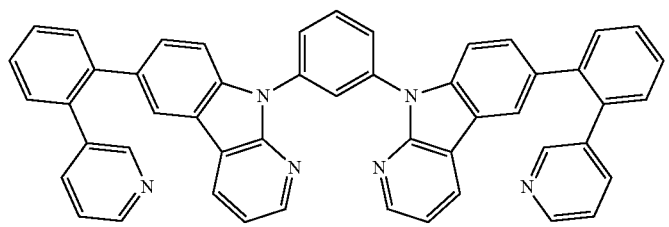
53

-continued
54
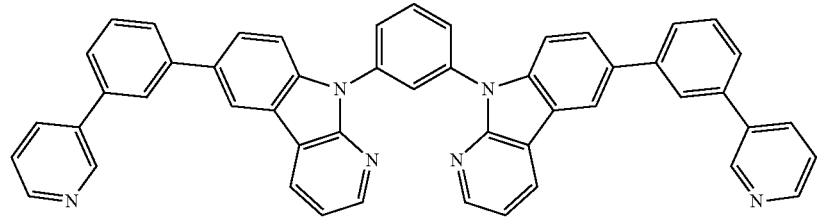
55
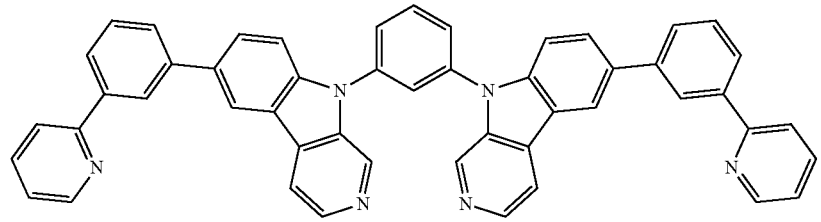
56
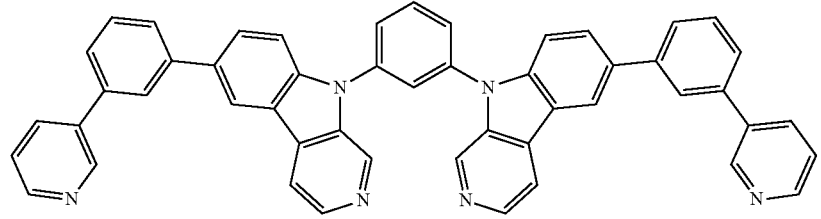
57
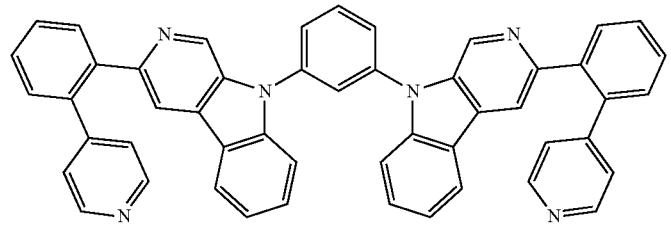
58
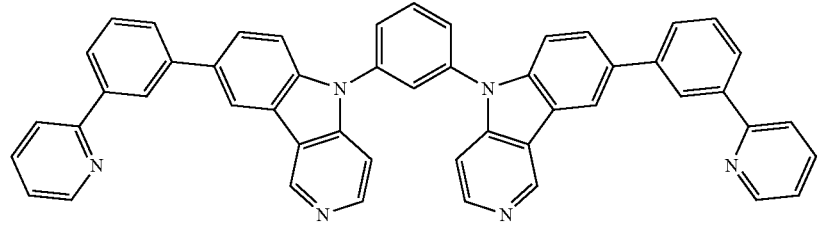
[Chem. 31]
59
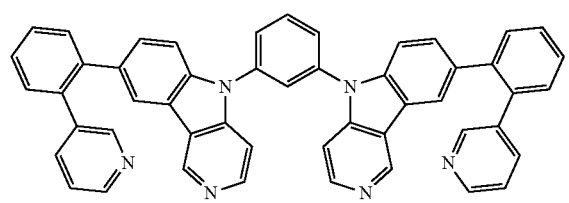
60
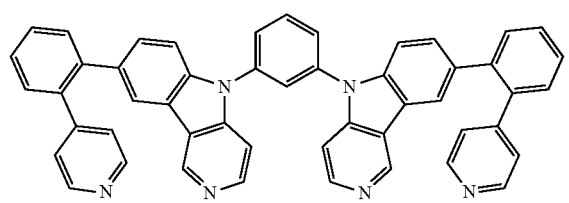

-continued
61
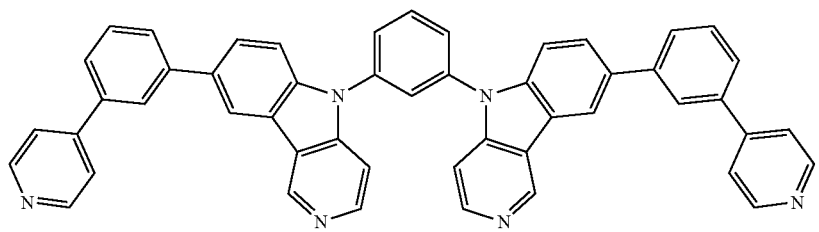
62
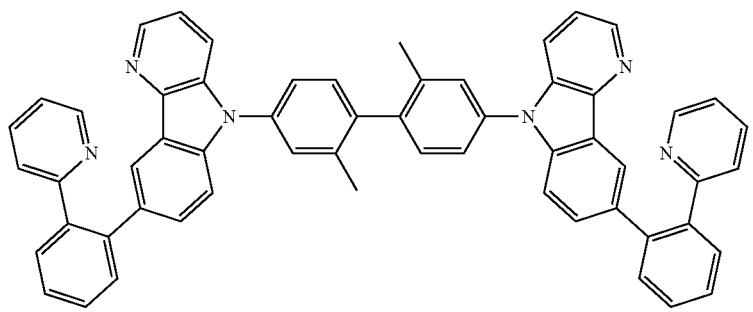
63
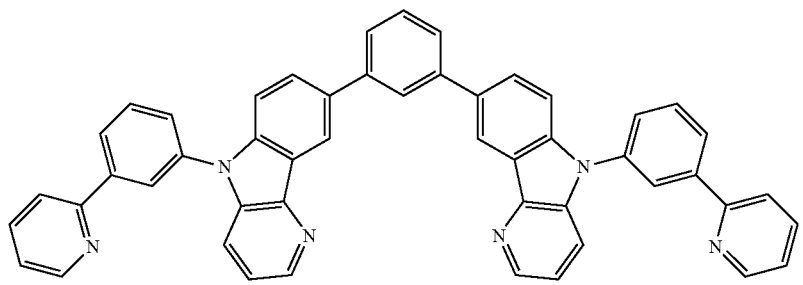
64
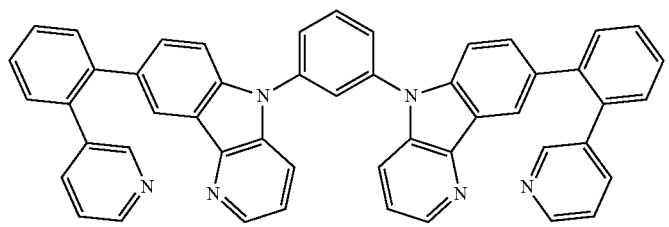
[Chem. 32]
65
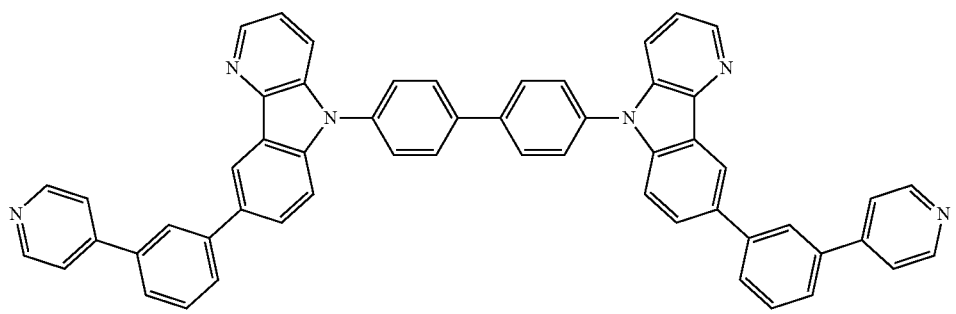

-continued
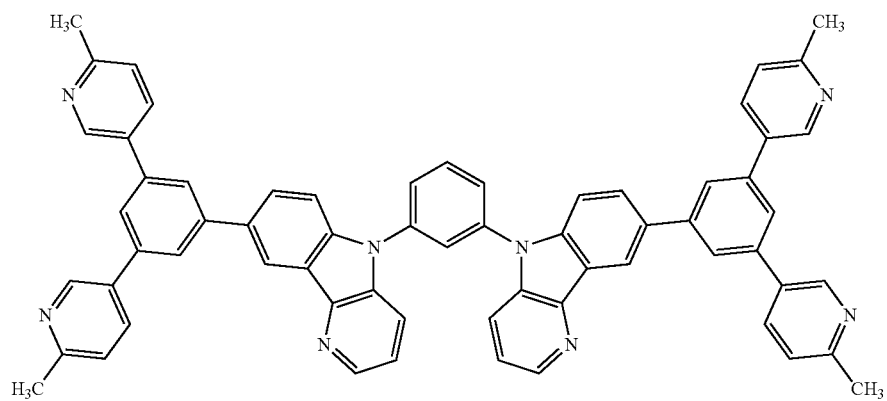
66
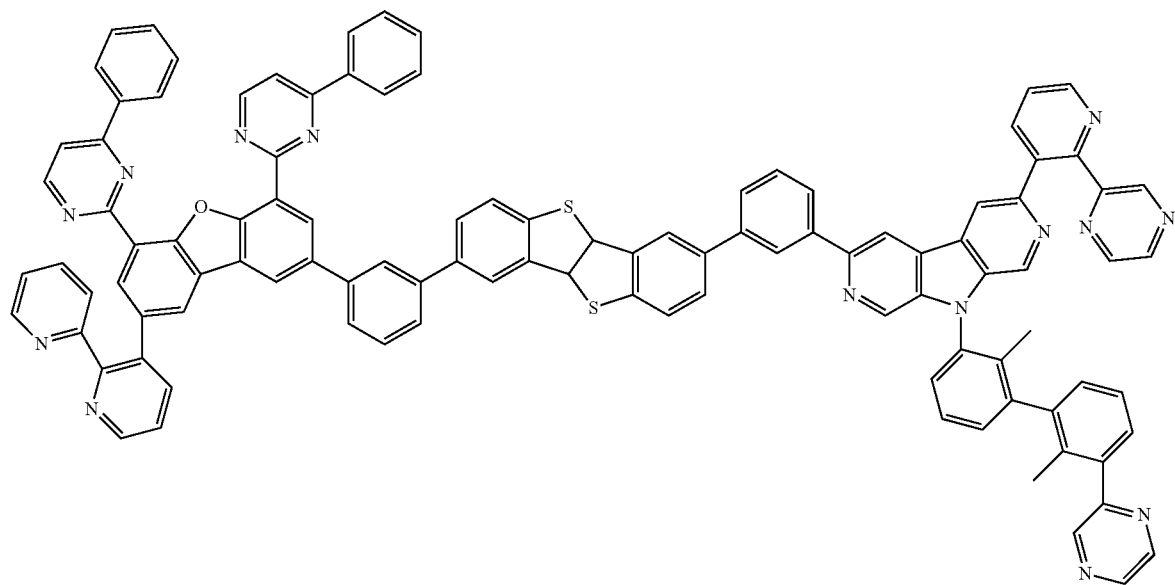
67
[Chem. 33]
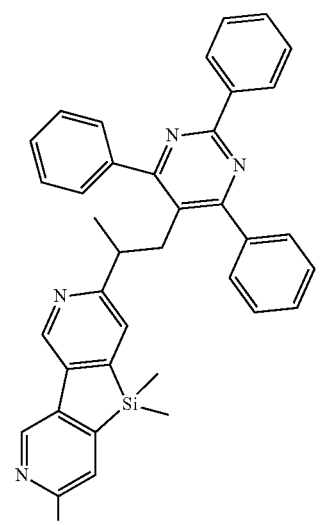
68

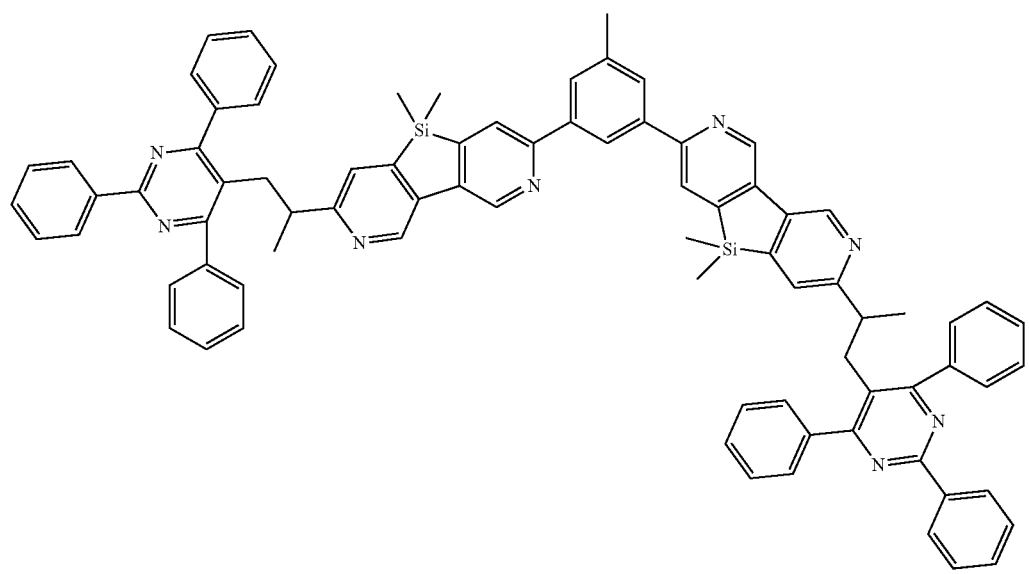
69
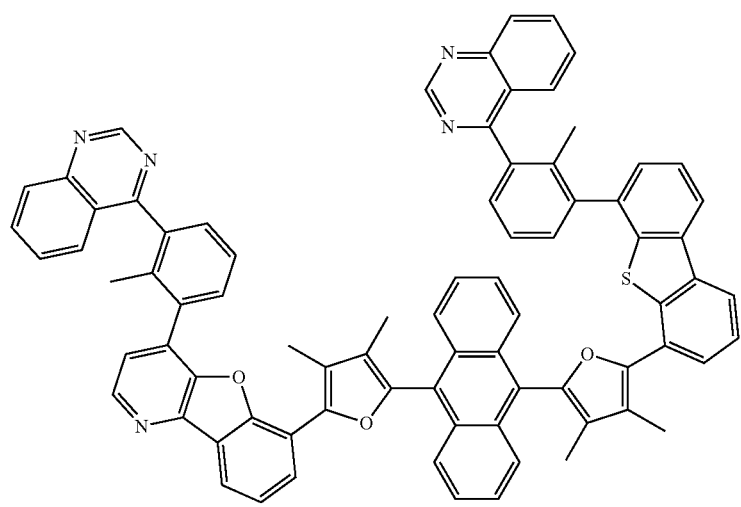
[Chem. 34]
70
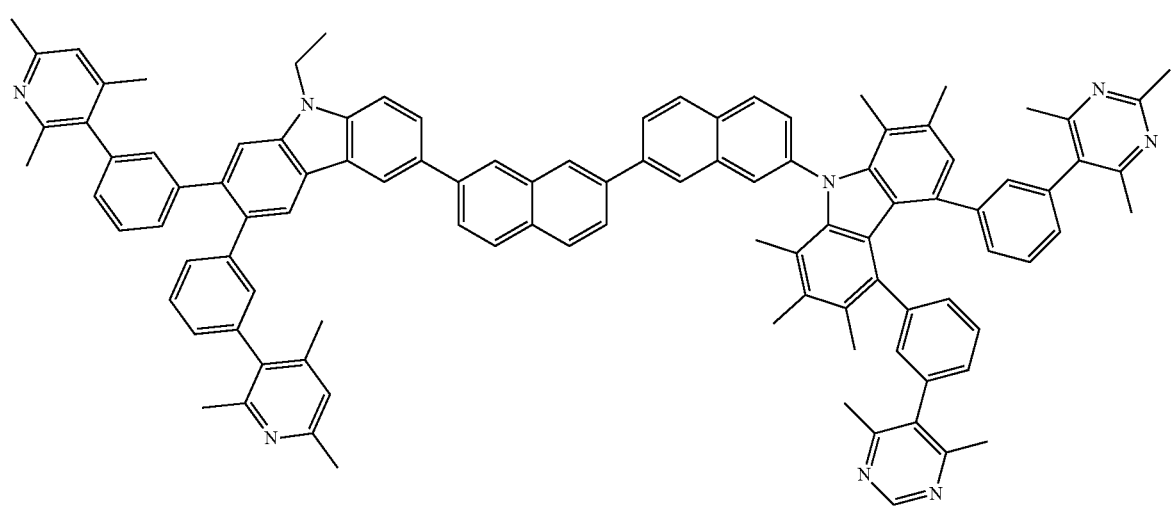

71
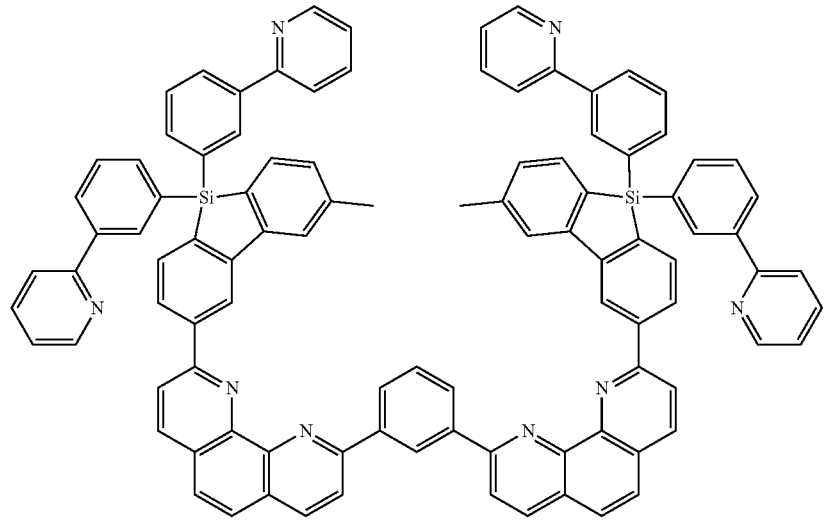
72
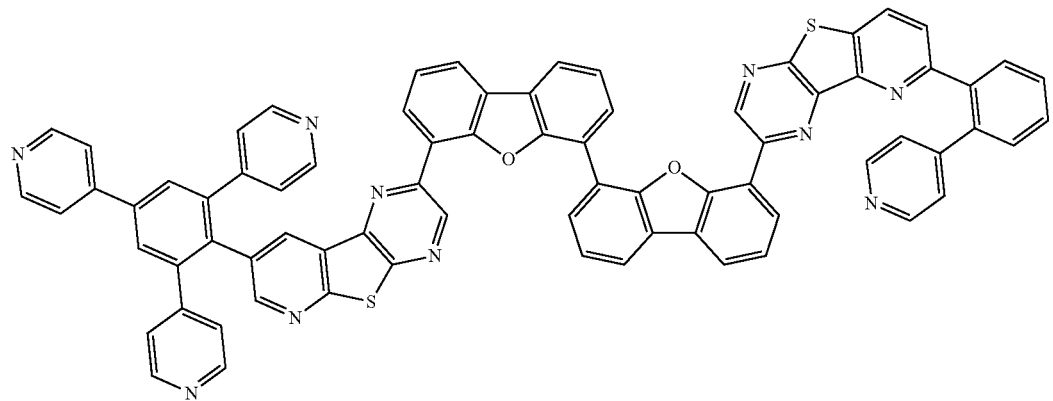
[Chem. 35]
73
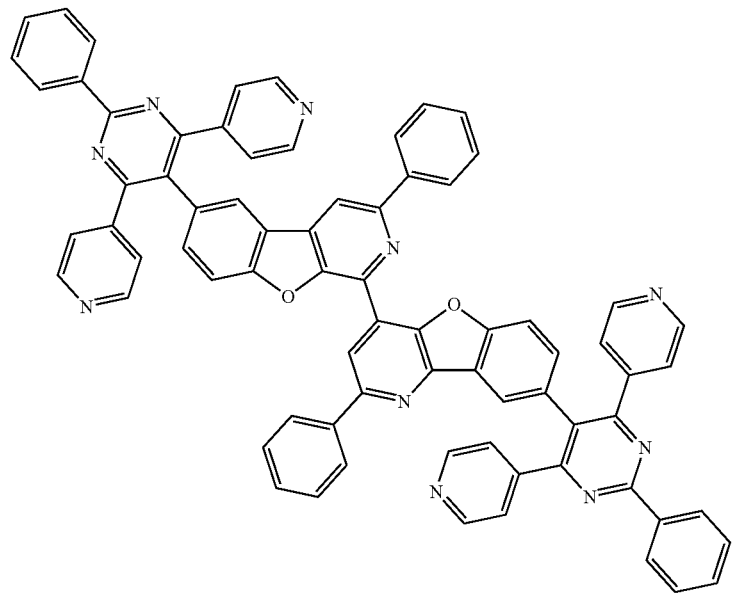

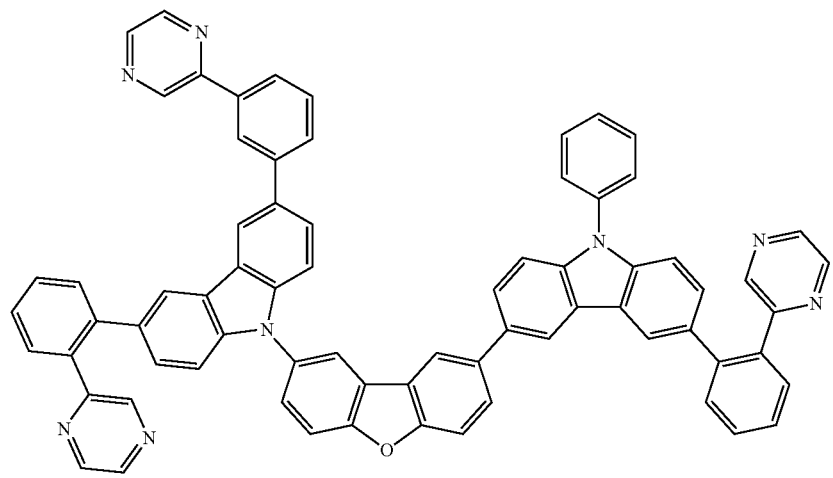
74
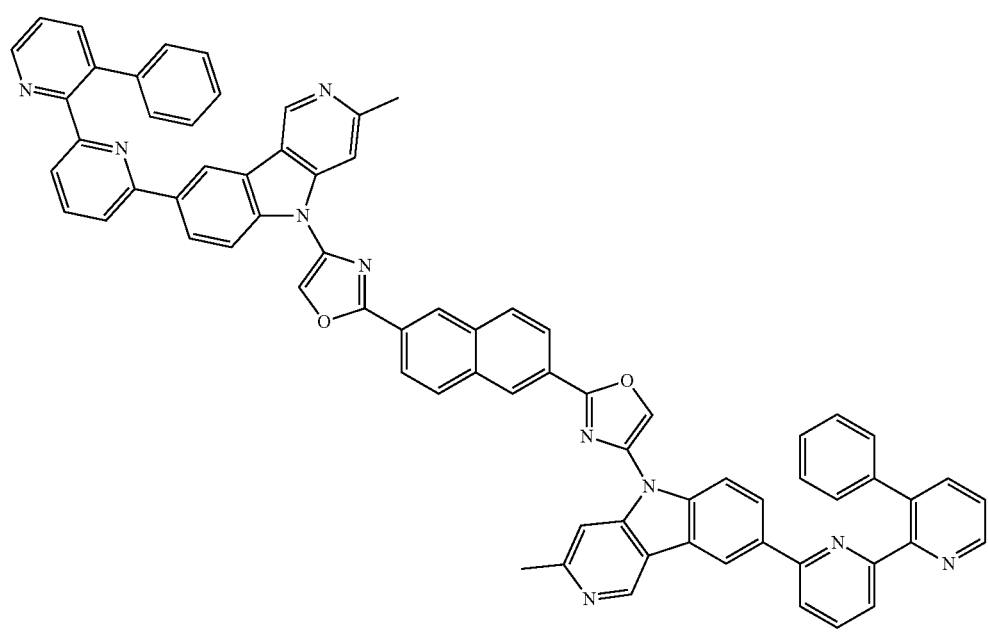
75

[Chem. 36]
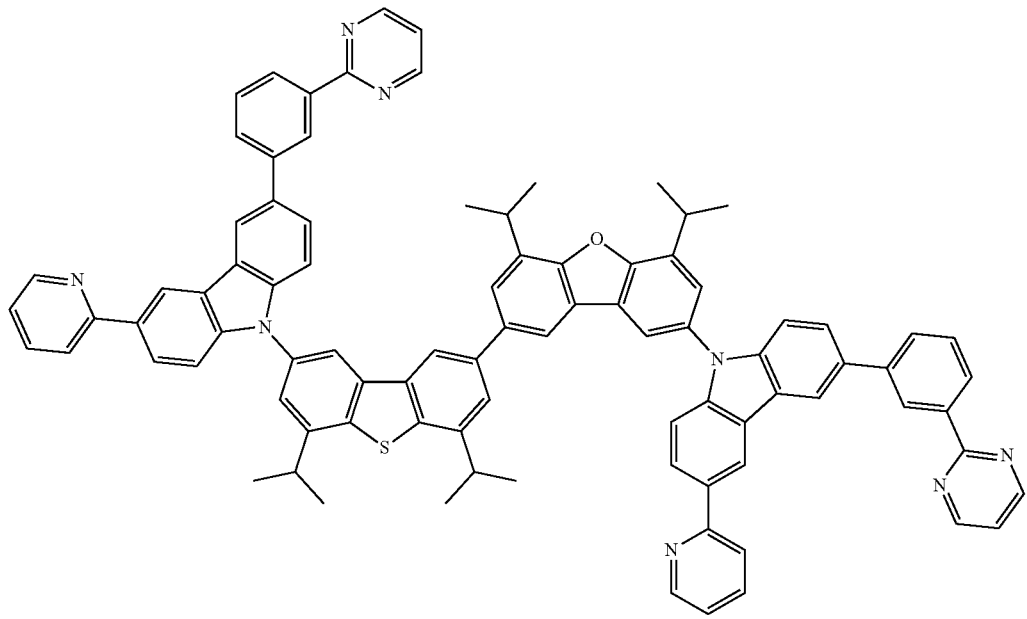
76
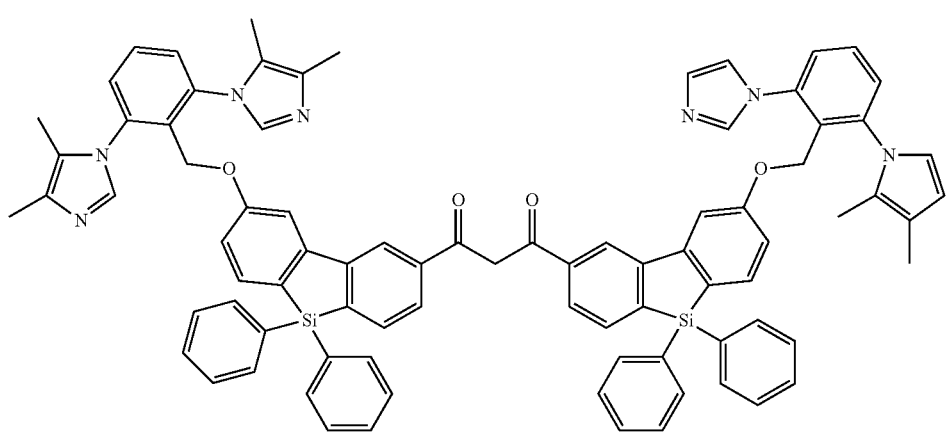
77

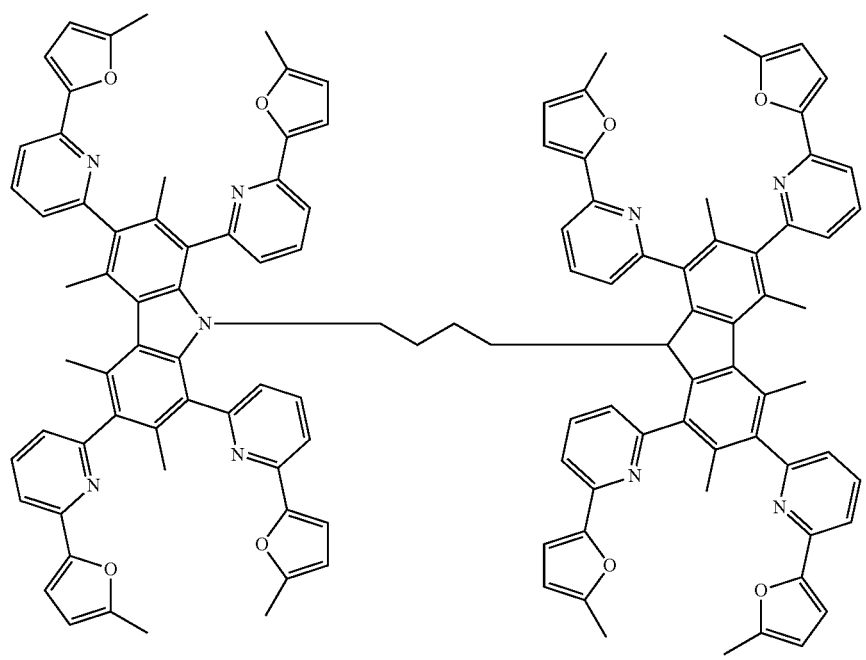
78
[Chem. 37]
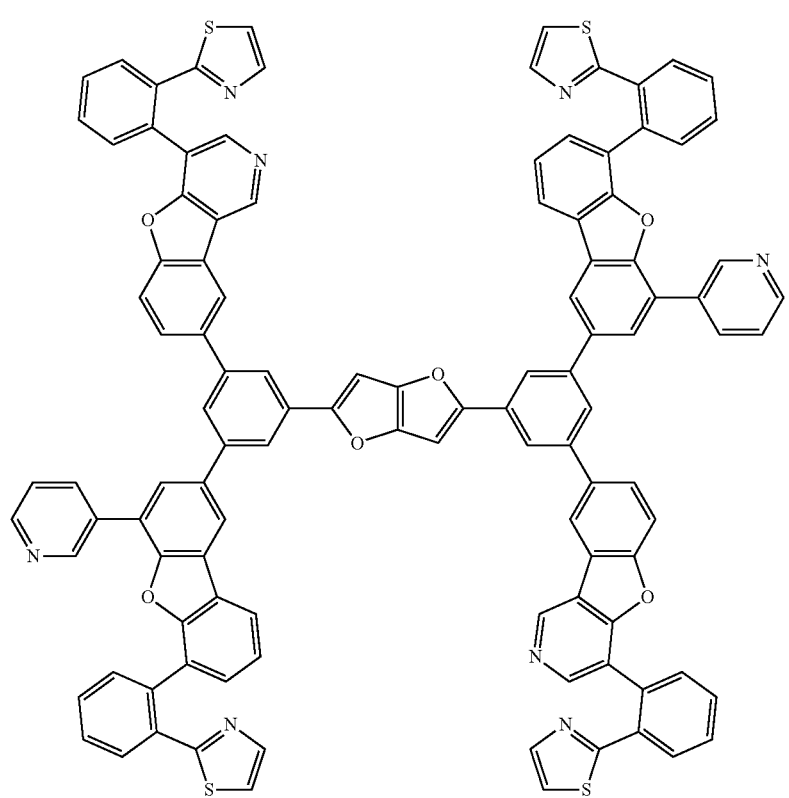
79

-continued
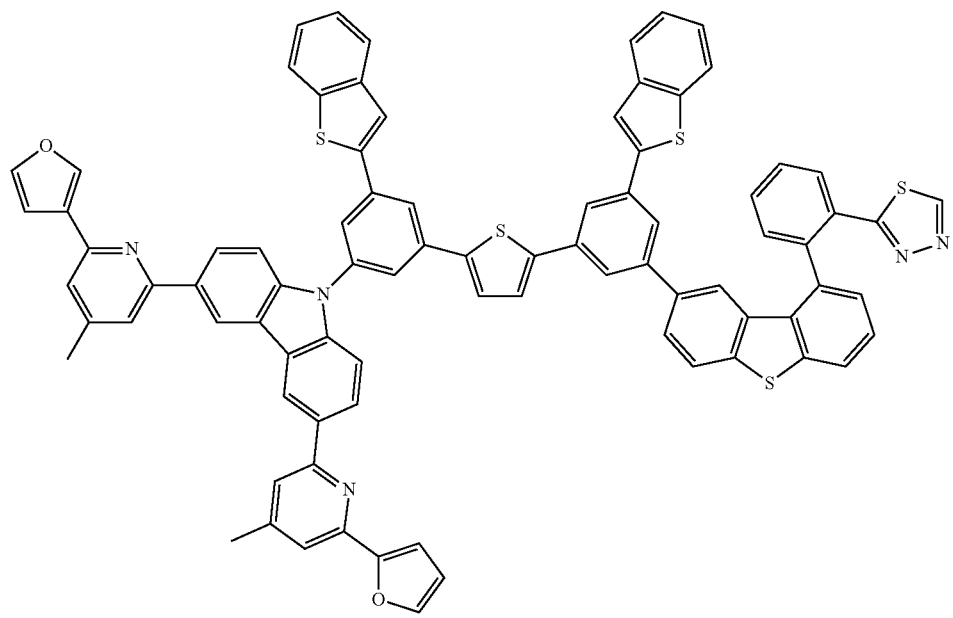
80
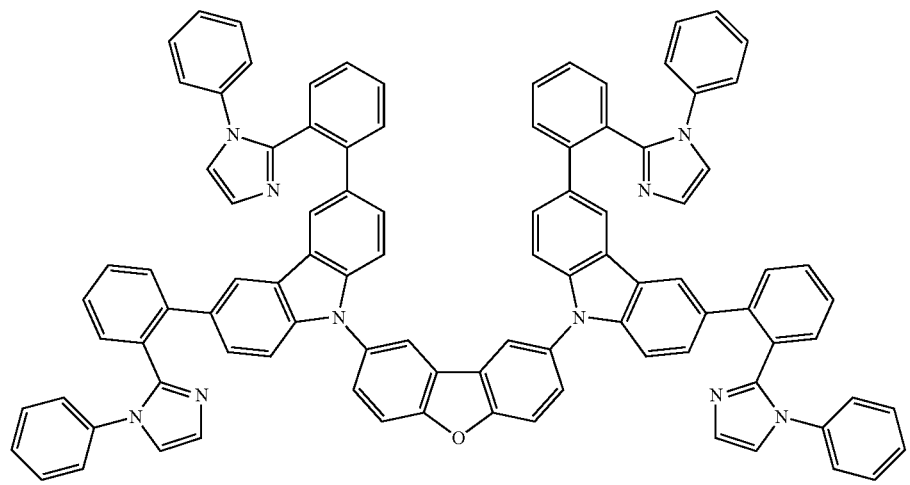
81
[Chem. 38]
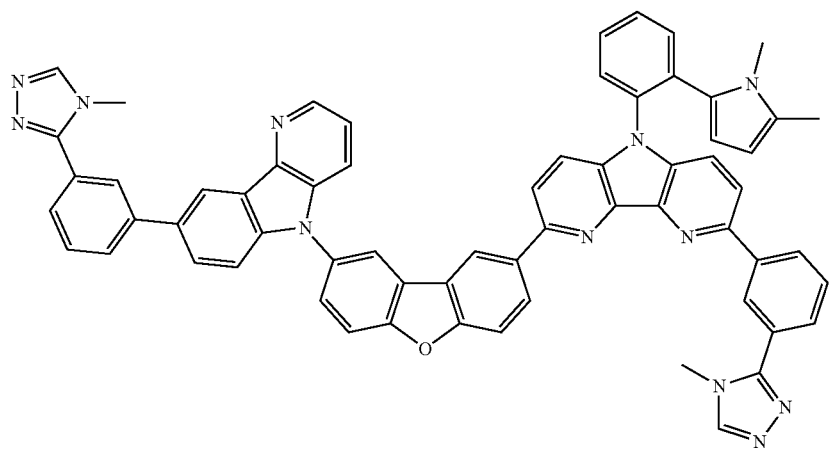
82

83
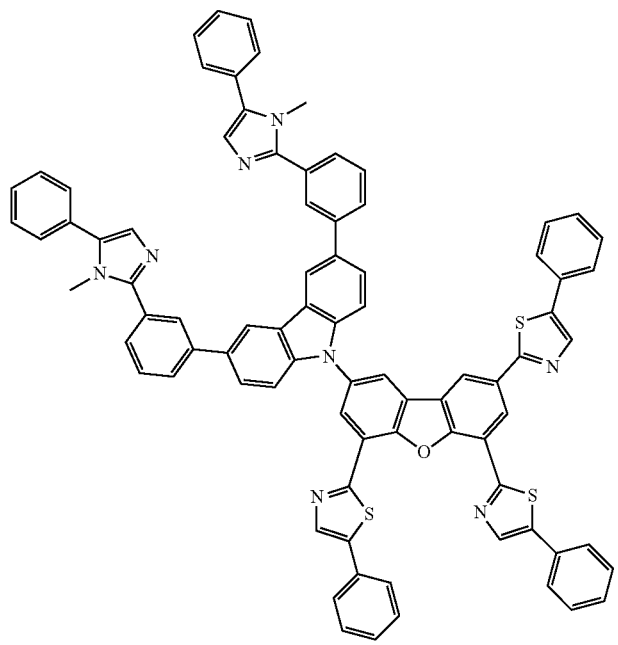
[Chem. 39]
84
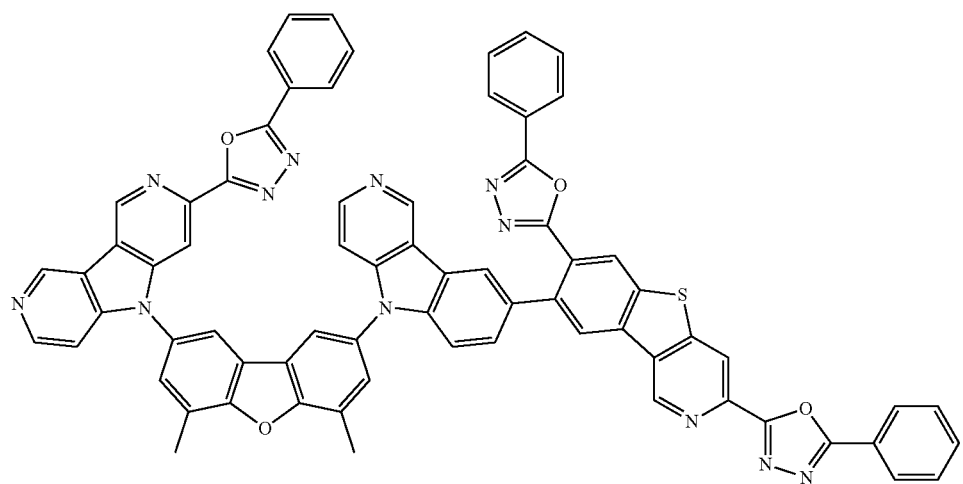

85
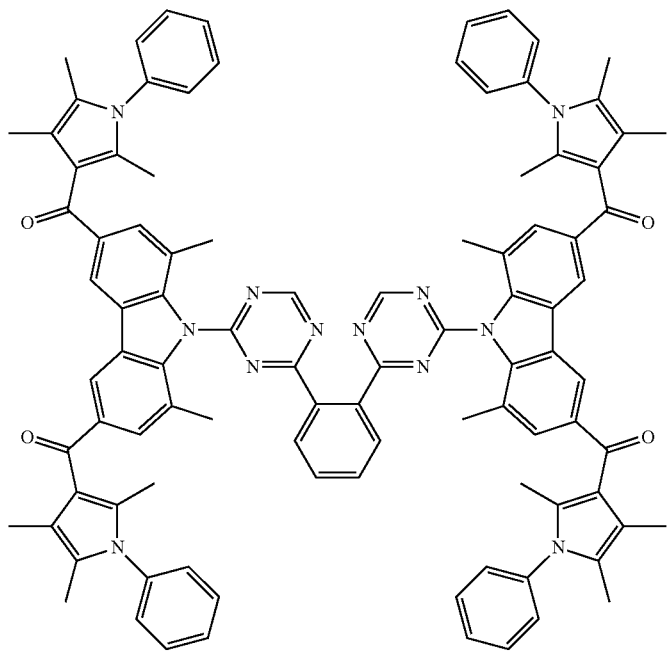
[Chem. 40]
86
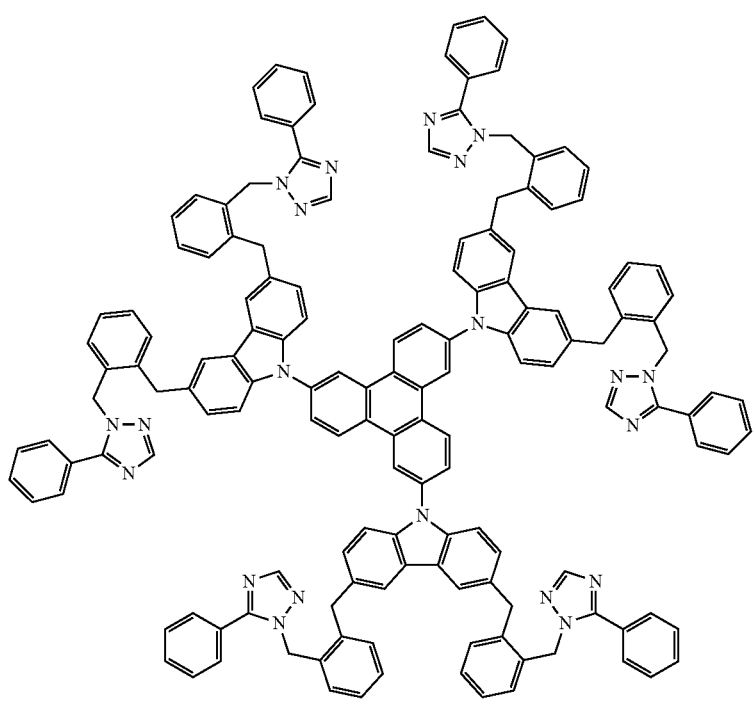

87
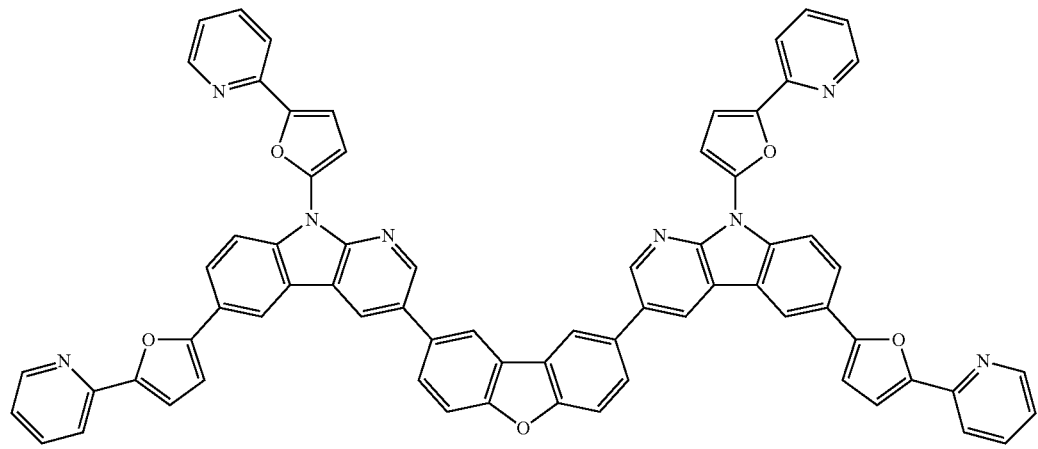
88
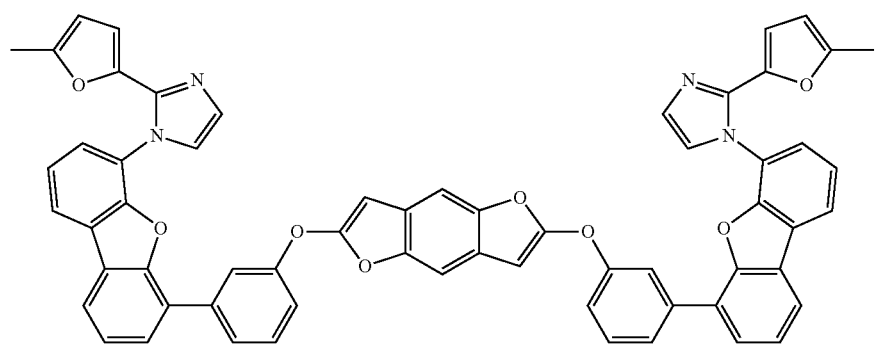
[Chem. 41]
89
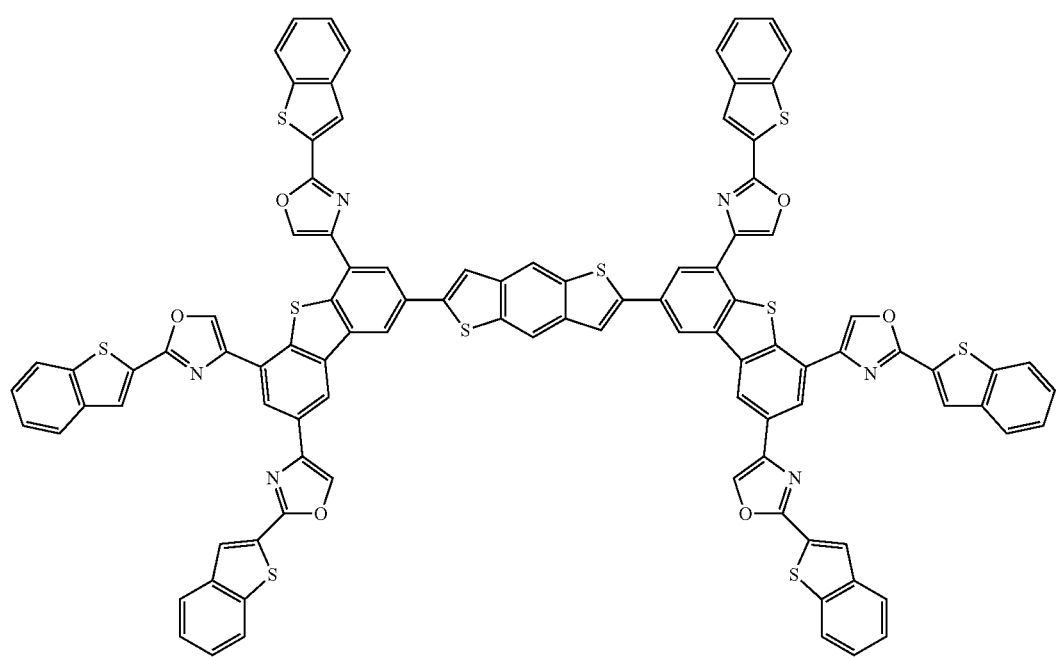

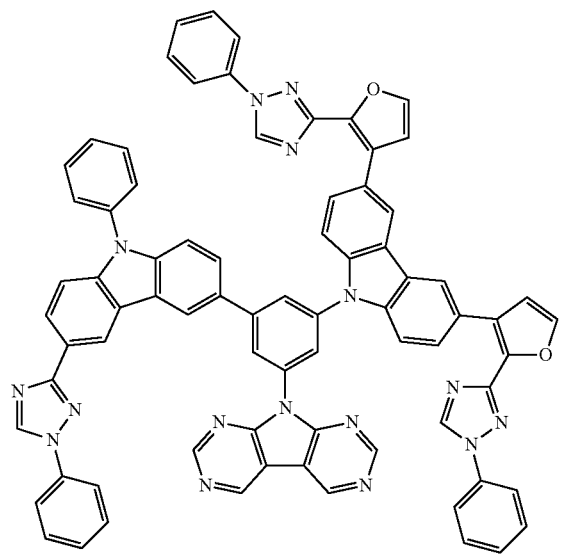
90
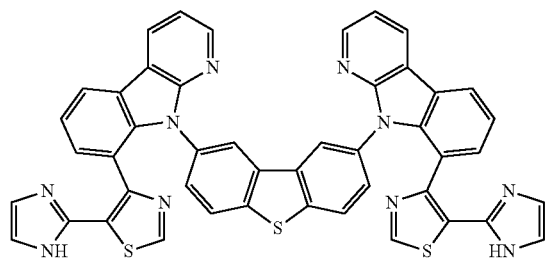
91
[Chem. 42]
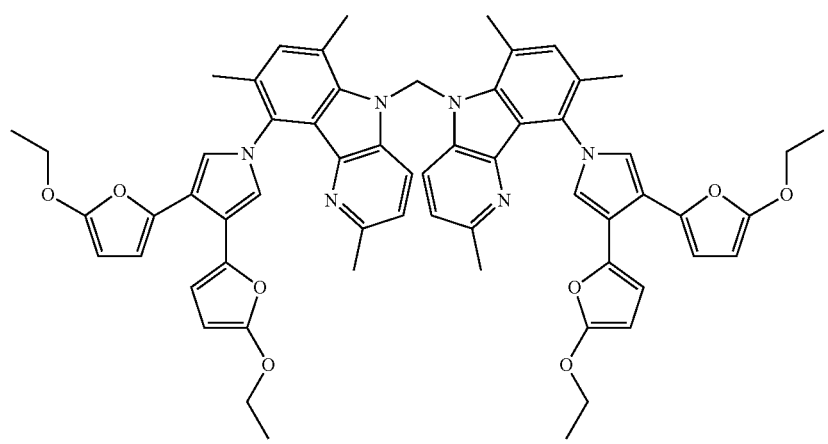
92
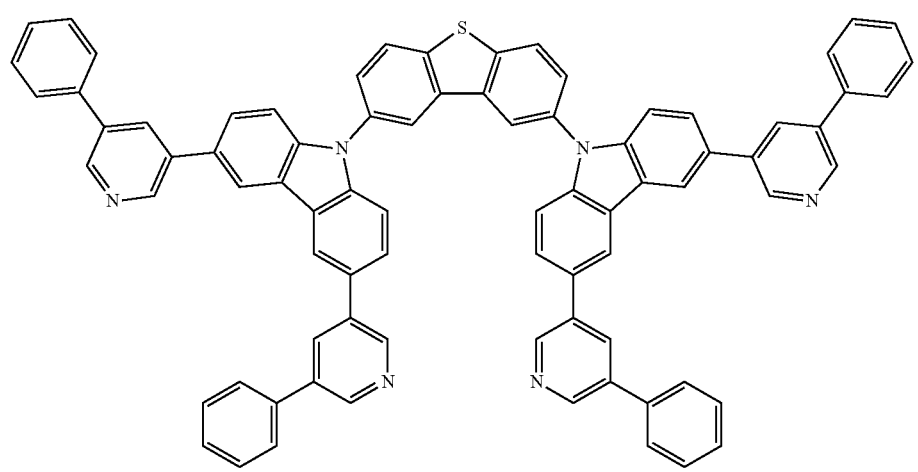
93

94
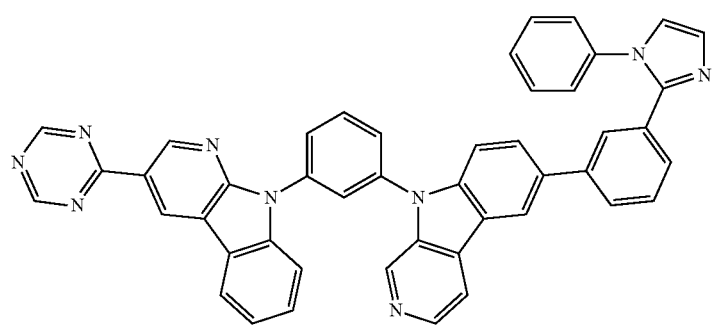
95
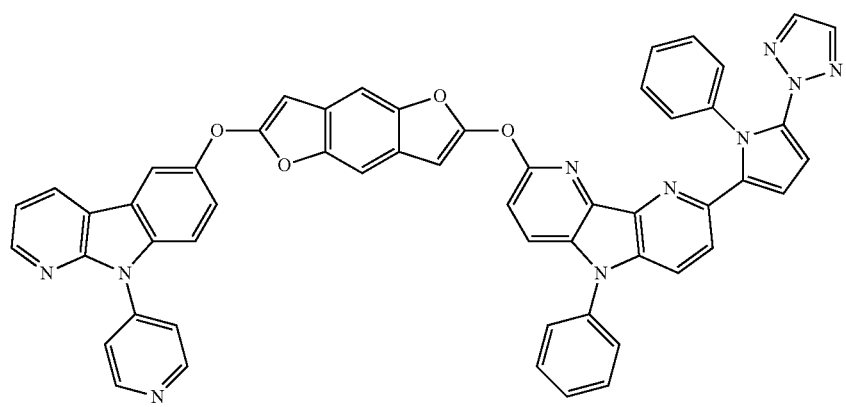
[Chem. 43]
96
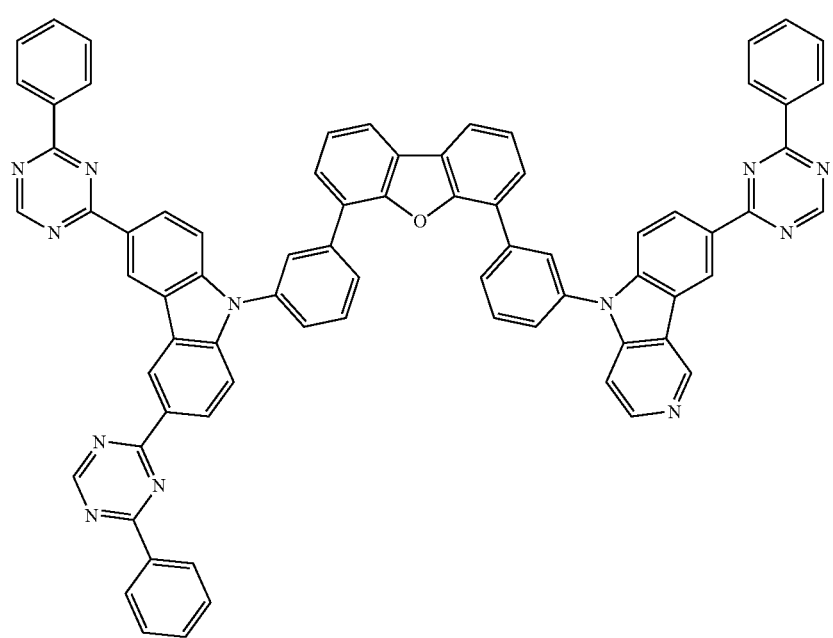

97
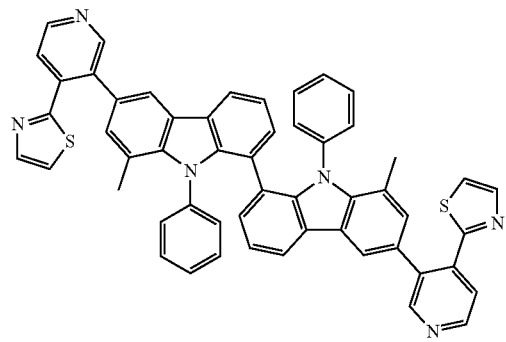
98
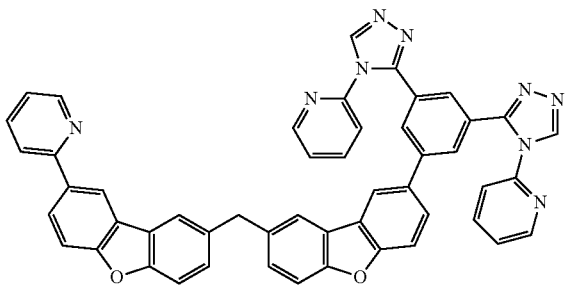
99
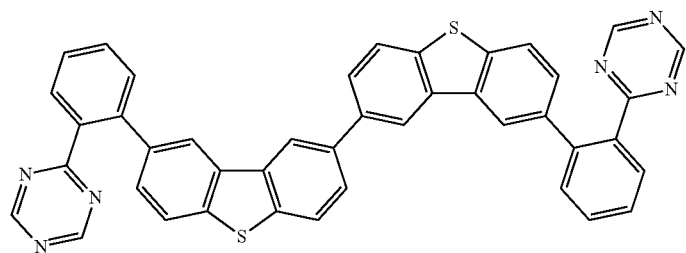
[Chem. 44]
100
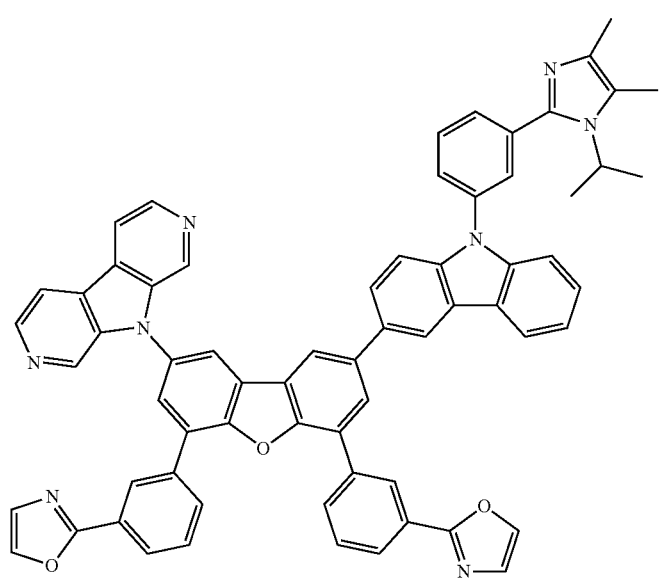

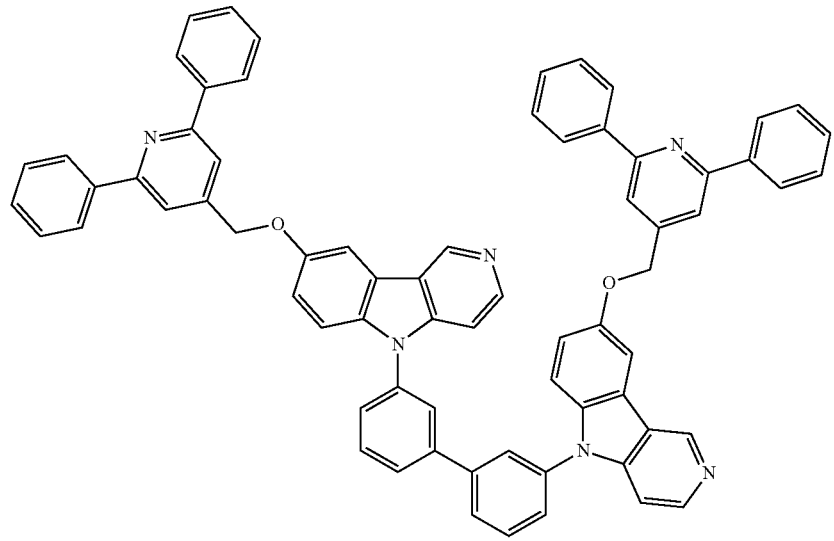
101
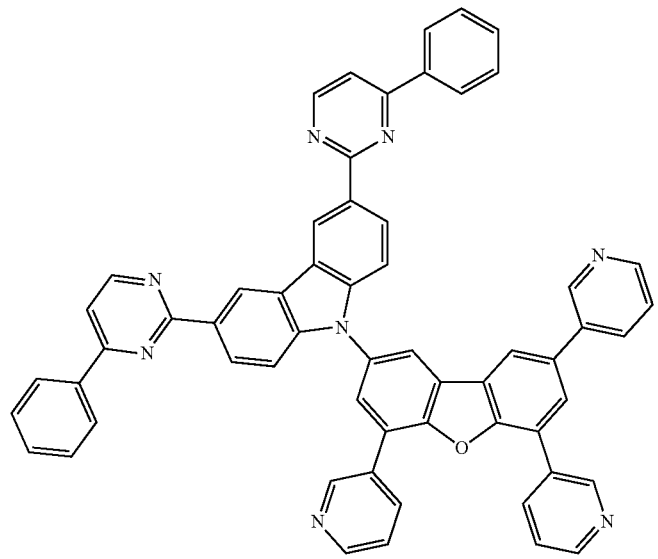
102
[Chem. 45]
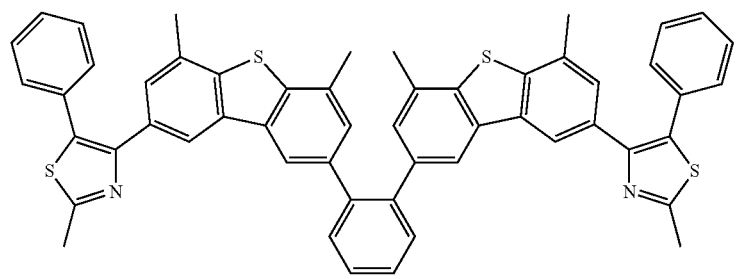
103

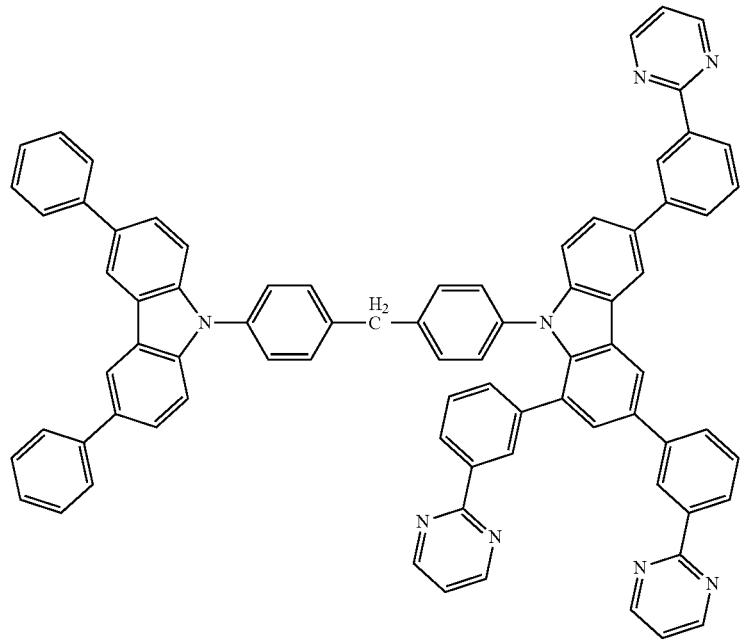
104
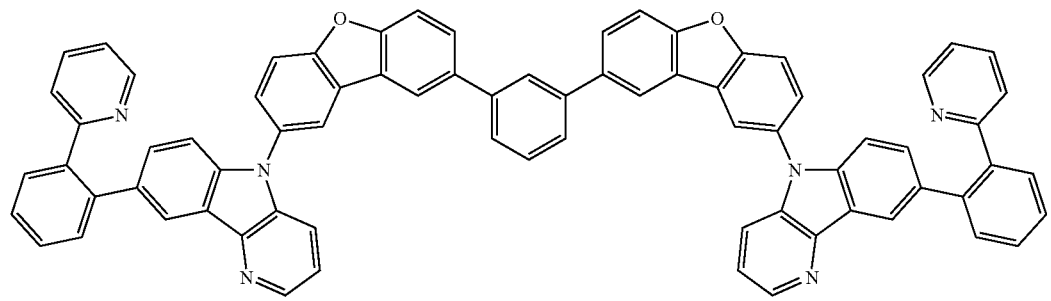
105
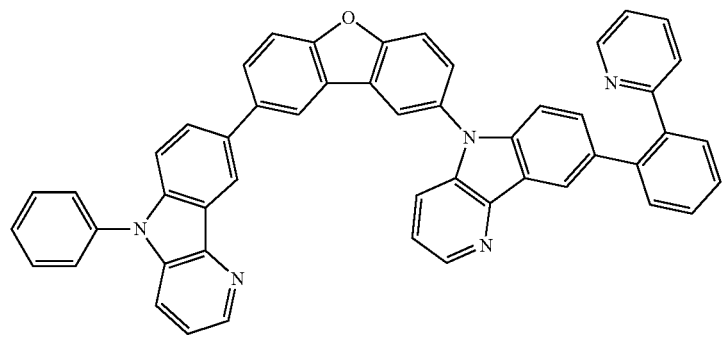
106

[Chem. 46]
107
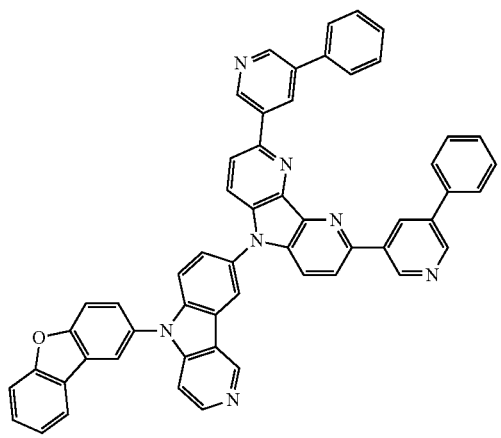
108
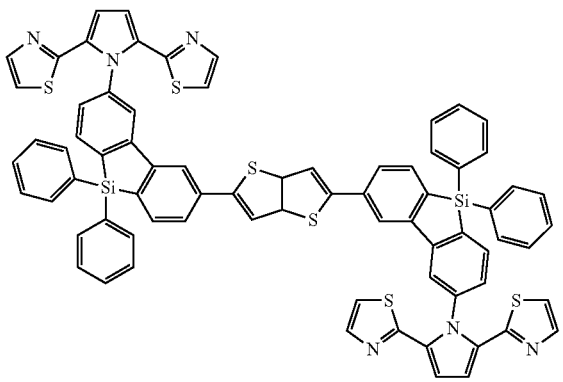
109
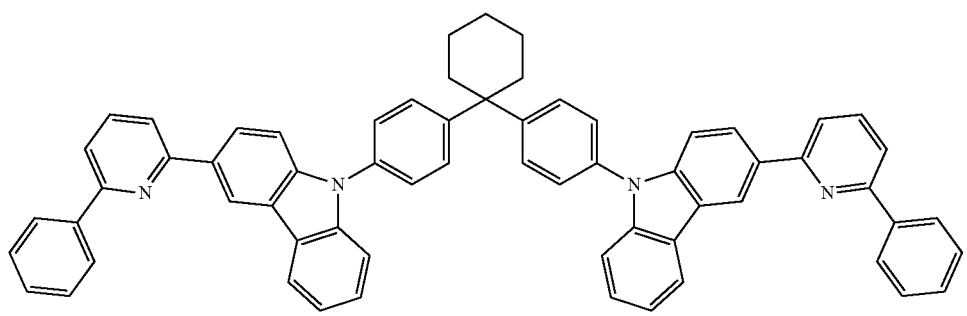
[Chem. 47]
110
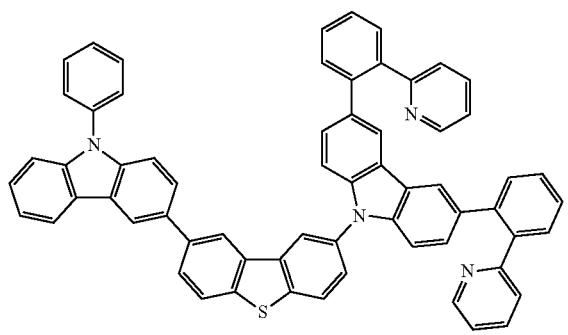
111
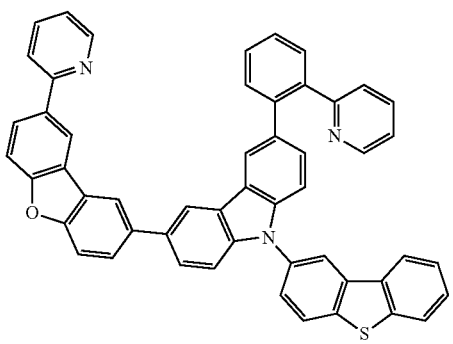
112
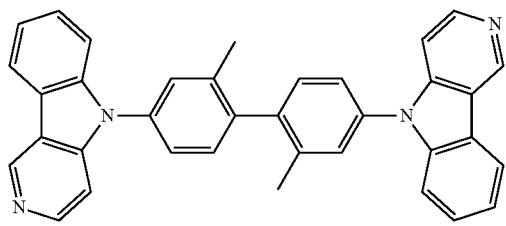
113
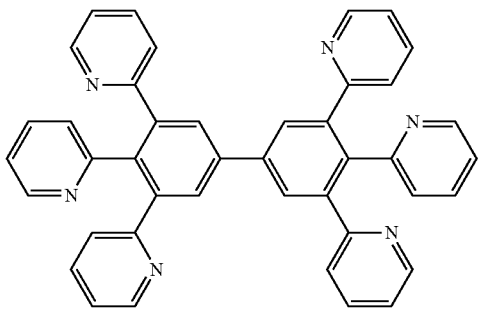

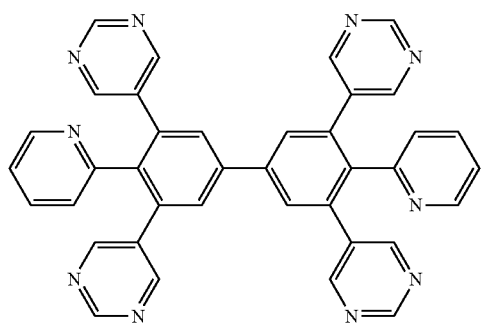
114
[Chem. 48]
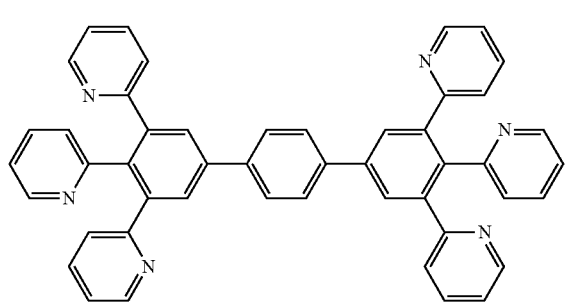
115
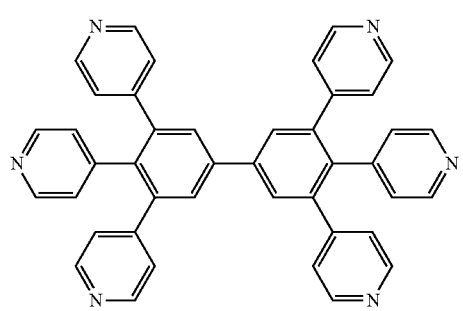
116
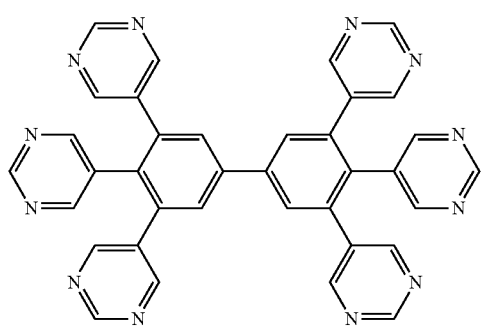
117
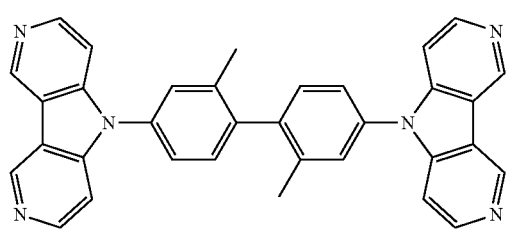
118
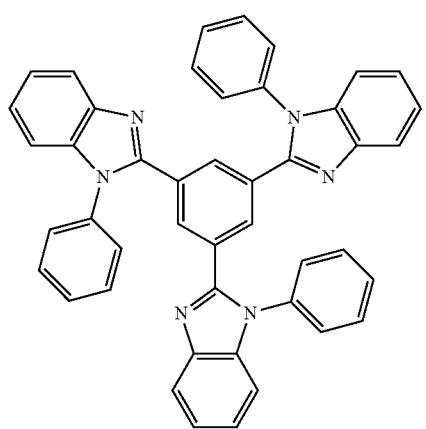
119
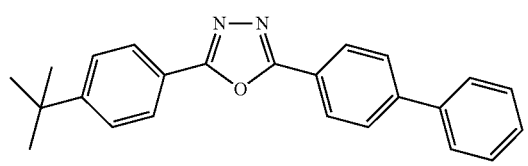
120

-continued
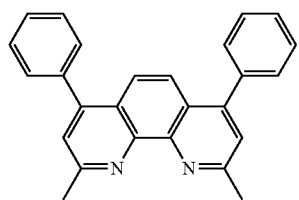
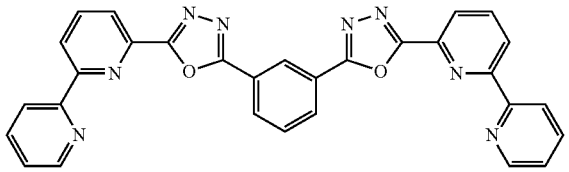
[Chem. 49]
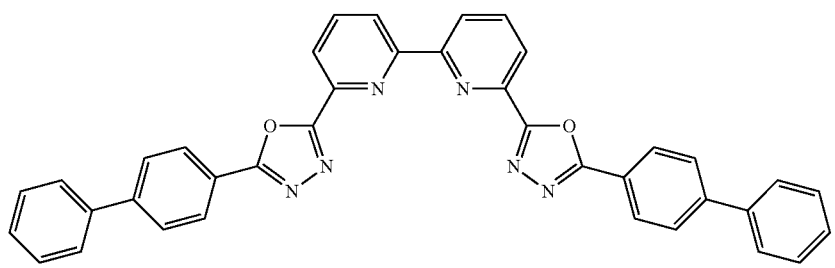
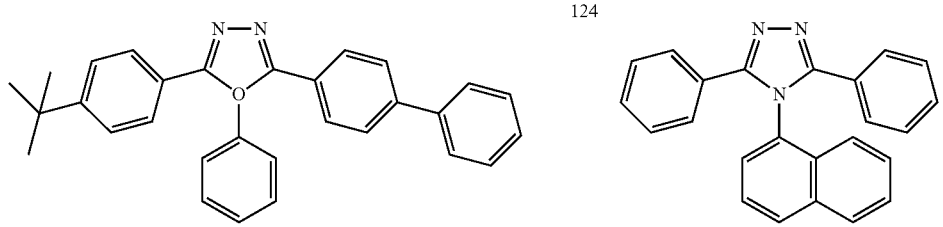
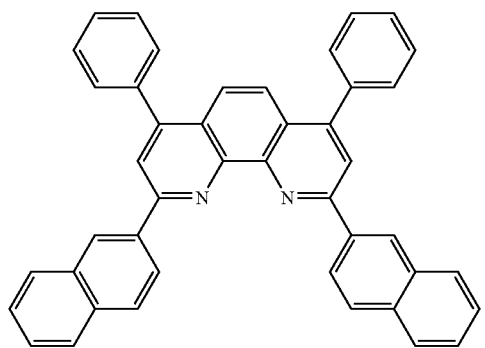
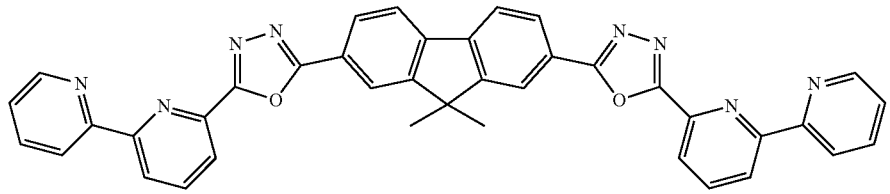
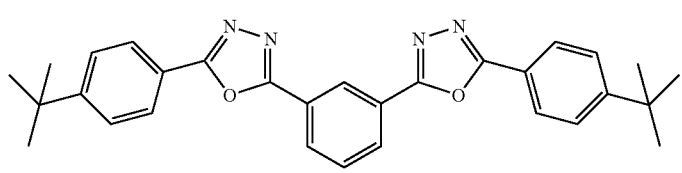

[Chem. 50]
129 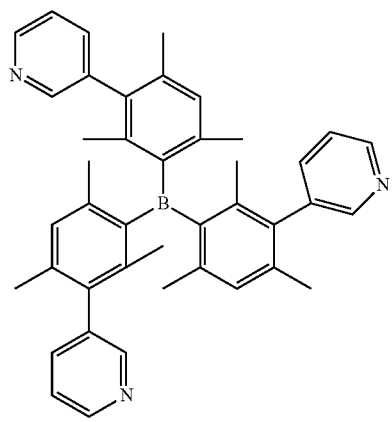
130 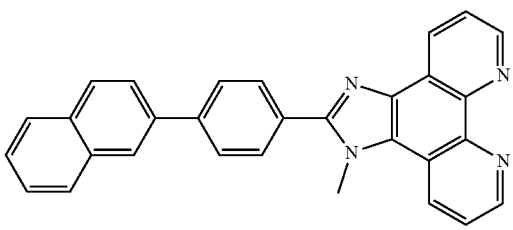
131 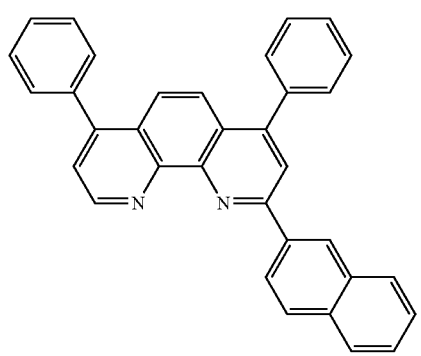
132 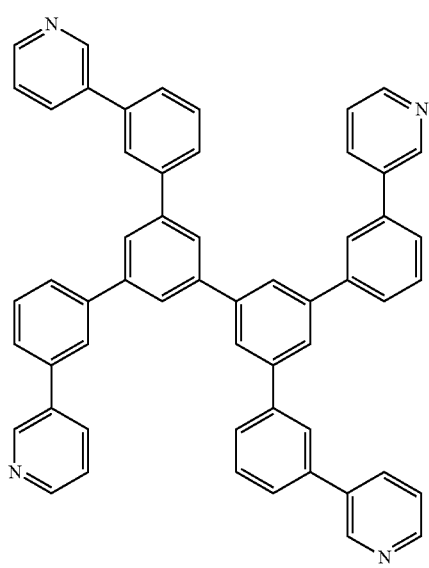
133 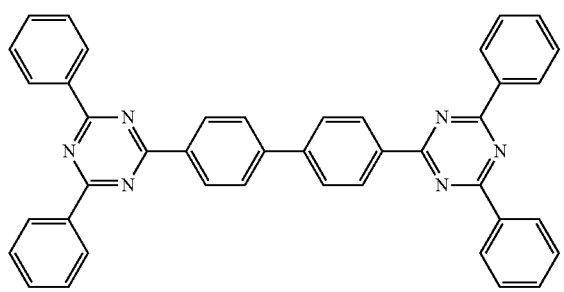
134 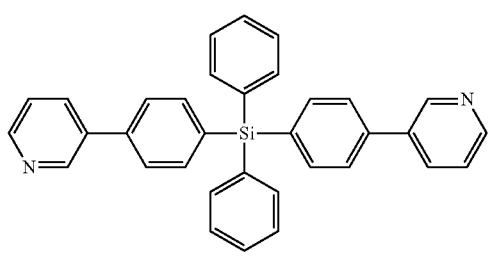
[Chem. 51]
135 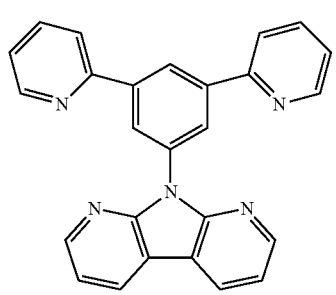
136 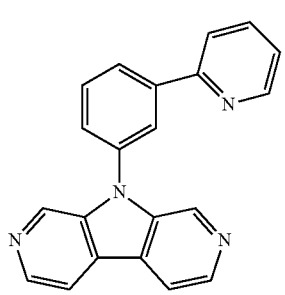

-continued
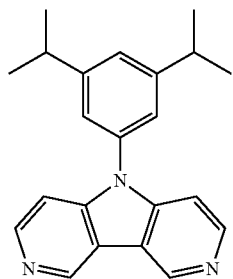
137
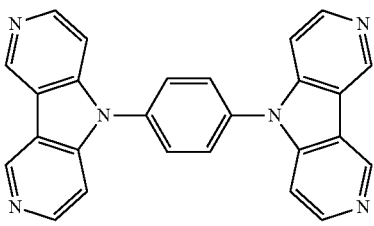
138
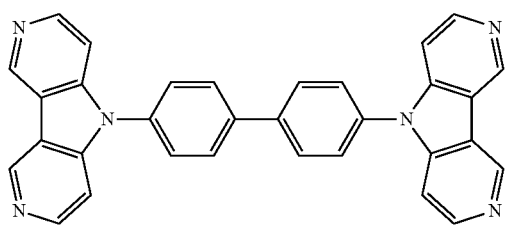
139
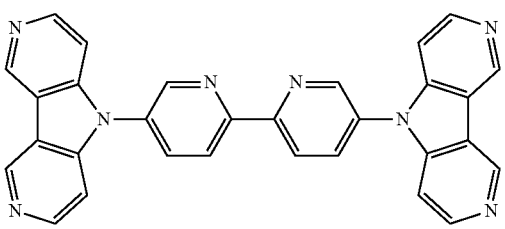
140
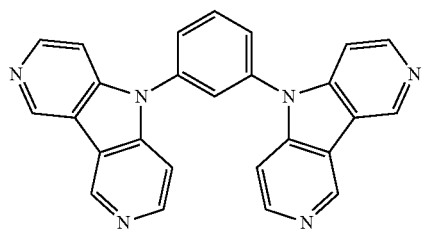
141
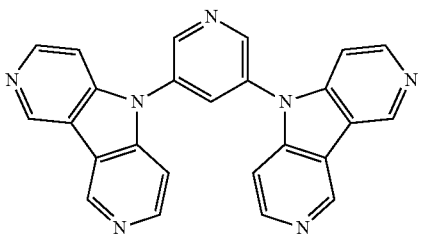
142
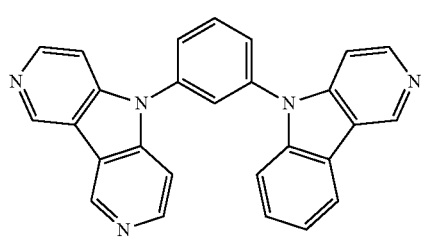
143
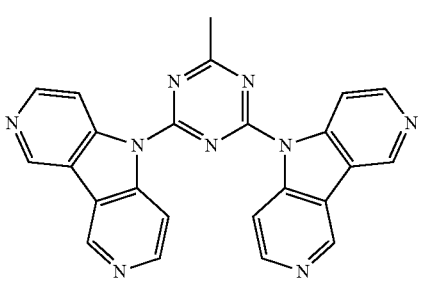
144
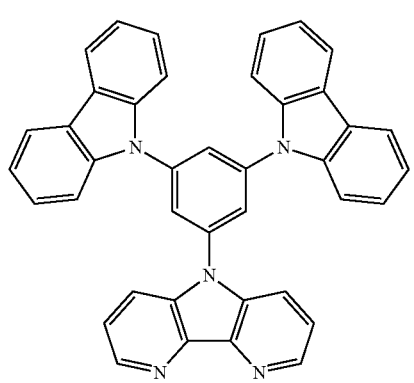
145

[Chem. 52]
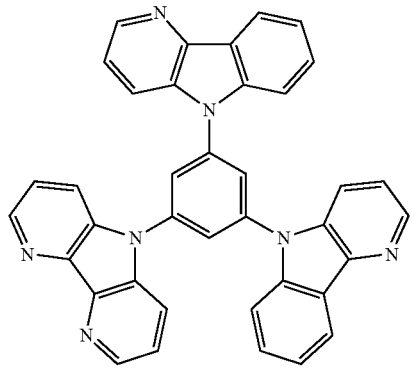
146
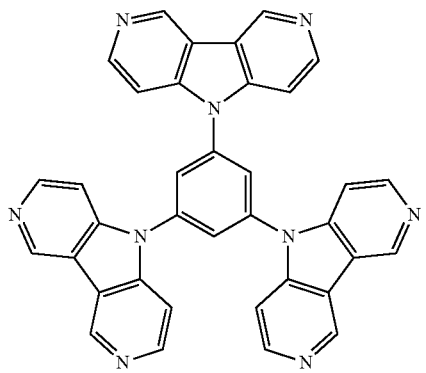
147
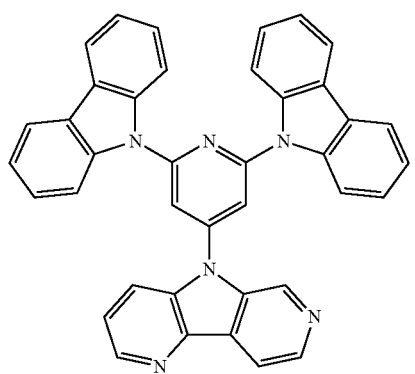
148
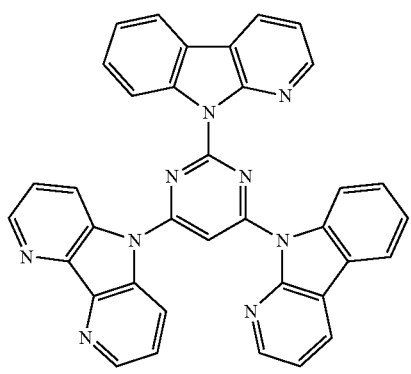
149
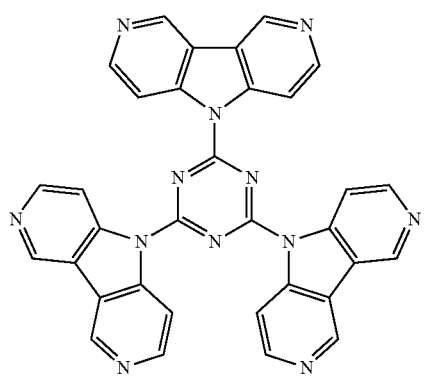
150
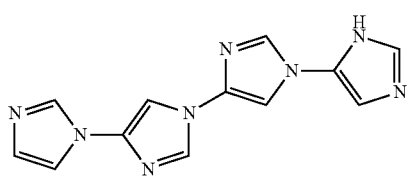
151
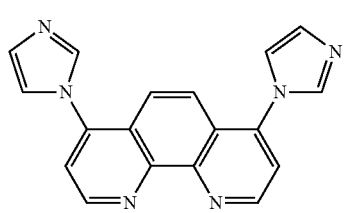
152
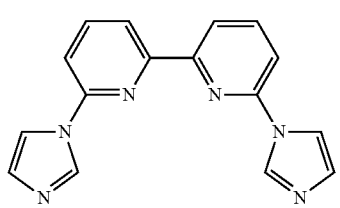
153

[Chem. 53]
154
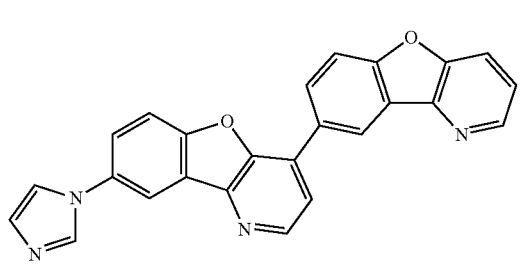
155
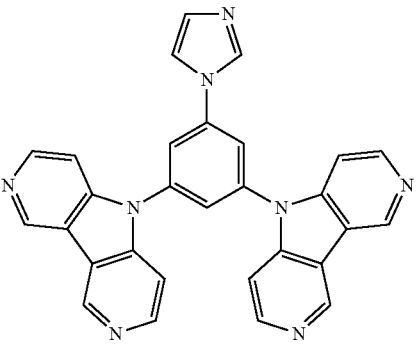
156
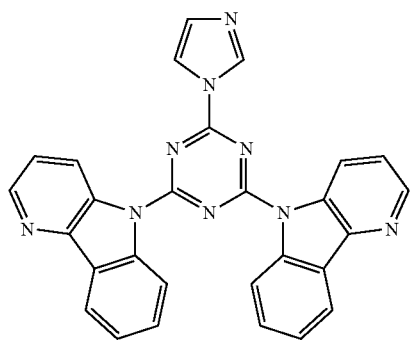
157
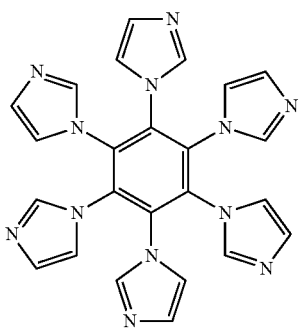
158
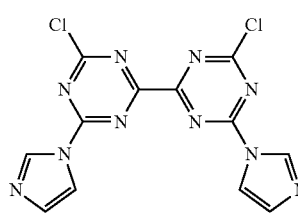
159
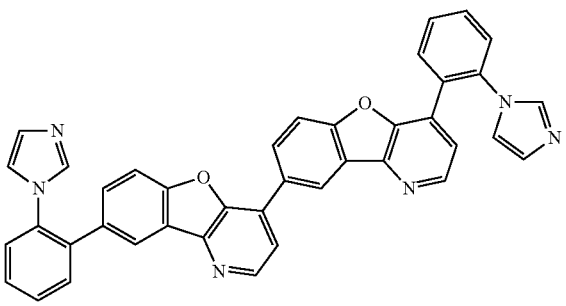
160
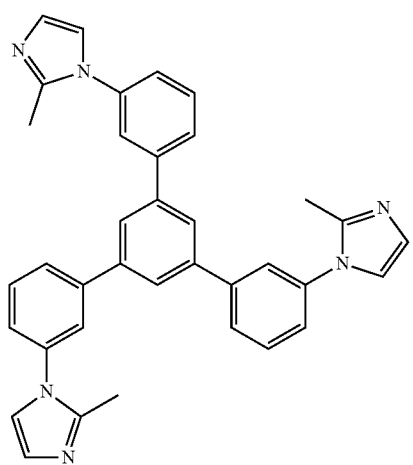
161
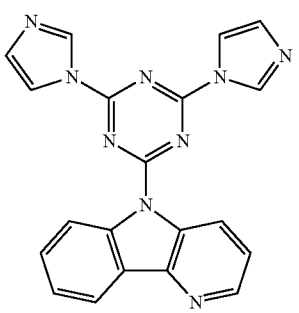

[Chem. 54]
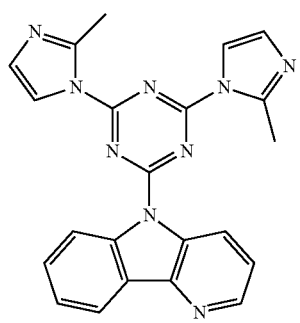
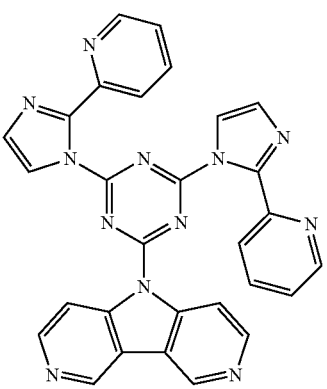
162
163
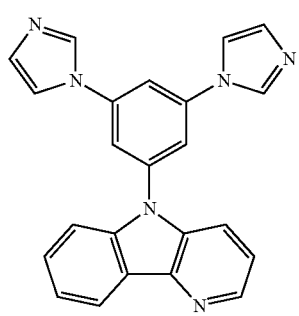
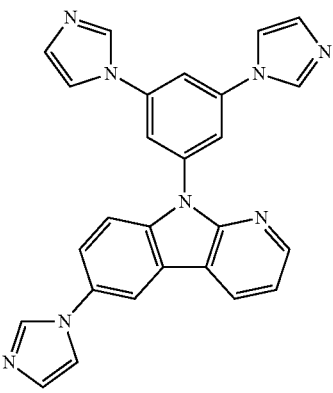
164
165
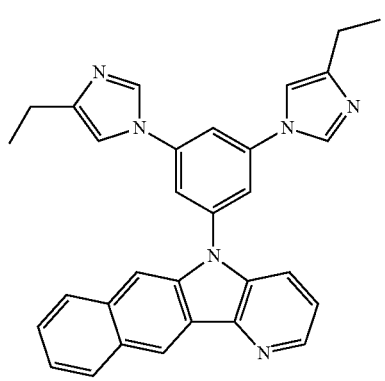
166
[Synthetic Example of Compound]
Hereinafter, as a synthetic example of a typical compound, a specific synthetic example of Compound 5 will be described, but the present invention is not limited thereto.
[Chem. 55]
Synthesis of Compound 5
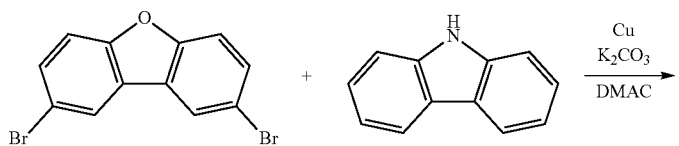

-continued

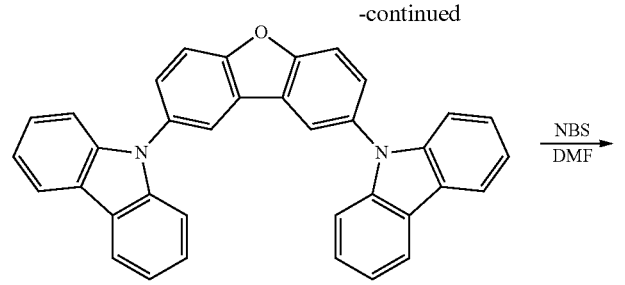

Intermediate 1

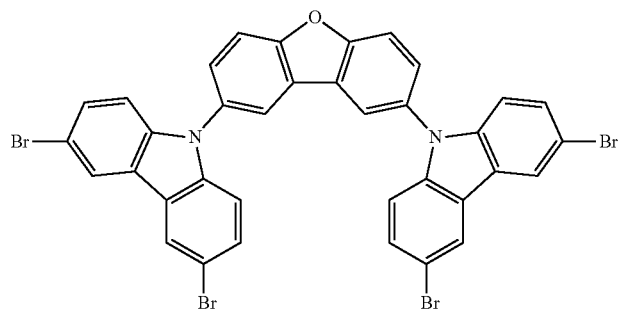

Intermediate 2

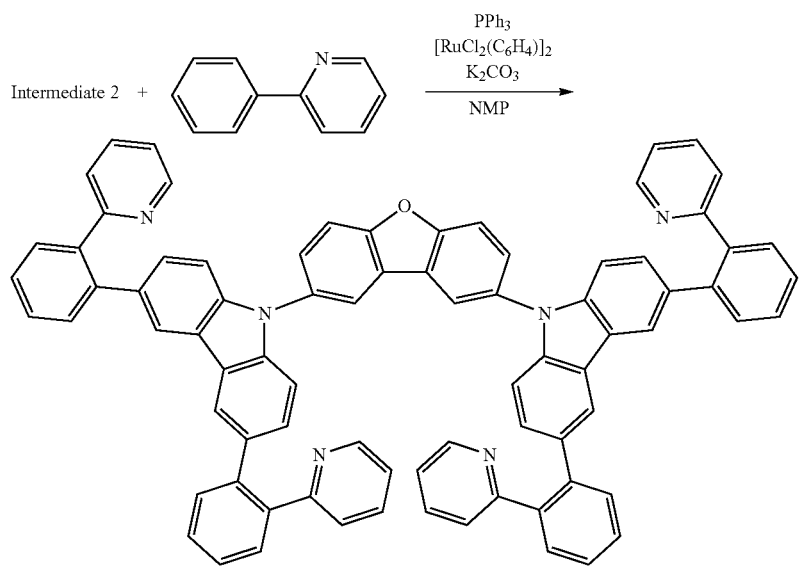

Compound 5

Process 1: (Synthesis of Intermediate 1)

Under nitrogen atmosphere, 2,8-dibromodibenzofuran (1.0 mole), of carbazole (2.0 moles), copper powder (3.0 moles), potassium carbonate (1.5 moles) were mixed in 300 ml of DMAc (dimethylacetamide) and then stirred for 24 hours at 130° C. After the reaction liquid thus obtained was cooled to room temperature, 1 L of toluene was added to the liquid, the resultant liquid was washed three times with distilled water, the solvent was distilled away from the washed layer under reduced pressure, and purification of the residue with silica gel flash chromatography (n-heptane:toluene=4:1 to 3:1) gave Intermediate 1 at a yield of 85%.

Process 2: (Synthesis of Intermediate 2)

At room temperature under atmospheric pressure, Intermediate 1 (0.5 mole) was dissolved into 100 ml of DMF (dimethylformamide), NBS (N-bromosuccinic acid imide) (2.0 moles) was added, and then stirred over one night at room temperature. The obtained precipitate was filtered and washed with methanol, and thus Intermediate 2 was obtained at a yield of 92%.

Process 3: (Synthesis of Compound 5)

Under nitrogen atmosphere, Intermediate 2 (0.25 mole), 2-phenylpyridine (1.0 mole), ruthenium complex [(η6-C6H6)RuCl2]2 (0.05 mole), triphenylphosphine (0.2 mole), potassium carbonate (12 moles) were mixed in 3 L of NMP (N-methyl-2-pyrrolidone), and then stirred over one night at 140° C.

After the reaction liquid was cooled to room temperature, 5 L of dichloromethane was added, and then the liquid was filtered. The solvent was distilled away from the filtrate under reduced pressure (800 Pa, 80° C.), and the residue was purified with silica gel flash chromatography (CH$_2$Cl$_2$: Et$_3$N=20:1 to 10:1).

After the solvent was distilled away under reduced pressure, the residue was again dissolved into dichloromethane and washed three times with water. After the substance obtained by the washing was dried with anhydrous magnesium sulfate, the solvent was distilled away under reduced pressure from the dried substance and thus Compound 5 was obtained at a yield of 68%.

[Method of Film Formation of Nitrogen-Containing Layer]

In the case where the nitrogen-containing layer 14 is formed on the high refractive index layer 13 as described above, examples of the formation method include a wet process such as a coating method, an inkjet method or a dipping method, and a dry process such as a vapor deposition method (resister heating, EB method or the like), a sputtering method or a CVD method, and the like. Among them, the vapor deposition method is preferably applied.

Particularly, in the case where the nitrogen-containing layer 14 is formed by using a plurality of compounds, a co-deposition method may be employed in which a plurality of compounds is supplied at the same time from a plurality of deposition sources. In case of using a high molecular weight compound, the coating method is preferably employed. In the case, a coating solution in which the compound is dissolved in a solvent is used. The solvent to dissolve the compound is not limited. In the case in which the nitrogen-containing layer 14 is formed by using a plurality of compounds, a coating solution may be prepared by using a solvent which can dissolve such a plurality of compounds.

[Conductive Layer]

The conductive layer 15 is a layer constituted by silver as a main component, and is a layer constituted using silver or an alloy having silver as a main component and formed adjacent to the nitrogen-containing layer 14. Examples of the formation method of the conductive layer 15 include a wet process such as a coating method, an inkjet method or a dipping method, and a dry process such as a vapor deposition method (resister heating, EB method, or the like), a sputtering method or a CVD method, and the like. Among them, the vapor deposition method is preferably applied. Although the feature of the conductive layer 15 is to have a sufficient electrical conductivity without a high-temperature annealing treatment after formation of the conductive layer 15 on the nitrogen-containing layer 14, the high temperature annealing treatment may be carried out after formation, as necessary.

Examples of the alloy having silver (Ag) as a main component constituting the conductive layer 15 include silver magnesium (AgMg), silver copper (AgCu), silver palladium (AgPd), silver copper palladium (AgPdCu), silver indium (AgIn), or the like.

The conductive layer 15 as described above may have a configuration in which layers of silver or an alloy having silver as a main component are laminated by being divided into a plurality of layers.

Furthermore, the conductive layer 15 preferably has a film thickness within the range of 4 to 12 nm. When the thickness is 12 nm or less, since an absorption component or a reflection component of the layer can be suppressed at a low level, the light transmittance of the conductive layer 15 is maintained, thereby being preferable. When the thickness is 4 nm or more, the electrical conductivity of the layer is also ensured.

The transparent electrode 10 having a lamination structure including the low refractive index layer 12, the high refractive index layer 13, the nitrogen-containing layer 14 and the conductive layer 15 provided adjacent to the nitrogen-containing layer 14 may be covered with a protective film in the upper portion of the conductive layer 15, or may be laminated with another conductive layer. In this case, the protective film and the conductive layer preferably have a light transmittance so as not to spoil the light transmittance of the transparent electrode 10. Additionally, a layer as required may be provided in the lower portion of the low refractive index layer 12, namely, also between the low refractive index layer 12 and the base material 11.

[Aluminum Layer]

In addition, in the transparent electrode 10 having the above configuration, an aluminum (Al) layer not shown may be provided between the nitrogen-containing layer 14 and the conductive layer 15. The aluminum layer is formed so that its thickness does not hinder the interaction of the conductive layer 15 and the nitrogen-containing layer. Additionally, the aluminum layer may not be a continuous layer, and may be a layer of island or have pores. In this case, a part of the silver layer is provided adjacent to the nitrogen-containing layer. In this way, it is possible to have a configuration in which other metal is sandwiched between the nitrogen-containing layer and the layer having silver as a main component. In this case, it is possible to have a configuration in which an alloy layer is formed between the silver or an alloy having silver as a main component, constituting the conductive layer 15, and the aluminum layer provided on the nitrogen-containing layer 14.

[Effects of Transparent Electrode]

The transparent electrode 10 constituted as described above has a configuration in which a conductive layer 15 having silver as a main component is provided adjacent to the nitrogen-containing layer 14 constituted using a compound containing a nitrogen atom. Thereby, when forming the conductive layer 15 adjacent to the nitrogen-containing layer 14, the silver atom constituting the conductive layer 15 interacts with the compound containing a nitrogen atom constituting the nitrogen-containing layer 14 to thereby reduce a diffusion distance of the silver atom on the surface of the nitrogen-containing layer 14, which causes suppression of aggregation of silver. As a result, generally, a thin silver layer that tends to be easily isolated in an island shape as the result of the growth by a nuclear growth-type (Volumer-Weber: VW type) is formed by the growth of a single layer growth type (Frank-van der Merwe: FM type). Accordingly, a conductive layer 15 having a uniform thickness can be obtained even though the layer is thin.

Additionally, particularly, as an index of bonding stability of the silver constituting the conductive layer 15 with respect to the nitrogen-containing layer 14, the above-described effective unshared electron pair content [n/M] is applied, and the nitrogen-containing layer 14 is constituted using the compound having the value of $2.0 \times 10^{-3} \leq [n/M]$. As a result, it becomes possible to provide the nitrogen-containing layer 14 in which the above-described "suppression of aggregation of silver" effect can be reliably obtained. As will be explained in examples mentioned below in detail, this has been confirmed by the fact that a sheet resistance-measurable conductive layer 15 despite being a remarkably thin layer having a thickness of 6 nm is formed on such a nitrogen-containing layer 14.

As a result, the conductive layer 15 ensuring an electrical conductivity due to a uniform thickness while ensuring a light transmission property due to a small thickness can be obtained in the upper portion of such a nitrogen-containing layer 14, and thus it becomes possible to establish both of the improvement of electrical conductivity and improvement of light transmission property in the transparent electrode 10 made by using silver.

The transparent electrode 10 has a configuration having the low refractive index layer 12 and the high refractive index layer 13; and the low refractive index layer 12, the high refractive index layer 13, the nitrogen-containing layer 14 and the conductive layer 15 are laminated in this order. As a result, a possible reflection caused on the conductive layer having silver as a main component is suppressed.

The transparent electrode 10 is low in cost because indium (In) which is a rare metal is not used, and is excellent in long-term reliability because a chemically unstable material such as ZnO is not used.

[Use of Transparent Electrode]

The transparent electrode 10 having each of the above-described configurations can be used for various electronic devices. Examples of the electronic device include an organic electroluminescent element, an LED (light-emitting Diode), a liquid crystal element, a solar cell, a touch panel, and the like. The above-described transparent electrode 10 can be used as an electrode member, for which a light transmission property is required in the electronic device.

Hereinafter, as one use application, there will be explained an embodiment of the organic electroluminescent element in which the electrodes are used as an anode and a cathode.

<2. Organic Electroluminescent Element (Bottom Emission Type)>

[Configuration of Organic Electroluminescent Element]

Figure 7:
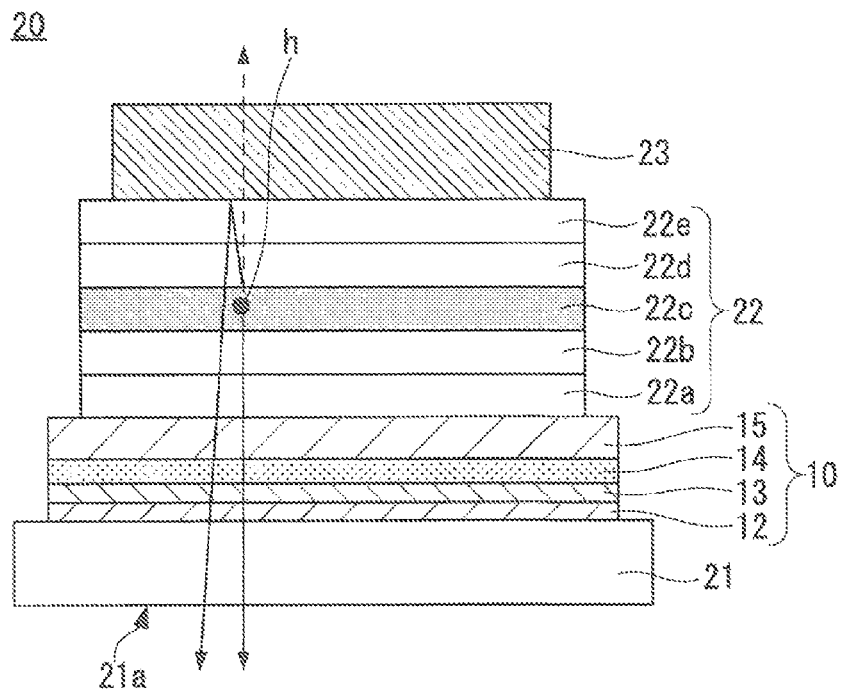
FIG. 7 is a cross-sectional view showing a configuration of an organic electroluminescent element of the embodiment.

Next, an embodiment of the electronic device of the present invention will be explained. In the present embodiment, an organic electroluminescent element using the above-described transparent electrode 10 will be explained as an example of electronic devices. In FIG. 7, a cross-sectional configuration diagram of the organic electroluminescent element in the present embodiment is shown. Hereinafter, the configuration of the organic electroluminescent element will be explained based on the drawing.

The organic electroluminescent element 20 shown in FIG. 7 is provided on a transparent substrate 21, and there are laminated the transparent electrode 10 serving as an anode, the light-emitting functional layer 22 and the counter electrode 23 serving as a cathode, in order from the transparent substrate 21 side. Among them, the transparent electrode 10 of the above-described embodiment is used as the transparent electrode 10. Therefore, the organic electroluminescent element 20 is constituted as a bottom emission type that extracts emitted light (hereinafter, described as emitted light h) at least from transparent substrate 21 side.

In addition, the whole layer configuration of the organic electroluminescent element 20 is not limited to the above and may be a general layer configuration. Here, the transparent electrode 10 is disposed on the side of anode (namely, positive electrode) and mainly, the conductive layer 15 functions as the anode, whereas the counter electrode 23 functions as the cathode (namely, negative electrode).

In the case, for example, the light-emitting functional layer 22 can have an exemplified configuration in which [positive hole injection layer 22a/positive hole transport layer 22b/light-emitting layer 22c/electron transport layer 22d/electron injection layer 22e] are laminated in this order in the upper portion of the transparent electrode 10 being the anode. Among them, it is necessary to have a light-emitting layer 22c constituted using at least organic material. The positive hole injection layer 22a and the positive hole transport layer 22b may be provided as a positive transport/injection layer having positive hole transport property and positive hole injection property. The electron transport layer 22d and the electron injection layer 22e may be provided as one layer having electron transport property and electron injection property. Among the light-emitting functional layers 22, for example, the electron injection layer 22e may be constituted by an inorganic material.

In addition, in the light-emitting functional layer 22, a positive hole blocking layer, an electron blocking layer and the like also other than these layers may be laminated on a necessary portion, as necessary. Furthermore, the light-emitting layer 22c may have light-emitting layers of each color corresponding to the respective range of wavelength, and a light-emitting layer unit may be formed by laminating the light-emitting layers via an intermediate layer having non-light-emitting property. The intermediate layer may function as the positive hole blocking layer and the electron blocking layer. Moreover, the counter electrode 23 being an cathode may have a lamination structure as necessary. In these configurations, only the portion in which the light-emitting functional layer 22 is sandwiched between the transparent electrode 10 and the counter electrode 23 serves as the light-emitting region in the organic electroluminescent element 20.

Additionally, in the above layer configuration, in order to reduce electric resistance of the transparent electrode 10, an auxiliary electrode may be provided in contact with the conductive layer 15 of the transparent electrode 10.

The organic electroluminescent element 20 having the above configuration is sealed by a transparent sealing material described below on the transparent substrate 21 in order to prevent the degradation of the light-emitting functional layer 22 constituted using organic materials. The transparent sealing material is fixed on the transparent substrate 21 side via an adhesive. However, terminal portions of the transparent electrode 10 and the counter electrode 23 are set to be provided in a state where they are exposed from the transparent sealing material while maintaining electric insulation with each other by the light-emitting functional layer 22 on the transparent substrate 21.

Hereinafter, the details of the main layers for constituting the above organic electroluminescent element 20 will be explained in order of the transparent substrate 21, the transparent electrode 10, the counter electrode 23, the light-emitting layer 22c of the light-emitting functional layer 22, other layers of the light-emitting functional layer 22, the auxiliary electrode, and the transparent sealing material. After that, production method of the organic electroluminescent element 20 is explained.

[Transparent Substrate]

The transparent substrate 21 is formed by using a transparent material having a light transmittance among the substrates where the transparent electrode 10 of the embodiment shown in the above FIG. 1. is provided.

[Transparent Electrode (Anode Side)]

The transparent electrode 10 is the transparent electrode 10 of the above-described embodiment, and has the construction where the low refractive index layer 12, the high refractive index layer 13, the nitrogen-containing layer 14 and the conductive layer 15 are formed from the transparent electrode 21 in this order. Particularly here, the conductive layer 15 of the transparent electrode 10 is substantially the cathode.

[Counter Electrode (Cathode)]

The counter electrode 23 is an electrode layer having a function as a cathode for supplying an electron to the light-emitting functional layer 22, and a metal, an alloy, an organic or inorganic conductive compound, and a mixture thereof are used. Specific examples include gold, aluminum, silver, magnesium, lithium, a mixture of magnesium/copper, a mixture of magnesium/silver, a mixture of magnesium/ aluminum, a mixture of magnesium/indium, indium, a mixture of lithium/aluminum, a rare-earth metal, an oxide semiconductor such as ITO, ZnO, $TiO_2$ or $SnO_2$.

The counter electrode 23 can be produced by forming a thin film from the conductive material through the use of a method such as vapor deposition or sputtering. In addition, the sheet resistance as the counter electrode 23 is preferably several hundreds of Q/sq. or less. The thickness is generally selected within the range of 5 nm to 5 μm, preferably within the range of 5 nm to 200 nm.

Note that, when the organic electroluminescent element 20 is a top-and-bottom emission type in which emitted light h can also be extracted from the counter electrode 23 side, the counter electrode 23 may be constituted by selecting a conductive material having a good light transmission property among the above-mentioned conductive materials.

[Light-Emitting Layer]

The light-emitting layer 22c used for the organic electroluminescent element of the present embodiment contains a phosphorescence-emitting compound as a light-emitting material.

The light-emitting layer 22c of the present invention is a layer which emits light through recombination of electrons injected from an electrode or an electron transport layer 22d and positive holes injected from the positive hole transport layer 22b. A portion that emits light may be either the inside of the light-emitting layer 22c or an interface between the light-emitting layer 22c and its adjacent layer.

The configuration of the light-emitting layer 22c is not particularly limited as long as the light-emitting material contained therein satisfies a light emission requirement. In addition, there may be a plurality of light-emitting layers having the same emission spectrum and/or emission maximum wavelength. In the case, it is preferable that non-luminescent intermediate layers (not shown) are present between the light-emitting layers 22c.

The total thickness of the light-emitting layers 22c is preferably within a range of 1 to 100 nm and, more preferably within a range of 1 to 30 nm from the viewpoint of obtaining a lower driving voltage. Note that the total thickness of the light-emitting layers 22c means a thickness including the thickness of the intermediate layers when the non-luminescent intermediate layers are present between the light-emitting layers 22c.

In the case of the light-emitting layer 22c constituted by lamination of a plurality of layers, it is preferable to adjust the thickness of individual light-emitting layer to be within a range of 1 to 50 nm and it is more preferable to adjust the thickness thereof to be within a range of 1 to 20 nm. When the plurality of the laminated light-emitting layers corresponds to the emitted color of blue, green and red, respectively, the relationship between the respective thickness of the light-emitting layers of blue, green and red is not particularly limited.

The above light-emitting layer 22c can be formed through the film-formation of a light-emitting material and a host compound, which are mentioned below, by a well-known thin film forming method such as a vacuum vapor deposition method, a spin coating method, a casting method, an LB method or an ink-jet method.

In addition, in the light-emitting layer 22c, a plurality of light-emitting materials may be mixed. Furthermore, a fluorescence-emitting material and a fluorescence-emitting material (also referred to as fluorescence-emitting dopant, fluorescence-emitting compound) may be mixed in the same light-emitting layer 22c.

It is preferable that the light-emitting layer 22c is constituted so as to contain a host compound (also referred to as emitting host) and a light-emitting material (also referred to as light-emitting dopant compound, a guest compound), and emit light through the light-emitting material.

(Host Compound)

The host compound contained in the light-emitting layer 22c is preferably a compound having a phosphorescence quantum yield in phosphorescence emission of less than 0.1 at room temperature (25° C.). Furthermore, the host compound more preferably has a phosphorescent quantum yield of less than 0.01. In addition, a volume ratio in the layer of 50% or more is preferable among the compounds contained in the light-emitting layer 22c.

A well-known host compound may be used as the host compound, alone or in combination of a plurality of kinds. The use of a plurality of host compounds makes it possible to adjust transfer of charges, and to increase an efficiency of the organic electroluminescent element 20. In addition, the use of a plurality of light-emitting materials mentioned below makes it possible to mix different colors of light to be emitted, and to thereby produce any luminous color.

The host compound to be used may be a well-known low molecular weight compound, a high molecular compound having a repeating unit or a low-molecular-weight compound having a polymerizable group such as a vinyl group or an epoxy group (vapor deposition-polymerizable light emission host) may be used.

The well-known host compound is preferably a compound preventing a light emission wavelength from becoming longer and having a high Tg (glass transition temperature), while having a positive hole transport ability and an electron transport ability. The glass transition temperature Tg herein is a value measured using DSC (Differential Scanning Colorimetry) in accordance with JIS-K-7121.

Hereinafter, specific examples of the host compounds (H1 to H79) applicable to the organic electroluminescent element will be shown. Note that the host compounds applicable to the organic electroluminescent element are not limited to these.

In the host compound H68 to H79, x and y represent ratio of random copolymer. The ratio can be set to, for example, x:y=1:10.

[Chem. 56]

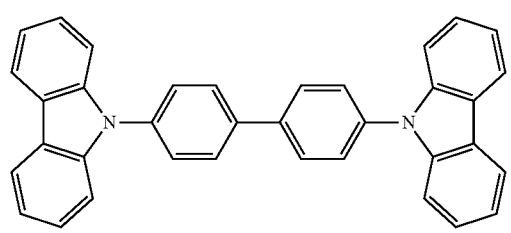

H1

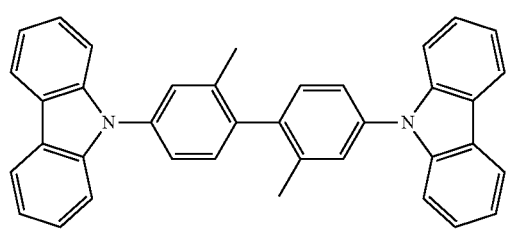

H2

-continued
H3 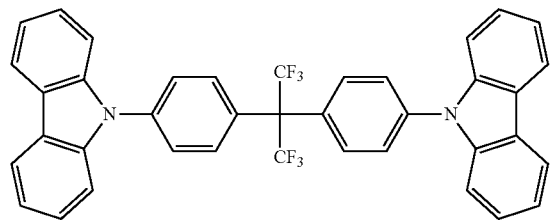
H4 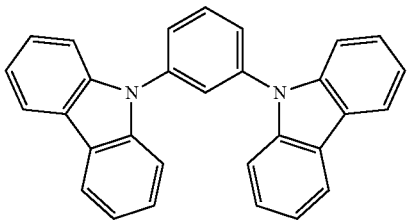
H5 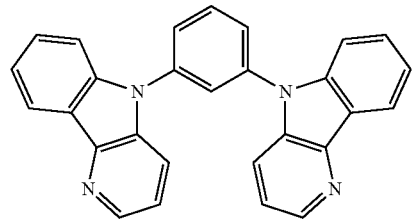
H6 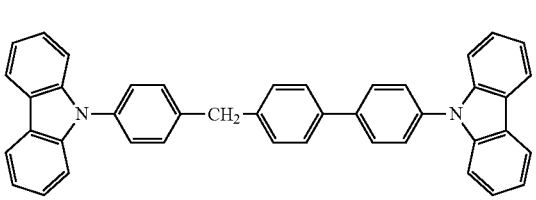
H7 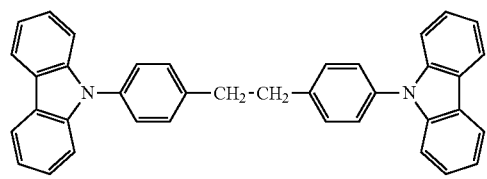
H8 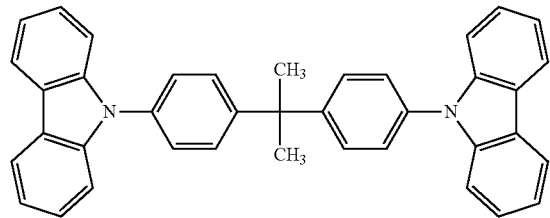
H9 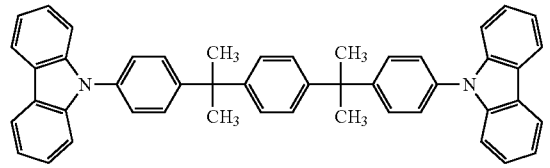
[Chem. 57]
H10 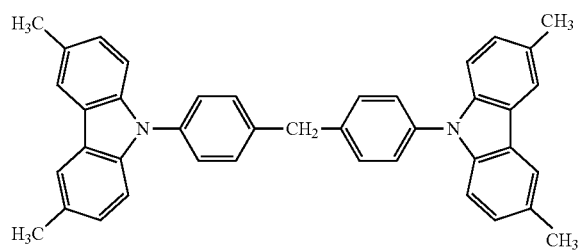
H11 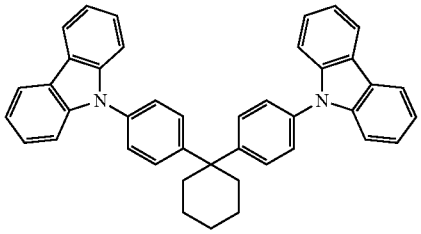
H12 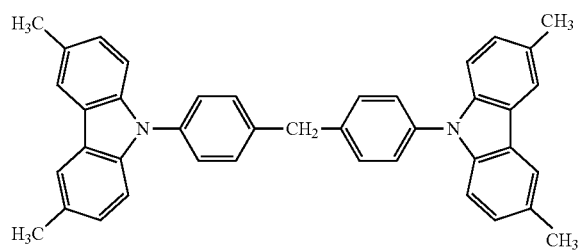
H13 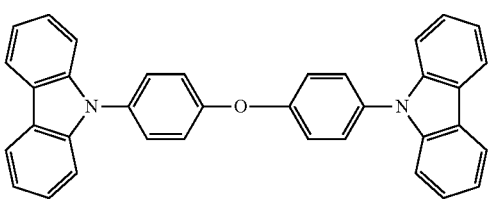

-continued
H14
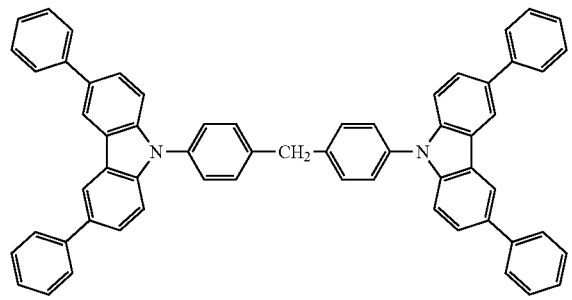
[Chem. 58]
H15 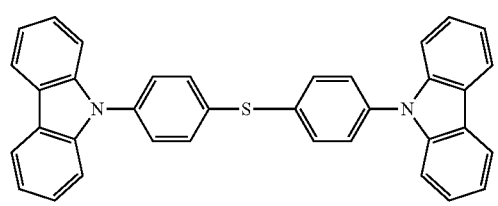   H16 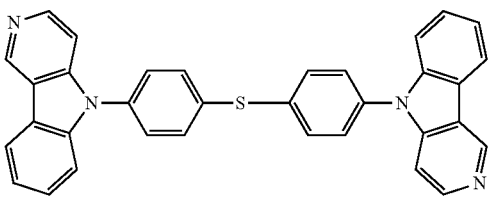
H17 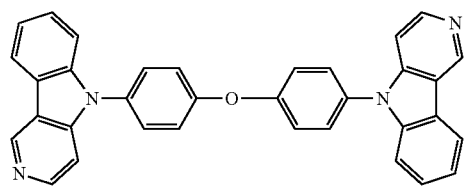   H18 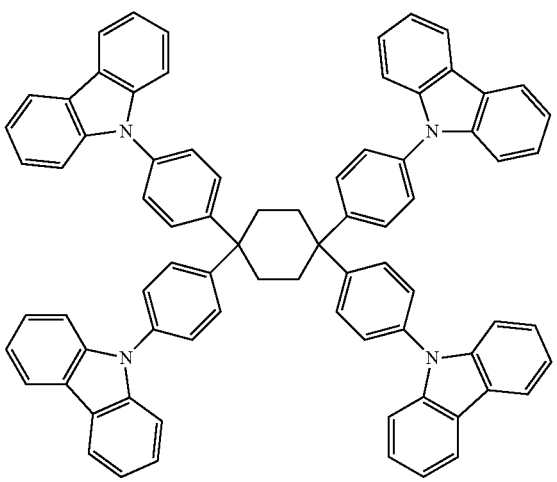
H19
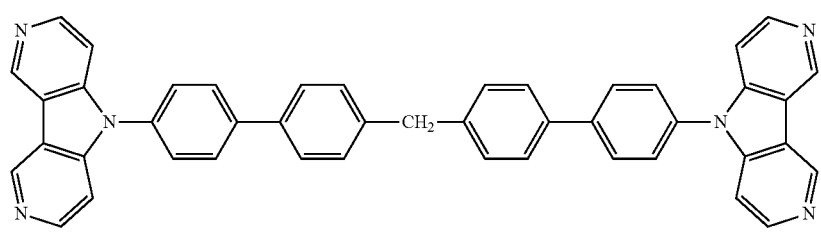
H20
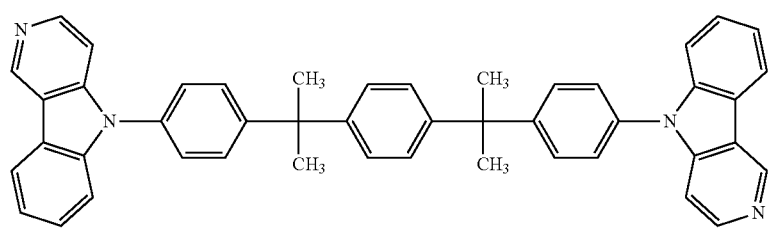

-continued
H21 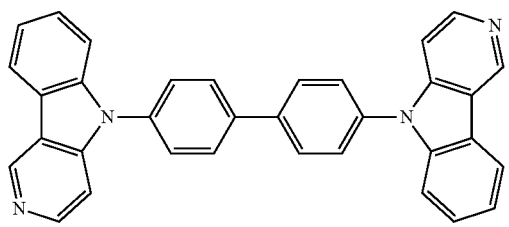 H22 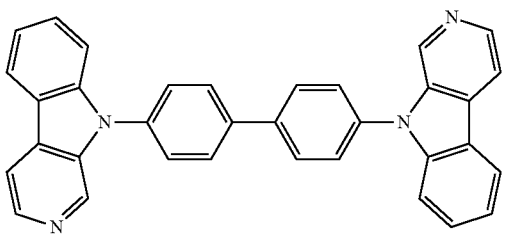
[Chem. 59]
H23 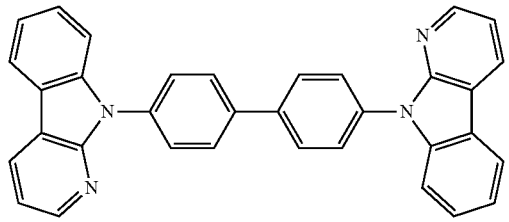 H24 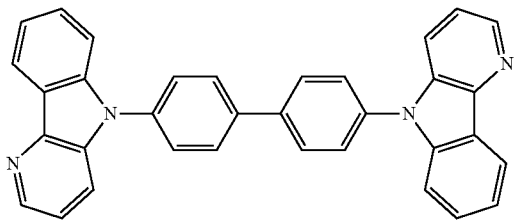
H25 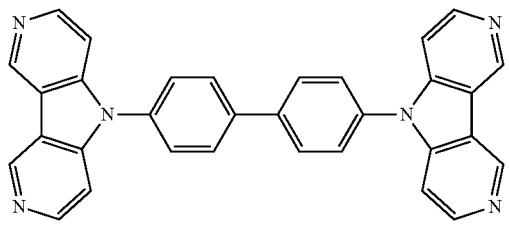 H26 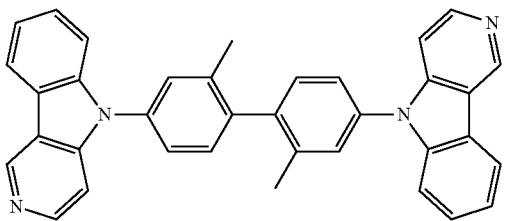
H27 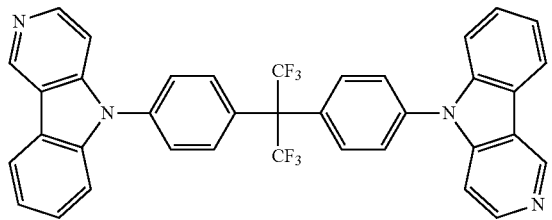 H28 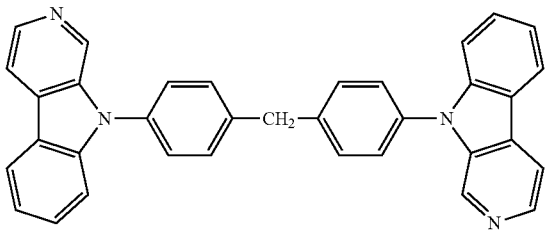
H29 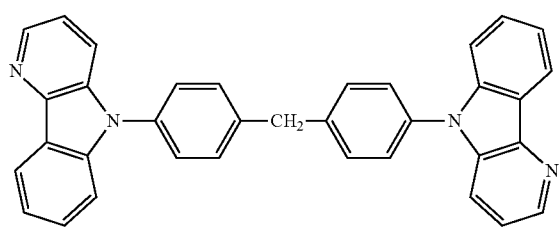 H30 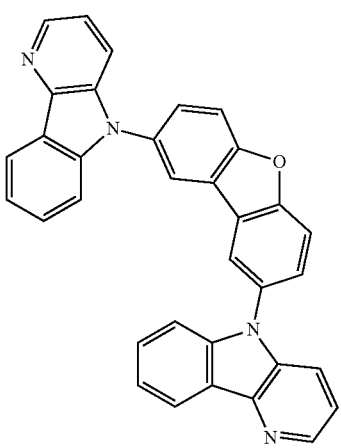

[Chem. 60]
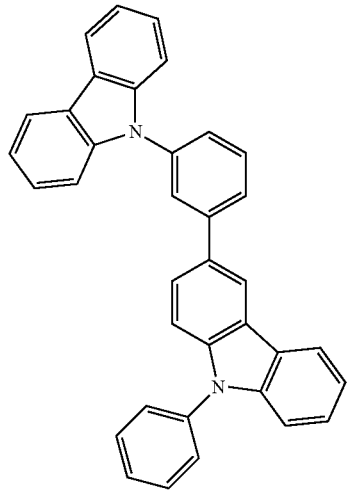
H31
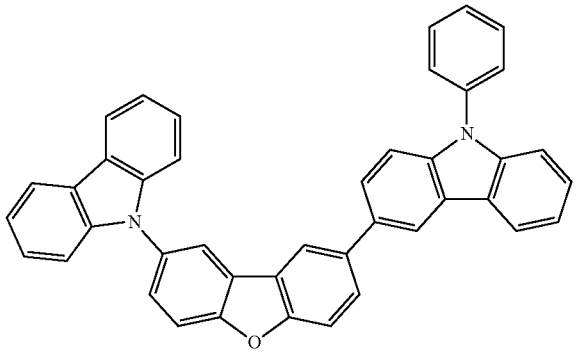
H32
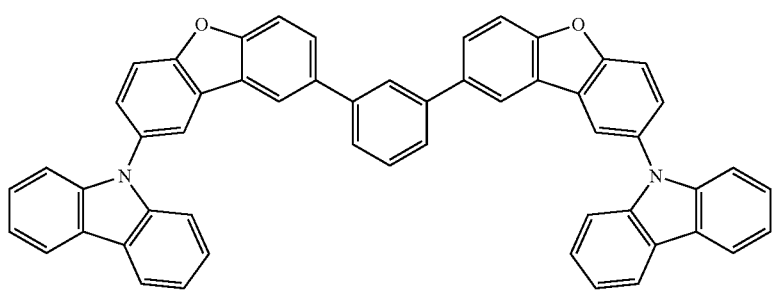
H33
[Chem. 61]
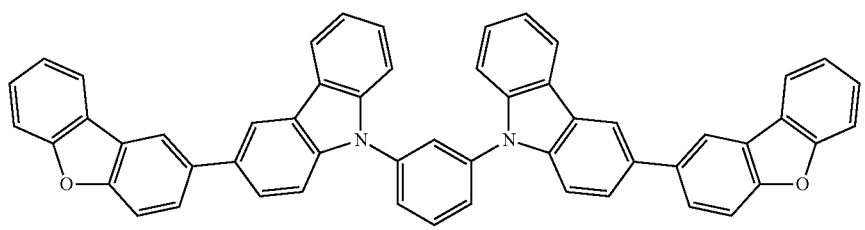
H34
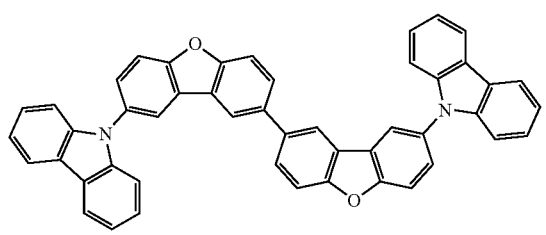
H35
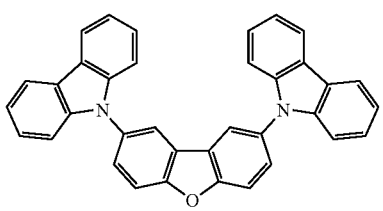
H36

-continued
H37
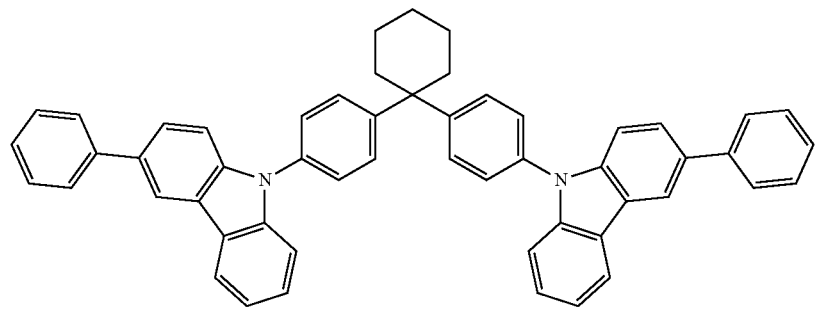
H38
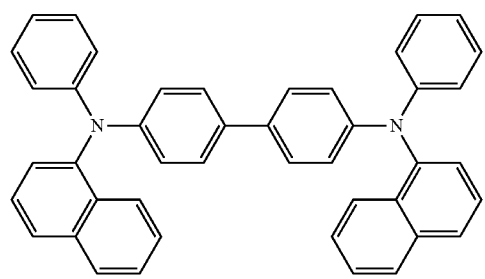
H39
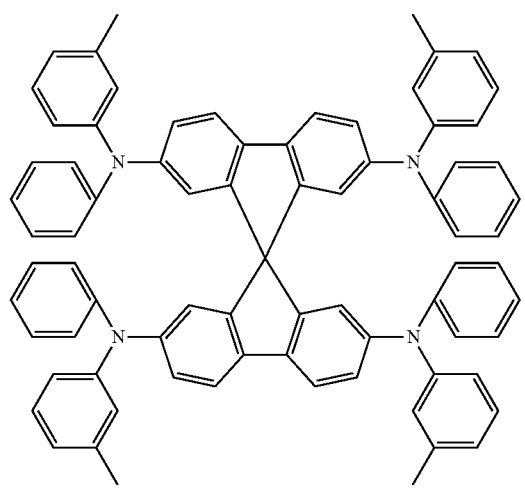
[Chem. 62]
H40
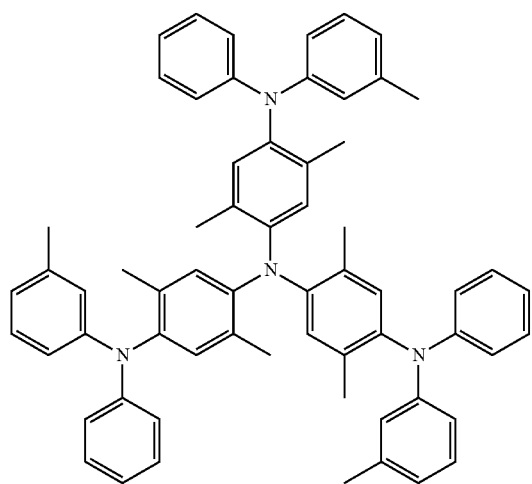
H41
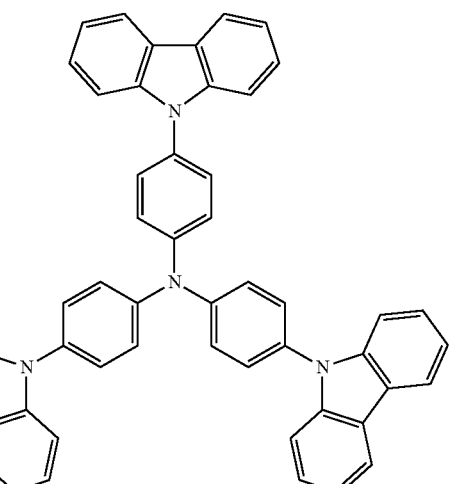
H42
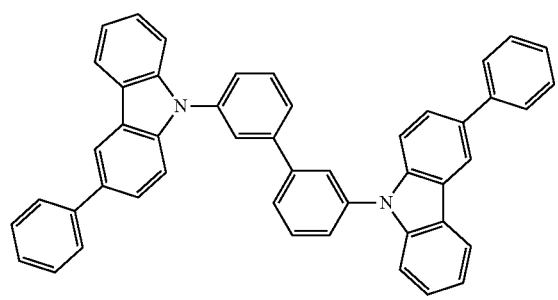
H43
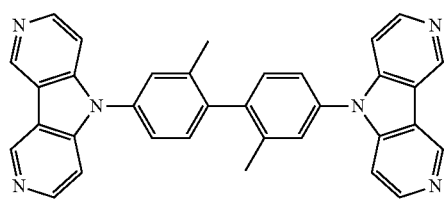

-continued
H44
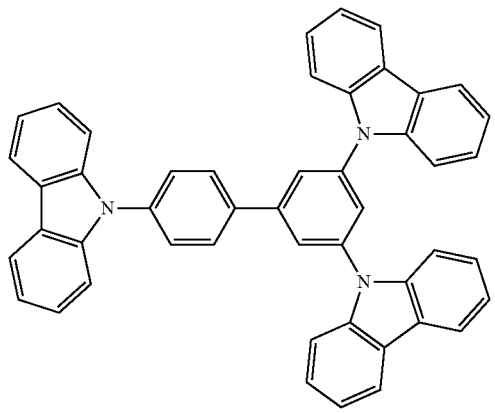
H45
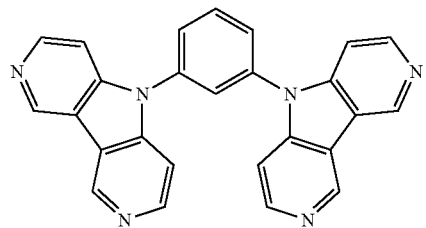
H46
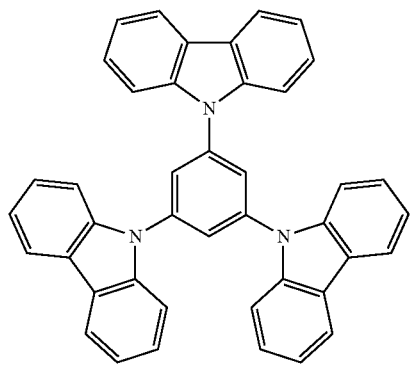
H47
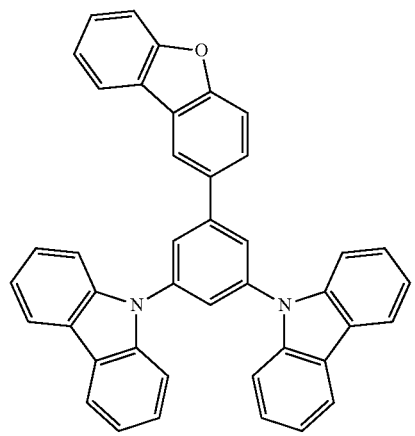
[Chem. 63]
H48
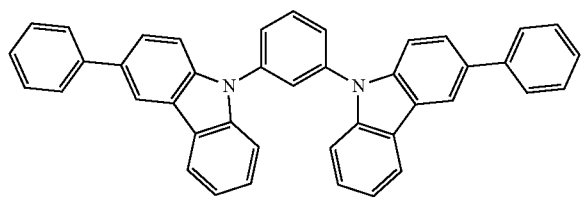
H49
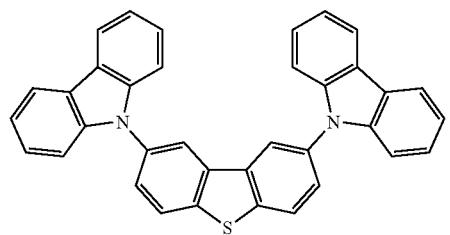
H50
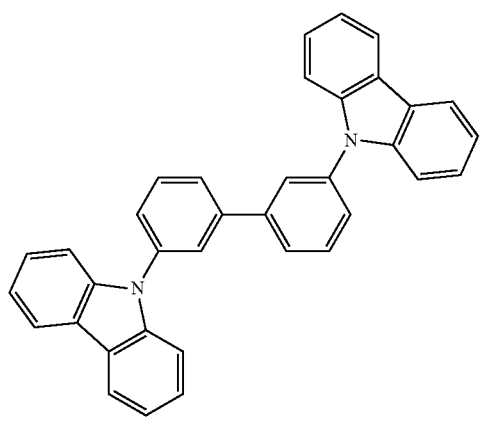
H51
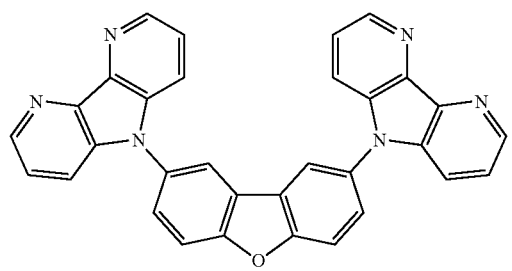

-continued
H52
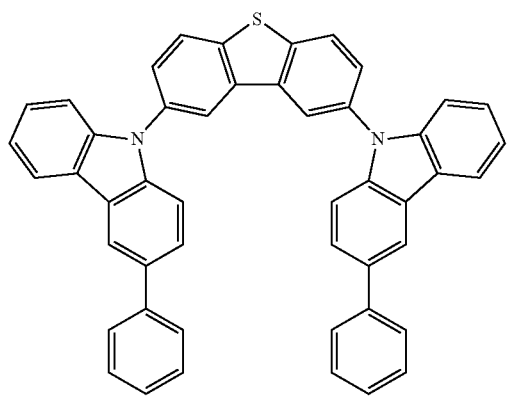
H53
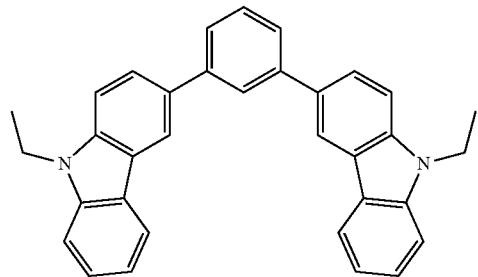
H54
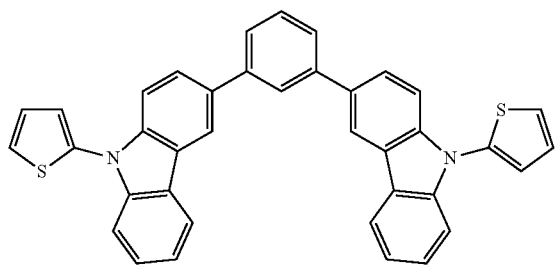
H55
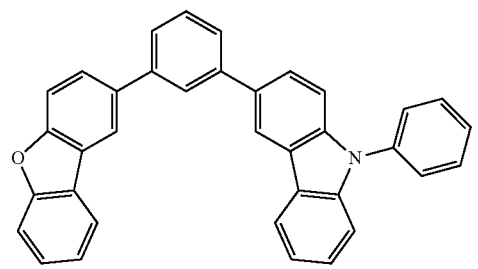
[Chem. 64]
H56
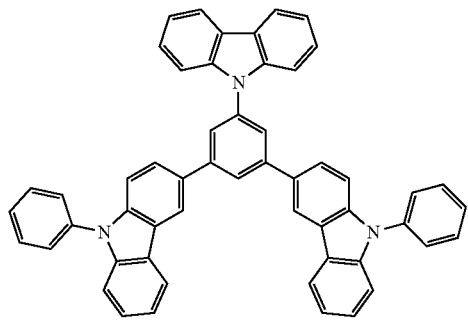
H57
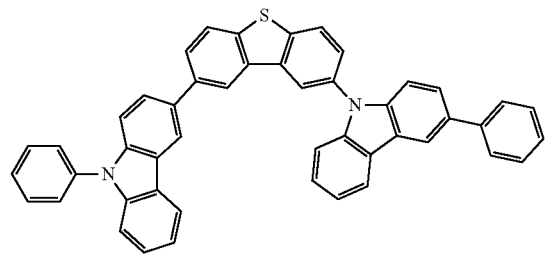
H58
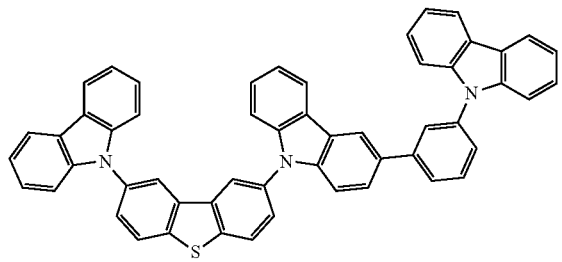
H59
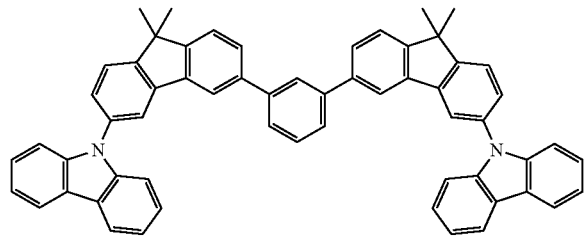
[Chem. 65]
H60
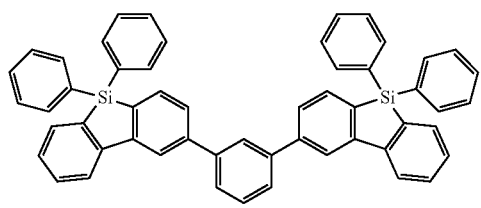
H61
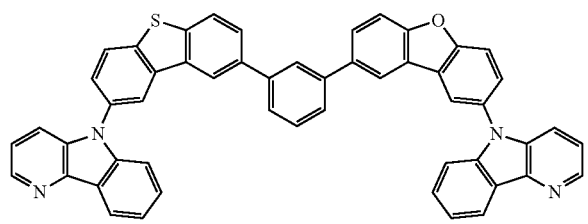

-continued
H62
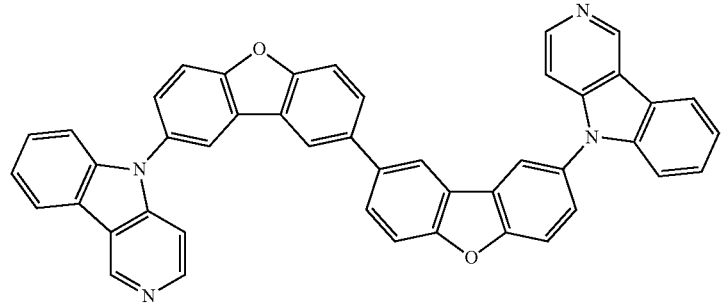
H63
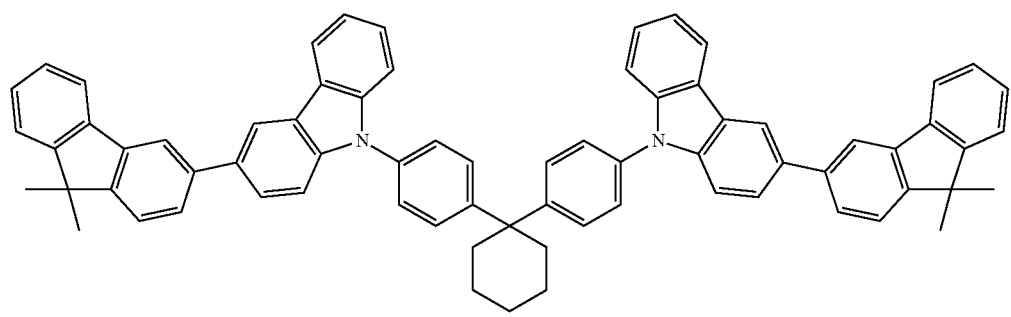
H64
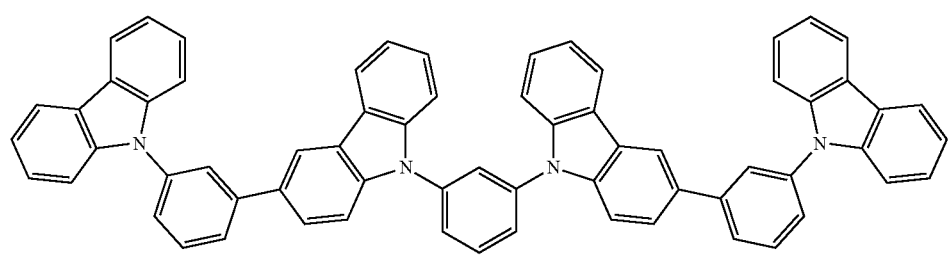
[Chem. 66]
H65
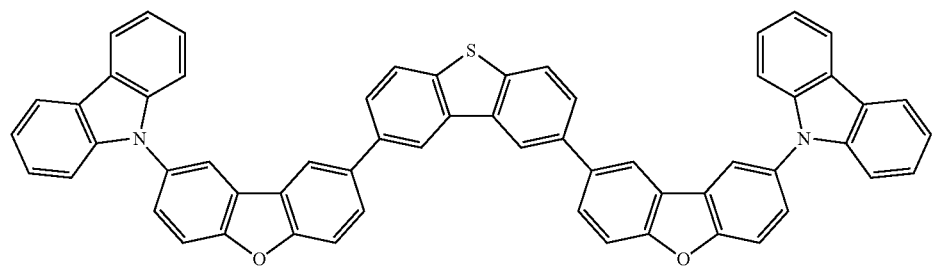
H66
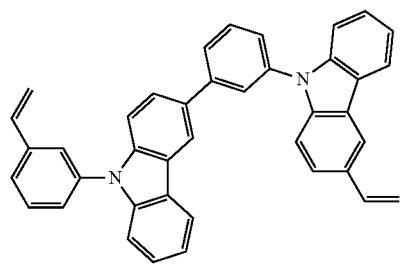
H67
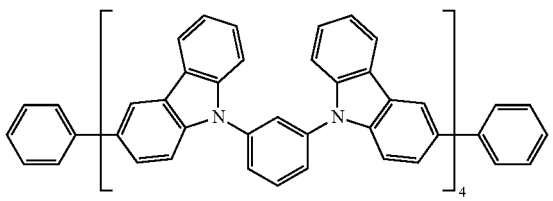

-continued
[Chem. 67]
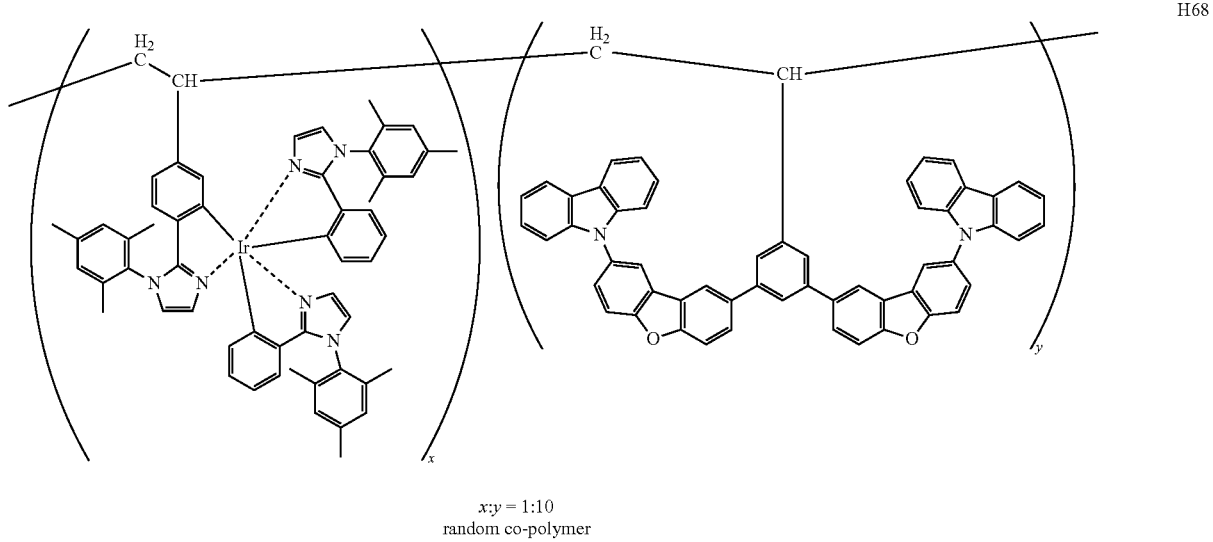
H68
x:y = 1:10
random co-polymer
[Chem. 68]
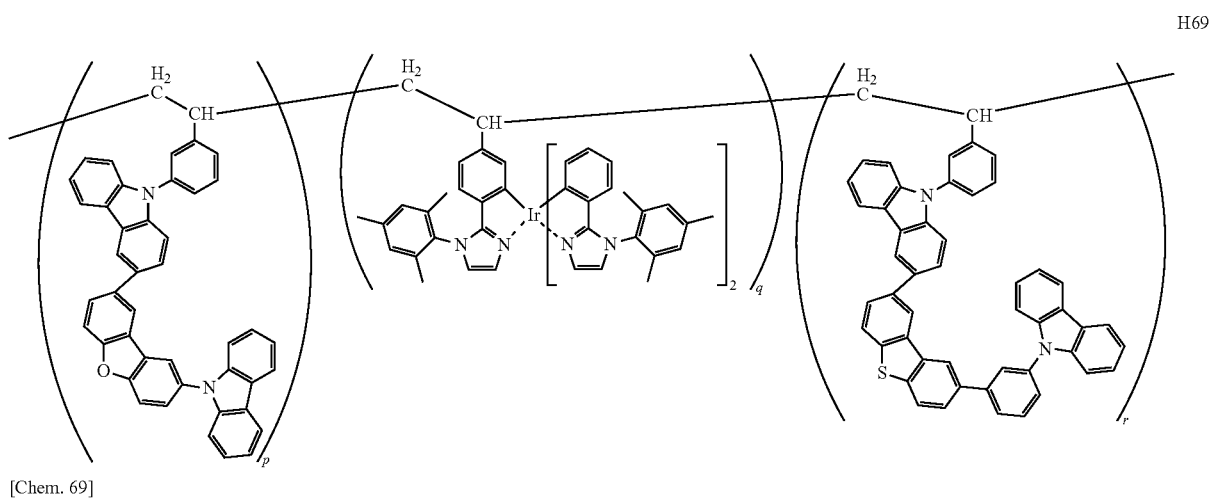
H69
[Chem. 69]
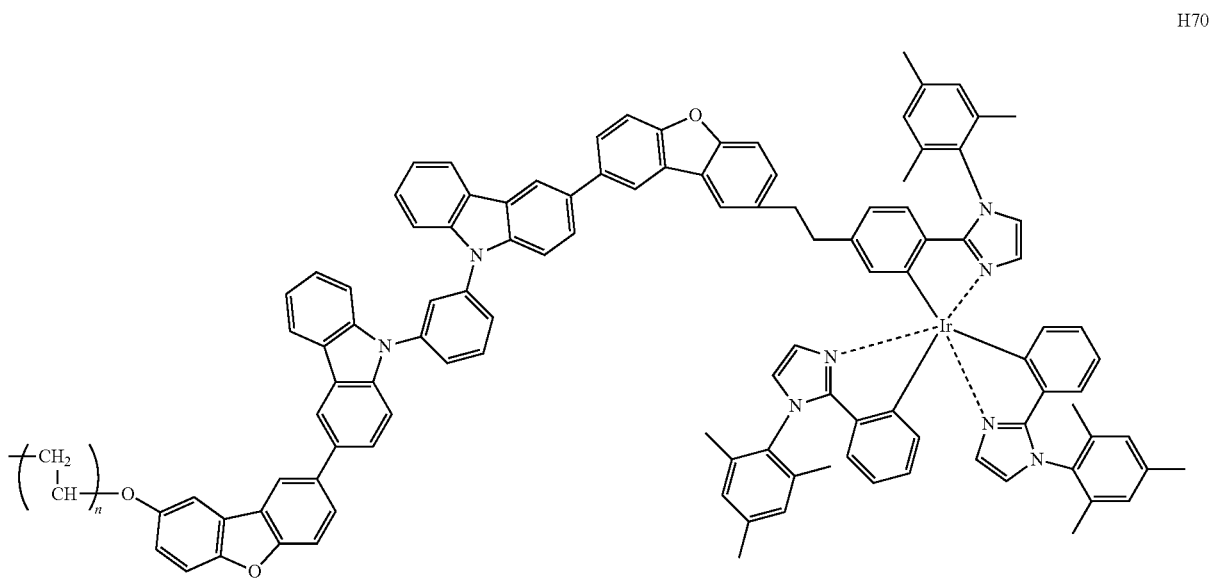
H70

[Chem. 70]
H71
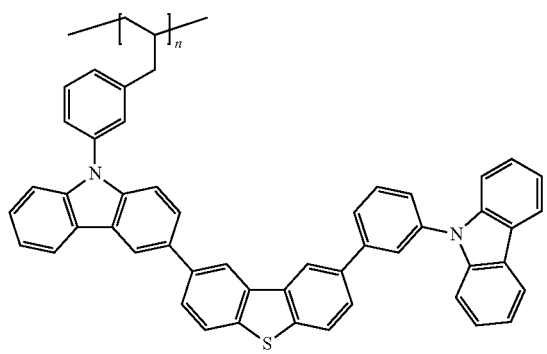
H72
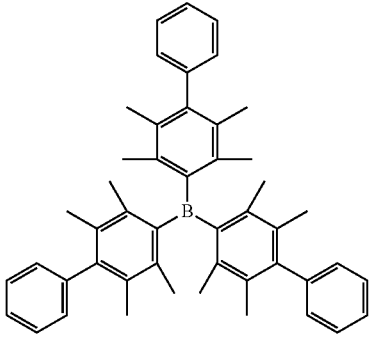
H73
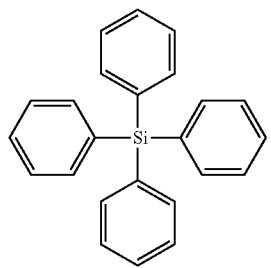
H74
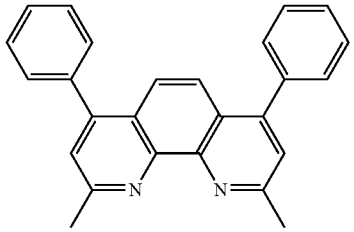
H75
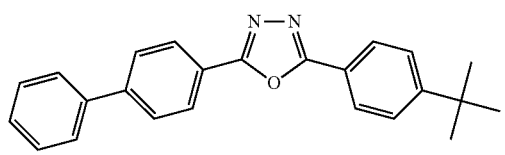
H76
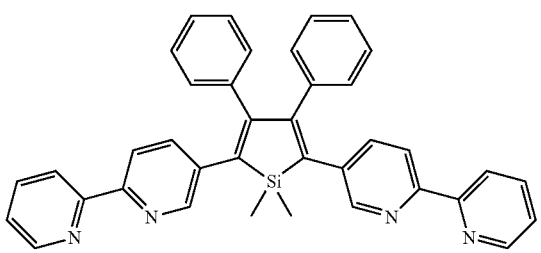
H77
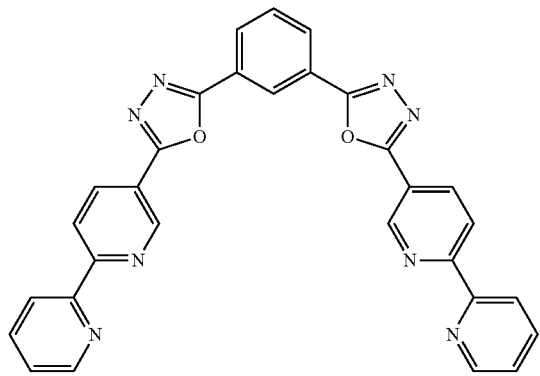
H78
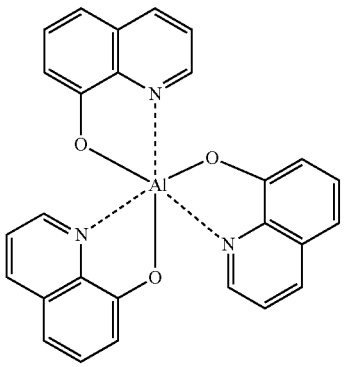

H79

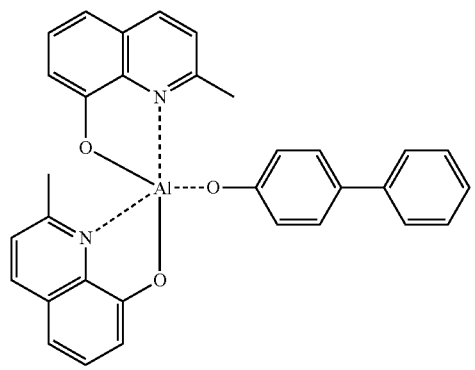

Specific examples of the well-known host compound are compounds described in the following documents; for example, Japanese Patent Application Laid-Open Publication Nos. 2001-257076, 2002-308855, 2001-313179, 2002-319491, 2001-357977, 2002-334786, 2002-8860, 2002-334787, 2002-15871, 2002-334788, 2002-43056, 2002-334789, 2002-75645, 2002-338579, 2002-105445, 2002-343568, 2002-141173, 2002-352957, 2002-203683, 2002-363227, 2002-231453, 2003-3165, 2002-234888, 2003-27048, 2002-255934, 2002-260861, 2002-280183, 2002-299060, 2002-302516, 2002-305083, 2002-305084, 2002-308837, and the like.

(Light-Emitting Material)

Te light-emitting material that can be used for the organic electroluminescent element of the present embodiment includes a phosphorescence-emitting material (also referred to as a phosphorescent compound or a phosphorescence-emitting compound).

The phosphorescence-emitting material is defined as a compound in which light emission from an excited triplet state is observed, and specifically, a compound which emits phosphorescence at room temperature (25° C.) and a phosphorescence quantum yield at 25° C. is 0.01 or more, and preferable phosphorescence quantum yield is 0.1 or more.

The phosphorescence quantum yield can be measured by a method described on page 398 of Bunko II of Dai 4 Han Jikken Kagaku Koza 7 (Spectroscopy II of Lecture of Experimental Chemistry vol. 7, 4th edition) (1992, published by Maruzen Co., Ltd.). The phosphorescence quantum yield in a solution can be measured by using various solvents, and in the present example, when the phosphorescence-emitting material is used, it is only necessary to achieve the above-described phosphorescence quantum yield (0.01 or more) in any of appropriate solvents.

There are two kinds of principles regarding light emission of the phosphorescence-emitting material. One is an energy transfer type, in which carriers recombine on a host compound transferring the carriers to thereby produce an excited state of the host compound, this energy is transferred to a phosphorescence-emitting material, and then light emission from the phosphorescence-emitting material is carried out. The other is a carrier trap type, in which a phosphorescence-emitting material serves as a carrier trap, carriers recombine on the phosphorescence-emitting material, and then light emission from the phosphorescence-emitting material is carried out. In either case, the excited state energy of the phosphorescence-emitting material is required to be lower than that of the host compound.

The phosphorescence-emitting material can be suitably selected from the well-known phosphorescence-emitting compounds used for light-emitting layers of organic electroluminescent elements, preferably a complex compound containing metal of the groups 8 to 10 in the element periodic table. More preferably, the phosphorescence-emitting material is an iridium compound, an osmium compound, a platinum compound (a platinum complex compound) or a rare earth complex, and most preferably, is an iridium compound.

In the organic electroluminescent element of the present embodiment, at least one light-emitting layer 22c may contain two or more types of light-emitting materials, and a ratio of concentration of the phosphorescence-emitting material in the light-emitting layer 22c may vary in the direction of thickness of the light-emitting layer 22c.

An amount of the phosphorescence-emitting material is preferably 0.1% by volume or more and 30% by volume or less to the total volume of the light-emitting layer 22c.

(Compound Represented by the General Formula (9))

The compound contained in the light-emitting layer 22c (phosphorescence-emitting compound) is preferably a compound represented by the following general formula (9).

In a preferable embodiment, the phosphorescence-emitting compound (also referred to as a phosphorescence-emitting metal complex) represented by the general formula (9) is contained in the light-emitting layer 22c of the organic electroluminescent element 20 as a light-emitting dopant, and may be contained in a light-emitting functional layer in the layer other than the light-emitting layer 22c.

[Chem. 71]

General formula (9)

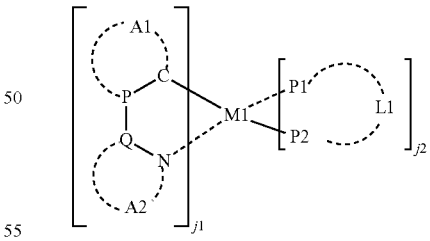

In the general formula (9), P and Q each represent a carbon atom or a nitrogen atom, A1 represents an atom group which forms an aromatic hydrocarbon ring or an aromatic heterocyclic ring with P—C. A2 represents an atom group which forms an aromatic heterocyclic ring with Q-N. P1-L1-P2 represents a bidentate ligand, P1 and P2 each independently represent carbon atom, nitrogen atom or oxygen atom. L1 represents an atom group which forms a bidentate ligand with P1 and P2. j1 represents an integer of 1 to 3, j2 represents an integer of 0 to 2, but the sum of j1 and j2 is 2 or 3. M1 represents a transition metal element of the groups 8 to 10 in the element periodic table.

Examples of the aromatic hydrocarbon ring which is formed by A1 with P—C in the general formula (9) include benzene ring, biphenyl ring, naphthalene ring, azulene ring, anthracene ring, phenanthrene ring, pyrene ring, chrysene ring, naphthacene ring, triphenylene ring, o-terphenyl ring, m-terphenyl ring, p-terphenyl ring, acenaphthene ring, coronene ring, fluorene ring, fluoranthrene ring, naphthacene ring, pentacene ring, perylene ring, pentaphene ring, picene ring, pyrene ring, pyranthrene ring, anthranthrene ring, and the like.

These rings may have a substituent which is exemplified as R11, R12 in general formula (1).

Examples of the aromatic heterocyclic ring which is formed by A1 with P—C in the general formula (9) include furan ring, thiophene ring, oxazole ring, pyrrole ring, pyridine ring, pyridazine ring, pyrimidine ring, pyrazine ring, triazine ring, benzimidazole ring, oxadiazole ring, triazole ring, imidazole ring, pyrazole ring, triazole ring, indole ring, benzimidazole ring, benzothiazole ring, benzoxazole ring, quinoxaline ring, quinazoline ring, phthalazine ring, carbazole ring, azacarbazole ring, and the like.

Here, the azacarbazole ring indicates a ring obtained by substituting one or more carbon atoms of benzene ring constituting carbazole ring with a nitrogen atom.

These rings may have a substituent which is exemplified as R11, R12 in general formula (1).

Examples of the aromatic heterocyclic ring which is formed by A2 with Q-N in the general formula (9) include oxazole ring, oxadiazole ring, oxatriazole ring, isoxazole ring, tetrazole ring, thiadiazole ring, thiatriazole ring, isothiazole ring, pyrrole ring, pyridine ring, pyridazine ring, pyrimidine ring, pyrazine ring, triazine ring, imidazole ring, pyrazole ring, triazole ring, and the like.

These rings may have a substituent which is exemplified as R11, R12 in general formula (1).

Examples of the bidentate ligand represented by P1-L1-P2 include phenylpyridine, phenylpyrazole, phenylimidazole, phenyltriazole, phenyltetrazole, pyrazabole, acetylacetone, picolinic acid, and the like.

In the general formula (9), j1 represents an integer of 1 to 3, and j2 represents an integer of 0 to 2, but the sum of j1 and j2 is 2 or 3. Particularly, j2 is preferably 0.

In the general formula (9), M1 represents a transition metal element (simply called a transition metal) of the groups 8 to 10 in the element periodic table. Particularly, M1 is preferably iridium.

(Compound Represented by the General Formula (10))

Among the compounds represented by the general formula (9), the compound represented by the general formula (10) is preferable.

[Chem. 72]

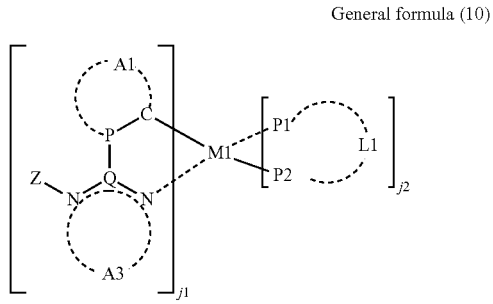

General formula (10)

In the above general formula (10), Z represents a hydrocarbon ring group or a heterocyclic ring group. P and Q each represent carbon atom or nitrogen atom, A1 represents an atom group which forms an aromatic hydrocarbon ring or an aromatic heterocyclic ring with P—C. A3 represents —C(R01)=C(R02)-, —N=C(R02)-, —C(R01)=N— or —N=N—, and R01 and R02 each represent hydrogen atom or a substituent. P1-L1-P2 represents a bidentate ligand, P1 and P2 each independently represent carbon atom, nitrogen atom or oxygen atom. L1 represents an atom group which forms the bidentate ligand with P1 and P2. j1 represents an integer of 1 to 3, j2 represents an integer of 0 to 2, but the sum of j1 and j2 is 2 or 3. M1 represents a transition metal element of the groups 8 to 10 in the element periodic table.

Examples of the hydrocarbon ring group represented by Z in the general formula (10) include a non-aromatic hydrocarbon ring group and an aromatic hydrocarbon ring group, and examples of the non-aromatic hydrocarbon ring group include cyclopropyl group, cyclopentyl group, cyclohexyl group, and the like. These groups may be a non-substituted group, or may have a substituent which is exemplified as R11, R12 in general formula (1). Preferably, the group represented by Z is an aromatic hydrocarbon ring group or an aromatic heterocyclic ring group.

Examples of the aromatic hydrocarbon ring group (also referred to as an aromatic hydrocarbon group, an aryl group or the like) include phenyl group, p-chlorophenyl group, mesityl group, tolyl group, xylyl group, naphthyl group, anthryl group, azulenyl group, acenaphthenyl group, fluorenyl group, phenanthryl group, indenyl group, pyrenyl group, biphenyl group, and the like.

These groups may be a non-substituted group, or may have a substituent which is exemplified as R11, R12 in general formula (1).

Examples of the heterocyclic ring group represented by Z in the general formula (10) include a non-aromatic heterocyclic ring group and an aromatic heterocyclic ring group. Examples of the non-aromatic heterocyclic ring group include a group derived from: epoxy ring, aziridine ring, thiirane ring, oxetane ring, azetidine ring, thietane ring, tetrahydrofuran ring, dioxorane ring, pyrrolidine ring, pyrazolidine ring, imidazolidine ring, oxazolidine ring, tetrahydrothiophene ring, sulforane ring, thiazolidine ring, ϵ-caprolactone ring, ϵ-caprolactam ring, piperidine ring, hexahydropyridazine ring, hexahydropyrimidine ring, piperazine ring, morpholine ring, tetrahydropyrane ring, 1,3-dioxane ring, 1,4-dioxane ring, trioxane ring, tetrahydrothiopyrane ring, thiomorpholine ring, thiomorpholine-1,1-dioxide ring, pyranose ring, diazabicyclo[2,2,2]-octane ring, and the like.

These groups may be a non-substituted group, or may have a substituent which is exemplified as R11, R12 in general formula (1).

Examples of the aromatic heterocyclic ring group include pyridyl group, pyrimidinyl group, furyl group, pyrrolyl group, imidazolyl group, benzimidazolyl group, pyrrazolyl group, pyradinyl group, triazolyl group (for example, 1, 2, 4-triazole-1-yl group or 1,2,3-triazole-1-yl group and the like), oxazolyl group, benzoxazolyl group, triazolyl group, isooxazolyl group, isothiazolyl group, furazanyl group, thienyl group, quinolyl group, benzofuryl group, dibenzofuryl group, benzothienyl group, dibenzothienyl group, indolyl group, carbazolyl group, carbolinyl group, diazacarbazolyl group (indicating a ring obtained by substituting, with a nitrogen atom, one of carbon atoms constituting carboline ring of carbolinyl group), quinoxalinyl group, pyridazinyl group, triazinyl group, quinazolinyl group, phthalazinyl group, and the like.

These groups may be a non-substituted group, or may have a substituent which is exemplified as R11, R12 in general formula (1).

Examples of the aromatic hydrocarbon ring which is formed by A1 with P—C in the general formula (10) include benzene ring, biphenyl ring, naphthalene ring, azulene ring, anthracene ring, phenanthrene ring, pyrene ring, chrysene ring, naphthacene ring, triphenylene ring, o-terphenyl ring, m-terphenyl ring, p-terphenyl ring, acenaphthene ring, coronene ring, fluorene ring, fluoranthrene ring, naphthacene ring, pentacene ring, perylene ring, pentaphene ring, picene ring, pyrene ring, pyranthrene ring, anthranthrene ring, and the like.

Furthermore, these rings may have a substituent which is exemplified as R11, R12 in general formula (1).

Examples of the aromatic heterocyclic ring which is formed by A1 with P—C in the general formula (10) include furan ring, thiophene ring, oxazole ring, pyrrole ring, pyridine ring, pyridazine ring, pyrimidine ring, pyrazine ring, triazine ring, benzimidazole ring, oxadiazole ring, triazole ring, imidazole ring, pyrazole ring, triazole ring, indole ring, benzimidazole ring, benzothiazole ring, benzoxazole ring, quinoxaline ring, quinazoline ring, phthalazine ring, carbazole ring, carboline ring, azacarbazole ring, and the like.

Here, the azacarbazole ring indicates a ring obtained by substituting, with a nitrogen atom, one or more carbon atoms of benzene ring constituting the above-described carbazole ring.

Furthermore, these rings may have a substituent which is exemplified as R11, R12 in general formula (1).

A substituent each represented by R01 and R02 in —C(R01)=C(R02)-, —N=C(R02)- and —C(R01)=N— which are represented by A3 in the general formula (10) has the same definition as the substituent which is exemplified as R11, R12 in general formula (1).

In the general formula (10), examples of the bidentate ligand represented by P1-L1-P2 include phenylpyridine, phenylpyrazole, phenylimidazole, phenyltriazole, phenyltetrazole, pyrazabole, acetylacetone, picolinic acid, and the like.

In addition, j1 represents an integer of 1 to 3, and j2 represents an integer of 0 to 2, but the sum of j1 and j2 is 2 or 3. Among them, j2 is preferably 0.

In the general formula (10), the transition metal element (simply called a transition metal) of the groups 8 to 10 in the element periodic table represented by M1 has the same definition as the transition metal element of the groups 8 to 10 in the element periodic table represented by M1 in the general formula (9).

(Compound represented by the general formula (11))

The following compound represented by the general formula (10) is shown as one of preferable embodiments represented by the general formula (11).

[Chem. 73]

General formula (11)

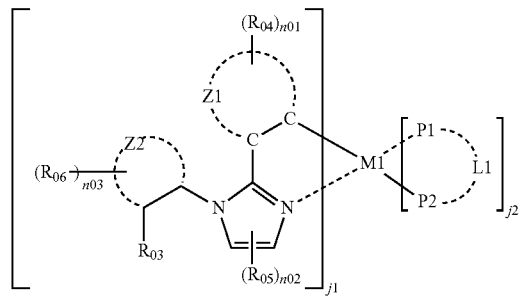

In the above general formula (11), $R_{03}$ represents a substituent, $R_{04}$ represents hydrogen atom or a substituent, a plurality of $R_{04}$s may bond to each other to form a ring. n01 represents an integer of 1 to 4. R05 represents hydrogen atom or a substituent, a plurality of $R_{05}$s may bond to each other to form a ring. n02 represents an integer of 1 to 2. $R_{06}$ represents hydrogen atom or a substituent, and may bond to each other to form a ring. n03 represents an integer of 1 to 4. Z1 represents an atom group which is necessary to form a six-membered aromatic hydrocarbon ring together with C—C, or a five- or six-membered aromatic heterocyclic ring. Z2 represents a hydrocarbon ring group or a heterocyclic ring group. P1-L1-P2 represents a bidentate ligand, P1 and P2 each independently represent carbon atom, nitrogen atom or oxygen atom. L1 represents an atom group which forms the bidentate ligand with P1 and P2. j1 represents an integer of 1 to 3, j2 represents an integer of 0 to 2, but the sum of j1 and j2 is 2 or 3. M1 represents a transition metal element of the groups 8 to 10 in the element periodic table. $R_{03}$ and $R_{06}$, $R_{04}$ and $R_{06}$, and $R_{05}$ and $R_{06}$ may bond to each other to thereby form a ring.

The substituent each represented by $R_{03}$, $R_{04}$, $R_{05}$, $R_{06}$ in the general formula (11) may have a substituent which is exemplified as R11, R12 in general formula (1).

In the general formula (11), examples of the six-membered aromatic hydrocarbon ring which is formed by Z1 with C—C include benzene ring, and the like.

These rings may have a substituent which is exemplified as R11, R12 in general formula (1).

Examples of the five-membered or six-membered aromatic heterocyclic ring which is formed by Z1 together with C—C in the general formula (11) include oxazole ring, oxadiazole ring, oxatriazole ring, isoxazole ring, tetrazole ring, thiadiazole ring, thiatriazole ring, isothiazole ring, thiophene ring, furan ring, pyrrole ring, pyridine ring, pyridazine ring, pyrimidine ring, pyrazine ring, triazine ring, imidazole ring, pyrazole ring, triazole ring, and the like.

These rings may have a substituent which is exemplified as R11, R12 in general formula (1).

Examples of the hydrocarbon ring group represented by Z2 in the general formula (11) include a non-aromatic hydrocarbon ring group and an aromatic hydrocarbon ring group. Examples of the non-aromatic hydrocarbon ring group include cyclopropyl group, cyclopentyl group, cyclohexyl group, and the like. These groups may be a non-substituted group, or may have a substituent which is exemplified as R11, R12 in general formula (1).

Additionally, examples of the aromatic hydrocarbon ring group (also referred to as an aromatic hydrocarbon group, an aryl group or the like) include phenyl group, p-chlorophenyl group, mesityl group, tolyl group, xylyl group, naphthyl group, anthryl group, azulenyl group, acenaphthenyl group, fluorenyl group, phenanthryl group, indenyl group, pyrenyl group, biphenyl group, and the like. These groups may be a non-substituted group, or may have a substituent which is exemplified as R11, R12 in general formula (1).

Examples of the heterocyclic ring group represented by Z2 in the general formula (11) include a non-aromatic heterocyclic ring group and an aromatic heterocyclic ring group. Examples of the non-aromatic heterocyclic ring group include a group derived from epoxy ring, aziridine ring, thiirane ring, oxetane ring, azetidine ring, thietane ring, tetrahydrofuran ring, dioxorane ring, pyrrolidine ring, pyrazolidine ring, imidazolidine ring, oxazolidine ring, tetrahydrothiophene ring, sulforane ring, thiazolidine ring, ε-caprolactone ring, ε-caprolactam ring, piperidine ring, hexahydropyridazine ring, hexahydropyrimidine ring, piperazine ring, morpholine ring, tetrahydropyrane ring, 1,3-dioxane ring, 1,4-dioxane ring, trioxane ring, tetrahydrothiopyrane ring, thiomorpholine ring, thiomorpholine-1,1-dioxide ring, pyranose ring, diazabicyclo[2,2,2]-octane ring, and the like. These groups may be a non-substituted group, or may have a substituent which is exemplified as R11, R12 in general formula (1).

Examples of the aromatic heterocyclic ring group include pyridyl group, pyrimidinyl group, furyl group, pyrrolyl group, imidazolyl group, benzimidazolyl group, pyrrazolyl group, pyradinyl group, triazolyl group (for example, 1,2,4-triazole-1-yl group or 1,2,3-triazole-1-yl group and the like), oxazolyl group, benzoxazolyl group, triazolyl group, isooxazolyl group, isothiazolyl group, furazanyl group, thienyl group, quinolyl group, benzofuryl group, dibenzofuryl group, benzothienyl group, dibenzothienyl group, indolyl group, carbazolyl group, carbolinyl group, diazacarbazolyl group (indicating a ring obtained by substituting, with a nitrogen atom, a carbon atom constituting carboline ring of carbolinyl group), quinoxalinyl group, pyridazinyl group, triazinyl group, quinazolinyl group, phthalazinyl group, and the like.

These groups may be a non-substituted group, or may have a substituent which is exemplified as R11, R12 in general formula (1).

In the general formula (11), a group formed by Z1 and Z2 is preferably benzene ring.

In the general formula (11), the bidentate ligand represented by P1-L1-P2 has the same definition as the bidentate ligand represented by P1-L1-P2 in the general formula (9).

In the general formula (11), the transition metal element of the groups 8 to 10 in the element periodic table represented by M1 has the same definition as the transition metal element of the groups 8 to 10 in the element periodic table represented by M1 in the general formula (9).

In addition, the phosphorescence-emitting material can be suitably selected from the well-known phosphorescence-emitting compounds used for light-emitting layers 22c of organic electroluminescent elements 20.

The phosphorescence-emitting material to be applied to the organic electroluminescent element of the present embodiment is preferably a complex compound containing metal of the groups 8 to 10 in the element periodic table, and more preferably an iridium compound, an osmium compound, a platinum compound (a platinum complex compound) or a rare earth complex, and most preferably an iridium compound.

Hereinafter, the examples of the phosphorescence-emitting material (Pt-1 to Pt-3, A-1, Ir-1 to Ir-50) will be shown. Note that the phosphorescence-emitting material to be applied to the organic electroluminescent element of the present embodiment is not limited thereto. In the compounds, m and n represent the number of repeating unit.

[Chem. 74]

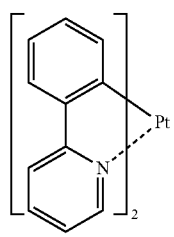

Pt-1

-continued

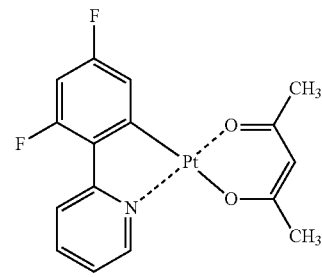

Pt-2

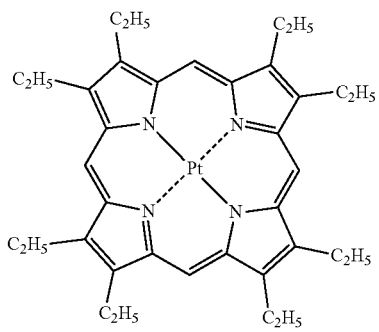

Pt-3

[Chem. 75]

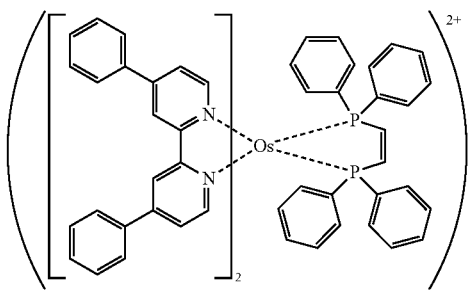

A-1

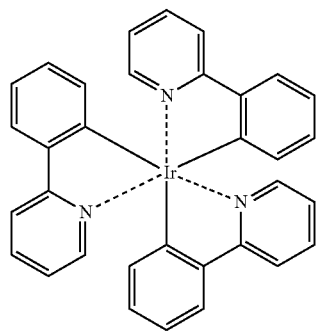

Ir-1

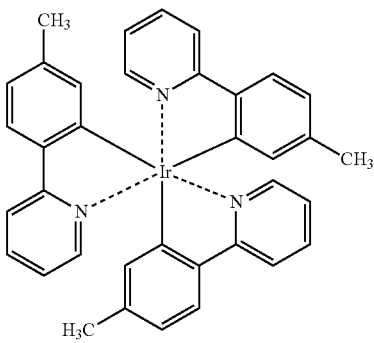

Ir-2

Ir-3
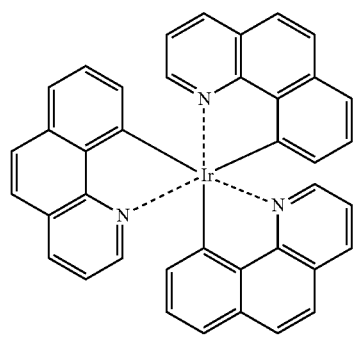
Ir-4
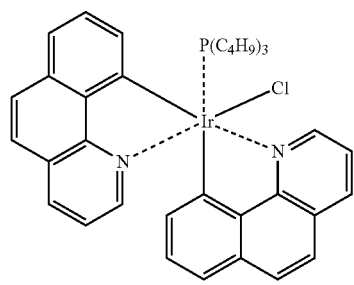
Ir-5
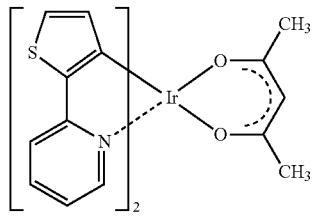
Ir-6
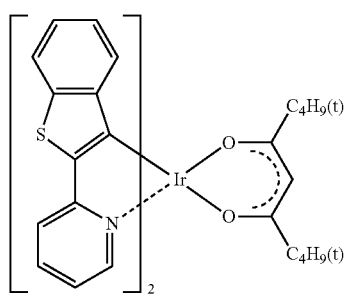
[Chem. 76]
Ir-7
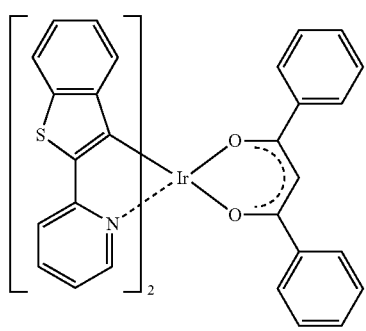
Ir-8
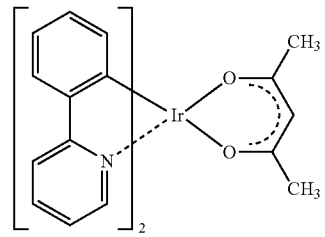
Ir-9
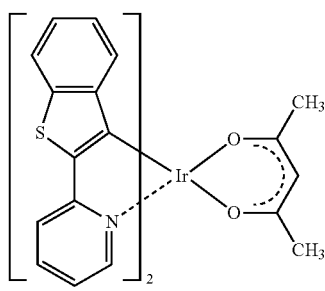
Ir-10
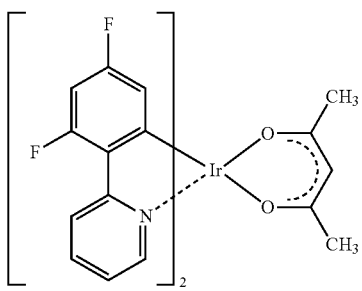
Ir-11
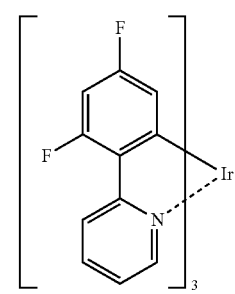
Ir-12
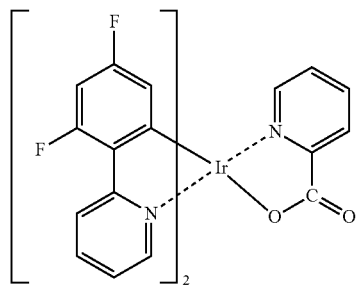

Ir-13
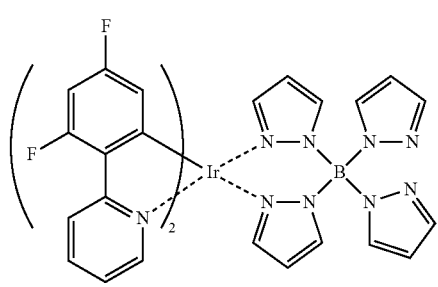
Ir-14
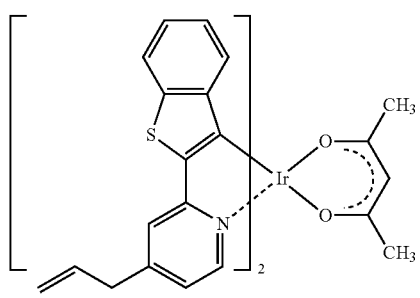
[Chem. 77]
Ir-15
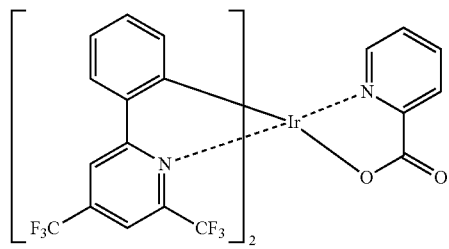
Ir-16
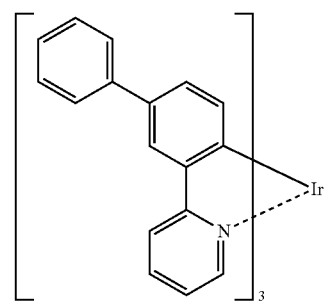
Ir-17
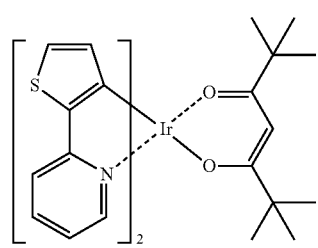
Ir-18
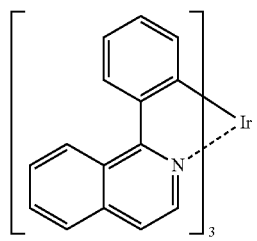
Ir-19
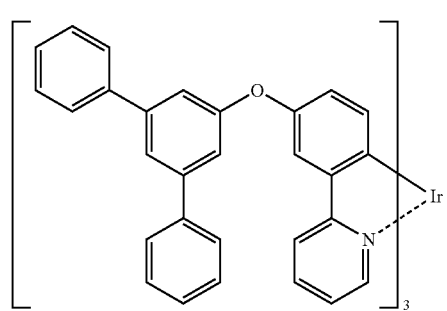
Ir-20
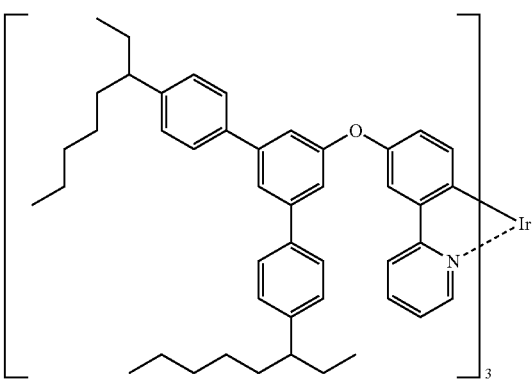
Ir-21
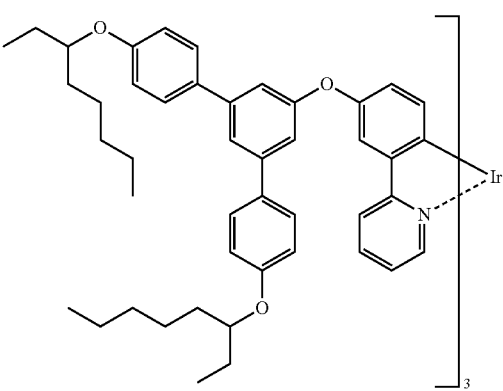

[Chem. 78]
Ir-22
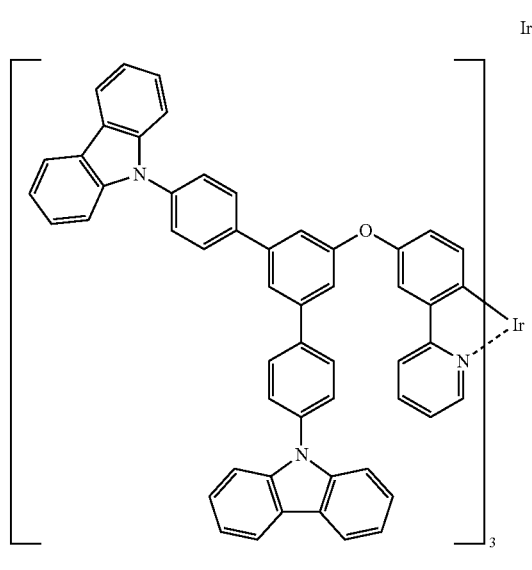
Ir-23
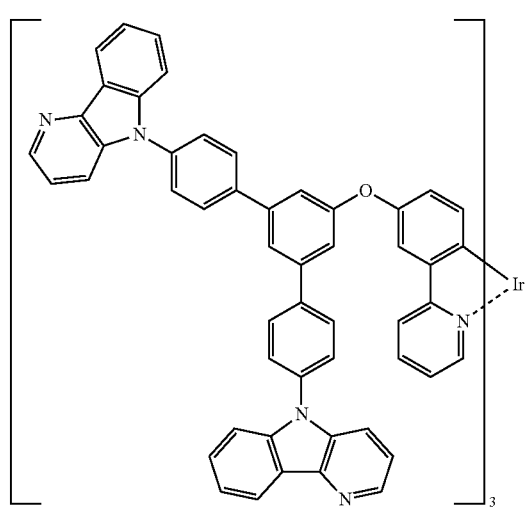
Ir-24
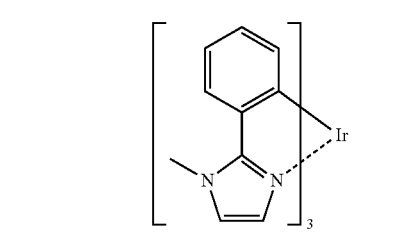
Ir-25
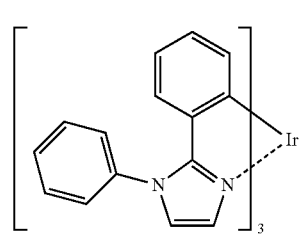
Ir-26
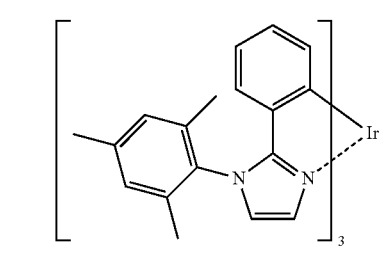
[Chem. 79]
Ir-27
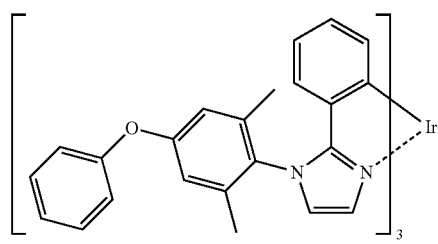
Ir-28
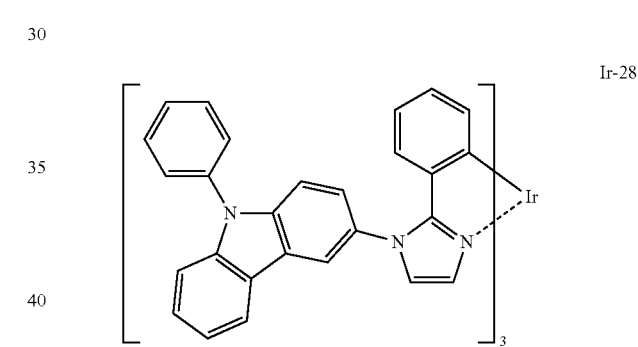
Ir-29
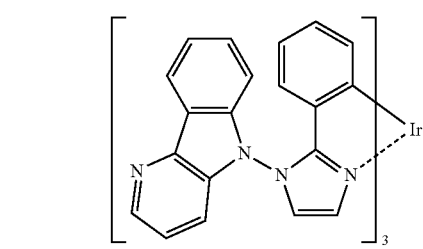
Ir-30
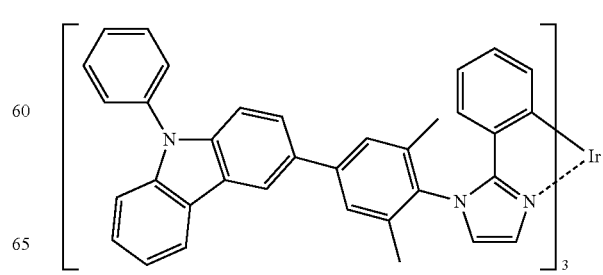

Ir-31
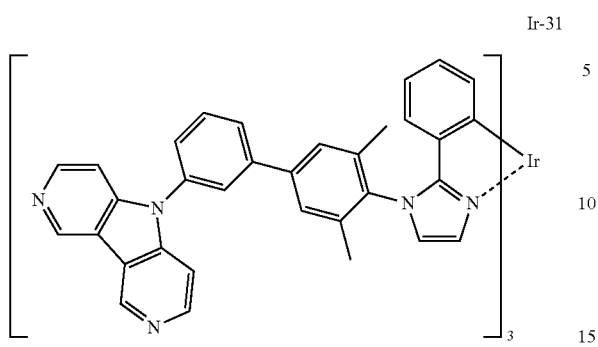
Ir-32
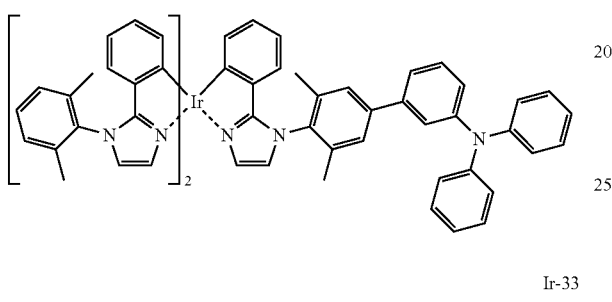
Ir-33
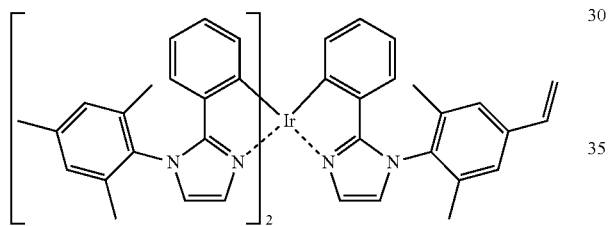
[Chem. 80]
Ir-34
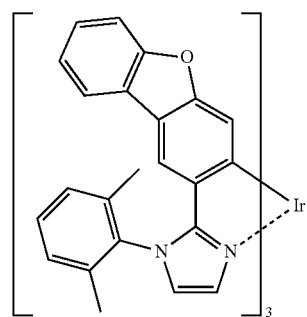
Ir-35
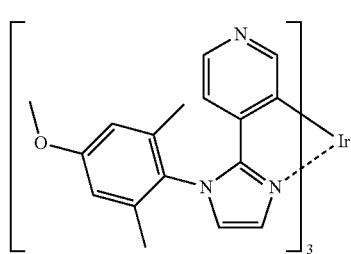
Ir-36
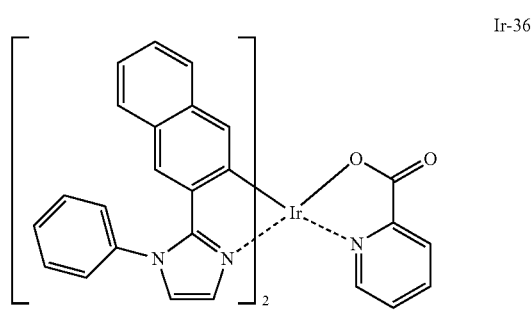
Ir-37
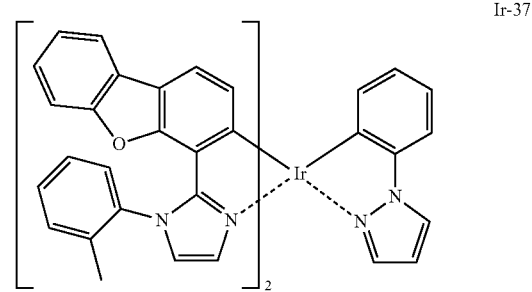
Ir-38
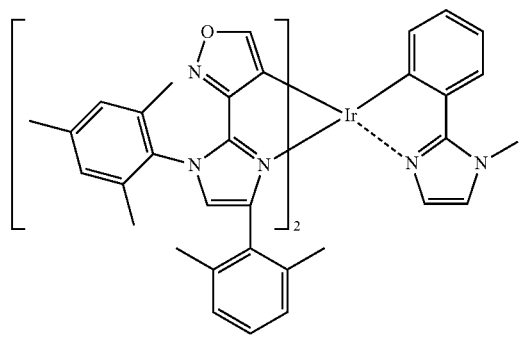
Ir-39
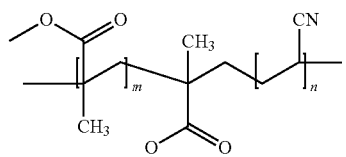

[Chem. 81]
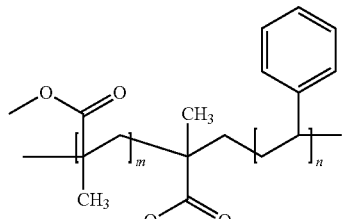
Ir-40
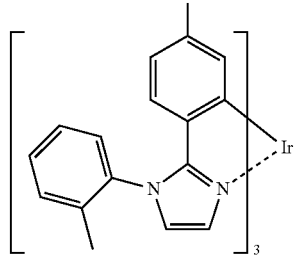
Ir-41
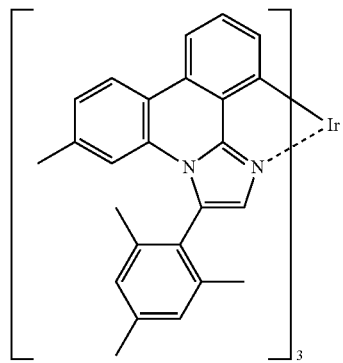
Ir-42
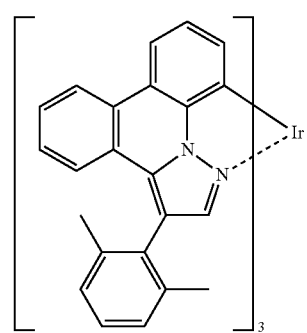
Ir-43
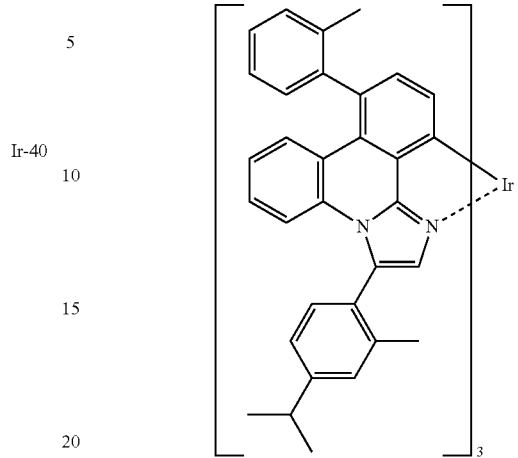
Ir-44
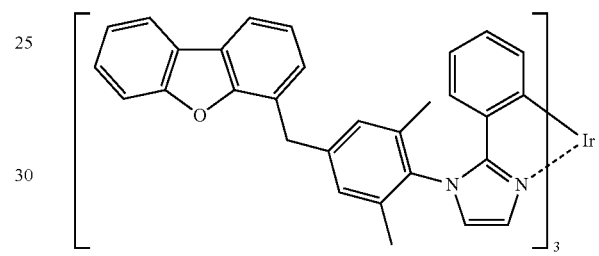
Ir-45
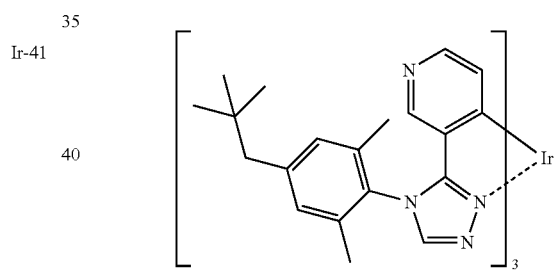
[Chem. 82]
Ir-46
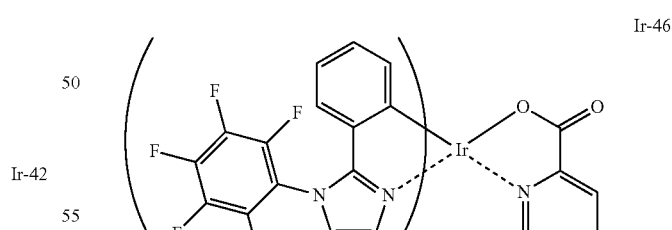
Ir-47
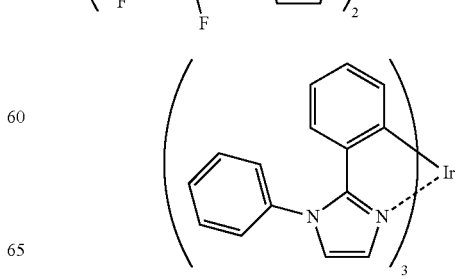

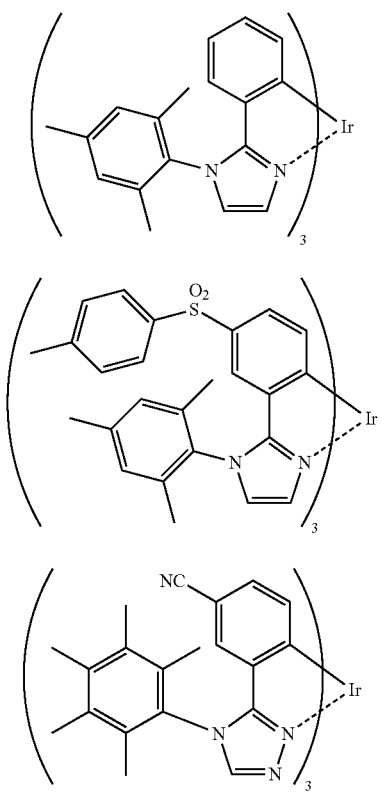

The above-mentioned phosphorescence-emitting compounds (also referred to as phosphorescence-emitting metal complexes and the like) can be synthesized by employing methods described in documents such as Organic Letter, vol. 3, No. 16, pp. 2579-2581 (2001); Inorganic Chemistry, vol. 30, No. 8, pp. 1685-1687 (1991); J. Am. Chem. Soc., vol. 123, p. 4304 (2001); Inorganic Chemistry, vol. 40, No. 7, pp. 1704-1711 (2001); Inorganic Chemistry, vol. 41, No. 12, pp. 3055-3066 (2002); New Journal of Chemistry, vol. 26, p. 1171 (2002); and European Journal of Organic Chemistry, vol. 4, pp. 695-709 (2004); and reference documents described in these documents.

(Fluorescence-Emitting Material)

Examples of the fluorescence-emitting material include a coumarin-based coloring matter, a pyran-based coloring matter, a cyanine-based coloring matter, a croconium-based coloring matter, a squarylium-based coloring matter, an oxobenzanthracene-based coloring matter, a fluorescein-based coloring matter, a rhodamine-based coloring matter, a pyrylium-based coloring matter, a perylene-based coloring matter, a stilbene-based coloring matter, a polythiophene-based coloring matter, or a rare earth complex-based fluorescent material or the like.

[Injection Layer: Positive Hole Injection Layer, Electron Injection Layer]

The injection layer is a layer disposed between an electrode and the light-emitting layer 22c to decrease a driving voltage and to improve luminance of light emitted, which is detailed in Part 2, Chapter 2 "Denkyoku Zairyo" (pp. 123-166) of "Yuki EL Soshi To Sono Kogyoka Saizensen (Nov. 30, 1998, published by N. T. S Co., Ltd.)", and examples thereof include a positive hole injection layer 22a and an electron injection layer 22e.

The injection layer is provided as necessary. The positive hole injection layer 22a may be present between an anode and the light-emitting layer 22c or the positive transport layer 22b, and the electron injection layer 22e may be present between a cathode and the light-emitting layer 22c or the electron transport layer 22d.

The positive hole injection layer 22a is also detailed in documents such as Japanese Patent Application Laid-Open Publication Nos. 09-45479, 09-260062 and 08-288069, and examples include a phthalocyanine layer represented by copper phthalocyanine, an oxide layer represented by vanadium oxide, an amorphous carbon layer, a polymer layer employing a conductive polymer such as polyaniline (emeraldine) or polythiophene, and the like.

The electron injection layer 22e is also detailed in documents such as Japanese Patent Application Laid-Open Publication Nos. 06-325871, 09-17574 and 10-74586 and examples include: a metal layer represented by strontium or aluminum, an alkali metal halide layer represented by potassium fluoride, an alkali earth metal compound layer represented by magnesium fluoride, an oxide layer represented by molybdenum oxide, and the like. It is preferable that the electron injection layer 22e is a very thin film, and the thickness thereof is within a range of 1 nm to 10 μm although it depends on the material thereof.

[Positive Hole Transport Layer]

The positive hole transport layer 22b is formed of a positive hole transport material having a function of transporting positive holes, and a positive hole injection layer 22a and an electron blocking layer are also included in the positive hole transport layer 22b in the broad sense of the word. The positive hole transport layer 22b can be provided as a sole layer or as a plurality of layers.

The positive hole transport material is a material having an injection capability or transport capability of positive holes, and barrier property against electrons and either an organic substance or an inorganic substance may be used. Examples include a triazole derivative, an oxadiazole derivative, an imidazole derivative, a polyarylalkane derivative, a pyrazoline derivative and a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline-based copolymer, and a conductive high-molecular oligomer, particularly, a thiophene oligomer and the like.

Those described above can be used as the positive hole transport material. However, it is preferable to use a porphyrin compound, an aromatic tertiary amine compound and a styrylamine compound, particularly, an aromatic tertiary amine compound.

Typical examples of the aromatic tertiary amine compound and the styrylamine compound include N,N,N',N'-tetraphenyl-4,4'-diaminophenyl; N,N'-diphenyl-N,N'-bis(3-methylphenyl)-[1,1'-biphenyl]-4,4'-diamine (TDP); 2,2-bis(4-di-p-tolylaminophenyl)propane; 1,1-bis(4-di-p-tolylaminophenyl)cyclohexane; N,N,N',N'-tetra-p-tolyl-4,4'-diaminobiphenyl; 1,1-bis(4-di-p-tolylaminophenyl)-4-phenylcyclohexane; bis(4-dimethylamino-2-metyl)phenylmethane; bis(4-di-p-tolylaminophenyl)phenylmethane; N,N'-diphenyl-N,N'-di(4-methoxyphenyl)-4,4'-diaminobiphenyl; N,N,N',N'-tetraphenyl-4,4'-diaminodiphenylether; 4,4'-bis(diphenylamino)quadriphenyl; N,N,N-tri(p-tolyl)amine; 4-(di-p-tolylamino)-4'-[4-(di-p-tolylamino) styryl]stilbene; 4-N,N-diphenylamino-(2-diphenylvinyl)benzene; 3-methoxy-4'-N,N-diphenylaminostilbene; N-phenylcarbazole; those having two condensed aromatic rings in a molecule described in U.S. Pat. No. 5,061,569, for instance, 4,4'-bis[N-(1-naphthyl)-N-phenylamino]biphenyl (NPD), 4,4',4''-tris [N-(3-methylphenyl)-N-phenylamino]triphenylamine (MTDATA) in which three triphenylamine units are bonded in a star burst form described in Japanese Patent Application Laid-Open Publication No. 04-308688 and the like.

Furthermore, polymer materials in which these materials are introduced into a polymer chain or constitute a main chain of a polymer can also be used. Moreover, inorganic compounds such as a p type-Si and a p type-SiC can also be used as the positive hole injection material and the positive hole transport material.

In addition, it is also possible to use so-called p type positive hole transport materials described in documents such as Japanese Patent Application Laid-Open Publication No. 11-251067 and Applied Physics Letters 80 (2002), p. 139 by J. Huang et. al. It is preferable to use these materials from the viewpoint of obtaining a light-emitting element having high efficiency.

The positive hole transport layer 22b can be formed by making the above-mentioned positive hole transport material a thin film by a well-known method such as the vacuum vapor deposition method, the spin coating method, the casting method, the printing method including the ink-jet method or the LB method. The thickness of the positive hole transport layer 22b is not particularly limited, but the thickness is generally within a range about of 5 nm to 5 µm, preferably within a range of 5 nm to 200 nm. This positive hole transport layer 22b may have a single layer configuration constituted of one or two or more of the above-mentioned materials.

Furthermore, it is possible to enhance the p property by doping the material of the positive hole transport layer 22b with impurities. Examples include those described in documents such as Japanese Patent Application Laid-Open Publication Nos. 04-297076, 2000-196140, 2001-102175 and J. Appl. Phys., 95, 5773 (2004).

As described above, it is preferable that enhancement of a high p property of the positive hole transport layer 22b makes it possible to produce an element which consumes lower electric power.

[Electron Transport Layer]

The electron transport layer 22d is formed of a material having a function of transporting electrons, and, in a broad sense, the electron injection layer 22e and a positive hole blocking layer (not shown) are included in the electron transport layer 22d. The electron transport layer 22d can be provided as a single layer or a laminated layer of a plurality of layers.

In the electron transport layer 22d having a single layer configuration and the electron transport layer 22d having a laminated layer configuration, the electron transport material constituting a layer provided adjacent to the light-emitting layer 22c has a function of transporting electrons injected from the cathode to the light-emitting layer 22c. The material to be used can be optionally selected from well-known compounds. Examples include a nitro-substituted fluorene derivative, a diphenylquinone derivative, a thiopyrandioxide derivative, carbodiimide, a fluorenylidenemethane derivative, anthraquinonedimethane, an anthrone derivative, and an oxadiazole derivative and the like. Furthermore, in the above-mentioned oxadiazole derivative, a thiadiazole derivative which is formed by substituting the oxygen atom of the above oxadiazole ring by a sulfur atom, and a quinoxaline derivative having a quinoxaline ring which is well-known as an electron withdrawing group can be used as the material of the electron transport layer 22d. Moreover, polymer materials in which these materials are introduced into a polymer chain or constitute a main chain of a polymer can also be used.

Additionally, metal complexes of an 8-quinolinol derivative such as: tris(8-quinolinol)aluminum (Alq3), tris(5,7-dichloro-8-quinolinol)aluminum, tris(5,7-dibromo-8-quinolinol)aluminum, tris(2-methyl-8-quinolinol)aluminum, tris (5-methyl-8-quinolinol)aluminum and bis(8-quinolinol) zinc (Znq), and metal complexes in which the central metal of these metal complexes is substituted by In, Mg, Cu, Ca, Sn, Ga or Pb can also be used as the material of the electron transport layer 22d.

Besides, a metal-free or metalphthalocyanine and those in which the terminals thereof are substituted by an alkyl group, a sulfonic acid group or the like can be preferably used as the material of the electron transport layer 22d. Moreover, the distyrylpyrazine derivative mentioned as an example of the material of the light-emitting layer 22c can also be used as the material of the electron transport layer 22d. As same as the positive hole injection layer 22a and the positive hole transfer layer 22b, inorganic semiconductors such as an n type-Si and an n type-SiC can also be used as the material of the electron transport layer 22d.

The electron transport layer 22d can be formed by thinning the above-mentioned electron transport material by a well-known method such as the vacuum vapor deposition method, the spin coating method, the casting method, the printing method including the ink-jet method or the LB method. The thickness of the electron transport layer 22d is not particularly limited, but the thickness is generally within a range of 5 nm to 5 µm, preferably within a range of 5 nm to 200 nm. This electron transport layer 22d may have a single layer configuration constituted of one or two or more of the above-mentioned materials.

Furthermore, it is possible to enhance the n property by doping the material of the electron transport layer 22d with impurities. Examples thereof include those described in documents such as Japanese Patent Application Laid-Open Publication Nos. 04-297076, 10-270172, 2000-196140 and 2001-102175 and J. Appl. Phys., 95, 5773 (2004). Moreover, it is preferable to introduce potassium or a potassium compound into the electron transport layer 22d. Examples of the potassium compound that can be used include, for example, potassium fluoride, and the like. As described above, an element which consumes lower electric power can be produced by enhancement of an n property of the electron transport layer 22d.

In addition, the compound represented by the general formula (12) can be preferably used as the material of the electron transport layer 22d (electron transport compound).

$$(Ar1)_{n1}\text{-}Y1 \qquad \text{General formula (12)}$$

In the general formula (12), n1 represents an integer of 1 or more, Y1 represents a substituent when n1 is 1, and represents a bond or an n1-valent linking group when n1 is 2 or more. Ar1 represents a group represented by the following general formula (A), and a plurality of Ar1s is identical or different when n1 is 2 or more. However, the compound represented by the above-described general formula (12) has, in a molecule, at least two condensed aromatic heterocyclic rings obtained by condensing three or more rings.

In the general formula (12), an example of the substituent represented by Y1 has the same meaning as the substituent exemplified as R11, R12 of the general formula (1) which is shown as the compound constituting the nitrogen-containing layer 14 of the transparent electrode 10.

Examples of an n1-valent linking group represented by Y1 in the general formula (12) include a divalent linking group, a trivalent linking group and a tetravalent linking group, and the like.

Examples of the divalent linking group represented by Y1 in the general formula (12) include: an alkylene group (for example, ethylene group, trimethylene group, tetramethylene group, propylene group, ethylethylene group, pentamethylene group, hexamethylene group, 2,2,4-trimethylhexamethylene group, heptamethylene group, octamethylene group, nonamethylene group, decamethylene group, undecamethylene group, dodecamethylene group, a cyclohexylene group (for example, 1,6-cyclohexanediyl group and the like) and a cyclopenthylene group (for example, 1,5-cyclopentanediyl group and the like)), an alkenylene group (for example, vinylene group, propenylene group, butenylene group, pentenylene group, 1-methylvinylene group, 1-methylpropenylene group, 2-methylpropenylene group, 1-methylpentenylene group, 3-methylpentenylene group, 1-ethylvinylene group, 1-ethylpropenylene group, 1-ethylbutenylene group, 3-ethylbutenylene group and the like), an alkynylene group (for example, ethynylene group, 1-propynylene group, 1-butynylene group, 1-pentynylene group, 1-hexynylene group, 2-butynylene group, 2-pentynylene group, 1-methylethynylene group, 3-methyl-1-propynylene group, 3-methyl-1-butynylene group and the like), an arylene group (for example, o-phenylene group, p-phenylene group, naphthalenediyl group, anthracenediyl group, naphthacenediyl group, pyrenediyl group, naphthylnaphthalenediyl group, a biphenyldiyl group (for example, [1,1'-biphenyl]-4,4'-diyl group, 3,3'-biphenyldiyl group, 3,6-biphenyldiyl group and the like), terphenyldiyl group, quaterphenyldiyl group, quinquephenyldiyl group, sexiphenyldiyl group, septiphenyldiyl group, octiphenyldiyl group, nobiphenyldiyl group, deciphenyldiyl group and the like), a heteroarylene group (for example, a divalent group derived from a group consisting of carbazole group, carboline ring, diazacarbazole ring (also referred to as monoazacarboline group, exhibiting a ring structure obtained by substituting, with a nitrogen atom, a carbon atom constituting the carboline rin), triazole ring, pyrrole ring, pyridine ring, pyrazine ring, quinoxaline ring, thiophene ring, oxadiazole ring, dibenzofuran ring, dibenzothiophene ring, indole ring and the like), a chalcogen atom such as oxygen or sulfur, a group or the like derived from a condensed aromatic heterocyclic ring obtained by condensing three or more rings (here, the condensed aromatic heterocyclic ring formed by condensing three or more rings preferably contains a hetero atom selected from N, O and S as an element constituting a condensed ring, for example, acridine ring, benzoquinoline ring, carbazole ring, phenazine ring, phenanthridine ring, phenanthroline ring, carboline ring, cycladine ring, quindoline ring, thebenidine ring, quinindoline ring, triphenodithiazine ring, triphenodioxazine ring, phenanthrazine ring, anthrazine ring, perimizine ring, diazacarbazole ring (exhibiting a ring obtained by substituting, with a nitrogen atom, optional one of carbon atoms constituting the carboline ring), phenanthroline ring, dibenzofuran ring, dibenzothiophene ring, naphthofuran ring, naphthothiophene ring, benzodifuran ring, benzodithiophene ring, naphthodifuran ring, naphthodithiophene ring, anthrafuran ring, anthradifuran ring, anthrathiophene ring, anthradithiophene ring, thianthrene ring, phenoxathiin ring, thiophanthrene ring (naphthothiophene ring) and the like).

Examples of the trivalent linking group represented by Y1 in the general formula (12) include ethanetriyl group, propanetriyl group, butanetriyl group, pentanetriyl group, hexanetriyl group, heptanetriyl group, octanetriyl group, nonanetriyl group, decanetriyl group, undecanetriyl group, dodecanetriyl group, cyclohexanetriyl group, cyclopentanetriyl group, benzenetriyl group, naphthalenetriyl group, pyridinetriyl group, carbazoletriyl group, and the like.

The tetravalent linking group represented by Y1 in the general formula (12) is a group having a combining group added to the above-mentioned trivalent linking group. Examples include propandiylidene group, 1,3-propandiyl-2-ylidene group, butanediylidene group, pentanediylidene group, hexanediylidene group, heptanediylidene group, octanediylidene group, nonanediylidene group, decanediylidene group, undecanediylidene group, dodecanediylidene group, cyclohexanediylidene group, cyclopentanediylidene group, benzenetetrayl group, naphthalenetetrayl group, pyridinetetrayl group, carbazoletetrayl group, and the like.

Note that each of the above-mentioned divalent, trivalent and tetravalent linking groups may further have a substituent exemplified as R11 and R12 of the general formula (1).

As the preferable aspect of the compound represented by the general formula (12), it is preferable that Y1 represent a group which is derived from a condensed aromatic heterocyclic ring formed by condensing three or more rings. Examples of the condensed aromatic heterocyclic ring formed by condensing three or more rings preferably include dibenzofuran ring or dibenzothiophene ring. In addition, preferably n1 is 2 or more.

Furthermore, the compound represented by the general formula (12) has, in the molecule, at least two condensed aromatic heterocyclic rings formed by condensing three or more rings, described above.

Moreover, when Y1 represents an n1-valent linking group, Y1 is preferably non-conjugated in order to keep the triplet excitation energy of the compound represented by the general formula (12) high, and is preferably constituted of aromatic rings (aromatic hydrocarbon ring+aromatic heterocyclic ring) from the viewpoint of improving Tg (also referred to as glass transition point, or glass transition temperature).

Here, the "non-conjugated" means a case in which a linking group cannot be expressed by repetition of a single bond (single bond) and a double bond, or a case in which a conjugation of aromatic rings constituting a linking group is sterically broken.

[Group Represented by the General Formula (A)]

Ar1 in the general formula (12) represents the group represented by the general formula (A) below.

[Chem. 83]

General formula (A)

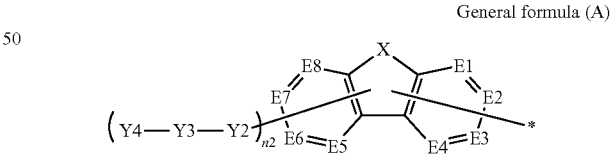

where X represents —N(R)—, —O—, —S— or —Si(R)(R')—, E1 to E8 each represent —C(R1)= or —N=, R, R' and R1 each represent hydrogen atom, a substituent or a linking moiety with Y1. * represents a linking moiety with Y1. Y2 represents simply a bond or a divalent linking group. Y3 and Y4 each represent a group derived from a five-membered or six-membered aromatic ring, and at least one represents a group derived from an aromatic heterocyclic ring containing a nitrogen atom as a ring constituent atom. n2 represents an integer of 1 to 4.

Here, in —N(R)— or —Si(R)(R')— represented by X of the general formula (A), and further in —C(R1)= represented by E1 to E8, a substituent represented by each of R, R' and R1 has the same meaning as the substituent represented by R11, R12 of the general formula (1).

In addition, a divalent linking group represented by Y2 in the general formula (A) has the same meaning as the divalent linking group represented by Y1 in the general formula (12).

Furthermore, examples of a five-membered or six-membered aromatic ring which is used for the formation of a group derived from a five-membered or six-membered aromatic ring represented by each of Y3 and Y4 in the general formula (A) include benzene ring, oxazole ring, thiophene ring, furan ring, pyrrole ring, pyridine ring, pyridazine ring, pyrimidine ring, pyrazine ring, diazine ring, triazine ring, imidazole ring, isoxazole ring, pyrazole ring, triazole ring, and the like.

Moreover, at least one of the groups derived from five-membered or six-membered aromatic rings each represented by Y3 and Y4 represents a group derived from the aromatic heterocyclic ring containing a nitrogen atom as a ring constituent atom, and examples of the aromatic heterocyclic ring containing a nitrogen atom as a ring constituent atom include oxazole ring, pyrrole ring, pyridine ring, pyridazine ring, pyrimidine ring, pyrazine ring, diazine ring, triazine ring, imidazole ring, isoxazole ring, pyrazole ring, triazole ring, and the like.

(Preferred Aspect of the Group Represented by Y3)

In the general formula (A), the group represented by Y3 is preferably a group derived from the above-mentioned six-membered aromatic ring, and is more preferably a group derived from a benzene ring.

(Preferred Aspect of the Group Represented by Y4)

In the general formula (A), the group represented by Y4 is preferably a group derived from the above-mentioned six-membered aromatic ring, is more preferably a group derived from the aromatic heterocyclic ring containing nitrogen atom as a ring constituent atom, and is particularly preferably a group derived from a pyridine ring.

(Preferred Aspect of the Group Represented by the General Formula (A))

The preferable aspect of the group represented by the general formula (A) includes a group represented by any of the general formulae (A-1), (A-2), (A-3) or (A-4).

[Chem. 84]

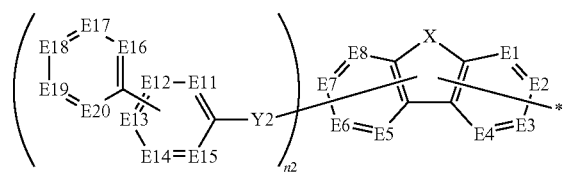

General formula (A-1)

In the general formula (A-1), X represents —N(R)—, —O—, —S— or —Si(R)(R')—, E1 to E8 each represent —C(R1)= or —N=, and R, R' and R1 each represent hydrogen atom, a substituent or a linking moiety with Y1. Y2 represents simply a bond or a divalent linking group. E11 to E20 each represent —C(R2)= or —N=, and at least one represents —N=. R2 represents hydrogen atom, a substituent or a linking moiety. However, at least one of E11 and E12 represents —C(R2)=, and R2 represents a linking moiety. n2 represents an integer of 1 to 4. The symbol * represents a linking moiety with Y1 in the general formula (12).

[Chem. 85]

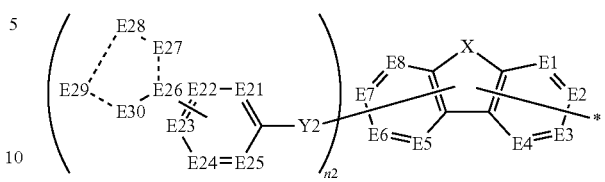

General formula (A-2)

In the general formula (A-2), X represents —N(R)—, —O—, —S— or —Si(R)(R')—, E1 to E8 each represent —C(R1)= or —N=, and R, R' and R1 each represent a hydrogen atom, a substituent or a linking moiety with Y1. Y2 represents simply a bond or a divalent linking group. E21 to E25 each represent —C(R2)= or —N=, E26 to E30 each represent —C(R2)=, —N=, —O—, —S— or —Si(R3)(R4)-, and at least one of E21 to E30 represents —N=. R2 represents hydrogen atom, a substituent or a linking moiety, and R3 and R4 each represent hydrogen atom or a substituent. However, at least one of E21 or E22 represents —C(R2)= and R2 represents a linking moiety. n2 represents an integer of 1 to 4. * represents a linking moiety with Y1 in the general formula (12).

[Chem. 86]

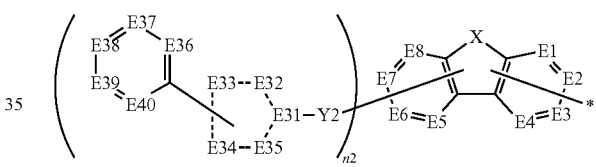

General formula (A-3)

In the general formula (A-3), X represents —N(R)—, —O—, —S— or —Si(R)(R')—, E1 to E8 each represent —C(R1)= or —N=, and R, R' and R1 each represent hydrogen atom, a substituent or a linking moiety with Y1. Y2 represents simply a bond or a divalent linking group. E31 to E35 each represent —C(R2)=, —N=, —O—, —S— or —Si(R3)(R4)-, and E36 to E40 each represent —C(R2)= or —N=, and at least one of E31 to E40 represents —N=. R2 represents hydrogen atom, a substituent or a linking moiety, and R3 and R4 each represent hydrogen atom or a substituent. However, at least one of E32 or E33 represents —C(R2)= and R2 represents a linking moiety. n2 represents an integer of 1 to 4. * represents a linking moiety with Y1 in the general formula (12).

[Chem. 87]

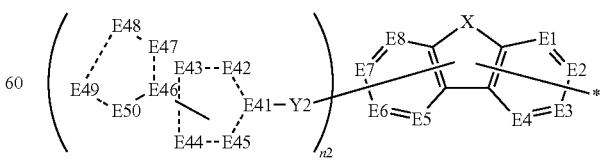

General formula (A-4)

In the general formula (A-4), X represents —N(R)—, —O—, —S— or —Si(R)(R')—, E1 to E8 each represent —C(R1)= or —N=, and R, R' and R1 each represent hydrogen atom, a substituent or a linking moiety with Y1. Y2 represents simply a bond or a divalent linking group. E41 to E50 each represent —C(R2)=, —N=, —O—, —S— or —Si(R3) (R4)-, and at least one represents —N=. R2 represents hydrogen atom, a substituent or a linking moiety, and R3 and R4 each represent hydrogen atom or a substituent. However, at least one of E42 or E43 represents —C(R2)= and R2 represents a linking moiety. n2 represents an integer of 1 to 4. * represents a linking moiety with Y1 in the general formula (12).

Hereinafter, the group represented by any of the general formulae (A-1) to (A-4) will be explained.

In —N(R)— or —Si(R)(R')— represented by X in any of the group represented by the general formulae (A-1) to (A-4), and further in —C(R1)=represented by E1 to E8, a substituent represented by each of R, R' and R1 has the same definition as the substituent represented by R11, R12 of the general formula (1).

In any of the group represented by the general formulae (A-1) to (A-4), the divalent linking group represented by Y2 has the same definition as the divalent linking group represented by Y1 of the general formula (12).

The substituent represented by R2 in —C(R2)=represented by each of E11 to E20 in the general formula (A-1), each of E21 to E30 in the general formula (A-2), each of E31 to E40 in the general formula (A-3) and each of E41 to E50 in the general formula (A-4) has the same definition as the substituent represented by R11, R12 of the general formula (1).

Next, further preferable embodiments of the compound represented by the general formula (12) according to the present invention will be explained.

[Compound Represented by the General Formula (13)]

According to the present invention, among the compounds represented by the above-mentioned general formula (12), the compound represented by the following general formula (13) is preferable. The general formula (13) includes the general formula (2) representing the compound constituting the nitrogen-containing layer 14 of the transparent electrode 10. Hereinafter, the compound represented by the general formula (13) will be explained.

[Chem. 88]

General formula (13)

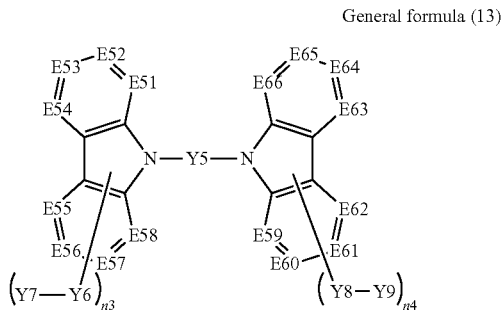

In the general formula (13), Y5 represents a divalent linking group formed of an arylene group, a heteroarylene group or a combination thereof. E51 to E66 each represent —C(R3)= or —N=, and R3 represents hydrogen atom or a substituent. Y6 to Y9 each represent a group derived from an aromatic hydrocarbon ring or a group derived from an aromatic heterocyclic ring, and at least one of Y6 or Y7 and at least one of Y8 or Y9 each represent a group derived from an aromatic heterocyclic ring containing N atom. n3 and n4 each represent an integer of 0 to 4, but n3+n4 is an integer of 2 or more.

Y5 in the general formula (13) has the same definition as Y21 in the general formula (2).

Each of E51 to E66 in the general formula (13) has the same definition as E201 to E216 in the general formula (2), and when R3 of —C(R3)=represented by each of E51 to E66 is a substituent, as examples of the substituent, one exemplified as R11, R12 of the general formula (1) is applied in the same way.

In the general formula (13), it is preferable that as groups represented by E51 to E66, six or more among E51 to E58 and six or more among E59 to E66 each represent —C(R3)=.

In the general formula (13), examples of the aromatic hydrocarbon ring which is used for the formation of a group derived from the aromatic hydrocarbon ring represented by Y6 to Y9 include benzene ring, biphenyl ring, naphthalene ring, azulene ring, anthracene ring, phenanthrene ring, pyrene ring, chrysene ring, naphthacene ring, triphenylene ring, o-terphenyl ring, m-terphenyl ring, p-terphenyl ring, acenaphthene ring, coronene ring, fluorene ring, fluoranthrene ring, naphthacene ring, pentacene ring, perylene ring, pentaphene ring, picene ring, pyrene ring, pyranthrene ring, anthranthrene ring and the like.

Furthermore, the above-described aromatic hydrocarbon ring may also have a substituent represented by R11, R12 of the general formula (1).

In the general formula (13), examples of the aromatic heterocyclic ring used for the formation of a group derived from the aromatic heterocyclic ring represented by each of Y6 to Y9 include furan ring, thiophene ring, oxazole ring, pyrrole ring, pyridine ring, pyridazine ring, pyrimidine ring, pyrazine ring, triazine ring, benzimidazole ring, oxadiazole ring, triazole ring, imidazole ring, pyrazole ring, triazole ring, indole ring, indazole ring, benzimidazole ring, benzothiazole ring, benzoxazole ring, quinoxaline ring, quinazoline ring, cinnoline ring, quinoline ring, isoquinoline ring, phthalazine ring, naphthylidine ring, carbazole ring, carboline ring, diazacarbazole ring (represents a ring obtained by further substituting, with a nitrogen atom, one of carbon atoms constituting the carboline ring), and the like.

Moreover, the above-described aromatic hydrocarbon ring may have the substituent exemplified as R11, R12 of the general formula (1).

In the general formula (13), examples of the aromatic heterocyclic ring containing N atom which is used for the formation of a group derived from the aromatic heterocyclic ring containing N atom represented by at least one of Y6 or Y7 and at least one of Y8 or Y9 include oxazole ring, pyrrole ring, pyridine ring, pyridazine ring, pyrimidine ring, pyrazine ring, triazine ring, benzimidazole ring, oxadiazole ring, triazole ring, imidazole ring, pyrazole ring, triazole ring, indole ring, indazole ring, benzimidazole ring, benzothiazole ring, benzoxazole ring, quinoxaline ring, quinazoline ring, cinnoline ring, quinoline ring, isoquinoline ring, phthalazine ring, naphthylidine ring, carbazole ring, carboline ring, diazacarbazole ring (represents a ring obtained by further substituting, with a nitrogen atom, one of carbon atoms constituting the carboline ring), and the like.

In the general formula (13), it is preferable that the group each represented by Y7, Y9 is represented by a group derived from each pyridine ring.

In addition, in the general formula (13), it is preferable that the group each represented by Y6 and Y8 is represented by a group derived from each benzene ring.

More preferable embodiment among the compounds represented by the general formula (13) as explained above includes the compound represented by the general formula (2) exemplified as the compounds constituting the nitrogen-containing layer 14 of the transparent electrode 10.

Specific examples of the compound represented by each of the above general formulae (12), (13) or the general formula (2) include the above-mentioned compounds (1 to 118).

[Blocking Layer: Positive Hole Blocking Layer, Electron Blocking Layer]

The blocking layer is provided as necessary in addition to the basic constituent layers of thin organic compound films described above. Examples thereof include a positive hole blocking layer described in documents such as Japanese Patent Application Laid-Open Publication Nos. 11-204258, 11-204359, and p. 237 of "Yuki EL Soshi To Sono Kogyoka Saizensen (Organic EL Element and Front of Industrialization thereof) (Nov. 30, 1998, published by N. T. S Co., Ltd.)", and the like.

The positive hole blocking layer has a function of the electron transport layer 22d in a broad sense. The positive hole blocking layer is formed of a positive hole blocking material having a remarkably small capability to transport positive holes while having a function of transporting electrons and can increase recombination probability of electrons and positive holes by blocking positive holes while transporting electrons. Furthermore, as necessary, the configuration of an electron transport layer 22d described below can be used as the positive hole blocking layer according to the present invention. It is preferable that the positive hole blocking layer be disposed adjacent to the light-emitting layer 22c.

On the other hand, the electron blocking layer has a function as the positive hole transport layer 22b in a broad sense. The electron blocking layer is formed of a material having a very little capability to transport electrons while having a function of transporting positive holes, and can increase the recombination probability of electrons and positive holes by blocking electrons while transporting positive holes. Furthermore, as necessary, the configuration of a positive hole transport layer 22b described below can be applied to the electron blocking layer. The thickness of the positive hole blocking layer according to the present invention is preferably 3 to 100 nm, more preferably 5 to 30 nm.

[Auxiliary Electrode]

An auxiliary electrode is provided in order to lower an electric resistance of the transparent electrode 10 and is provided in contact with the conductive layer 15 of the transparent electrode 10. As a material forming the auxiliary electrode, a metal having a low electric resistance such as gold, platinum, silver, copper or aluminum is preferable. These metals may be patterned within a range not affecting the extraction of the emitted light h from a light extraction surface 21a due to the low light transmission property. Examples of a method for forming the auxiliary electrode include the vapor deposition method, the sputtering method, the printing method, the ink-jet method, an aerosol jet method and the like. It is preferable that the line width of the auxiliary electrode is 50 µm or less in view of an aperture ratio for the light extraction, and the thickness of the auxiliary electrode is 1 µm or more in view of electric conductivity.

[Sealing Material]

A sealing material is a material for covering the organic electroluminescent element 20, and may be a plate-like (film-like) sealing member which is fixed to a transparent substrate 21 by an adhesive, or may be a sealing membrane. The sealing material is provided in a state where the terminal portions of transparent electrode 10 and the counter electrode 23 of the organic electroluminescent element 20 are exposed and at least the light-emitting functional layer 22 is covered. Alternatively, the transparent sealing material may be constituted so that an electrode is provided on the sealing material, and the electrode is electrically conducted with the terminal portions of transparent electrode 10 and the counter electrode 23 of the organic electroluminescent element 20.

Specific examples of the plate-like (film-like) transparent sealing material include a glass substrate, a polymer substrate, and the transparent sealing material may be used by making these substrates into thinner-type films. Examples of glass substrate can include particularly soda lime glass, barium strontium-containing glass, lead glass, alminosilicate glass, borosilicate glass, barium borosilicate glass, quartz and the like. In addition, examples of the polymer substrate can include polycarbonate, acryl, polyethylene terephthalate, polyethersulfide, polysulfone and the like.

Among them, from the viewpoint of thinning the element, the polymer substrate in the form of a thin film is preferably used as the sealing material.

Furthermore, the polymer substrate in the form of a thin film preferably has an oxygen transmittance measured in accordance with the method of JIS-K-7126-1987 of $1 \times 10^{-3}$ ml/(m$^2$·24 hr·atm) or less and a water vapor transmittance (25±0.5° C., relative humidity (90±2) % RH) measured in accordance with the method of JIS-K-7129-1992 of $1 \times 10^{-3}$ g/(m$^2$·24 hr) or less.

Moreover, the above substrate material may also be processed into the form of a recessed plate to thereby be used as the sealing material. In this case, processing such as sandblast processing or chemical etching processing is performed on the substrate member to thereby form recessed portions.

Not to limit to those, a metallic material may be used. Examples of the metallic material include one or more of kinds selected from the group consisting of stainless steel, iron, copper, aluminum, magnesium, nickel, zinc, chromium, titanium, molybdenum, silicon, germanium and tantalum or an alloy thereof. Since the metallic material is made thin film to be used as the sealing material, the whole of the light-emitting panel where the organic electroluminescent element is provided can be made thinner.

In addition, the adhesive for fixing the plate-like transparent sealing material to the transparent substrate 21 side is also used as a sealant for sealing the organic electroluminescent element 20 sandwiched between the sealing material and the transparent substrate 21. Examples of the adhesive can include a photo curable and thermosetting-type adhesive such as an acrylic acid-based oligomer or methacrylic acid-based oligomer having a reactive vinyl group, a moisture curable type adhesive such as 2-cyanoacrylic acid ester and the like.

In addition, examples of the adhesive can include a thermosetting or chemical curable (two liquids mixing type) adhesive such as epoxy-based adhesive. In addition, there can be included a hot-melt type adhesive such as polyamide, polyester, polyolefin, or the like. Additionally, there can be included an ultraviolet curable-type epoxy resin adhesive of cationic curable-type.

Note that there is a case in which the organic materials constituting the organic electroluminescent element 20 degrade through heat treatment. Therefore, it is preferable that the adhesive can be caused to adhere and be cured at temperatures from room temperature to 80° C. In addition, a drying agent may be dispersed in the adhesive.

Coating of the adhesive on the adhesion portion of the sealing material and the transparent substrate 21 may be carried out using a commercially available dispenser, or by printing such as screen-printing.

Furthermore, when a gap is formed among the plate-like sealing material and the transparent substrate 21 and the adhesive, it is preferable to inject an inert gas such as nitrogen or argon, or an inert liquid such as a fluorinated hydrocarbon or a silicone oil to the gap, in gaseous phase and liquid phase. In addition, it is also possible to be set vacuum. Additionally, it is also possible to enclose a hydroscopic compound into the gap.

Examples of the hydroscopic compound include, for instance, a metal oxide (for example, sodium oxide, potassium oxide, calcium oxide, barium oxide, magnesium oxide, aluminum oxide and the like), a sulfate (for example, sodium sulfate, calcium sulfate, magnesium sulfate, cobalt sulfate and the like), a metal halide (for example, calcium chloride, magnesium chloride, cesium fluoride, tantalum fluoride, cesium brominate, magnesium brominate, barium iodide, magnesium iodide and the like), a perchloric acid (for example, barium perchloric acid salt, magnesium perchloric acid salt and the like), and the like. In the sulfate, metal halide and the perchloric acid, an anhydrous salt is suitably used.

In contrast, when using the sealing layer as the sealing material, the sealing membrane is formed on the transparent substrate 21 in a state where the light-emitting functional layer 22 of the organic electroluminescent element 20 is completely covered and the terminal portions of the transparent electrode 10 and the counter electrode 23 of the organic electroluminescent element 20 are exposed.

The sealing layer is constituted using an inorganic material or an organic material. Particularly, the sealing membrane should be constituted by a material having function of suppressing the immersion of a substance which causes degradation of the light-emitting functional layer 22 in the organic electroluminescent element 20, such as moisture and oxygen. For example, an inorganic material such as silicon oxide, silicon dioxide or silicon nitride is used as such a material. Furthermore, in order to improve its fragility of the sealing layer, a lamination structure may be formed by using a layer formed of an organic material, in addition to the layer formed of the inorganic material.

The method for forming the layer is not particularly limited, and there can be used, for example, a vacuum deposition method, a sputtering method, a reactive sputtering method, a molecular beam epitaxy method, a cluster ion beam method, an ion plating method, a plasma polymerization method, an atmospheric plasma polymerization method, a plasma CVD method, a laser CVD method, a heat CVD method, a coating method, and the like.

[Protective Layer, Protective Plate]

Note that, although the illustration here is omitted, a protective layer or a protective plate may be provided by sandwiching the organic electroluminescent element EL and the sealing material between the transparent substrate 21. The protective layer or the protective plate is to mechanically protect the organic electroluminescent element EL, and particularly when the transparent sealing material is the protective layer, it is preferable to provide the protective layer or the protective plate since the mechanical protection of the organic electroluminescent element EL is not sufficient.

Examples of the protective layer or the protective plate to be applied include a glass plate, a polymer plate, a thinner polymer film, a metal plate, a thinner metal plate, or a membrane of polymer material and a membrane of metal material. Among them, from the viewpoint of light weight and small thickness, the polymer film is preferably used.

[Production Method of Organic Electroluminescent Element]

Here, as one example, the manufacturing method of the organic electroluminescent element 20 shown in FIG. 7 will be explained.

First, the low refractive index layer 12 is formed on the transparent substrate 21 in a thickness of about 90 nm. Next, the high refractive index layer 13 is formed on the low refractive index layer 12 in a thickness of about 30 nm. Next, the nitrogen-containing layer 14 is formed so that a thickness is 10 nm or less, preferably 3 nm to 5 nm. Thereafter, the conductive layer 15 made of silver (or alloy having silver as a main component) is formed so that a thickness is 4 nm to 12 nm to produce the transparent electrode 10 of the anode side on the transparent electrode 21. For the formation of the low refractive index layer 12, the high refractive index layer 13, the nitrogen-containing layer 14 and the conductive layer 15, there are employed a spin coating method, a casting method, an inkjet printing method, a vapor deposition method, a sputtering method, a printing method, and the like. From the viewpoints that a homogeneous layer can be obtained and a pinhole is hard to be generated, the vacuum deposition method is particularly preferable. In addition, before and after the formation of the conductive layer 15, occasion demand, pattern formation of an auxiliary electrode may be done.

Next, a light-emitting functional layer 22 was formed on the auxiliary electrode by the formation of a positive hole injection layer 22a, a positive hole transport layer 22b, a light-emitting layer 22c, an electron transport layer 22d and an electron injection layer 22e in the order. There are employed, for the film formation of the layers, a spin coating method, a casting method, an inkjet printing method, a vapor deposition method, a sputtering method, a printing method, and the like. From the viewpoints of obtaining a homogeneous membrane easily, of not generating a pinhole easily and the like, the vacuum deposition method or the spin coating method is particularly preferable. In addition, a different formation method may be employed to each layer. When employing the vapor deposition method for formation of each layer, although the vapor deposition conditions are varied depending on the kind of the compound to be used, it is desirable to select each condition optionally within the ranges of a heating temperature of boat for housing a compound of 50° C. to 450° C., a degree of vacuum of $10^{-6}$ Pa to $10^{-2}$ Pa, a vapor deposition rate of 0.01 nm/sec. to 50 nm/sec., a temperature of substrate of −50° C. to 300° C., and a thickness of membrane of 0.1 μm to 5 μm.

Next, a counter electrode 23 constituting a cathode is formed. At this time, pattern is formed from upper side of the light emitting functional layer 22 so that a terminal portion is pulled out from the peripheral of the transparent substrate 21, while keeping insulation state against the transparent electrode 10 by the light emitting functional layer 22.

As a result, the organic electroluminescent element 20 is obtained. Moreover, after that, there is provided the sealing material covering at least the light-emitting functional layer 22, in a state where the terminal portions of the transparent electrode 10 and the counter electrode 23 of the organic electroluminescent element 20 are exposed. At this time, the organic electroluminescent element 20 is sealed between the sealing material and the transparent substrate 21 by causing the sealing material to adhere to the transparent substrate 21 side with the adhesive.

By the above procedures, a desired organic electroluminescent element 20 is obtained on the transparent substrate 21. In the production of the organic electroluminescent element 20, although it is preferable to perform production consistently from the light-emitting functional layer 22 to the counter electrode 23 through one-time vacuum drawing, it may be possible that the transparent substrate 21 is extracted from the vacuum atmosphere to thereby be subjected to other different formation methods. At this time, it is necessary to consider that the procedures are carried out under a dry inert gas atmosphere.

In the case of applying a direct voltage to the organic electroluminescent element 20 thus obtained, while setting the conductive layer 15 of the anode as +polarity and the counter electrode 23 of the cathode as −polarity, a light emission can be observed when applying a voltage of 2 V or more to 40 V or less to the electrodes. In addition, an alternating voltage may be applied. Note that a waveform of the alternating voltage to be applied may be optional.

[Effects of Organic Electroluminescent Element]

The above-mentioned organic electroluminescent element 20 has the configuration in which the transparent electrode 10 of the present invention having both electrical conductivity and light transmission property is used as the anode, and the light-emitting functional layer 22 and the counter electrode 23 serving as the cathode are provided in this order in the portion thereof. Accordingly, while a light emission with a high luminance of the organic electroluminescent element 20 can be implemented by applying a sufficient voltage between the transparent electrode 10 and the counter electrode 23, it is possible to achieve a high luminance by enhancing an extraction efficiency of the emitted light h from the transparent electrode 10. Furthermore, it also becomes possible to achieve enhancement of emission life by reducing a driving voltage for obtaining a given luminance.

<3. Organic Electroluminescent Element (Reverse Laminate Configuration)>

[Configuration of Organic Electroluminescent Element]

Figure 8:
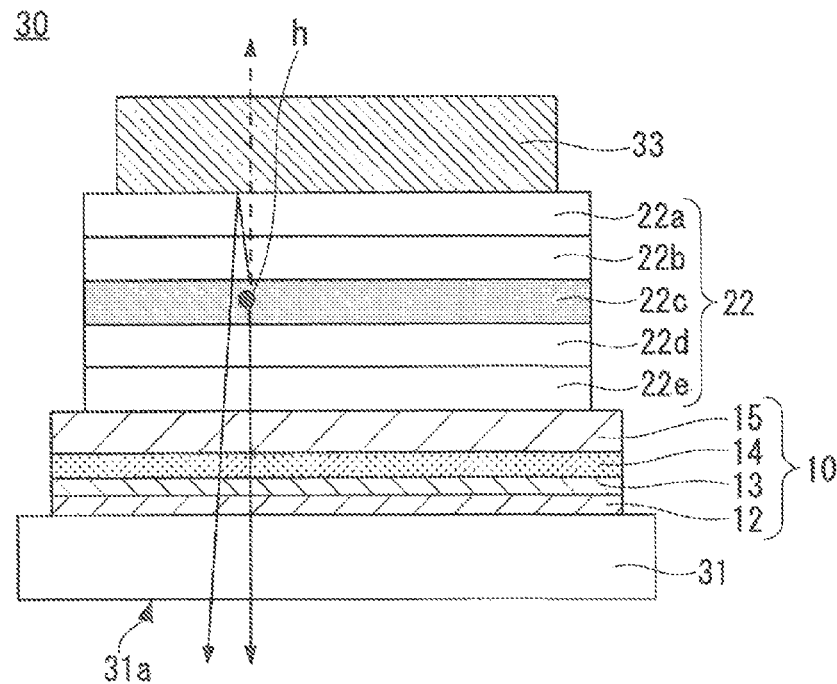
FIG. 8 is a cross-sectional view showing the configuration of the organic electroluminescent element of the embodiment.

FIG. 8 shows a cross-sectional configuration view of the second example of the organic electroluminescent element using the above-mentioned transparent electrode as one example of the electronic device according to the present invention. The organic electroluminescent element 30 of the second example shown in FIG. 8 is different from the organic electroluminescent element 20 of the first example explained using the above-described FIG. 7 in that the lamination order is reversed in such a manner that the cathode (transparent electrode 10), the light emitting functional layer 22 and the anode (counter electrode 33) are provided from the transparent substrate 31 side. Hereinafter, the repeated detailed explanation as to the same elements as the first example is omitted, and the characteristic configurations of the organic electroluminescent element 30 of the second example will be explained.

The organic electroluminescent element 30 shown in FIG. 8 is provided on the transparent substrate 31, there are laminated the transparent electrode 10 serving as a cathode, the light emitting functional layer 22 and the counter electrode 33 serving as an anode in this order, from the transparent substrate 31 side. In the construction, the distinctive feature is the use of the transparent electrode 10 of the above-described embodiment as the conductive layer on the light extraction surface 31*a* side. Accordingly, the organic electroluminescent element 30 is constituted as the bottom emission type in which emitted light h is taken out from at least the transparent substrate 31 side.

The whole layer structure of the organic electroluminescent element 30 is not limited in the same way as in the first example, and a general layer structure may be employed. The organic electroluminescent element 30 of the second case has a configuration in which the electron injection layer 22*e*/the electron transport layer 22*d*/the light emitting layer 22*c*/the positive hole transport layer 22*b*/the positive hole injection layer 22*a* are laminated in the upper portion of the transparent electrode 10 serving as a cathode, in this order, and further the counter electrode 33 serving as an anode is laminated in the upper portion thereof.

Meanwhile, various configurations are employed, as necessary, as the light-emitting functional layer 22, other than the layers in the same way as that explained in the first example, and the positive hole blocking layer and the electron blocking layer whose drawings are omitted may be provided. In the above-mentioned configurations, in the same way as in the first example, only the portion in which the light-emitting functional layer 22 is sandwiched between the transparent electrode 10 and the counter electrode 33 serves as the light-emitting region in the organic electroluminescent element 30.

Furthermore, in the above layer configuration, in the same way as in the first example, the auxiliary electrode may be provided in contact with the conductive layer 15 of the transparent electrode 10 in order to lower the electric resistance of the transparent electrode 10.

Moreover, the counter electrode 33 provided as an anode above the light-emitting functional layer 22 is made of a metal, an alloy, a conductive organic or inorganic compound, and a mixture thereof, which are the same as in the anode of the first example.

[Effects of Organic Electroluminescent Element 30]

The above-mentioned organic electroluminescent element 30 has a configuration in which the transparent electrode 10 of the present invention having both electrical conductivity and light transmission property is used as a cathode, and the light-emitting functional layer 22 and the counter electrode 33 serving as the anode are provided in the upper portion thereof. Accordingly, in the same way as in the first embodiment, while a light emission with a high luminance of the organic electroluminescent element 30 can be implemented by applying a sufficient voltage between the transparent electrode 10 and the counter electrode 33, it is possible to achieve a high luminance by enhancing an extraction efficiency of the emitted light h from the transparent electrode 10 side. Furthermore, it is also possible to achieve improvement of emission life by reducing a driving voltage for obtaining a given luminance.

Note that, although in the above-described embodiment, there is explained the configuration in which the transparent electrode formed of the low refractive index layer, the high refractive index layer, the nitrogen-containing layer and the conductive layer is applied to the organic elelctroluminescent element of the bottom emission type, the organic electroluminescent element to which the transparent electrode is applied is not limited to the bottom emission type but may have a configuration of, for example, a top emission type in which light is taken out from the counter electrode side. When the organic electroluminescent element is the top emission type, the organic electroluminescent element may have a configuration in which a transparent material is used for the counter electrode and also an opaque substrate having reflective property is used in instead of the transparent substrate, and emitted light h is taken out from the counter electrode side by reflecting on the substrate. Moreover, in the top emission type, there can be employed each of the configuration in which the transparent electrode is used as an anode as in the case of the organic electroluminescent element of the above-described first example, and the configuration in which the transparent electrode is used as a cathode as in the case of the organic electroluminescent element of the second example.

[Use of Organic Electroluminescent Element]

The organic electroluminescent elements having the above-mentioned various configurations are surface emitting elements, and thus are usable for light-emitting sources of various types. Examples include a lighting device such as a home lighting device or a car lighting device, a backlight for a timepiece or a liquid crystal, a signboard for advertisement, a light source for a signal, a light source for an optical storage medium, a light source for an electrophotographic copier, a light source for an optical communication processor, a light source for an optical sensor, and the like. The organic electroluminescent elements are not limited to these light-emitting sources and can be used as other light-emitting sources.

Particularly, the organic electroluminescent element can be effectively used as a backlight for a liquid crystal display device which is combined with a color filter and as a light source for lighting.

Furthermore, the organic electroluminescent element of each of the embodiment examples may be used as a kind of lamp such as a lighting device or an exposure light source, or may be used as a projection device of an image projecting type, or a display of a type by which a still image or moving image is visually recognized directly. In this case, a light-emitting surface area may be enlarged by so-called tiling in which light-emitting panels provided with the organic electroluminescent element are combined flatly in response to the recent increasing in size of a lighting device and a display device.

When using the organic electroluminescent element as a display device for reproducing a moving image, a driving system is either a simple matrix (passive matrix) system or active matrix system. In addition, when using two or more kinds of the organic electroluminescent element having a different emission color, it is possible to produce a color or full color display device.

Hereinafter, a lighting device will be explained as one example of the uses, and next, a lighting device having an emission area enlarged by tiling will be explained.

<4. Lighting Device>

[Lighting Device-1]

An embodiment of the lighting device of the present invention is explained. The lighting device of the embodiment is constituted by providing the organic electroluminescent element in each above-described embodiment.

An organic electroluminescent element used in the lighting device of the present embodiment may be designed so as to impart a resonator structure to the each organic electroluminescent element of the above-mentioned configuration. The objects of using the organic electroluminescent element having the resonator structure include a light source for an optical storage medium, a light source for an electrophotographic copier, a light source for an optical communication processor, a light source for an optical sensor, and the like, but is not limited thereto. Alternatively, the organic electroluminescent element may be used for the above-mentioned purpose by oscillating laser beam.

Note that the material used for the organic electroluminescent element can be applied to an organic electroluminescent element which emits a substantial white light (also referred to as white organic electroluminescent element). For example, the simultaneous emission of a plurality of luminescent colors from a plurality of light-emitting materials can also give a white color emission by color mixing. Examples of the combination of a plurality of luminescent colors may include a combination containing three maximum emission wavelengths of three primary colors of red, green and blue, or a combination containing two maximum emission wavelengths which are in a complementary color relationship such as blue and yellow, bluish green and orange, or the like.

Furthermore, combinations of light-emitting materials for obtaining a plurality of luminescent colors are either a combination of light-emitting materials which emit a plurality of phosphorescence or fluorescence, or a combination of a light-emitting material which emit a plurality of phosphorescence or fluorescence and a material of coloring matter which emits an excitation light from a light-emitting material. In the white color organic electroluminescent element, a plurality of light-emitting dopants may be combined.

The white color organic electroluminescent element has a configuration different from the configuration of obtaining a white color emission by arranging, in parallel, organic electroluminescent elements each of which emits an individual color light, in an array form, and the organic electroluminescent element itself can emit a white color light. Therefore, it is not necessary to use a mask for formation of most of layers constituting the element, and thus, for example, the electrode layer can be formed all over by a vapor deposition method, a casting method, a spin coating method, an ink-jet method, a printing method, and the like, which enhances productivity.

Furthermore, the materials to be used for the light-emitting layers of the white color organic electroluminescent element are not particularly limited, and for example, as to a backlight in a liquid crystal display element, whiting is performed by selection and combination of arbitrary materials from among the metal complexes described in the above-described embodiment of the organic electroluminescent element or well-known light-emitting materials so as to be suited to a wavelength range corresponding to a CF (color filter) property.

It is possible to produce a lighting device which emits substantial white light, by using the white color organic electroluminescent element explained above.

[Lighting Device-2]

Furthermore, the organic electroluminescent element can be used as a lighting device having an enlarged light-emitting area by, for example, using a plurality of the elements. In this case, the enlargement of the light-emitting area can be done by arranging (that is, tiling), on a support substrate, a plurality of light-emitting panels provided with the organic electroluminescent elements on a transparent substrate. The support substrate may also double as a sealing material, and the light-emitting panels are tiled in a state where the organic electroluminescent elements are sandwiched between the support substrate and a transparent electrode of the light-emitting panel. The organic electroluminescent element may be sealed by filling an adhesive between the support substrate and the transparent electrode. Note that terminals of the transparent electrode and the counter electrode are exposed around the light-emitting panel.

In the lighting device having such a configuration, a non-light-emitting region is generated between the light-emitting panels since the center region of the light-emitting panel serves as the light-emitting region. Therefore, in order to increase an amount of light to be extracted from the non-light-emitting region, a light extraction member may be provided in the non-light-emitting region of the light extraction surface. A light condensing sheet or a light diffusing sheet can be used for the light extraction member.

Example 1

Hereinafter, the present invention will be explained by referring examples, but is not limited thereto.

[Production of Transparent Electrode]

Each of transparent electrodes of Samples 101 to 143 was produced so that an area of an electrical conductivity region was 5 cm×5 cm. The following Table 2 shows the configuration of each layer in each of the transparent electrode of Samples 101 to 143.

[Production of Transparent Electrodes of Samples 101 and 102]

In the following way, a conductive layer formed of silver having a film thickness shown in Table 2 was formed on a glass substrate.

First, a transparent substrate formed of an alkali-free glass was fixed onto a substrate holder of a commercial vacuum evaporator, and then attached to a vacuum tank of the vacuum evaporator. Silver (Ag) was placed in a tungsten resistive heating boat. After reducing a pressure of the vacuum tank to $4 \times 10^{-4}$ Pa, the heating boat was heated by applying an electric current, and there was formed a conductive layer constituted of silver having each of desired thicknesses at a vapor deposition rate of 0.1 nm/sec to 0.2 nm/sec. The thickness of Sample 101 was 5 nm, and the thickness of Sample 102 was 15 nm.

[Production of Transparent Electrode of Sample 103]

In the following way, the high refractive layer made of titanium oxide ($TiO_2$) having a thickness of 30 nm was formed on the glass base material, and the conductive layer made of silver having a thickness of 5 nm was formed in the upper portion thereof.

First, a transparent substrate made of an alkali-free glass was fixed onto a substrate holder of a commercial electron beam evaporator, titanium oxide ($TiO_2$) was placed in the heating boat, and then the substrate holder and the heating boat were attached to a vacuum tank of the electron beam evaporator. In addition, silver (Ag) was placed in a tungsten resistive heating boat, and was attached to the vacuum tank of the commercial vacuum evaporator.

Next, after reducing a pressure of the vacuum tank of the electron beam evaporator to $4 \times 10^{-4}$ Pa, the heating boat obtained by placing titanium oxide ($TiO_2$) was irradiated with the electron beam for heating, and the high refractive layer made of titanium oxide having a film thickness of 30 nm was provided on the base material, at a vapor deposition rate of 0.1 nm/sec to 0.2 nm/sec.

Subsequently, the base material obtained by forming the high refractive layer was transferred to the vacuum tank of the vacuum evaporator under vacuum, and after reducing a pressure of the vacuum tank to $4 \times 10^{-4}$ Pa, the heating boat containing silver was heated by applying an electric current. Therefore, the conductive layer made of silver having a thickness of 5 nm was formed at a vapor deposition rate of 0.1 nm/sec to 0.2 nm/sec, with the result that there was obtained the transparent electrode of Sample 103 having a lamination structure of the high refractive layer and the conductive layer in the upper portion thereof.

[Production of Transparent Electrode of Sample 104 to 108]

In the following way, the high refractive layer made of titanium oxide ($TiO_2$) having a thickness of 30 nm was formed on the glass base material, and a layer (underlying layer) having a thickness of 10 nm and made of the compound shown in the following No.-1 to No.-5 was formed in the upper portion thereof, and the conductive layer made of silver having a thickness of 5 nm was formed in the upper portion thereof.

First, a transparent substrate made of an alkali-free glass was fixed onto a substrate holder of a commercial electron beam evaporator, titanium oxide ($TiO_2$) was placed in the heating boat, and then the substrate holder and the heating boat were attached to a vacuum tank of the electron beam evaporator. Next, the compound No.-1 to No.-5 was placed in a tantalum resistive heating boat, and was attached to the first vacuum tank of the vacuum evaporator. In addition, silver (Ag) was placed in the tungsten resistive heating boat, and was attached to the second vacuum tank of the vacuum evaporator.

Subsequently, after reducing a pressure of the vacuum tank of the electron beam evaporator to $4 \times 10^{-4}$ Pa, the heating boat obtained by placing each compound was irradiated with the electron beam for heating, and the high refractive layer made of titanium oxide having a thickness of 30 nm was provided on the base material, at a vapor deposition rate of 0.1 nm/sec to 0.2 nm/sec.

After that, the base material obtained by forming the high refractive layer was transferred to the first vacuum tank of the vacuum evaporator in a vacuum state, and after reducing a pressure of the first vacuum tank to $4 \times 10^{-4}$ Pa, the heating boat in which each compound was placed was heated by applying an electric current, and then, the underlying layer constituted by each compound and having the respective thicknesses of 10 nm was provided on the base material, at a vapor deposition rate of 0.1 nm/sec to 0.2 nm/sec.

Next, the base material obtained by forming the underlying layer was transferred to the second vacuum tank in a vacuum state, and after reducing a pressure of the second vacuum tank to $4 \times 10^{-4}$ Pa, the heating boat obtained by placing silver was heated by applying an electric current, and then a conductive layer made of silver having a thickness of 5 nm was formed at a vapor deposition rate of 0.1 nm/sec to 0.2 nm/sec, with the result that each of transparent electrodes of Sample 104 to 108 obtained by laminating the high refractive layer, the underlying layer and the conductive layer was obtained in this order.

Among the compounds used herein, Compounds No.-1 to No.-5 are shown in the following, and a nitrogen atom having an [effective unshared electron pair] is indicated by 0. Among them, Compound No.-1 is anthracene containing no nitrogen atom, and Compounds No.-2 to No.-5 are compound containing a nitrogen atom but has an effective unshared electron pair content [n/M] of [n/M]<$2.0 \times 10^{-3}$.

[Chem. 89]

No.-1

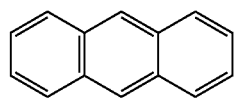

(Anthracene)

No.-2

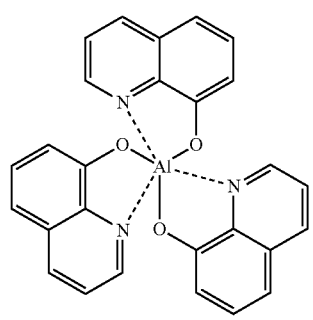

(Alq3)

No.-3

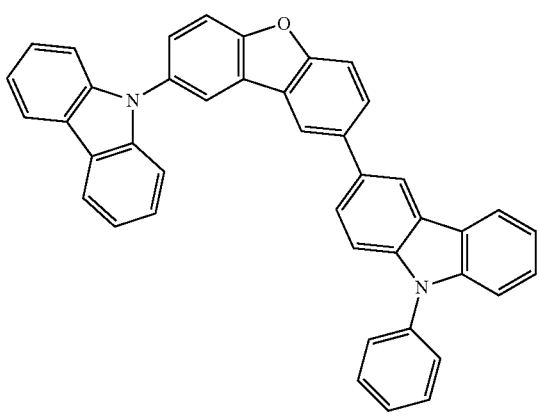

No.-4

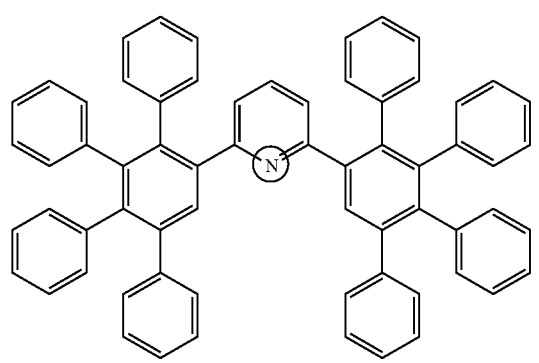

No.-5

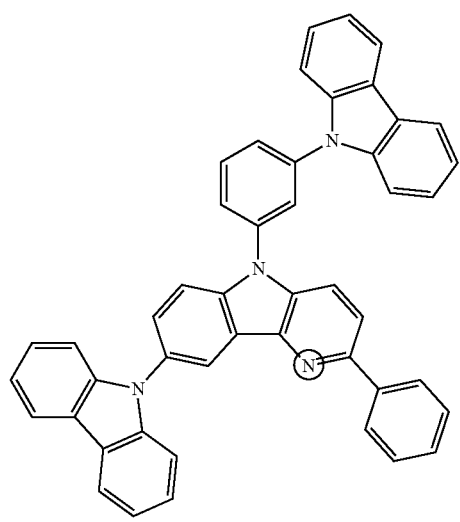

[Production of Transparent Electrode of Sample 109]

In the following way, the low refractive layer made of magnesium fluoride (MgF$_2$) having a thickness of 90 nm was formed on the glass base material, the high refractive layer made of titanium oxide (TiO$_2$) having a thickness of 30 nm was formed, and a layer having a thickness of 10 nm and made of the compound No.-1 was formed in the upper portion thereof, and the conductive layer made of silver having a thickness of 5 nm was formed in the upper portion thereof.

First, a transparent base material made of an alkali-free glass was fixed onto a substrate holder of a commercial electron beam evaporator, magnesium fluoride (MgF$_2$) was placed in the heating boat, and then the substrate holder and the heating boat were attached to a vacuum tank of the electron beam evaporator. In addition, titanium oxide (TiO$_2$) was placed in the heating boat, and then was attached to a vacuum tank of the electron beam evaporator. Next, the compound No.-1 was placed in the tantalum resistive heating boat, and was attached to the first vacuum tank of the vacuum evaporator. Additionally, silver (Ag) was placed in the tungsten resistive heating boat, and was attached to the second vacuum tank of the vacuum evaporator.

Subsequently, after reducing a pressure of the vacuum tank of the electron beam evaporator to 4×10$^{-4}$ Pa, the heating boat obtained by placing magnesium fluoride (MgF$_2$) was irradiated with the electron beam for heating, and the low refractive layer made of magnesium fluoride having a thickness of 90 nm was provided on the base material, at a vapor deposition rate of 0.1 nm/sec to 0.2 nm/sec.

Furthermore, the heating boat obtained by placing titanium oxide (TiO$_2$) was irradiated with the electron beam for heating, and the high refractive layer made of titanium oxide having a thickness of 30 nm was provided on the low refractive index layer, at a vapor deposition rate of 0.1 nm/sec to 0.2 nm/sec.

Subsequently, the base material obtained by forming the high refractive layer was transferred to the first vacuum tank of the vacuum evaporator under vacuum, and after reducing a pressure of the first vacuum tank to 4×10$^{-4}$ Pa, the heating boat obtained by placing the compound No.-1 was heated by applying an electric current, and then the underlying layer constituted of the compound No and having a thickness of 10 nm was provided on the base material at a vapor deposition rate of 0.1 nm/sec to 0.2 nm/sec.

After that, the base material obtained by forming the underlying layer was transferred to the second vacuum tank under vacuum, and after reducing a pressure of the second vacuum tank to 4×10$^{-4}$ Pa, the heating boat which contained silver was heated by applying an electric current, and then a conductive layer made of silver having a thickness of 5 nm was formed at a vapor deposition rate of 0.1 nm/sec to 0.2 nm/sec, with the result that there was obtained a transparent electrode of Sample 109 obtained by laminating the low refractive index layer, the high refractive layer, the nitrogen-containing layer and the conductive layer in this order.

[Production of Transparent Electrode of Sample 110 to 129]

Each of transparent electrodes of Samples 110 to 129 was obtained in the same procedures as in the above-described Sample 109 except that the layer formed on the high refractive index layer was the nitrogen-containing layer of the compounds No. 1 to No. 18 shown in Table 1, and was formed at a thickness shown in the following Table 2 (10 nm, 5 nm, or 3 nm).

[Production of Transparent Electrode of Sample 130 and 131]

Each transparent electrode of Sample 130 and 131 was obtained in the same procedures as in the above Sample 112 except that the thickness of the conductive layer made of silver was 8 nm. Note that, in the formation of the nitrogen-containing layer, the compound No. 7 was used in Sample 130, and the compound No. 14 was used in Sample 131.

[Production of Transparent Electrode of Sample 132]

A transparent electrode of Sample 132 was obtained in the same procedures as in the above Sample 130 except that the high refractive index layer was formed of niobium oxide (Nb$_2$O$_5$). Note that, in Sample 132, the high refractive index layer of niobium oxide ($Nb_2O_5$) was formed on the low refractive index layer by sputtering method of using niobium oxide ($Nb_2O_5$) as a target.

[Production of Transparent Electrode of Sample 133]

A transparent electrode of Sample 133 was obtained in the same procedures as in the above Sample 130 except that the high refractive index layer was constituted of zirconium oxide (ZrO).

[Production of Transparent Electrode of Sample 134]

A transparent electrode of Sample 134 was obtained in the same procedures as in the above Sample 130 except that the high refractive index layer was constituted of cadmium oxide (CdO).

[Production of Transparent Electrode of Sample 135]

A transparent electrode of Sample 135 was obtained in the same procedures as in the above Sample 130 except that the high refractive index layer was constituted of indium tin oxide (ITO). Note that, in Sample 135 the high refractive index layer of ITO was formed on the low refractive index layer by sputtering method of using ITO as a target.

[Production of Transparent Electrode of Sample 136]

A transparent electrode of Sample 136 was obtained in the same procedures as in the above Sample 132 except that the low refractive index layer was constituted of lithium fluoride (LiF).

[Production of Transparent Electrode of Sample 137]

A transparent electrode of Sample 137 was obtained in the same procedures as in the above Sample 132 except that the low refractive index layer was constituted of calcium fluoride ($CaF_2$).

[Production of Transparent Electrode of Sample 138]

A transparent electrode of Sample 138 was obtained in the same procedures as in the above Sample 132 except that the low refractive index layer was constituted of aluminum fluoride ($AlF_2$).

[Production of Transparent Electrode of Sample 139]

A transparent electrode of Sample 139 was obtained in the same procedures as in the above Sample 132 except that a polyethylene terephthalate (PET) was used as the base material.

[Production of Transparent Electrode of Sample 140]

A transparent electrode of Sample 140 was obtained in the same procedures as in the above Sample 139 except that the nitrogen-containing layer was constituted using the compound No. 14.

[Production of Transparent Electrode of Sample 141]

A transparent electrode of Sample 141 was obtained in the same procedures as in the above Sample 112 except that the layer formed on the high refractive index layer was the nitrogen-containing layer of the compound No. 48 shown in Table 1.

[Production of Transparent Electrode of Sample 142]

A transparent electrode of Sample 142 was obtained in the same procedures as in the above Sample 112 except that the layer formed on the high refractive index layer was the nitrogen-containing layer of the compound No. 46 shown in Table 1.

[Production of Transparent Electrode of Sample 143]

A transparent electrode of Sample 143 was obtained in the same procedures as in the above Sample 112 except that the layer formed on the high refractive index layer was the nitrogen-containing layer of the compound No. 47 shown in Table 1.

[Evaluation of Each Sample in EXAMPLE 1]

With respect to each of the transparent electrodes of Sample 101 to 143 produced above, a light transmittance and a sheet resistance value were measured. The light transmittance was measured at a wavelength of 550 nm, by using a spectrophotometer (U-3300 manufactured by HITACHI) and was carried out by using a baseline of a base material used in the same way for the sample. The sheet resistance value was measured by using a resistivity meter (MCP-T610 manufactured by MITSUBISHI CHEMICALS), and carried out by 4 terminals 4 probes method constant current applying system. The results are shown in the following Table 2 together.

Note that the compound No. 1 to No. 18 and compound No. 46 to No. 48 used in the above samples are the exemplified compounds in the prior embodiment, shown that the effective unshared electron pair content [n/M] is $[n/M] \geq 2.0 \times 10^{-3}$. In the following Table 2, the number [n] of effective unshared electron pair, a molecular weight [M] and also an effective unshared electron pair content [n/M] of the compounds used are shown.

TABLE 2

| | | CONFIGURATION OF EXAMPLE TRANSPARENT ELECTRODE | | | | | | |
|---|---|---|---|---|---|---|---|---|
| | | LOW REFRACTIVE INDEX LAYER | | HIGH REFRACTIVE INDEX LAYER | | LAYER HAVING COMPOUND CONTAINING NITROGEN ATOM | | |
| EXAMPLE NO. | SUBSTRATE MATERIAL | COMPOUND | LAYER THICKNESS NM | COMPOUND | LAYER THICKNESS NM | COMPOUND | LAYER THICKNESS NM | NUMBER (N) OF EFFECTIVE UNSHARED ELECTRON PAIRS |
| 101 | GLASS | — | — | — | — | — | — | — |
| 102 | ↓ | — | — | — | — | — | — | — |
| 103 | ↓ | — | — | $TiO_2$ | 30 | — | — | — |
| 104 | ↓ | — | — | ↓ | ↓ | No. −1 | 10 | 0 |
| 105 | ↓ | — | — | ↓ | ↓ | No. −2 | ↓ | 0 |
| 106 | ↓ | — | — | ↓ | ↓ | No. −3 | ↓ | 0 |
| 107 | ↓ | — | — | ↓ | ↓ | No. −4 | ↓ | 1 |
| 108 | ↓ | — | — | ↓ | ↓ | No. −5 | ↓ | 1 |
| 109 | ↓ | $MgF_2$ | 90 | ↓ | ↓ | No. −1 | 10 | 0 |
| 110 | ↓ | ↓ | ↓ | ↓ | ↓ | No. 1 | ↓ | 1 |
| 111 | ↓ | ↓ | ↓ | ↓ | ↓ | ↓ | 5 | 1 |
| 112 | ↓ | ↓ | ↓ | ↓ | ↓ | ↓ | 3 | 1 |
| 113 | ↓ | ↓ | ↓ | ↓ | ↓ | No. 2 | ↓ | 2 |
| 114 | ↓ | ↓ | ↓ | ↓ | ↓ | No. 3 | ↓ | 2 |
| 115 | ↓ | ↓ | ↓ | ↓ | ↓ | No. 4 | ↓ | 2 |
| 116 | ↓ | ↓ | ↓ | ↓ | ↓ | No. 5 | ↓ | 3 |
| 117 | ↓ | ↓ | ↓ | ↓ | ↓ | No. 6 | ↓ | 3 |

TABLE 2-continued

| 118 | ↓ | ↓ | ↓ | ↓ | ↓ | No. 7 | ↓ | 4 |
|---|---|---|---|---|---|---|---|---|
| 119 | ↓ | ↓ | ↓ | ↓ | ↓ | No. 8 | ↓ | 6 |
| 120 | ↓ | ↓ | ↓ | ↓ | ↓ | No. 9 | ↓ | 4 |
| 121 | ↓ | ↓ | ↓ | ↓ | ↓ | No. 10 | ↓ | 4 |
| 122 | ↓ | ↓ | ↓ | ↓ | ↓ | No. 11 | ↓ | 5 |
| 123 | ↓ | ↓ | ↓ | ↓ | ↓ | No. 12 | ↓ | 8 |
| 124 | ↓ | ↓ | ↓ | ↓ | ↓ | No. 13 | ↓ | 4 |
| 125 | ↓ | ↓ | ↓ | ↓ | ↓ | No. 14 | ↓ | 5 |
| 126 | ↓ | ↓ | ↓ | ↓ | ↓ | No. 15 | ↓ | 5 |
| 127 | ↓ | ↓ | ↓ | ↓ | ↓ | No. 16 | ↓ | 6 |
| 128 | ↓ | ↓ | ↓ | ↓ | ↓ | No. 17 | ↓ | 9 |
| 129 | ↓ | ↓ | ↓ | ↓ | ↓ | No. 18 | ↓ | 6 |
| 130 | ↓ | ↓ | ↓ | ↓ | ↓ | No. 7 | ↓ | 4 |
| 131 | ↓ | ↓ | ↓ | ↓ | ↓ | No. 14 | ↓ | 6 |
| 132 | ↓ | ↓ | ↓ | $Nb_2O_5$ | ↓ | No. 7 | ↓ | 4 |
| 133 | ↓ | ↓ | ↓ | ZrO | ↓ | No. 7 | ↓ | 4 |
| 134 | ↓ | ↓ | ↓ | CdO | ↓ | No. 7 | ↓ | 4 |
| 135 | ↓ | ↓ | ↓ | ITO | ↓ | No. 7 | ↓ | 4 |
| 136 | ↓ | LiF | ↓ | $Nb_2O_5$ | ↓ | No. 7 | ↓ | 4 |
| 137 | ↓ | $CaF_2$ | ↓ | ↓ | ↓ | No. 7 | ↓ | 4 |
| 138 | ↓ | $AlF_3$ | ↓ | ↓ | ↓ | No. 7 | ↓ | 4 |
| 139 | PET | $MgF_2$ | ↓ | $Nb_2O_5$ | ↓ | No. 7 | ↓ | 4 |
| 140 | ↓ | ↓ | ↓ | ↓ | ↓ | No. 14 | ↓ | 5 |
| 141 | GLASS | $MgF_2$ | 90 | $TiO_2$ | 30 | No. 48 | 3 | 6 |
| 142 | ↓ | ↓ | ↓ | ↓ | ↓ | No. 46 | ↓ | 3 |
| 143 | ↓ | ↓ | ↓ | ↓ | ↓ | No. 47 | ↓ | 3 |

| | CONFIGURATION OF EXAMPLE TRANSPARENT ELECTRODE | | | | | | |
|---|---|---|---|---|---|---|---|
| | LAYER HAVING COMPOUND CONTAINING NITROGEN ATOM | | CONDUCTIVE LAYER | | RESULT OF EVALUATION | | |
| EXAMPLE NO. | MOLECULAR WEIGHT [M] | [N/M] | COMPOUND | LAYER THICKNESS NM | TRANSMITTANCE % (550 NM) | SURFACE RESISTANCE Ω/SQ | NOTE |
| 101 | — | — | Ag | 5 | 45 | CANNOT BE MEASURED | COMPARATIVE |
| 102 | — | — | ↓ | 15 | 25 | 5.0 | COMPARATIVE |
| 103 | — | — | ↓ | 5 | 48 | CANNOT BE MEASURED | COMPARATIVE |
| 104 | 178.23 | 0.0E+00 | ↓ | ↓ | 45 | CANNOT BE MEASURED | COMPARATIVE |
| 105 | 459.44 | 0.0E+00 | ↓ | ↓ | 50 | CANNOT BE MEASURED | COMPARATIVE |
| 106 | 574.67 | 0.0E+00 | ↓ | ↓ | 46 | CANNOT BE MEASURED | COMPARATIVE |
| 107 | 839.00 | 1.2E−03 | ↓ | ↓ | 47 | CANNOT BE MEASURED | COMPARATIVE |
| 108 | 650.77 | 1.5E−03 | ↓ | ↓ | 48 | CANNOT BE MEASURED | COMPARATIVE |
| 109 | 178.23 | 0.0E+00 | ↓ | ↓ | 40 | CANNOT BE MEASURED | COMPARATIVE |
| 110 | 500.55 | 2.0E−03 | ↓ | ↓ | 60 | 270 | PRESENT INVENTION |
| 111 | 500.55 | 2.0E−03 | ↓ | ↓ | 65 | 269 | PRESENT INVENTION |
| 112 | 500.55 | 2.0E−03 | ↓ | ↓ | 68 | 258 | PRESENT INVENTION |
| 113 | 790.95 | 2.5E−03 | ↓ | ↓ | 71 | 246 | PRESENT INVENTION |
| 114 | 655.81 | 3.0E−03 | ↓ | ↓ | 72 | 200 | PRESENT INVENTION |
| 115 | 655.81 | 3.0E−03 | ↓ | ↓ | 73 | 180 | PRESENT INVENTION |
| 116 | 974.18 | 3.1E−03 | ↓ | ↓ | 76 | 150 | PRESENT INVENTION |
| 117 | 808.99 | 3.7E−03 | ↓ | ↓ | 78 | 100 | PRESENT INVENTION |
| 118 | 716.83 | 5.6E−03 | ↓ | ↓ | >80 | 25.0 | PRESENT INVENTION |
| 119 | 1036.19 | 5.8E−03 | ↓ | ↓ | >80 | 23.8 | PRESENT INVENTION |
| 120 | 551.64 | 7.3E−03 | ↓ | ↓ | >80 | 22.5 | PRESENT INVENTION |
| 121 | 516.60 | 7.7E−03 | ↓ | ↓ | >80 | 20.2 | PRESENT INVENTION |
| 122 | 539.63 | 9.3E−03 | ↓ | ↓ | >80 | 19.0 | PRESENT INVENTION |
| 123 | 646.76 | 9.3E−03 | ↓ | ↓ | >80 | 19.5 | PRESENT INVENTION |
| 124 | 412.45 | 9.7E−03 | ↓ | ↓ | >80 | 18.7 | PRESENT INVENTION |
| 125 | 616.71 | 9.7E−03 | ↓ | ↓ | >80 | 18.5 | PRESENT INVENTION |
| 126 | 463.53 | 1.1E−02 | ↓ | ↓ | >80 | 16.0 | PRESENT INVENTION |
| 127 | 540.62 | 1.1E−02 | ↓ | ↓ | >80 | 15.0 | PRESENT INVENTION |
| 128 | 543.58 | 1.7E−02 | ↓ | ↓ | >80 | 14.0 | PRESENT INVENTION |
| 129 | 312.30 | 1.9E−02 | ↓ | ↓ | >80 | 12.0 | PRESENT INVENTION |
| 130 | 716.83 | 5.6E−03 | ↓ | 8 | >80 | 9.5 | PRESENT INVENTION |
| 131 | 616.71 | 9.7E−03 | ↓ | ↓ | >80 | 9.8 | PRESENT INVENTION |
| 132 | 716.83 | 5.6E−03 | ↓ | ↓ | >80 | 9.5 | PRESENT INVENTION |
| 133 | 716.83 | 5.6E−03 | ↓ | ↓ | 78 | 9.5 | PRESENT INVENTION |
| 134 | 716.83 | 5.6E−03 | ↓ | ↓ | 78 | 9.5 | PRESENT INVENTION |
| 135 | 716.83 | 5.6E−03 | ↓ | ↓ | 55 | 9.4 | PRESENT INVENTION |

TABLE 2-continued

| 136 | 716.83 | 5.6E-03 | ↓ | ↓ | >80 | 9.8 | PRESENT INVENTION |
|---|---|---|---|---|---|---|---|
| 137 | 716.83 | 5.6E-03 | ↓ | ↓ | >80 | 9.7 | PRESENT INVENTION |
| 138 | 716.83 | 5.6E-03 | ↓ | ↓ | >80 | 9.8 | PRESENT INVENTION |
| 139 | 716.83 | 5.6E-03 | ↓ | ↓ | >80 | 15.0 | PRESENT INVENTION |
| 140 | 616.71 | 9.7E-03 | ↓ | ↓ | >80 | 18.0 | PRESENT INVENTION |
| 141 | 379.38 | 1.6E-02 | Ag | 5 | >80 | 10.5 | PRESENT INVENTION |
| 142 | 576.65 | 5.2E-03 | ↓ | ↓ | >80 | 10.3 | PRESENT INVENTION |
| 143 | 545.55 | 5.5E-03 | ↓ | ↓ | >80 | 10.8 | PRESENT INVENTION |

[Results of Evaluation of EXAMPLE 1]

As is clear from Table 2, with respect to the transparent electrodes of Samples 110 to 143 in which the nitrogen-containing layer was constituted by using Compound No. 1 to No. 18 and compound No. 46 to No. 48 having the effective unshared electron pair content [n/M] within the predetermined range of $2.0 \times 10^{-3} \leq [n/M] \leq 1.9 \times 10^{-2}$, even if the conductive layer obtained by using silver and having a role of substantial electrical conductivity was a very thin layer of 5 nm or 8 nm, the sheet resistance was able to be measured, and it has been confirmed that the layer is formed at an approximately uniform thickness through the monolayer growth type (Frank-van der Merwe: FM type).

In contrast, with respect to Sample 101 having only mono-layer structure of the conductive layer, and the transparent electrode of Sample 103 formed without a nitrogen-containing layer and having a structure obtained by laminating the conductive layer in the upper portion of the high refractive index layer, the sheet resistance cannot be measured, and thus the use as an electrode is not possible. In addition, also with respect to the transparent electrode of Sample 104 to 108 obtained by constituting the nitrogen-containing layer by using Compound No.-1 to No.-5 of $2.0 \times 10^{-3} > [n/M]$, the sheet resistance cannot be measured, and thus the use as an electrode is not possible. Furthermore, also with respect to Sample 109 having the low refractive index layer and the high refractive index layer, but using Compound No.-1 of $2.0 \times 10^{-3} > [n/M]$ as the nitrogen-containing layer, the sheet resistance cannot be measured, and thus the use as an electrode is not possible.

Additionally, with respect to Sample 102 in which a nitrogen-containing layer such as a nitrogen-containing layer was not provided, the conductive layer had a large thickness of 15 nm, and thus a light transmittance is low although the sheet resistance is low, and the use as a transparent electrode is not possible.

As described above, it has been confirmed that the transparent electrodes of Samples 110 to 143 having the effective unshared electron pair content [n/M] within the predetermined range also have a light transmission of 50% or more, and can be used as the transparent electrode. The same results were obtained with respect to the glass substrate and the plastic materials (PET) substrate. Furthermore, with respect to the transparent electrodes of Samples 110 to 143, even if the conductive layer had a thickness of 5 nm or 8 nm, the light transmittance was maintained at a high value of about 70%. Moreover, the lowering of the sheet resistance of the conductive layer was confirmed due to enlargement of the thickness from 5 nm to 8 nm. Therefore, in the transparent electrodes of Samples 110 to 143, it was confirmed that the enhancement of the light transmission property and the enhancement of the electric conductivity were achieved at the same time.

In addition, with respect to the transparent electrodes of Sample 110 to 112 being different only in the thicknesses of the nitrogen-containing layer, it was confirmed that when the thickness of the nitrogen-containing layer became smaller, the light transmittance was high and the sheet resistance was low.

Additionally, with respect to the transparent electrodes of Sample 130, and 132 to 135 which were different only in the compound used for the high refractive layer, the refractive index of each of the compounds is n=2.3 to 2.4 in the case of $TiO_2$, n=2.3 in the case of $Nb_2O_5$, n=2.49 in the case of CdO, and n=2.1 to 2.2 in the case of ITO. As described above, every compound has a higher refractive index than the nitrogen-containing layer (n=1.7 to 1.8) by 0.3 or more. Accordingly, in Sample 130, 132 to 134, it was confirmed that the light transmittance was kept 70% or more, and the sheet resistance value was kept as low as one digit. In addition, with respect to Sample 135, a sufficiently low sheet resistance was confirmed although the transmittance was low because the light transmittance of the ITO is lower than the other materials.

In addition, with respect to the transparent electrodes of Sample 132, 136 to 138 which were different only in the compound used for the low refractive layer, the refractive index of each of the compounds is n=1.37 in the case of $MgF_2$, n=1.39 in the case of LiF, n=1.43 in the case of $CaF_2$, and n=1.38 in the case of $AlF_3$. As described above, each compound has a lower refractive index than the high refractive index layer ($Nb_2O_5$, n=2.3), and thus it was confirmed that the light transmittance was kept 80% or more, and the sheet resistance value was kept as low as one digit.

Furthermore, with respect to the transparent electrode of Sample 142, the nitrogen-containing layer was formed by using the compound No. 47 having a nitro group, and it was confirmed that results excellent in light transmittance and sheet resistance were obtained. Accordingly, it was confirmed that the unshared electron pair of the nitro group (—$NO_2$) is utilized for resonance structure, but is an unshared electron pair which is not involved in aromaticity and which is not coordinated to a metal, and exerts effects on bonding to silver (Ag) as the "effective unshared electron pair".

From the above results, it was confirmed that the low resistive electrode layer (namely, the transparent electrode) despite having a small layer thickness for obtaining a light transmittance property was obtained by selecting and using the compound which constitutes the nitrogen-containing layer provided in contact with the conductive layer by using the effective unshared electron pair content [n/M] as an indicator.

Example 2

[Production of Bottom Emission Type Organic Electroluminescent Element]

Figure 9:
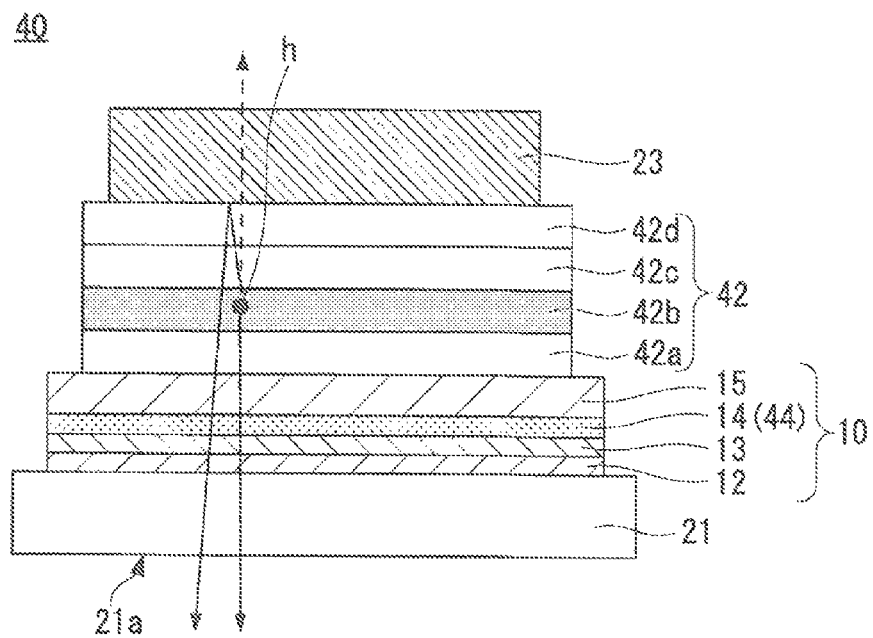
FIG. 9 is a cross-sectional view showing the configuration of the organic electroluminescent element of an Example.

There was produced a bottom emission-type organic electroluminescent element obtained by providing each transparent electrode having the configuration produced in EXAMPLE 1 under the light-emitting functional layer as an anode. The production procedures are explained by referring to FIG. 9. Note that the following Table 3 shows the configuration of the transparent electrode used in the organic electroluminescent element of Samples 201 to 235.

[Production Procedures of Organic Electroluminescent Elements of Samples 201 and 202]

(Conductive Layer of Transparent Electrode: Formation of Anode)

First, in the production of Samples 201 and 202, a conductive layer 15 made of silver was formed at a thickness of 5 nm or 15 nm in the upper portion of a transparent electrode 21 made of a transparent substrate made of an alkali-free glass. Each conductive layer 15 was formed in the same procedures as in Samples 101 and 102 of EXAMPLE 1.

(Formation of Positive Hole Transport-Injection Layer)

First, the heating boat in which α-NPD represented by the following structural formula was placed as a positive hole transport injection material was heated by applying an electric current, and thus the positive hole transport-injection layer 42a constituted of α-NPD and combining the positive hole injection layer with the positive hole transport layer was formed on the transparent electrode 10. At this time, the vapor deposition rate was 0.1 nm/sec to 0.2 nm/sec, and the thickness was 20 nm.

[Chem. 90]

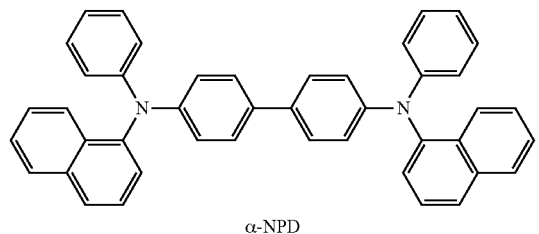

α-NPD (Formation of Light-Emitting Layer)

Next, the heating boat in which the host material H4 previously represented by the structural formula was placed and the heating boat in which the phosphorescence-emitting compound Ir-4 previously represented by the structural formula was placed were independently heated by applying an electric current, and the light-emitting layer 42b constituted of the host material H4 and the phosphorescence-emitting compound Ir-4 were formed on the positive hole transport-injection layer 42a. At that time, the current to be applied was controlled so that the vapor deposition rate of the host material H4:the phosphorescence-emitting compound Ir-4=100:6 holds. The film thickness was set to be 30 nm.

(Formation of Positive Hole Blocking Layer)

Next, the heating boat in which BAlq represented by the following structural formula was placed as a positive hole block material was heated by applying an electric current, and thus the positive hole blocking layer 42c constituted of BAlq was formed on the light-emitting layer 42b. At this time, the vapor deposition rate was set to be 0.1 nm/sec to 0.2 nm/sec, and the thickness was set to be 10 nm.

[Chem. 91]

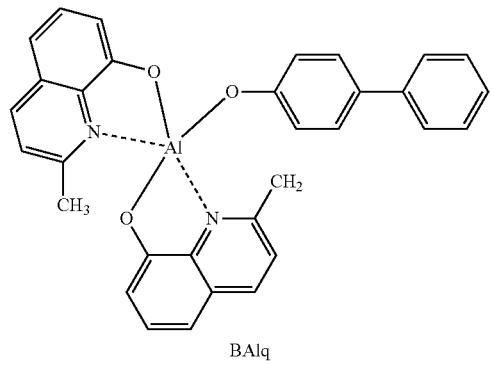

BAlq (Formation of Electron Transport-Injection Layer)

After that, the heating boat in which Compound 10 represented by the structural formula before as the electron transport material was placed and the heating boat in which potassium fluoride was placed were independently heated by applying an electric current, and thus the electron transport-injection layer 42d constituted of Compound 10 and the potassium fluoride, and combining electron transport layer with the electron injection layer was formed on the positive hole blocking layer 42c. At that time, the current to be applied was controlled so that the vapor deposition rate of Compound 10:the potassium fluoride=75:25 holds. In addition, the thickness was set to be 30 nm. Note that Compound 10 is also Compound No. 7 which has the effective unshared electron pair content [n/M] within the predetermined range.

(Counter Electrode: Formation of Cathode)

Next, the transparent substrate 21 obtained by forming the light-emitting functional layer 42 was transferred to the vacuum tank of the vacuum evaporator, and after reducing a pressure of the vacuum tank to $4 \times 10^{-4}$ Pa, the heating boat provided in the vacuum tank and containing aluminum was heated by applying an electric current. Thereby, a counter electrode 23 of aluminum having a thickness of 100 nm was formed at a vapor deposition rate of 0.3 nm/sec. The counter electrode 23 is used as a cathode. According to the above procedures, an organic electroluminescent element 40 of bottom emission type was formed on the transparent substrate 21.

(Sealing of Element)

After that, the organic electroluminescent element 40 was covered by a sealing material formed of a glass substrate having a thickness of 300 μm, and an adhesive (sealing material) was filled in the space between the transparent sealing material and the transparent substrate 21 in a state of covering the organic electroluminescent element 40. An epoxy-based photocurable adhesive (Lackstrack LC0629B manufactured by TOAGOSEI) was used as the adhesive. The adhesive filled in the space between the transparent sealing material and the transparent substrate 21 was irradiated with UV light from the glass substrate (sealing material) side, the organic electroluminescent element 40 was sealed by curing the adhesive.

Note that, in the formation of the organic electroluminescent element 40, by using a vapor deposition mask for forming each layer, 4.5 cm×4.5 cm in the center of the transparent substrate 21 of 5 cm×5 cm was set as a light-emitting region A, and a non-light-emitting region B was provided around the whole peripheral of the light-emitting region A with a width of 0.25 cm. Furthermore, the conductive layer 15 of the transparent electrode 10 of an anode and the counter electrode 23 of a cathode were formed in a state of being insulated by the positive hole transport-injection layer 42a to the elevctron transport-injection layer 42d, and in the form of pulling out the terminal portion to the peripheral of the transparent substrate 21.

As described above, each of the light-emitting panels of the organic electroluminescent element of Samples 201 and 202 was obtained by providing the organic electroluminescent element 40 on the transparent substrate 21, and sealing with the transparent sealing material and the adhesive. In the respective light-emitting panel, the emitted light h of each color generated in the light-emitting layer 42b was extracted from the transparent substrate 21 side.

[Production Procedures of Organic Electroluminescent Element of Sample 203]

(Formation of High Refractive Index Layer of Transparent Electrode)

First, in the production of Sample 203, a high refractive index layer 13 made of titanium oxide was formed at a thickness of 30 nm in the upper portion of a transparent substrate 21 made of an alkali-free glass. In this case, the high refractive index layer 13 was formed in the same procedure as in Sample 103 of EXAMPLE 1.

(Conductive Layer of Transparent Electrode: Formation of Anode)

Next, a conductive layer 15 formed of silver and having a thickness of 5 nm was formed on the high refractive index layer 13 in the same way as in Sample 103 of EXAMPLE 1. This conductive layer 15 was used as an anode.

In the following, in the same way as in Samples 201 and 202, a positive hole transport injection layer 42a to an electron transport injection layer 42d were formed on the transparent electrode 10, and then a counter electrode 23 (cathode) were formed. Thereby, an organic electroluminescent element 40 of bottom emission type was formed on the transparent substrate 21. Subsequently, in the same way as in Sample 201, 202, the organic electroluminescent element 40 was sealed by a sealing material and an adhesive to obtain a light-emitting panel of the organic electroluminescent element of Sample 303. In the each of light-emitting panels, the emitted light h of each color generated in the light emitting layer 42b was taken out from the transparent substrate 21 side.

[Production Procedures of Organic Electroluminescent Elements of Samples 204 and 205]

(Formation of High Refractive Index Layer of Transparent Electrode)

First, in the production of Samples 204 and 205, a high refractive index layer 13 made of titanium oxide was formed at a thickness of 30 nm in the upper portion of a transparent substrate 21 made of an alkali-free glass. At this time, the high refractive index layer 13 was formed in the same procedures as in Samples 104 and 107 of EXAMPLE 1.

(Formation of Underlying Layer of Transparent Electrode)

Next, an underlying layer 44 made of each compound was formed at a thickness of 10 nm in the upper portion of the high refractive index layer 13. The underlying layer 44 was formed in the same procedures as in Samples 104 and 107 of EXAMPLE 1.

(Conductive Layer of Transparent Electrode: Formation of Anode)

Next, a conductive layer 15 formed of silver and having a thickness of 5 nm was formed on the underlying layer 44 in the same way as in Samples 104 and 107 of EXAMPLE 1. This conductive layer 15 was used as an anode.

In the following, in the same way as in Sample 201, a positive hole transport injection layer 42a to an electron transport injection layer 42d were formed on the transparent electrode 10, and furthermore, a counter electrode 23 (cathode) was formed. Thereby, an organic electroluminescent element 40 of bottom emission type was formed on the transparent substrate 21. Subsequently, in the same way as in Sample 201, the organic electroluminescent element 40 was sealed by a sealing material and an adhesive, with the result that a light-emitting panel of the organic electroluminescent element of each of Samples 204 and 205 was obtained.

[Production Procedures of Organic Electroluminescent Element of Sample 206]

(Formation of Low Refractive Index Layer of Transparent Electrode)

First, in the production of Sample 206, a low refractive index layer 12 made of magnesium fluoride was formed at a thickness of 90 nm in the upper portion of a transparent substrate 21 made of an alkali-free glass. At this time, the low refractive index layer 12 was formed in the same procedure as in Sample 109 of EXAMPLE 1.

(Formation of High Refractive Index Layer of Transparent Electrode)

Next, a high refractive index layer 13 made of titanium oxide was formed at a thickness of 30 nm in the upper portion of the low refractive index layer 12. In this case, the high refractive index layer 13 was formed in the same procedure as in Sample 109 of EXAMPLE 1.

(Formation of Underlying Layer of Transparent Electrode)

Subsequently, an underlying layer 44 made of each compound was formed at a thickness of 10 nm in the upper portion of the high refractive index layer 13. The underlying layer 44 was formed in the same procedure as in Sample 109 of EXAMPLE 1.

(Conductive Layer of Transparent Electrode: Formation of Anode)

Next, a conductive layer 15 formed of silver and having a thickness of 5 nm was formed on the underlying layer 44 in the same way as in Sample 109 of EXAMPLE 1. This conductive layer 15 was used as an anode.

In the following, in the same way as in Sample 201, a positive hole transport injection layer 42a to an electron transport injection layer 42d were formed on the transparent electrode 10, and furthermore, a counter electrode 23 (cathode) was formed. Thereby, an organic electroluminescent element 40 of bottom emission type was formed on the transparent substrate 21. Subsequently, in the same way as in Sample 201, the organic electroluminescent element 40 was sealed by a sealing material and an adhesive, with the result that a light-emitting panel of the organic electroluminescent element of Sample 206 was obtained.

(Production Procedures of Organic Electroluminescent Elements of Samples 207 to 209]

(Formation of Low Refractive Index Layer of Transparent Electrode)

First, in the production of Samples 207 to 209, a low refractive index layer 12 made of magnesium fluoride was formed at a thickness of 90 nm in the upper portion of a transparent substrate 21 made of an alkali-free glass. In this case, the low refractive index layer 12 was formed in the same procedures as in Samples 110 to 112 of EXAMPLE 1.

(Formation of High Refractive Index Layer of Transparent Electrode)

Next, a high refractive index layer 13 made of titanium oxide was formed at a thickness of 30 nm in the upper portion of the low refractive index layer 12. In this case, the high refractive index layer 13 was formed in the same procedures as in Samples 110 to 112 of EXAMPLE 1.

(Formation of Nitrogen-Containing Layer of Transparent Electrode)

Subsequently, a nitrogen-containing layer 14 made of each compound was formed at a thickness of 10 nm, 5 nm or 3 nm in the upper portion of the high refractive index layer 13. The nitrogen-containing layer 14 was formed in the same procedures as in Samples 110 to 112 of EXAMPLE 1.

(Conductive Layer of Transparent Electrode: Formation of Anode)

Then, a conductive layer 15 formed of silver and having a thickness of 5 nm was formed on nitrogen-containing layer 14 in the same way as in Samples 110 to 112 of EXAMPLE 1. This conductive layer 15 was used as an anode.

In the following, in the same way as in Sample 201, a positive hole transport injection layer 42a to an electron transport injection layer 42d were formed on the transparent electrode 10, and furthermore, a counter electrode 23 (cathode) was formed. Thereby, an organic electroluminescent element 40 of bottom emission type was formed on the transparent substrate 21. Subsequently, in the same way as in Sample 201, the organic electroluminescent element 40 was sealed by a sealing material and an adhesive, with the result that a light-emitting panel of the organic electroluminescent element of each of Samples 207 to 209 was obtained.

[Production Procedures of Organic Electroluminescent Elements of Samples 210 to 225]

(Formation of Low Refractive Index Layer of Transparent Electrode)

First, in the production of Samples 210 to 225, a low refractive index layer 12 made of magnesium fluoride was formed at a thickness of 90 nm in the upper portion of a transparent substrate 21 made of an alkali-free glass. In this case, the low refractive index layer 12 was formed in the same procedures as in Samples 114 to 129 of EXAMPLE 1.

(Formation of High Refractive Index Layer of Transparent Electrode)

Next, a high refractive index layer 13 made of titanium oxide was formed at a thickness of 30 nm in the upper portion of the low refractive index layer 12. In this case, the high refractive index layer 13 was formed in the same procedures as in Samples 114 to 129 of EXAMPLE 1.

(Formation of Nitrogen-Containing Layer of Transparent Electrode)

Subsequently, a nitrogen-containing layer 14 made of each compound was formed at a thickness of 3 nm in the upper portion of the high refractive index layer 13. The nitrogen-containing layer 14 was formed in the same procedures as in Samples 114 to 129 of EXAMPLE 1.

(Conductive Layer of Transparent Electrode: Formation of Anode)

Then, a conductive layer 15 formed of silver and having a thickness of 8 nm was formed on nitrogen-containing layer 14 in the same way as in Samples 114 to 129 of EXAMPLE 1. This conductive layer 15 was used as an anode.

In the following, in the same way as in Sample 201, a positive hole transport injection layer 42a to an electron transport injection layer 42d were formed on the transparent electrode 10, and furthermore, a counter electrode 23 (cathode) was formed. Thereby, an organic electroluminescent element 40 of bottom emission type was formed on the transparent substrate 21. Subsequently, in the same way as in Sample 201, the organic electroluminescent element 40 was sealed by a sealing material and an adhesive, with the result that a light-emitting panel of the organic electroluminescent element of each of Samples 210 to 225 was obtained.

[Production Procedures of Organic Electroluminescent Elements of Samples 226 to 229]

(Formation of Low Refractive Index Layer of Transparent Electrode)

First, in the production of Samples 226 to 229, a low refractive index layer 12 made of magnesium fluoride was formed at a thickness of 90 nm in the upper portion of a transparent substrate 21 made of an alkali-free glass. In this case, the low refractive index layer 12 was formed in the same procedures as in Samples 132 to 135 of EXAMPLE 1.

(Formation of High Refractive Index Layer of Transparent Electrode)

Next, a high refractive index layer 13 made of niobium oxide, zirconium oxide, cadmium oxide or ITO was formed at a thickness of 30 nm in the upper portion of the low refractive index layer 12. In this case, the high refractive index layer 13 was formed in the same procedures as in Samples 132 to 135 of EXAMPLE 1.

(Formation of Nitrogen-Containing Layer of Transparent Electrode)

Subsequently, a nitrogen-containing layer 14 made of each compound was formed at a thickness of 3 nm in the upper portion of the high refractive index layer 13. The nitrogen-containing layer 14 was formed in the same procedures as in Samples 132 to 135 of EXAMPLE 1.

(Conductive Layer of Transparent Electrode: Formation of Anode)

Then, a conductive layer 15 formed of silver and having a thickness of 8 nm was formed on nitrogen-containing layer 14 in the same way as in Samples 132 to 135 of EXAMPLE 1. This conductive layer 15 was used as an anode.

In the following, in the same way as in Sample 201, a positive hole transport injection layer 42a to an electron transport injection layer 42d were formed on the transparent electrode 10, and furthermore, a counter electrode 23 (cathode) was formed. Thereby, an organic electroluminescent element 40 of bottom emission type was formed on the transparent substrate 21. Subsequently, in the same way as in Sample 201, the organic electroluminescent element 40 was sealed by a sealing material and an adhesive, with the result that a light-emitting panel of the organic electroluminescent element of each of Samples 226 to 229 was obtained.

[Production Procedures of Organic Electroluminescent Elements of Samples 230 to 232]

(Formation of Low Refractive Index Layer of Transparent Electrode)

First, in the production of Samples 230 to 232, a low refractive index layer 12 made of lithium fluoride, calcium fluoride or aluminum fluoride was formed at a thickness of 90 nm in the upper portion of a transparent substrate 21 made of an alkali-free glass. In this case, the low refractive index layer 12 was formed in the same procedures as in Samples 136 to 138 of EXAMPLE 1.

(Formation of High Refractive Index Layer of Transparent Electrode)

Next, a high refractive index layer 13 made of niobium oxide was formed at a thickness of 30 nm in the upper portion of the low refractive index layer 12. In this case, the high refractive index layer 13 was formed in the same procedures as in Samples 136 to 138 of EXAMPLE 1.

(Formation of Nitrogen-Containing Layer of Transparent Electrode)

Next, a nitrogen-containing layer 14 made of each compound was formed at a thickness of 3 nm in the upper portion of the high refractive index layer 13. The nitrogen-containing layer 14 was formed in the same procedures as in Samples 136 to 138 of EXAMPLE 1.

(Conductive Layer of Transparent Electrode: Formation of Anode)

Next, a conductive layer 15 formed of silver and having a thickness of 8 nm was formed on nitrogen-containing layer 14 in the same way as in Samples 136 to 138 of EXAMPLE 1. This conductive layer 15 was used as an anode.

In the following, in the same way as in Sample 201, a positive hole transport injection layer 42a to an electron transport injection layer 42d were formed on the transparent electrode 10, and furthermore, a counter electrode 23 (cathode) was formed. Thereby, an organic electroluminescent element 40 of bottom emission type was formed on the transparent substrate 21. Subsequently, in the same way as in Sample 201, the organic electroluminescent element 40 was sealed by a sealing material and an adhesive, with the result that a light-emitting panel of the organic electroluminescent element of each of Samples 230 to 232 was obtained.

[Production Procedures of Organic Electroluminescent Elements of Samples 233 to 235]

(Formation of Low Refractive Index Layer of Transparent Electrode)

First, in the production of Sample 233 to 235, a low refractive index layer 12 made of magnesium fluoride was formed at a thickness of 90 nm in the upper portion of a transparent substrate 21 made of an alkali-free glass. In this case, the low refractive index layer 12 was formed in the same procedures as in Samples 141 to 143 of EXAMPLE 1.

(Formation of High Refractive Index Layer of Transparent Electrode)

Next, a high refractive index layer 13 made of titanium oxide was formed at a thickness of 30 nm in the upper portion of the low refractive index layer 12. In this case, the high refractive index layer 13 was formed in the same procedures as in Samples 141 to 143 of EXAMPLE 1.

(Formation of Nitrogen-Containing Layer of Transparent Electrode)

Next, a nitrogen-containing layer 14 made of each compound was formed at a thickness of 3 nm in the upper portion of the high refractive index layer 13. The nitrogen-containing layer 14 was formed in the same procedures as in Samples 141 to 143 of EXAMPLE 1.

(Conductive Layer of Transparent Electrode: Formation of Anode)

Next, a conductive layer 15 formed of silver and having a thickness of 5 nm was formed on nitrogen-containing layer 14 in the same way as in Samples 141 to 143 of EXAMPLE 1. This conductive layer 15 was used as an anode.

In the following, in the same way as in Sample 201, a positive hole transport injection layer 42a to an electron transport injection layer 42d were formed on the transparent electrode 10, and furthermore, a counter electrode 23 (cathode) was formed. Thereby, an organic electroluminescent element 40 of bottom emission type was formed on the transparent substrate 21. Subsequently, in the same way as in Sample 201, the organic electroluminescent element 40 was sealed by a sealing material and an adhesive, with the result that a light-emitting panel of the organic electroluminescent element of each of Samples 233 to 235 was obtained.

[Evaluation of Each Sample of EXAMPLE 2]

With respect to the organic electroluminescent element 40 (light-emitting panel) produced in Samples 201 to 235, a driving voltage and a color change were measured. The results are shown in the following Table 3 together.

In the measurement of the driving voltage, a voltage in which a front luminance at the transparent electrode 10 side (namely, the transparent substrate 21 side) of the organic electroluminescent element 40 is 1000 cd/m$^2$ is the driving voltage. The spectral emission luminance meter CS-1000 (manufactured by CONIKA MINOLTA SENCING) was used in order to measure the luminance. The smaller the obtained voltage is, the better the result is.

Furthermore, in the measurement of the color change, the chromaticity in the CIE1931 colorimetric system was measured from positions of different angles, by applying a current of 2.5 mA/cm$^2$ to the organic electroluminescent element 40. At this time, there were measured chromaticities at the position of 0 degree which correspond to the normal direction with respect to the light-emitting surface on the transparent electrode 10 side, and at the positions of 45 degrees from the vertical and horizontal (up and down, right and left) directions. The difference in chromaticities measured at the positions of different angles is shown in the following Table 3 as the chromaticity difference. The chromaticity difference indicates viewing angle characteristics, and the smaller the value is, the more preferable the result becomes.

TABLE 3

| | | \multicolumn{6}{c|}{CONFIGURATION OF EXAMPLE TRANSPARENT ELECTRODE} |
|---|---|---|---|---|---|---|---|
| EXAMPLE NO. | SUBSTRATE MATERIAL | LOW REFRACTIVE INDEX LAYER | | HIGH REFRACTIVE INDEX LAYER | | LAYER HAVING COMPOUND CONTAINING NITROGEN ATOM | |
| | | COMPOUND | LAYER THICKNESS NM | COMPOUND | LAYER THICKNESS NM | COMPOUND | LAYER THICKNESS NM | NUMBER (N) OF EFFECTIVE UNSHARED ELECTRON PAIRS |
| 201 | GLASS | — | — | — | — | — | — | — |
| 202 | ↓ | — | — | — | — | — | — | — |
| 203 | ↓ | — | — | TiO$_2$ | 30 | — | — | — |
| 204 | ↓ | — | — | ↓ | ↓ | No. -1 | 10 | 0 |
| 205 | ↓ | — | — | ↓ | ↓ | No. -4 | ↓ | 1 |
| 206 | ↓ | MgF$_2$ | 90 | ↓ | ↓ | No. -1 | ↓ | 0 |
| 207 | ↓ | ↓ | ↓ | ↓ | ↓ | No. 1 | 10 | 1 |
| 208 | ↓ | ↓ | ↓ | ↓ | ↓ | ↓ | 5 | 1 |

TABLE 3-continued

| | | | | | | | | |
|---|---|---|---|---|---|---|---|---|
| 209 | ↓ | ↓ | ↓ | ↓ | ↓ | ↓ | 3 | 1 |
| 210 | ↓ | ↓ | ↓ | ↓ | ↓ | No. 3 | ↓ | 2 |
| 211 | ↓ | ↓ | ↓ | ↓ | ↓ | No. 4 | ↓ | 2 |
| 212 | ↓ | ↓ | ↓ | ↓ | ↓ | No. 5 | ↓ | 3 |
| 213 | ↓ | ↓ | ↓ | ↓ | ↓ | No. 6 | ↓ | 3 |
| 214 | ↓ | ↓ | ↓ | ↓ | ↓ | No. 7 | ↓ | 4 |
| 215 | ↓ | ↓ | ↓ | ↓ | ↓ | No. 8 | ↓ | 6 |
| 216 | ↓ | ↓ | ↓ | ↓ | ↓ | No. 9 | ↓ | 4 |
| 217 | ↓ | ↓ | ↓ | ↓ | ↓ | No. 10 | ↓ | 4 |
| 218 | ↓ | ↓ | ↓ | ↓ | ↓ | No. 11 | ↓ | 5 |
| 219 | ↓ | ↓ | ↓ | ↓ | ↓ | No. 12 | ↓ | 6 |
| 220 | ↓ | ↓ | ↓ | ↓ | ↓ | No. 13 | ↓ | 4 |
| 221 | ↓ | ↓ | ↓ | ↓ | ↓ | No. 14 | ↓ | 6 |
| 222 | ↓ | ↓ | ↓ | ↓ | ↓ | No. 15 | ↓ | 5 |
| 223 | ↓ | ↓ | ↓ | ↓ | ↓ | No. 16 | ↓ | 6 |
| 224 | ↓ | ↓ | ↓ | ↓ | ↓ | No. 17 | ↓ | 9 |
| 225 | ↓ | ↓ | ↓ | ↓ | ↓ | No. 18 | ↓ | 6 |
| 226 | ↓ | ↓ | ↓ | $Nb_2O_5$ | ↓ | No. 7 | ↓ | 4 |
| 227 | ↓ | ↓ | ↓ | ZrO | ↓ | ↓ | ↓ | 4 |
| 228 | ↓ | ↓ | ↓ | CdO | ↓ | ↓ | ↓ | 4 |
| 229 | ↓ | ↓ | ↓ | ITO | ↓ | ↓ | ↓ | 4 |
| 230 | ↓ | LiF | ↓ | $Nb_2O_5$ | ↓ | ↓ | ↓ | 4 |
| 231 | ↓ | $CaF_2$ | ↓ | ↓ | ↓ | ↓ | ↓ | 4 |
| 232 | ↓ | $AlF_3$ | ↓ | ↓ | ↓ | ↓ | ↓ | 4 |
| 233 | GLASS | $MgF_2$ | 90 | $TiO_2$ | 30 | No. 48 | 3 | 6 |
| 234 | ↓ | ↓ | ↓ | ↓ | ↓ | No. 46 | ↓ | 3 |
| 235 | ↓ | ↓ | ↓ | ↓ | ↓ | No. 47 | ↓ | 3 |

| | CONFIGURATION OF EXAMPLE TRANSPARENT ELECTRODE | | | | | | |
|---|---|---|---|---|---|---|---|
| | LAYER HAVING COMPOUND CONTAINING NITROGEN ATOM | | CONDUCTIVE LAYER | | RESULT OF EVALUATION | | |
| EXAMPLE NO. | MOLECULAR WEIGHT [M] | [N/M] | COMPOUND | LAYER THICKNESS NM | DRIVING VOLTAGE V | COLOR CHANGE Δxy | NOTE |
| 201 | — | — | Ag | 5 | NOT EMITTED | | COMPARATIVE |
| 202 | — | — | ↓ | 15 | <5 | 0.15 | COMPARATIVE |
| 203 | — | — | ↓ | 5 | NOT EMITTED | | COMPARATIVE |
| 204 | 178.23 | 0.0E+00 | ↓ | ↓ | NOT EMITTED | | COMPARATIVE |
| 205 | 839.00 | 1.2E−03 | ↓ | ↓ | NOT EMITTED | | COMPARATIVE |
| 206 | 178.23 | 0.0E+00 | ↓ | ↓ | NOT EMITTED | | COMPARATIVE |
| 207 | 500.55 | 2.0E−03 | ↓ | ↓ | 6 | 0.10 | PRESENT INVENTION |
| 208 | 500.55 | 2.0E−03 | ↓ | ↓ | 6 | 0.06 | PRESENT INVENTION |
| 209 | 500.55 | 2.0E−03 | ↓ | ↓ | 6 | 0.03 | PRESENT INVENTION |
| 210 | 655.81 | 3.0E−03 | ↓ | 8 | 5.5 | 0.03 | PRESENT INVENTION |
| 211 | 655.81 | 3.0E−03 | ↓ | ↓ | 5.5 | 0.03 | PRESENT INVENTION |
| 212 | 974.18 | 3.1E−03 | ↓ | ↓ | 5.5 | 0.03 | PRESENT INVENTION |
| 213 | 808.99 | 3.7E−03 | ↓ | ↓ | 5.5 | 0.03 | PRESENT INVENTION |
| 214 | 716.83 | 5.6E−03 | ↓ | ↓ | <5 | <0.03 | PRESENT INVENTION |
| 215 | 1036.19 | 5.8E−03 | ↓ | ↓ | <5 | <0.03 | PRESENT INVENTION |
| 216 | 551.64 | 7.3E−03 | ↓ | ↓ | <5 | <0.03 | PRESENT INVENTION |
| 217 | 516.60 | 7.7E−03 | ↓ | ↓ | <5 | <0.03 | PRESENT INVENTION |
| 218 | 539.63 | 9.3E−03 | ↓ | ↓ | <5 | <0.03 | PRESENT INVENTION |
| 219 | 646.76 | 9.3E−03 | ↓ | ↓ | <5 | <0.03 | PRESENT INVENTION |
| 220 | 412.45 | 9.7E−03 | ↓ | ↓ | <5 | <0.03 | PRESENT INVENTION |
| 221 | 616.71 | 9.7E−03 | ↓ | ↓ | <5 | <0.03 | PRESENT INVENTION |
| 222 | 463.53 | 1.1E−02 | ↓ | ↓ | <5 | <0.03 | PRESENT INVENTION |
| 223 | 540.62 | 1.1E−02 | ↓ | ↓ | <5 | <0.03 | PRESENT INVENTION |
| 224 | 543.58 | 1.7E−02 | ↓ | ↓ | <5 | <0.03 | PRESENT INVENTION |
| 225 | 312.30 | 1.9E−02 | ↓ | ↓ | <5 | <0.03 | PRESENT INVENTION |
| 226 | 716.83 | 5.6E−03 | ↓ | ↓ | <5 | <0.03 | PRESENT INVENTION |
| 227 | 716.83 | 5.6E−03 | ↓ | ↓ | <5 | 0.03 | PRESENT INVENTION |
| 228 | 716.83 | 5.6E−03 | ↓ | ↓ | <5 | 0.03 | PRESENT INVENTION |
| 229 | 716.83 | 5.6E−03 | ↓ | ↓ | <5 | 0.05 | PRESENT INVENTION |
| 230 | 716.83 | 5.6E−03 | ↓ | ↓ | <5 | <0.03 | PRESENT INVENTION |
| 231 | 716.83 | 5.6E−03 | ↓ | ↓ | <5 | <0.03 | PRESENT INVENTION |
| 232 | 716.83 | 5.6E−03 | ↓ | ↓ | <5 | <0.03 | PRESENT INVENTION |
| 233 | 379.38 | 1.6E−02 | Ag | 5 | <5 | <0.03 | PRESENT INVENTION |
| 234 | 576.65 | 5.2E−03 | ↓ | ↓ | <5 | <0.03 | PRESENT INVENTION |
| 235 | 545.55 | 5.5E−03 | ↓ | ↓ | <5 | <0.03 | PRESENT INVENTION |

[Evaluation Results of EXAMPLE 2]

As is clear from Table 3, it was confirmed that the organic electroluminescent element of each of Samples 207 to 235 having the nitrogen-containing layer 14 using Compounds No. 1 to No. 18 and Compounds No. 46 to No. 48 having the effective unshared electron pair content [n/M] of $2.0 \times 10^{-3} \leq$ [n/M] was able to give a front luminance of 1000 cd/m$^2$ at a low driving voltage of 6V or less. Furthermore, it was confirmed that each of the organic electroluminescent elements of these Samples 207 to 235 has a value of the color change having been suppressed to 0.12 or less.

Moreover, it was confirmed that the organic electroluminescent element of each of Samples 214 to 235 having the nitrogen-containing layer 14 using Compounds No. 7 to No. 18 and Compounds No. 46 to No. 48 having the effective unshared electron pair content [n/M] of $3.9 \times 10^{-3} \leq$ [n/M] was able to give a front luminance of 1000 cd/m$^2$ at a low driving voltage of less than 5 V.

In contrast, it was confirmed that no light emission was not able to be obtained with respect to the organic electroluminescent element of Sample 201 having mono-layer structure formed only by the conductive layer, the organic electroluminescent element of Sample 203 in which the conductive layer was formed in the upper portion of the high refractive layer without a nitrogen-containing layer, and the organic electroluminescent elements of Samples 204 to 206 having the underlying layer using Compound No.-1, No.-4 having the effective unshared electron pair content [n/M] that is outside the above-described range.

In addition, with respect to the organic electroluminescent element of Sample 202 without an underlying layer, the organic electroluminescent element functions as an electrode due to its low sheet resistance since the conductive layer has a thickness of 15 nm, and thus it was confirmed that the light emission was able to be observed at a low driving voltage. However, it was confirmed that the conductive layer made of silver having a large thickness had a large chromaticity difference depending on the view angle.

Furthermore, with respect to the organic electroluminescent elements of Samples 207 to 209 which were different only in the thicknesses of the nitrogen-containing layer, it was confirmed that the smaller the thickness of the nitrogen-containing layer was, the smaller the color change was. It was confirmed that the smaller the thickness of the nitrogen-containing layer was, namely, the smaller the distance between the high refractive layer and the conductive layer was, the more the view angle dependency of chromaticity was suppressed.

Moreover, with respect to the organic electroluminescent elements of Samples 226 to 229 which were different only in the compound used for the high refractive layer, every compound has a higher refractivity than the nitrogen-containing layer by 0.3 or more as explained in the prior EXAMPLE 1. It was confirmed that the driving voltage and the color change of each of the organic electroluminescent elements of these Samples was suppressed at a low level.

According to the above results, it was confirmed that the organic electroluminescent element using the transparent electrode having the configuration according to the present invention was able to achieve a high luminance light emission at a low driving voltage and stable surface emission. Additionally, it was confirmed that the lowering of the driving voltage for obtaining a predetermined luminance and the improvement of light emission life were expected.

Note that the present invention is not to be limited to the configurations explained in the above-described embodiment examples, and various modifications and changes are possible within the scope not departing from the configurations of the present invention.

REFERENCE SIGNS LIST

10 Transparent electrode
11 Base material
12 Low refractive index layer
13 High refractive index layer
14 Nitrogen-containing layer
15 Conductive layer
20, 30, 40 Organic electroluminescent element
21, 31 Transparent substrate
21*a*, 31*a* Light extraction surface
22, 42 Light-emitting functional layer
22*a* Positive hole injection layer
22*b* Positive hole transport layer
22*c*, 42*b* Light-emitting layer
22*d* Electron transport layer
22*e* Electron injection layer
23, 33 Counter electrode
42*a* Positive transport injection layer
42*c* Positive block layer
42*d* Electron transport injection layer

The invention claimed is:

1. A transparent electrode, comprising
a nitrogen-containing layer constituted using a compound which includes nitrogen atoms, and has an effective unshared electron pair content [n/M] of $2.0 \times 10^{-3} \leq$ [n/M], when n is the number of unshared electron pairs which are not involved in aromaticity and which are not coordinated to a metal in the unshared electron pairs of the nitrogen atoms, and M is a molecular weight,
a conductive layer provided adjacent to the nitrogen-containing layer and having silver as a main component,
a high refractive index layer provided to sandwich the nitrogen-containing layer between the conductive layer and the high refractive index layer and having a higher refractive index than that of the nitrogen-containing layer,
a low refractive index layer provided in contact with the high refractive index layer and having a lower refractive index than that of the high refractive index layer, and
the nitrogen-containing layer contains a compound having a structure represented by the following General Formula (1), General Formula (1)

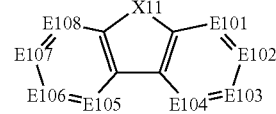

where,
X11 represents —N(R11) or —O—,
E101 to E108 each represent —C(R12)= or —N=,
at least one of E101 to E108 is —N=, and
the R11 and the R12 each represent a hydrogen atom (H) or a substituent.

2. The transparent electrode according to claim 1, wherein X11 in the General Formula (1) is —N(R11)-, as represented by the following General Formula (1a)

General Formula (1a)

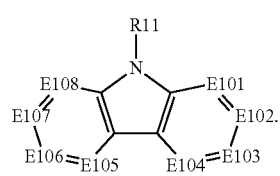

3. The transparent electrode according to claim 2, wherein the compound which includes nitrogen atoms also has a structure represented by General Formula 1a.

4. The transparent electrode according to claim 2, wherein E104 in the General Formula (1a) is —N═, as represented by the following General Formula (1a-1)

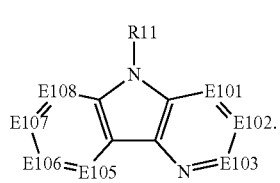

General Formula (1a-1)

5. The transparent electrode according to claim 4, wherein the compound which includes nitrogen atoms also has a structure represented by General Formula 1.

6. The transparent electrode according to claim 4, wherein the compound which includes nitrogen atoms also has a structure represented by General Formula 1a-1.

7. The transparent electrode according to claim 2, wherein E103 and E106 in the General Formula (1) is —N═, as represented by the following General Formula (1a-2)

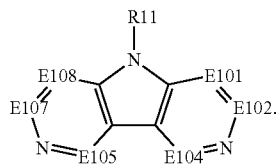

General Formula (1a-2)

8. The transparent electrode according to claim 7, wherein the compound which includes nitrogen atoms also has a structure represented by General Formula 1a-2.

9. The transparent electrode according to claim 1, wherein X11 in the General Formula (1) is —O— and E104 is —N═, as represented by the following General Formula (1b)

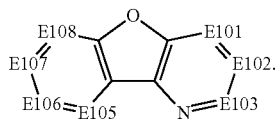

General Formula (1b)

10. The transparent electrode according to claim 9, wherein the compound which includes nitrogen atoms also has a structure represented by General Formula 1b.

11. A transparent electrode, comprising
a nitrogen-containing layer constituted using a compound which includes nitrogen atoms, and has an effective unshared electron pair content [n/M] of $2.0 \times 10^{-3} \leq [n/M]$, when n is the number of unshared electron pairs which are not involved in aromaticity and which are not coordinated to a metal in the unshared electron pairs of the nitrogen atoms, and M is a molecular weight,
a conductive layer provided adjacent to the nitrogen-containing layer and having silver as a main component,
a high refractive index layer provided to sandwich the nitrogen-containing layer between the conductive layer and the high refractive index layer and having a higher refractive index than that of the nitrogen-containing layer,
a low refractive index layer provided in contact with the high refractive index layer and having a lower refractive index than that of the high refractive index layer, and
the nitrogen-containing layer contains a compound having a structure represented by the following General Formula (2),

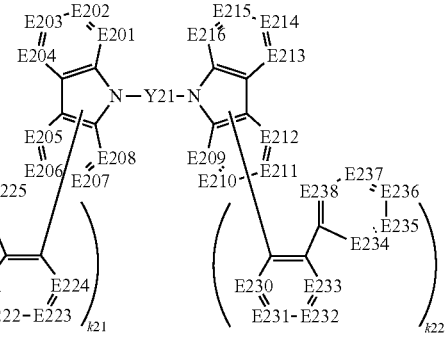

General Formula (2)

where,
Y21 represents a divalent linkage group of an arylene group, a heteroarylene group or combination thereof,
E201 to E216 and E221 to E238 each represent —C(R21)═ or —N═,
the R21 represents a hydrogen atom (H) or a substituent,
at least one of E221 to E229 and at least one of E230 to E238 represent —N═, and
k21 and k22 represent an integer of 0 to 4, and k21+k22 is an integer of 2 or more.

12. The transparent electrode according to claim 11, wherein the compound which includes nitrogen atoms also has a structure represented by General Formula 2.

13. A transparent electrode, comprising
a nitrogen-containing layer constituted using a compound which includes nitrogen atoms, and has an effective unshared electron pair content [n/M] of $2.0 \times 10^{-3} \leq [n/M]$, when n is the number of unshared electron pairs which are not involved in aromaticity and which are not coordinated to a metal in the unshared electron pairs of the nitrogen atoms, and M is a molecular weight,
a conductive layer provided adjacent to the nitrogen-containing layer and having silver as a main component,
a high refractive index layer provided to sandwich the nitrogen-containing layer between the conductive layer and the high refractive index layer and having a higher refractive index than that of the nitrogen-containing layer,
a low refractive index layer provided in contact with the high refractive index layer and having a lower refractive index than that of the high refractive index layer, and
the nitrogen-containing layer contains a compound having a structure represented by the following General Formula (3),

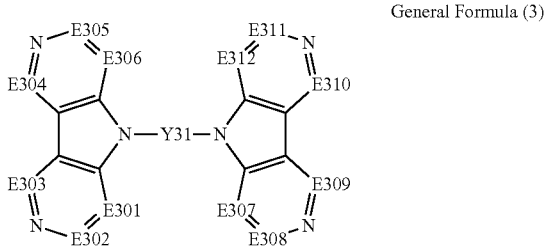

General Formula (3)

where,
E301 to E312 each represent —C(R31)=,
the R31 represents a hydrogen atom (H) or a substituent, and
Y31 represents a divalent linkage group of an arylene group, a heteroarylene group or combination thereof.

14. The transparent electrode according to claim 13, wherein the compound which includes nitrogen atoms also has a structure represented by General Formula 3.

15. A transparent electrode, comprising
a nitrogen-containing layer constituted using a compound which includes nitrogen atoms, and has an effective unshared electron pair content [n/M] of $2.0 \times 10^{-3} \leq [n/M]$, when n is the number of unshared electron pairs which are not involved in aromaticity and which are not coordinated to a metal in the unshared electron pairs of the nitrogen atoms, and M is a molecular weight,
a conductive layer provided adjacent to the nitrogen-containing layer and having silver as a main component,
a high refractive index layer provided to sandwich the nitrogen-containing layer between the conductive layer and the high refractive index layer and having a higher refractive index than that of the nitrogen-containing layer,
a low refractive index layer provided in contact with the Mali refractive index layer and having a lower refractive index than that of the high refractive index layer, and
the nitrogen-containing layer contains a compound having a structure represented by the following General Formula (4),

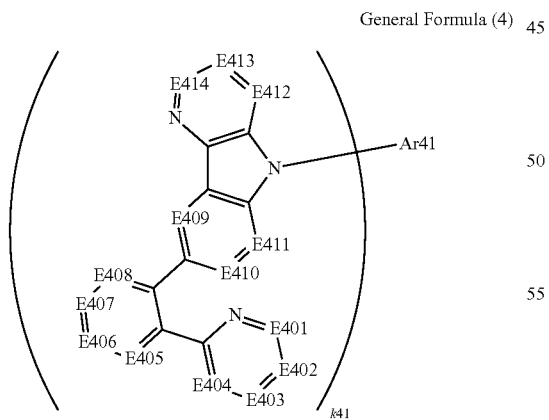

General Formula (4)

where,
E401 to E414 each represent —C(R41)=,
the R41 represents a hydrogen atom (H) or a substituent,
Ar41 represents a substituted or un-substituted aromatic hydrocarbon ring or a substituted or un-substituted aromatic heterocyclic ring, and
k41 represents an integer of 3 or more.

16. The transparent electrode according to claim 15, wherein the compound which includes nitrogen atoms also has a structure represented by General Formula 4.

17. A transparent electrode, comprising
a nitrogen-containing layer constituted using a compound which includes nitrogen atoms, and has an effective unshared electron pair content [n/M] of $2.0 \times 10^{-3} \leq [n/M]$, when n is the number of unshared electron pairs which are not involved in aromaticity and which are not coordinated to a metal in the unshared electron pairs of the nitrogen atoms, and M is a molecular weight,
a conductive layer provided adjacent to the nitrogen-containing layer and having silver as a main component,
a high refractive index layer provided to sandwich the nitrogen-containing layer between the conductive layer and the high refractive index layer and having a higher refractive index than that of the nitrogen-containing layer,
a low refractive index layer provided in contact with the high refractive index layer and having a lower refractive index than that of the high refractive index layer, and
the nitrogen-containing layer contains a compound having a structure represented by the following General Formula (5),

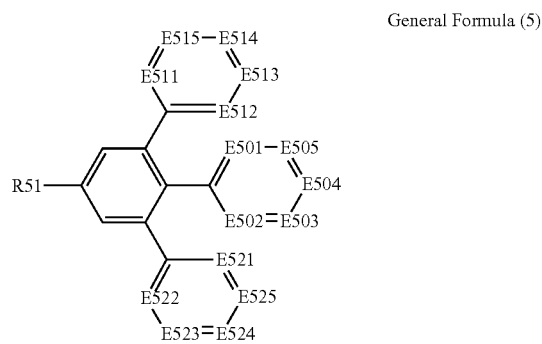

General Formula (5)

where,
R51 represents a substituent,
E501, E502, E511 to E515, and E521 to E525 each represent —C(R52)= or —N=,
E503 to E505 each represent —C(R52)=,
the R52 represents a hydrogen atom (H) or a substituent,
at least one of E501 and E502 is —N=,
at least one of E511 to E515 is —N=, and
at least one of E521 to E525 is —N=.

18. The transparent electrode according to claim 17, wherein the compound which includes nitrogen atoms also has a structure represented by General Formula 5.

19. A transparent electrode, comprising
a nitrogen-containing layer constituted using a compound which includes nitrogen atoms, and has an effective unshared electron pair content [n/M] of $2.0 \times 10^{-3} \leq [n/M]$, when n is the number of unshared electron pairs which are not involved in aromaticity and which are not coordinated to a metal in the unshared electron pairs of the nitrogen atoms, and M is a molecular weight,
a conductive layer provided adjacent to the nitrogen-containing layer and having silver as a main component, a high refractive index layer provided to sandwich the nitrogen-containing layer between the conductive layer and the high refractive index layer and having a higher refractive index than that of the nitrogen-containing layer, a low refractive index layer provided in contact with the high refractive index layer and having a lower refractive index than that of the high refractive index layer, and the nitrogen-containing layer contains a compound having a structure represented by the following General Formula (6),

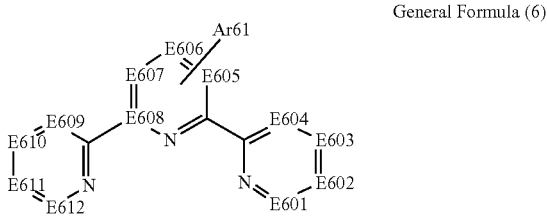

General Formula (6)

where,
E601 to E612 each represent —C(R61)= or —N=,
the R61 represents a hydrogen atom (H) or a substituent, and Ar61 represents a substituted or un-substituted aromatic hydrocarbon ring or a substituted or un-substituted aromatic heterocyclic ring.

20. The transparent electrode according to claim 19, wherein the compound which includes nitrogen atoms also has a structure represented by General Formula 6.

21. A transparent electrode, comprising
a nitrogen-containing layer constituted using a compound which includes nitrogen atoms, and has an effective unshared electron pair content [n/M] of $2.0\times10^{-3} \leq [n/M]$, when n is the number of unshared electron pairs which are not involved in aromaticity and which are not coordinated to a metal in the unshared electron pairs of the nitrogen atoms, and M is a molecular weight, a conductive layer provided adjacent to the nitrogen-containing layer and having silver as a main component, a high refractive index layer provided to sandwich the nitrogen-containing layer between the conductive layer and the high refractive index layer and having a higher refractive index than that of the nitrogen-containing layer, a low refractive index layer provided in contact with the high refractive index layer and having a lower refractive index than that of the high refractive index layer, and the nitrogen-containing layer contains a compound having a structure represented by the following General Formula (7),

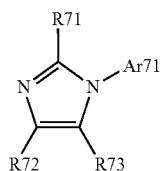

General Formula (7)

where,
R71 to R73 represent a hydrogen atom (H) or a substituent, and Ar71 represents an aromatic hydrocarbon ring or an aromatic heterocyclic ring.

22. The transparent electrode according to claim 21, wherein the compound which includes nitrogen atoms also has a structure represented by General Formula 7.

23. A transparent electrode, comprising
a nitrogen-containing layer constituted using a compound which includes nitrogen atoms, and has an effective unshared electron pair content [n/M] of $2.0\times10^{-3} \leq [n/M]$, when n is the number of unshared electron pairs which are not involved in aromaticity and which are not coordinated to a metal in the unshared electron pairs of the nitrogen atoms, and M is a molecular weight, a conductive layer provided adjacent to the nitrogen-containing layer and having silver as a main component, a high refractive index layer provided to sandwich the nitrogen-containing layer between the conductive layer and the high refractive index layer and having a higher refractive index than that of the nitrogen-containing layer, a low refractive index layer provided in contact with the high refractive index layer and having a lower refractive index than that of the high refractive index layer, and the nitrogen-containing layer contains a compound having a structure represented by the following General Formula (8),

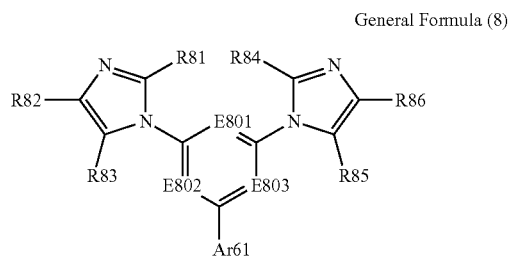

General Formula (8)

where,
R81 to R86 represent a hydrogen atom (H) or a substituent,
E801 to E803 each represent —C(R87)= or —N=,
R87 represents a hydrogen atom (H) or a substituent, and Ar81 represents an aromatic hydrocarbon ring or an aromatic heterocyclic ring.

24. The transparent electrode according to claim 23, wherein the compound having a structure represented by General Formula (8) has a structure represented by the following General Formula (8a)

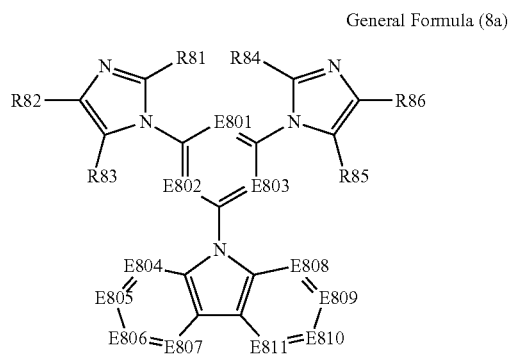

General Formula (8a)

where,
E804 to E811 each represent —C(R88)= or —N=,
R88 represents a hydrogen atom (H) or a substituent, at least one of E808 to E811 is —N=, and
E804 to E807 and E808 to E811 may bond each other to form a new ring.

25. The transparent electrode according to claim 24, wherein the compound which includes nitrogen atoms also has a structure represented by General Formula 8a.

26. The transparent electrode according to claim 23, wherein the compound which includes nitrogen atoms also has a structure represented by General Formula 8.

* * * * *